US010759854B2

(12) United States Patent
Chi et al.

(10) Patent No.: US 10,759,854 B2
(45) Date of Patent: Sep. 1, 2020

(54) INTERFERON ALPHA AND OMEGA ANTIBODY ANTAGONISTS

(71) Applicant: Janssen Biotech, Inc., Horsham, PA (US)

(72) Inventors: Ellen Chi, San Diego, CA (US); Judith Connor, San Diego, CA (US); Chichi Huang, Berwyn, PA (US); Jarrat Jordan, Norristown, PA (US); Xiefan Lin-Schmidt, Ambler, PA (US); Jinquan Luo, Malvern, PA (US); Lu Lu, Schwenksville, PA (US); Christian Martinez, San Diego, CA (US); Galina Obmolova, Phoenixville, PA (US); Ronald Swanson, San Diego, CA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 16/424,907

(22) Filed: May 29, 2019

(65) Prior Publication Data

US 2019/0359705 A1    Nov. 28, 2019

Related U.S. Application Data

(62) Division of application No. 16/222,285, filed on Dec. 17, 2018, now Pat. No. 10,358,491, which is a division of application No. 14/745,939, filed on Jun. 22, 2015, now Pat. No. 10,208,113.

(60) Provisional application No. 62/015,765, filed on Jun. 23, 2014.

(51) Int. Cl.
*C07K 16/24* (2006.01)
*A61K 38/13* (2006.01)
*A61K 45/06* (2006.01)
*A61K 39/395* (2006.01)
*A61K 39/00* (2006.01)

(52) U.S. Cl.
CPC ............ *C07K 16/249* (2013.01); *A61K 38/13* (2013.01); *A61K 39/3955* (2013.01); *A61K 45/06* (2013.01); *A61K 2039/505* (2013.01); *A61K 2039/507* (2013.01); *C07K 2317/21* (2013.01); *C07K 2317/31* (2013.01); *C07K 2317/33* (2013.01); *C07K 2317/52* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,683,195 | A  | 7/1987  | Mullis et al.     |
|-----------|----|---------|-------------------|
| 5,223,409 | A  | 6/1993  | Ladner et al.     |
| 5,225,539 | A  | 7/1993  | Winter            |
| 5,317,089 | A  | 5/1994  | Adolf             |
| 5,403,484 | A  | 4/1995  | Ladner et al.     |
| 5,427,908 | A  | 6/1995  | Dower et al.      |
| 5,474,771 | A  | 12/1995 | Lederman et al.   |
| 5,565,332 | A  | 10/1996 | Hoogenboom et al. |
| 5,571,698 | A  | 11/1996 | Ladner et al.     |
| 5,580,717 | A  | 12/1996 | Dower et al.      |
| 5,869,620 | A  | 2/1999  | Whitlow et al.    |
| 5,885,793 | A  | 3/1999  | Griffiths et al.  |
| 5,932,448 | A  | 8/1999  | Tso et al.        |
| 5,969,108 | A  | 10/1999 | McCafferty et al. |
| 6,150,584 | A  | 11/2000 | Kucherlapati et al. |
| 6,172,197 | B1 | 1/2001  | McCafferty et al. |
| 6,521,404 | B1 | 2/2003  | Griffiths et al.  |
| 6,544,731 | B1 | 4/2003  | Griffiths et al.  |
| 6,555,313 | B1 | 4/2003  | Griffiths et al.  |
| 6,582,915 | B1 | 6/2003  | Griffiths et al.  |
| 6,593,081 | B1 | 7/2003  | Griffiths et al.  |
| 6,737,056 | B1 | 5/2004  | Presta            |
| 6,747,037 | B1 | 6/2004  | Old et al.        |
| 6,818,749 | B1 | 11/2004 | Kashmiri et al.   |
| 6,833,441 | B2 | 12/2004 | Wang et al.       |
| 7,695,936 | B2 | 4/2010  | Carter et al.     |
| 7,709,226 | B2 | 5/2010  | Foote             |
| 8,460,668 | B2 | 6/2013  | Cardarelli        |
| 2007/0287170 | A1 | 12/2007 | Davis et al.   |
| 2009/0118127 | A1 | 5/2009  | Raghunathan    |
| 2009/0182127 | A1 | 7/2009  | Kjaergaard et al. |
| 2010/0015133 | A1 | 1/2010  | Igawa et al.   |
| 2010/0021477 | A1 | 1/2010  | Tsui et al.    |
| 2010/0261620 | A1 | 10/2010 | Almagro et al. |
| 2010/0286374 | A1 | 11/2010 | Kannan et al.  |

(Continued)

FOREIGN PATENT DOCUMENTS

EP          0 490 233 A1    3/1987
WO         WO 90/04026 A1   4/1990

(Continued)

OTHER PUBLICATIONS

Lech et al. JASN Sep. 2013, 24 (9) 1357-1366; DOI: https://doi.org/10.1681/ASN.2013010026 (Year: 2013).*

Günther R. Adolf, "Monoclonal Antibodies and Enzyme Immunoassays Specific for Human Interferon (IFN) w 1: Evidence that IFN-w1 is a Component of Human Leukocyte IFN," Virology, 175: 410-417 (1990).

Al-Lazikani, et al., "Standard Conformations for the Canonical Structures of Immunoglobulins," Journal of Molecular Biology, 273: 927-948 (1997).

(Continued)

*Primary Examiner* — Joanne Hama
*Assistant Examiner* — Jegatheesan Seharaseyon
(74) *Attorney, Agent, or Firm* — Eric Dichter

(57) ABSTRACT

The present invention relates to antibodies that broady neutralize interferon-α and interferon-ω, polynucleotides encoding the antibodies or fragments, and methods of making and using the foregoing.

13 Claims, 29 Drawing Sheets

Specification includes a Sequence Listing.

(56) References Cited

U.S. PATENT DOCUMENTS

| | | |
|---|---|---|
| 2011/0123532 A1 | 5/2011 | Gurney et al. |
| 2011/0206663 A1 | 8/2011 | Chuntharapai et al. |
| 2011/0206672 A1 | 8/2011 | Little et al. |
| 2012/0149876 A1 | 6/2012 | Von Kreudenstein et al. |
| 2014/0027648 A1 | 1/2014 | Petersson et al. |
| 2014/0271648 A1 | 9/2014 | Chi et al. |

FOREIGN PATENT DOCUMENTS

| | | |
|---|---|---|
| WO | WO 90/07861 A1 | 7/1990 |
| WO | WO 92/01047 A1 | 12/1992 |
| WO | WO 92/22653 A1 | 12/1992 |
| WO | WO 95/15388 A1 | 6/1995 |
| WO | WO 97/14719 A1 | 4/1997 |
| WO | WO 99/45962 A1 | 9/1999 |
| WO | WO 99/57150 A2 | 11/1999 |
| WO | WO 01/68860 A1 | 9/2001 |
| WO | WO 02/43478 A2 | 6/2002 |
| WO | WO 02/066630 A1 | 8/2002 |
| WO | WO 2013/138586 A1 | 9/2003 |
| WO | WO 2004/111233 A1 | 6/2004 |
| WO | WO 2006/013107 A1 | 2/2006 |
| WO | WO 2006/033702 A2 | 3/2006 |
| WO | WO 2006/054059 A1 | 5/2006 |
| WO | WO 2006/119115 A2 | 11/2006 |
| WO | WO 2007/005955 A2 | 1/2007 |
| WO | WO 2007/027714 A2 | 3/2007 |
| WO | WO 2007/070750 A1 | 6/2007 |
| WO | WO 2007/076927 A1 | 7/2007 |
| WO | WO 2007/106769 A2 | 9/2007 |
| WO | WO 2007/147019 A2 | 12/2007 |
| WO | WO 2007/149032 A1 | 12/2007 |
| WO | WO 2008/021156 A2 | 2/2008 |
| WO | WO 2008/047134 A2 | 4/2008 |
| WO | WO 2008/103432 A1 | 8/2008 |
| WO | WO 2008/118356 A2 | 10/2008 |
| WO | WO 2008/119353 A1 | 10/2008 |
| WO | WO 2008/134659 A2 | 11/2008 |
| WO | WO 2009/085462 A1 | 7/2009 |
| WO | WO 2009/130459 A2 | 10/2009 |
| WO | WO 2009/134776 A2 | 11/2009 |
| WO | WO 2009/135861 A2 | 11/2009 |
| WO | WO 2010/025400 A2 | 3/2010 |
| WO | WO 2010/056948 A2 | 5/2010 |
| WO | WO 2010/088444 A1 | 8/2010 |
| WO | WO 2011/036460 A1 | 3/2011 |
| WO | WO 2011/053763 A2 | 5/2011 |
| WO | WO 2011/066501 A1 | 6/2011 |
| WO | WO 2011/130434 A2 | 10/2011 |
| WO | WO 2011/131746 A2 | 10/2011 |
| WO | WO 2011/143545 A1 | 11/2011 |
| WO | WO 2012/004367 A1 | 1/2012 |
| WO | WO 2012/022811 A1 | 2/2012 |
| WO | WO 2012/095662 A1 | 7/2012 |
| WO | WO 2014/151422 A1 | 9/2014 |
| WO | WO 2015/001013 A2 | 1/2015 |

OTHER PUBLICATIONS

Juan C. Almagro, "Identification of differences in the specificity-determining residues of antibodies that recognize antigens of different size: implications for the rational design of antibody repertoires," Journal of Molecular Recognition, 17: 132-143 (2004).
Arico, et al., "Concomitant detection of IFNα-treated subjects at early times after repeated local cytokine treatments," Journal of Translations Medicine, 9: 67 (2011).
Baechler, et al., "Interferon-inducible gene expression signature in peripheral blood cells of patients with severe lupus," Proceedings of the National Academy of Science USA, 100(5): 2610-2615 (2003).
Bauer, et al., "Interferon-Regulated Chemokines as Biomarkers of Systemic Lupus Erythematosus Disease Activity," Arthritis & Rheumatism, 60(10): 3098-3107 (2009).
Bedu-Addo, et al, "Use of Biophysical Characterization in Preformulation Development of a Heavy-Chain Fragment of Botulinum Serotype B: Evaluation of Suitable Purification Process Conditions," Pharmaceutical Research, 21(8): 1353-1361 (2004).

Bennett, et al., "Interferon and Granulopoiesis Signatures in Systemic Lupus Erythematosus Blood," The Journal of Experimental Medicine, 197(6): 711-723 (2003).

Benoit, et al., "A Monoclonal Antibody to Recombinant Human IFN-α Receptor Inhibits Biologic Activity of Several Species of Human IFN-α, IFN-β, and IFN-ω," The Journal of Immunology, 150: 707-716 (1993).

Brüggemann, et al., "Production of human antibody repertoires in transgenic mice," Current Opinion in Biotechnology, 8: 455-456 (1997).

Brüggemann, et al., "Human antibody production in transgenic mice: expression from 100kb of the human IgH locus," European Journal of Immunology, 21: 1323-1326 (1991).

Chothia, et al., "Canonical Structures for the Hypervariable Regions of Immunoglobulins," Journal of Molecular Biology, 196: 901-917 (1987).

Dall'Acqua, et al., "Properties of Human IgG1s Engineered for Enhanced Binding to the Neonatal Fc Receptor (FcRN)," The Journal of Biological Chemistry, 281(33): 23514-23524 (2006).

Dall'Era, et al., "Type I interferon correlates with serological and clinical manifestations of SLE," Annals of Rheumatology Diseases, 64: 1692-1697 (2005).

Deonarain, et al., "Protective Role for Interferon-β in Coxsackievirus B3 Infection," Circulation, 110: 3540-3543 (2004).

Deonarain, et al., "Impaired Antiviral Response and Alpha/Beta Interferon Induction in Mice Lacking Beta Interferon," Journal of Virology, 74(7): 3404-3409 (2000).

Fishwild, et al., "High-avidity human IgGκ monoclonal antibodies from a novel strain of minilocus transgenic mice," Nature Biotechnology, 14: 845-851 (1996).

Gerlach, et al., "Effects of Type I Interferons on Friend Retrovirus Infection," Journal of Virology, 80(7): 3438-3444 (2006).

Goding, et al., Monoclonal Antibodies: Principles and Practice, Academic Press, 59-103 (1986).

Gonzalez-Navajas, et al., "Immunology functions of type I interferons," Nature Reviews Immunology, 12: 125-135 (2012).

Green, et al., "Antigen-specific human monoclonal antibodies from mice engineered with human Ig heavy and light chain YACs," Nature Genetics, 7: 13-21 (1994).

Larry L. Green, "Antibody engineering via genetic engineering of the mouse: XenoMouse strains are a vehicle for the facile generation of therapeutic human monoclonal antibodies," Journal of Immunological Methods, 231: 11-23 (1999).

Green, et al., "Regulation of B Cell Development by Variable Gene Complexity in Mice Reconstituted with Human Immunological Yeast Artificial Chromosomes," Journal of Experimental Medicine, 188(3): 483-495 (1998).

Gupta, et al., "Development of a Multidose Formulation for a Humanized Monoclonal Antibody Using Experimental Design Techniques," AAPS PharmSci, 5(2) (2003).

Han, et al., "Analysis of gene expression profiles in human systemic lupus erythematosus using oligonucleotide microarray," Genes and Immunity, 4: 177-186 (2003).

Hervas-Stubbs, et al., "Direct Effects of Type 1 Interferons on Cells of the Immune System," Clinical Cancer Research, 17(9): 2619-2627 (2011).

Hoogenboom, et al., "By-passing Immunisation Human Antibodies from Synthetic Repertoires of Germline $V_H$ Gene Segments Rearranged *in Vitro*," Journal of Molecular Biology, 227: 381-388 (1992).

Hooks, et al., "Multiple Interferons in the circulation of Patients with Systemic Lupus Erythematosus and Vasculitis," Arthritis and Rheumatism, 25(4): 396-400 (1982).

Hua, et al, "Functional Assay of Type I Interferon in Systemic Lupus Erythematosus Plasma and Association with Anti-RNA Binding Protein Autoantibodies," Arthritis & Rheumatism, 54(6): 1906-1916 (2006).

Isenberg, et al., "BILAG 2004. Development and initial validation of an updated version of the British Isles Lupus Assessment Group's disease activity index for patients with systemic lupus erythematosus," Rheumatology, 44: 902-906 (2005).

(56) References Cited

OTHER PUBLICATIONS

Kalunian, et al., "Efficacy and Safety of Rontalizumab (Anti-Interferon Alpha) in SLE Subjected with Restricted Immunosuppressant Use: Results of a Randomized, Double-Blind, Placebo-Controlled Phase 2 Study," American College of Rheumatology, Arthritis & Rheumatism Annual Scientific meeting, Nov. 9-14, 2012, Washington, DC. Abstract #2622.
Karageorgas, et al., "Activation of Type I Interferon Pathway in Systemic Lupus Erythematosus: Association with Distinct Clinical Phenotypes," Journal of Biomedicine and Biotechnology, vol. 2011, Article ID 273907, 13 pages.
Kennedy, et al., "Efficacy and safety of rontalizumab (anti-interferon-alpha) in sle patients with restricted immunosuppressant use: results of a randomized, double-blind, placebo-controlled phase 2 study," The $10^{th}$ International Congress on SLE, Buenos Aires, Argentina, Presentation 5, No. O22 (Apr. 20, 2013).
Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2000).
Knight, et al., "Pharmacodynamic enhancement of the anti-platelet antibody Fab abciximab by site-specific Pegylation," Platelets, 15(7): 409-418 (2004).
Kohler, et al., "Continuous cultures of fused cells secreting antibody of predefined specificity," Nature, 256: 495-497 (1975).
Kong, et al., "Enhanced expression of interferon-inducible protein-10 correlates with disease activity and clinical manifestations in systemic lupus erythematosus," Clinical & Experimental Immunology, 156: 134-140 (2009).
Krebs, et al., "High-throughput generation and engineering of recombinant human antibodies," Journal of Immunological Methods, 254: 67-84 (2001).
Kuhn, et al., "The classification and diagnosis of cutaneous lupus erythematosus," Journal of Autoimmunity, 48-49: 14-19 (2014).
Lazear, et al., "Beta Interferon Controls West Nile Virus Infection and Pathogenesis in Mice," Journal of Virology, 85(14): 7186-7194 (2011).
LeFranc, et al., "IMGT unique numbering for immunoglobulin and T cell receptor variable domains and Ig superfamily V-like domains," Developmental & Comparative Immunology, 27: 55-77 (2003).
Leong, et al., "Adapting Pharmacokinetic Properties of a Humanized Anti-Interleukin-8 Antibody for Therapeutic Applications Using Site-Specific Pegylation," Cytokine, 16(30: 106-199 (2001).
Lonberg, et al., "Human Antibodies from Transgenic Mice," International Review of Immunology, 13: 65-93 (1995).
Lonberg, et al., "Antigen-specific human antibodies from mice comprising four distinct genetic modifications," Nature, 368: 856-859 (1994).
Luo, et al., "Coevolution of Antibody Stability and $V_K$ CDR-L3 Canonical Structure," Journal of Molecular Biology, 402: 708-719 (2010).
Maa, et al., "Aggregation of recombinant human growth hormone induced by phenolic compounds," International Journal of Pharmaceutics, 140: 155-168 (1996).
MacLennan, et al., "Structure-Function Relationships in the $Ca^{2+}$-Binding and Translocation Domain of SERCA1: physiological correlates in Brody disease," Acta Physiological Scan. 163 (Supplement 643): 55-67 (1998).
Marks, et al., "By-passing Immunization Human Antibodies from V-gene Libraries Displayed on Phage," Journal of Molecular Biology, 222: 581-597 (1991).
Mendez, et al., "Functional transplant of megabase human immunoglobulin loci recapitulates human antibody response in mice," Nature Genetics, 15: 146-156 (1997).
Merrill, et al., "Safety profile and clinical activity of sifalimumab, a fully human anti-interferon α monoclonal antibody, in systemic lupus erythematosus: a phase I, multicenter, double-blind randomized study," Annals of Rheumatoid Disease, 70: 1905-1913 (2011).

Mohty, et al., "Induction of IP-10/CXCL10 secretion as an immunomodulatory effect of low-dose adjuvant interferon-alpha during treatment of melanoma," Immunobiology, 215: 113-123 (2010).
Niewold, et al., "High serum IFN-α activity is a heritable risk factor for systemic lupus erythematosus," Genes and Immunity, 8: 492-502 (2007).
Obmolova, et al., "Promoting crystallization of antibody-antigen complexes via microseed matrix screening," Biological Crystallography, D66: 927-933 (2010).
Osbourn, et al., "From rodent reagents to human therapeutics using antibody guided selection," Methods, 36: 61-68 (2005).
Eduardo Padlan, "A Possible Procedure for Reducing the Immunogenecity of Antibody Variable Domains While Preserving Their Ligand Binding Properties," Molecular Immunology, 28(4/5): 489-498 (1991).
Petri et al., "Sifalimumab, a Human Anti Interferon-α Monoclonal Antibody, in Systemic Lupus Erythematosus," Arthritis & Rheumatism, 65(4): 1011-1021 (2013).
Raghunathan, et al., "Antigen-binding site anatomy and somatic mutations in antibodies that recognize different types of antigens," Journal of Molecular Recognition, 25: 103-113 (2012).
Remmele, et al., "Interleukin-1 Receptor (IL-1R) Liquid Formulation Development Using Differential Scanning Calorimetry," Pharmaceutical Research, 15(2): 200-208 (1998).
Rice, et al., "Assessment of interferon-related biomarkers in Aicardi-Goutières syndrome associated with mutations in TREX1, RNASEH2A, RNASEH2B, RNASEH2C, SAMED1, and ADAR: a case-control study," Lancet Neurology, 12: 1159-1169 (2013).
Richardson, et al., "Development of a Quantitative PCR Method to Determine Interferon Signature Metric Status in SLE Patients: Distribution and Clinical & Serological Associations in Two Lupus Clinical Trials, Immunosuppressant Use: Results of a Randomized, Double-Blind, Placebo-Controlled Phase 2 Study," American College of Rheumatology, Arthritis & Rheumatism Annual Scientific meeting, Nov. 9-14, 2012, Washington, DC. Abstract #620.
Roberts, et al., "The Evolution of Type I Interferons," Journal of Interferon ad Cytokine Research, 18: 805-816 (1998).
Rose, et al., "IFNα and its response proteins, IP-10 and SIGLEC-1, are biomarkers of disease activity in systemic lupus erythematosus," Annals of the Rheumatic Diseases, 72: 1639-1645 (2013).
Sasaki, et al., "Structure-Mutation Analysis of the ATPaseSite of *Dictyostelium Discoideum* Myosin II," Advances in Bio physiology, 35: 1-24 (1998).
Sestak, et al., "The genetics of systemic lupus erythematosus and implications for targeted therapy," Annals of Rheumatic Diseases, 70(Supplement 1): i37-i43 (2011).
Sheets, et al., "Efficient construction of a large nonimmune phage antibody library: The production of high-affinity human single-chain antibodies to protein antigens," Proceedings of the National Academy of Science USA, 95: 6157-6162 (1998).
Shi, et al., "*De Novo* Selection of High-Affinity Antibodies from Synthetic Fab Libraries Displayed on Phage as pIX Fusion Proteins," Journal of Molecular Biology, 397: 385-396 (2010).
William R. Strohl, "Optimization of Fc-mediated effector functions of monoclonal antibodies," Current Opinion in Biotechnology, 20: 685-691 (2009).
Teijaro, et al., "Persistent LCMV Infection Is Controlled by Blockade of Type I Interferon Signaling," Science, 340: 207-211 (2013).
Tcherepanova, et al., "Results of a Randomized Placebo Controlled Phase IA Study of AGS-009, a Humanized Anti-Interferon-α Monoclonal Antibody in Subjects with Systemic Lupus Erythematosus," Annals of the Rheumatic Diseases, 71, Abstract SAT0193 (Jun. 9, 2012).
Vaughan, et al., "Human Antibodies with Sub-nanomolar Affinities Isolated from LargeNon-immunized Phage Display Library," Nature Biotechnology, 14: 309-314 (1996).
Josef Walker, et al., "Modification of TLR-induced activation of human dendritic cells by type I IFN: synergistic iteration with TLR4 but not FLR3 agonists," European Journal of Immunology, 36: 1827-1836 (2006).
Weissman, et al., "The Interferon Genes," Progress in Nucleic Acid Research and Molecular Biology, 33: 251-300 (1986).

(56) References Cited

OTHER PUBLICATIONS

Wilson, et al., "Blockade of Chronic Type I Interferon Signaling to Control Persistent LCMV Infection," Science, 340: 202-207 (2013).
Wörn, et al., "Stability Engineering of Antibody Single-chain Fv Fragments," Journal of Molecular Biology, 305: 989-1010 (2001).
Wu, et al., "An Analysis of the Sequences of the Variable Regions of Bence Jones Proteins and Myeloma Light Chains and Their Implications for Antibody Complementarity," Journal of Experimental Medicine, 132: 211-250 (1970).
Yang, et al., "Tailoring structure-function and pharmacokinetic properties of single-chain Fv proteins by site-specific PEGylation," Protein Engineering 16(10): 761-770 (2003).
Yao, et al., "Neutralization of Interferon-α/β-Inducible Genes and Downstream Effect in a Phase I Trial of an Anti-Interferon-α Monoclonal antibody in Systemic Lupus Erythematosus," Arthritis & Rheumatism, 60(6): 1785-1796 (2009).
Yao, et al., "Development of Potential Pharmacodynamic and Diagnostic Markers for Anti-IFN-α Monoclonal Antibody Trials in Systemic Lupus Erythematosus," Human Genomics and Proteomics, vol. 2009, Article ID 374312 (15 Pages).
Yasui, et al., "Effects of substitutions of amino acids on the thermal stability of the Fv fragments of antibodies," FEBS Letters, 353: 143-146 (1994).
Yee, et al., "Revised British Isles Lupus Assessment Group 2004 Index a Reliable Tool for Assessment of Systemic Lupus Erythematosus Activity," Arthritis & Rheumatism, 54(10): 3300-3305 (2006).
Zhang, et al., "Mechanism for benzyl Alcohol-Induced Aggregation of Recombinant Human Interleukin-1 Receptor Antagonist in Aqueous Solution," Journal of Pharmaceutical Sciences, 93(12): 3976-3089 (2004).
Haubitz, et al., "New and emerging treatment approaches to lupus," Biologics, 4: 263-271 (1020).
Jordan, et al., "Elevation and Functional Activity of Interferon Omega in Human Systemic Lupus Erythematosus," 2014 ACR/ARHP Annual meeting, Abstract No. 1976.
Soh, et al., "Expression of a Functional Human Type I Interferon Receptor in Hamster Cells: Application of Functional Yeast Artificial Chromosome (YAC)," Journal of Biological Chemistry, 8: 18102-18110 (1994.).
Kolchanov, et al., "Single Amino Acid Substitutions Producing Instability of Globular Calculation of Their Frequencies in the Entire Mutational Spectra of the α- and β-Subunits of Human Hemoglobin," Journal of Molecular Evolution, 27: 154-162 (1988).
Pasquo, et al., "Structural Stability of Human Protein Tyrosine Phosphatase p Catalytic Domain: Effect of Point Mutations," PLoS One, 7(2): e32555: 1-11 (2012).
Peer Bork, "Powers and Pitfalls in Sequence Analysis: The 70% Hurdle," Genome Research, 10: 398-400 (2000).
Peer Bork, "Go hunting in sequence databases but watch out for the traps," Genetwork, 12(10): 425-427 (1996).
Xuejun, et al., "Engineering human interferon α1c/86D with phage display technology," Science in China, 42(2): 191-201 (1999).
Thomas, et al., "Sructural Linkage between Ligand Discrimination and receptor Activation by Type I Interferons," Cell, 146: 621-632 (2011).

\* cited by examiner

Figure 10.

| mAb | ISRE IC50 (pM) | | | | | | | | | | | | | |
|---|---|---|---|---|---|---|---|---|---|---|---|---|---|---|
| | αA | αB2 | αC | αD | αF | αG | αH2 | αI | αJ1 | αK | αWA | α4a | β | ω |
| IFWM3308 | 94 | 230 | 996 | NT | 155 | 167 | 32 | 478 | 363 | 59 | 894 | 295 | NN | 40 |
| IFWM3307 | 73 | 247 | 583 | NN | 170 | 95 | 88 | 752 | 328 | 95 | 600 | 501 | NN | 100 |
| IFWM3410 | NT | 211 | 168 | NN | 77 | 55 | 33 | 183 | 217 | 41 | 538 | 192 | NN | 89 |
| IFWM3322 | 31 | 121 | 306 | NN | 117 | 83 | 46 | 460 | 169 | 71 | 382 | 352 | NN | 59 |
| IFWM3385 | 63 | 158 | 272 | NN | 66 | 77 | 29 | 225 | 251 | 65 | 839 | 414 | NN | 68 |
| IFWM3416 | 81 | 250 | 112 | NN | 64 | 49 | 35 | 158 | 61 | 43 | 779 | 201 | NN | 40 |
| IFWM3310 | 50 | 43 | 196 | NN | 111 | 73 | 45 | 258 | 166 | 96 | 473 | 169 | NN | 81 |
| IFWM3400 | 35 | 86 | 138 | NN | 43 | 35 | 15 | 137 | 154 | 35 | 376 | 220 | NN | 29 |
| IFWM3321 | 29 | 87 | 266 | NN | 54 | 34 | 28 | 301 | 114 | 46 | 267 | 295 | NN | 38 |
| IFWM3522 | 57 | 96 | 77 | NT | 225 | 57 | 34 | 124 | 134 | 29 | 185 | 163 | NT | 53 |
| IFWM3524 | 19 | 31 | 72 | | 25 | 21 | | | | | | 84 | | 22 |
| IFWM3320 | 45 | 18 | 392 | NT | 54 | 82 | 23 | 355 | 213 | 34 | 633 | 166 | NN | 53 |
| IFWM3304 | 29 | 39 | 117 | NN | 62 | 47 | 42 | 157 | 126 | 57 | 237 | 112 | NN | 31 |
| IFWM3520 | 17 | 21 | 31 | | 18 | 16 | | | | | | 23 | | 12 |
| IFWM3399 | 43 | 62 | 189 | NN | 29 | 29 | 13 | 18 | 106 | 32 | 189 | 111 | NN | 27 |
| IFWM3314 | 29 | 33 | 157 | NN | 58 | 57 | 40 | 163 | 86 | 65 | 188 | 137 | NN | 32 |
| IFWM3331 | 18 | 80 | 98 | NN | 48 | 27 | 33 | 198 | 94 | 28 | 109 | 117 | NN | 50 |
| IFWM3405 | 40 | 99 | 68 | NN | 35 | 26 | 16 | 72 | 26 | 22 | 216 | 86 | NN | 19 |
| IFWM3442 | 77 | 75 | 40 | NT | 14 | 16 | 16 | 8 | 20 | 2140 | 36 | 25 | NT | 18 |
| IFWM3525 | 23 | 25 | 34 | NN | 82 | 19 | 15 | 240 | 84 | 7 | 66 | 42 | NN | 19 |
| IFWM3423 | 12 | 11 | 12 | NN | 8 | 9 | 4 | 4 | 6 | 9 | 10 | 8 | NN | 6 |
| IFWM3444 | 28 | 27 | 55 | NN | 16 | 15 | 9 | 9 | 24 | 19 | 46 | 23 | NN | 9 |
| IFWM3421 | 13 | 16 | 20 | NN | 11 | 18 | 8 | 17 | 14 | 18 | 14 | 15 | NN | 8 |

NN= non-neutralizing

SEQUENCE LISTING

<160> NUMBER OF SEQ ID NOS: 162

<210> SEQ ID NO 1
<211> LENGTH: 172
<212> TYPE: PRT
<213> ORGANISM: Homo sapiens

<400> SEQUENCE: 1

```
Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
            20                  25                  30

Arg Arg Asp Phe Arg Phe Pro Gln Glu Met Val Lys Gly Ser Gln Leu
        35                  40                  45

Gln Lys Ala His Val Met Ser Val Leu His Glu Met Leu Gln Gln Ile
    50                  55                  60

Phe Ser Leu Phe His Thr Glu Arg Ser Ser Ala Ala Trp Asn Met Thr
65                  70                  75                  80

Leu Leu Asp Gln Leu His Thr Gly Leu His Gln Gln Leu Gln His Leu
                85                  90                  95

Glu Thr Cys Leu Leu Gln Val Val Gly Glu Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
    130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser
                165                 170
```

<210> SEQ ID NO 2
<211> LENGTH: 172
<212> TYPE: PRT
<213> ORGANISM: Homo sapiens

<400> SEQUENCE: 2

```
Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
            20                  25                  30

Arg Arg Asp Phe Arg Phe Pro Gln Glu Met Val Lys Gly Ser Gln Leu
        35                  40                  45

Gln Lys Ala His Val Met Ser Val Leu His Glu Met Leu Gln Gln Ile
    50                  55                  60

Phe Ser Leu Phe His Thr Glu Arg Ser Ser Ala Ala Trp Asn Met Glu
65                  70                  75                  80

Leu Leu Asp Gln Leu His Thr Gly Leu His Gln Gln Leu Gln His Leu
                85                  90                  95

Glu Thr Cys Leu Leu Gln Val Val Gly Glu Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
    130                 135                 140

Arg Met Glu Ile Met Lys Ser Leu Phe Leu Ser Thr Asn Met Gln Glu
```

```
                145                 150                 155                 160
Arg Leu Arg Ser Lys Asp Arg Asp Leu Gly Ser Ser
                    165                 170

<210> SEQ ID NO 3
<211> LENGTH: 177
<212> TYPE: PRT
<213> ORGANISM: Pan troglodytes

<400> SEQUENCE: 3

Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
                20                  25                  30

Arg Arg Asp Phe Arg Phe Pro Gln Glu Met Val Lys Gly Ser Gln Leu
            35                  40                  45

Gln Lys Ala Gln Val Met Ser Val Leu His Glu Met Leu Gln Gln Ile
        50                  55                  60

Phe Ser Leu Phe His Thr Glu Arg Ser Ser Ala Ala Trp Asn Met Thr
65                  70                  75                  80

Leu Leu Asp Gln Leu His Thr Gly Leu His Gln Gln Leu Gln His Leu
                85                  90                  95

Glu Thr Cys Leu Leu Gln Val Met Gly Glu Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser Arg Asn Asp Ser
                165                 170                 175

His

<210> SEQ ID NO 4
<211> LENGTH: 172
<212> TYPE: PRT
<213> ORGANISM: Macaca fascicularis

<400> SEQUENCE: 4

Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
                20                  25                  30

Arg Arg Asp Phe Arg Phe Pro Gln Glu Met Val Glu Gly Ser Gln Leu
            35                  40                  45

Gln Lys Ala Gln Val Met Ser Val Leu His Glu Met Leu Gln Gln Ile
        50                  55                  60

Phe Ser Leu Phe His Thr Glu His Ser Ser Ala Ala Trp Asn Thr Thr
65                  70                  75                  80

Leu Leu Asp His Leu His Thr Gly Leu His Arg Gln Leu Glu His Leu
                85                  90                  95

Glu Thr Cys Leu Val Gln Val Met Arg Glu Gly Glu Ser Ala Gly Ala
            100                 105                 110

Ile Arg Ser Pro Ala Leu Thr Leu Arg Arg Tyr Phe Gln Gly Ile Arg
        115                 120                 125
```

```
Val Tyr Leu Lys Glu Lys Lys Tyr Ser Asp Cys Ala Trp Val Val Val
    130                 135                 140

Arg Met Glu Ile Met Lys Ser Leu Phe Leu Ser Thr Asn Met Gln Glu
145                 150                 155                 160

Arg Leu Lys Ser Lys Asp Gly Asp Leu Gly Ser Ser
                165                 170

<210> SEQ ID NO 5
<211> LENGTH: 165
<212> TYPE: PRT
<213> ORGANISM: Homo sapiens

<400> SEQUENCE: 5

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 6
<211> LENGTH: 166
<212> TYPE: PRT
<213> ORGANISM: Homo sapiens

<400> SEQUENCE: 6

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
                20                  25                  30

Arg His Asp Phe Glu Phe Pro Gln Glu Glu Phe Asp Asp Lys Gln Phe
            35                  40                  45

Gln Lys Ala Gln Ala Ile Ser Val Leu His Glu Met Ile Gln Gln Thr
50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110
```

```
Tyr Glu Asp Ser Ile Leu Ala Val Arg Lys Tyr Phe Gln Arg Ile Thr
            115                 120                 125
Leu Tyr Leu Thr Glu Lys Lys Tyr Ser Ser Cys Ala Trp Glu Val Val
130                 135                 140
Arg Ala Glu Ile Met Arg Ser Phe Ser Leu Ser Ile Asn Leu Gln Lys
145                 150                 155                 160
Arg Leu Lys Ser Lys Glu
                165

<210> SEQ ID NO 7
<211> LENGTH: 166
<212> TYPE: PRT
<213> ORGANISM: Homo sapiens

<400> SEQUENCE: 7

Cys Asp Leu Pro Gln Thr His Ser Leu Gly Asn Arg Arg Ala Leu Ile
1               5                   10                  15
Leu Leu Gly Gln Met Gly Arg Ile Ser Pro Phe Ser Cys Leu Lys Asp
                20                  25                  30
Arg His Asp Phe Arg Ile Pro Gln Glu Glu Phe Asp Gly Asn Gln Phe
            35                  40                  45
Gln Lys Ala Gln Ala Ile Ser Val Leu His Glu Met Ile Gln Gln Thr
        50                  55                  60
Phe Asn Leu Phe Ser Thr Glu Asp Ser Ser Ala Ala Trp Glu Gln Ser
65                  70                  75                  80
Leu Leu Glu Lys Phe Ser Thr Glu Leu Tyr Gln Gln Leu Asn Asp Leu
                85                  90                  95
Glu Ala Cys Val Ile Gln Glu Val Gly Val Glu Glu Thr Pro Leu Met
            100                 105                 110
Asn Glu Asp Ser Ile Leu Ala Val Arg Lys Tyr Phe Gln Arg Ile Thr
        115                 120                 125
Leu Tyr Leu Ile Glu Arg Lys Tyr Ser Pro Cys Ala Trp Glu Val Val
130                 135                 140
Arg Ala Glu Ile Met Arg Ser Leu Ser Phe Ser Thr Asn Leu Gln Lys
145                 150                 155                 160
Arg Leu Arg Arg Lys Asp
                165

<210> SEQ ID NO 8
<211> LENGTH: 166
<212> TYPE: PRT
<213> ORGANISM: Homo sapiens

<400> SEQUENCE: 8

Cys Asp Leu Pro Glu Thr His Ser Leu Asp Asn Arg Arg Thr Leu Met
1               5                   10                  15
Leu Leu Ala Gln Met Ser Arg Ile Ser Pro Ser Ser Cys Leu Met Asp
                20                  25                  30
Arg His Asp Phe Gly Phe Pro Gln Glu Glu Phe Asp Gly Asn Gln Phe
            35                  40                  45
Gln Lys Ala Pro Ala Ile Ser Val Leu His Glu Leu Ile Gln Gln Ile
        50                  55                  60
Phe Asn Leu Phe Thr Thr Lys Asp Ser Ser Ala Ala Trp Asp Glu Asp
65                  70                  75                  80
Leu Leu Asp Lys Phe Cys Thr Glu Leu Tyr Gln Gln Leu Asn Asp Leu
                85                  90                  95
```

```
Glu Ala Cys Val Met Gln Glu Arg Val Gly Glu Thr Pro Leu Met
                100                 105                 110

Asn Val Asp Ser Ile Leu Ala Val Lys Lys Tyr Phe Arg Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 9
<211> LENGTH: 166
<212> TYPE: PRT
<213> ORGANISM: Homo sapiens

<400> SEQUENCE: 9

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Gln Leu Asn Asp Met
                85                  90                  95

Glu Ala Cys Val Ile Gln Glu Val Gly Val Glu Glu Thr Pro Leu Met
                100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 10
<211> LENGTH: 166
<212> TYPE: PRT
<213> ORGANISM: Homo sapiens

<400> SEQUENCE: 10

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Asp Glu Thr
65                  70                  75                  80
```

-continued

```
Leu Leu Asp Lys Phe Tyr Thr Glu Leu Tyr Gln Gln Leu Asn Asp Leu
                 85                  90                  95

Glu Ala Cys Met Met Gln Glu Val Gly Val Glu Asp Thr Pro Leu Met
            100                 105                 110

Asn Val Asp Ser Ile Leu Thr Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Ala Asn Leu Gln Glu
145                 150                 155                 160

Arg Leu Arg Arg Lys Glu
                165

<210> SEQ ID NO 11
<211> LENGTH: 166
<212> TYPE: PRT
<213> ORGANISM: Homo sapiens

<400> SEQUENCE: 11

Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Glu Phe Pro Gln Glu Glu Phe Asp Gly Asn Gln Phe
        35                  40                  45

Gln Lys Ala Gln Ala Ile Ser Val Leu His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Thr Pro Leu Met
            100                 105                 110

Asn Glu Asp Ser Ile Leu Ala Val Lys Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 12
<211> LENGTH: 166
<212> TYPE: PRT
<213> ORGANISM: Homo sapiens

<400> SEQUENCE: 12

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg Pro Asp Phe Gly Leu Pro Gln Glu Glu Phe Asp Gly Asn Gln Phe
        35                  40                  45

Gln Lys Thr Gln Ala Ile Ser Val Leu His Glu Met Ile Gln Gln Thr
    50                  55                  60
```

```
Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asn Leu
                 85                  90                  95

Glu Ala Cys Val Ile Gln Glu Val Gly Met Glu Glu Thr Pro Leu Met
                100                 105                 110

Asn Glu Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
            130                 135                 140

Arg Ala Glu Ile Met Arg Ser Leu Ser Phe Ser Thr Asn Leu Gln Lys
145                 150                 155                 160

Ile Leu Arg Arg Lys Asp
                165

<210> SEQ ID NO 13
<211> LENGTH: 166
<212> TYPE: PRT
<213> ORGANISM: Homo sapiens

<400> SEQUENCE: 13

Cys Asp Leu Pro Gln Thr His Ser Leu Arg Asn Arg Arg Ala Leu Ile
 1               5                  10                  15

Leu Leu Ala Gln Met Gly Arg Ile Ser Pro Phe Ser Cys Leu Lys Asp
                 20                  25                  30

Arg His Glu Phe Arg Phe Pro Glu Glu Glu Phe Asp Gly His Gln Phe
             35                  40                  45

Gln Lys Thr Gln Ala Ile Ser Val Leu His Glu Met Ile Gln Gln Thr
         50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                 85                  90                  95

Glu Ala Cys Val Ile Gln Glu Val Gly Val Glu Glu Thr Pro Leu Met
                100                 105                 110

Asn Glu Asp Phe Ile Leu Ala Val Arg Lys Tyr Phe Gln Arg Ile Thr
                115                 120                 125

Leu Tyr Leu Met Glu Lys Lys Tyr Ser Pro Cys Ala Trp Glu Val Val
            130                 135                 140

Arg Ala Glu Ile Met Arg Ser Phe Ser Phe Ser Thr Asn Leu Lys Lys
145                 150                 155                 160

Gly Leu Arg Arg Lys Asp
                165

<210> SEQ ID NO 14
<211> LENGTH: 166
<212> TYPE: PRT
<213> ORGANISM: Homo sapiens

<400> SEQUENCE: 14

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
                 20                  25                  30

Arg His Asp Phe Arg Phe Pro Gln Glu Glu Phe Asp Gly Asn Gln Phe
             35                  40                  45
```

```
Gln Lys Ala Glu Ala Ile Ser Val Leu His Glu Val Ile Gln Gln Thr
             50                  55                  60

Phe Asn Leu Phe Ser Thr Lys Asp Ser Ser Val Ala Trp Asp Glu Arg
 65                  70                  75                  80

Leu Leu Asp Lys Leu Tyr Thr Glu Leu Tyr Gln Gln Leu Asn Asp Leu
                 85                  90                  95

Glu Ala Cys Val Met Gln Glu Val Trp Val Gly Gly Thr Pro Leu Met
                100                 105                 110

Asn Glu Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
            130                 135                 140

Arg Ala Glu Ile Met Arg Ser Phe Ser Ser Arg Asn Leu Gln Glu
145                 150                 155                 160

Arg Leu Arg Arg Lys Glu
                165

<210> SEQ ID NO 15
<211> LENGTH: 166
<212> TYPE: PRT
<213> ORGANISM: Homo sapiens

<400> SEQUENCE: 15

Cys Asp Leu Pro Gln Thr His Ser Leu Gly Asn Arg Arg Ala Leu Ile
  1               5                  10                  15

Leu Leu Ala Gln Met Gly Arg Ile Ser His Phe Ser Cys Leu Lys Asp
                 20                  25                  30

Arg His Asp Phe Gly Phe Pro Glu Glu Glu Phe Asp Gly His Gln Phe
             35                  40                  45

Gln Lys Thr Gln Ala Ile Ser Val Leu His Glu Met Ile Gln Gln Thr
             50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                 85                  90                  95

Glu Ala Cys Val Ile Gln Glu Val Gly Val Glu Glu Thr Pro Leu Met
                100                 105                 110

Asn Val Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
            130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 16
<211> LENGTH: 166
<212> TYPE: PRT
<213> ORGANISM: Homo sapiens

<400> SEQUENCE: 16

Cys Asp Leu Pro Gln Thr His Ser Leu Gly Asn Arg Arg Ala Leu Ile
  1               5                  10                  15

Leu Leu Ala Gln Met Gly Arg Ile Ser His Phe Ser Cys Leu Lys Asp
                 20                  25                  30
```

```
Arg Tyr Asp Phe Gly Phe Pro Gln Glu Val Phe Asp Gly Asn Gln Phe
         35                  40                  45

Gln Lys Ala Gln Ala Ile Ser Ala Phe His Glu Met Ile Gln Gln Thr
 50                  55                  60

Phe Asn Leu Phe Ser Thr Lys Asp Ser Ser Ala Ala Trp Asp Glu Thr
 65                  70                  75                  80

Leu Leu Asp Lys Phe Tyr Ile Glu Leu Phe Gln Gln Leu Asn Asp Leu
                 85                  90                  95

Glu Ala Cys Val Thr Gln Glu Val Gly Val Glu Glu Ile Ala Leu Met
            100                 105                 110

Asn Glu Asp Ser Ile Leu Ala Val Arg Lys Tyr Phe Gln Arg Ile Thr
            115                 120                 125

Leu Tyr Leu Met Gly Lys Lys Tyr Ser Pro Cys Ala Trp Glu Val Val
        130                 135                 140

Arg Ala Glu Ile Met Arg Ser Phe Ser Phe Ser Thr Asn Leu Gln Lys
145                 150                 155                 160

Gly Leu Arg Arg Lys Asp
                165

<210> SEQ ID NO 17
<211> LENGTH: 165
<212> TYPE: PRT
<213> ORGANISM: Homo sapiens

<400> SEQUENCE: 17

Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 18
<211> LENGTH: 166
<212> TYPE: PRT
<213> ORGANISM: Homo sapiens

<400> SEQUENCE: 18

Cys Asp Leu Pro Glu Thr His Ser Leu Asp Asn Arg Arg Thr Leu Met
 1               5                  10                  15
```

```
Leu Leu Ala Gln Met Ser Arg Ile Ser Pro Ser Ser Cys Leu Met Asp
             20                  25                  30

Arg His Asp Phe Gly Phe Pro Gln Glu Glu Phe Asp Gly Asn Gln Phe
             35                  40                  45

Gln Lys Ala Pro Ala Ile Ser Val Leu His Glu Leu Ile Gln Gln Ile
     50                  55                  60

Phe Asn Leu Phe Thr Thr Lys Asp Ser Ser Ala Ala Trp Asp Glu Asp
 65                  70                  75                  80

Leu Leu Asp Lys Phe Cys Thr Glu Leu Tyr Gln Gln Leu Asn Asp Leu
                 85                  90                  95

Glu Ala Cys Val Met Gln Glu Glu Arg Val Gly Glu Thr Pro Leu Met
             100                 105                 110

Asn Ala Asp Ser Ile Leu Ala Val Lys Lys Tyr Phe Arg Arg Ile Thr
             115                 120                 125

Leu Tyr Leu Thr Glu Lys Lys Tyr Ser Pro Cys Ala Trp Glu Val Val
         130                 135                 140

Arg Ala Glu Ile Met Arg Ser Leu Ser Leu Ser Thr Asn Leu Gln Glu
145                 150                 155                 160

Arg Leu Arg Arg Lys Glu
                 165

<210> SEQ ID NO 19
<211> LENGTH: 166
<212> TYPE: PRT
<213> ORGANISM: Homo sapiens

<400> SEQUENCE: 19

Cys Asp Leu Pro Gln Thr His Ser Leu Gly Asn Arg Arg Ala Leu Ile
 1               5                  10                  15

Leu Leu Ala Gln Met Gly Arg Ile Ser His Phe Ser Cys Leu Lys Asp
             20                  25                  30

Arg His Asp Phe Gly Phe Pro Glu Glu Glu Phe Asp Gly His Gln Phe
             35                  40                  45

Gln Lys Ala Gln Ala Ile Ser Val Leu His Glu Met Ile Gln Gln Thr
     50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                 85                  90                  95

Glu Ala Cys Val Ile Gln Glu Val Gly Val Glu Glu Thr Pro Leu Met
             100                 105                 110

Asn Glu Asp Ser Ile Leu Ala Val Arg Lys Tyr Phe Gln Arg Ile Thr
             115                 120                 125

Leu Tyr Leu Thr Glu Lys Lys Tyr Ser Pro Cys Ala Trp Glu Val Val
         130                 135                 140

Arg Ala Glu Ile Met Arg Ser Leu Ser Phe Ser Thr Asn Leu Gln Lys
145                 150                 155                 160

Arg Leu Arg Arg Lys Asp
                 165

<210> SEQ ID NO 20
<211> LENGTH: 166
<212> TYPE: PRT
<213> ORGANISM: Homo sapiens

<400> SEQUENCE: 20
```

```
Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
                100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Ala Leu Thr Phe Tyr Leu Leu Val Ala Leu Val Val Leu Ser Tyr
1               5                   10                  15

Lys Ser Phe Ser Ser Leu Gly
            20

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Ala Arg Ser Phe Ser Leu Leu Met Val Val Leu Val Leu Ser Tyr
1               5                   10                  15

Lys Ser Ile Cys Ser Leu Gly
            20

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

```
Met Ala Leu Pro Phe Ala Leu Leu Met Ala Leu Val Val Leu Ser Cys
1               5                   10                  15

Lys Ser Ser Cys Ser Leu Asp
            20
```

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Met Ala Leu Ser Phe Ser Leu Leu Met Ala Val Leu Val Leu Ser Tyr
1               5                   10                  15

Lys Ser Ile Cys Ser Leu Gly
            20
```

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Met Ala Leu Thr Phe Ala Leu Leu Val Ala Leu Leu Val Leu Ser Cys
1               5                   10                  15

Lys Ser Ser Cys Ser Val Gly
            20
```

<210> SEQ ID NO 26
<211> LENGTH: 557
<212> TYPE: PRT
<213> ORGANISM: Homo sapiens

<400> SEQUENCE: 26

```
Met Met Val Val Leu Leu Gly Ala Thr Thr Leu Val Leu Val Ala Val
1               5                   10                  15

Ala Pro Trp Val Leu Ser Ala Ala Gly Gly Lys Asn Leu Lys Ser
            20                  25                  30

Pro Gln Lys Val Glu Val Asp Ile Ile Asp Asp Asn Phe Ile Leu Arg
            35                  40                  45

Trp Asn Arg Ser Asp Glu Ser Val Gly Asn Val Thr Phe Ser Phe Asp
50                  55                  60

Tyr Gln Lys Thr Gly Met Asp Asn Trp Ile Lys Leu Ser Gly Cys Gln
65                  70                  75                  80

Asn Ile Thr Ser Thr Lys Cys Asn Phe Ser Ser Leu Lys Leu Asn Val
                85                  90                  95

Tyr Glu Glu Ile Lys Leu Arg Ile Arg Ala Glu Lys Glu Asn Thr Ser
                100                 105                 110

Ser Trp Tyr Glu Val Asp Ser Phe Thr Pro Phe Arg Lys Ala Gln Ile
            115                 120                 125

Gly Pro Pro Glu Val His Leu Glu Ala Glu Asp Lys Ala Ile Val Ile
            130                 135                 140

His Ile Ser Pro Gly Thr Lys Asp Ser Val Met Trp Ala Leu Asp Gly
145                 150                 155                 160

Leu Ser Phe Thr Tyr Ser Leu Val Ile Trp Lys Asn Ser Ser Gly Val
```

```
              165                 170                 175
Glu Glu Arg Ile Glu Asn Ile Tyr Ser Arg His Lys Ile Tyr Lys Leu
                180                 185                 190

Ser Pro Glu Thr Thr Tyr Cys Leu Lys Val Lys Ala Ala Leu Leu Thr
                195                 200                 205

Ser Trp Lys Ile Gly Val Tyr Ser Pro Val His Cys Ile Lys Thr Thr
                210                 215                 220

Val Glu Asn Glu Leu Pro Pro Pro Glu Asn Ile Glu Val Ser Val Gln
225                 230                 235                 240

Asn Gln Asn Tyr Val Leu Lys Trp Asp Tyr Thr Tyr Ala Asn Met Thr
                245                 250                 255

Phe Gln Val Gln Trp Leu His Ala Phe Leu Lys Arg Asn Pro Gly Asn
                260                 265                 270

His Leu Tyr Lys Trp Lys Gln Ile Pro Asp Cys Glu Asn Val Lys Thr
                275                 280                 285

Thr Gln Cys Val Phe Pro Gln Asn Val Phe Gln Lys Gly Ile Tyr Leu
                290                 295                 300

Leu Arg Val Gln Ala Ser Asp Gly Asn Asn Thr Ser Phe Trp Ser Glu
305                 310                 315                 320

Glu Ile Lys Phe Asp Thr Glu Ile Gln Ala Phe Leu Leu Pro Pro Val
                325                 330                 335

Phe Asn Ile Arg Ser Leu Ser Asp Ser Phe His Ile Tyr Ile Gly Ala
                340                 345                 350

Pro Lys Gln Ser Gly Asn Thr Pro Val Ile Gln Asp Tyr Pro Leu Ile
                355                 360                 365

Tyr Glu Ile Ile Phe Trp Glu Asn Thr Ser Asn Ala Glu Arg Lys Ile
                370                 375                 380

Ile Glu Lys Lys Thr Asp Val Thr Val Pro Asn Leu Lys Pro Leu Thr
385                 390                 395                 400

Val Tyr Cys Val Lys Ala Arg Ala His Thr Met Asp Glu Lys Leu Asn
                405                 410                 415

Lys Ser Ser Val Phe Ser Asp Ala Val Cys Glu Lys Thr Lys Pro Gly
                420                 425                 430

Asn Thr Ser Lys Ile Trp Leu Ile Val Gly Ile Cys Ile Ala Leu Phe
                435                 440                 445

Ala Leu Pro Phe Val Ile Tyr Ala Ala Lys Val Phe Leu Arg Cys Ile
                450                 455                 460

Asn Tyr Val Phe Phe Pro Ser Leu Lys Pro Ser Ser Ser Ile Asp Glu
465                 470                 475                 480

Tyr Phe Ser Glu Gln Pro Leu Lys Asn Leu Leu Leu Ser Thr Ser Glu
                485                 490                 495

Glu Gln Ile Glu Lys Cys Phe Ile Ile Glu Asn Ile Ser Thr Ile Ala
                500                 505                 510

Thr Val Glu Glu Thr Asn Gln Thr Asp Glu Asp His Lys Lys Tyr Ser
                515                 520                 525

Ser Gln Thr Ser Gln Asp Ser Gly Asn Tyr Ser Asn Glu Asp Glu Ser
                530                 535                 540

Glu Ser Lys Thr Ser Glu Glu Leu Gln Gln Asp Phe Val
545                 550                 555

<210> SEQ ID NO 27
<211> LENGTH: 331
<212> TYPE: PRT
<213> ORGANISM: Homo sapiens
```

<400> SEQUENCE: 27

```
Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
        195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Ser Glu Ser Ala Glu
225                 230                 235                 240

Ser Ala Lys Ile Gly Gly Ile Ile Thr Val Phe Leu Ile Ala Leu Val
            245                 250                 255

Leu Thr Ser Thr Ile Val Thr Leu Lys Trp Ile Gly Tyr Ile Cys Leu
        260                 265                 270

Arg Asn Ser Leu Pro Lys Val Leu Arg Gln Gly Leu Ala Lys Gly Trp
    275                 280                 285

Asn Ala Val Ala Ile His Arg Cys Ser His Asn Ala Leu Gln Ser Glu
    290                 295                 300

Thr Pro Glu Leu Lys Gln Ser Ser Cys Leu Ser Phe Pro Ser Ser Trp
305                 310                 315                 320

Asp Tyr Lys Arg Ala Ser Leu Cys Pro Ser Asp
            325                 330
```

<210> SEQ ID NO 28
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Glu Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
65                   70                  75                  80

Leu Gln Trp Ser Ser Leu Lys Ala Ser Asp Thr Ala Met Tyr Tyr Cys
                85                  90                  95

Ala Arg His Pro Gly Leu Asn Trp Ala Pro Asp Phe Asp Tyr Trp Gly
            100                 105                 110

Gln Gly Thr Leu Val Thr Val Ser Ser
            115                 120

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 30
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Asp Pro Ser Asp Ser Asp Thr Ala Tyr Ser Pro Ser Phe
 50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg His Pro Gly Leu Asn Trp Ala Pro Asp Phe Asp Tyr Trp Gly
            100                 105                 110

Gln Gly Thr Leu Val Thr Val Ser Ser
        115                 120

<210> SEQ ID NO 31
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Gly Leu Ala Trp Ala Pro Asp Phe Asp Tyr Trp Gly
            100                 105                 110

Gln Gly Thr Leu Val Thr Val Ser Ser
        115                 120

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Gly Ser
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Phe Pro Leu
                85                  90                  95

Thr Phe Gly Gln Gly Thr Lys Val Glu Ile Lys
            100                 105

<210> SEQ ID NO 33
```

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Arg Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ile Asp Leu Pro Phe
                85                  90                  95

Thr Phe Gly Gln Gly Thr Lys Val Glu Ile Lys
            100                 105

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Phe
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Ile
                85                  90                  95

Thr Phe Gly Gln Gly Thr Lys Val Glu Ile Lys
            100                 105

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Ala
            20                  25                  30

```
Leu Asn Trp Tyr Gln Gln Lys Pro Gly Lys Ala Pro Lys Leu Leu Ile
            35                  40                  45

Tyr Phe Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Phe Pro Leu
                 85                  90                  95

Thr Phe Gly Gln Gly Thr Lys Val Glu Ile Lys
            100                 105
```

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Lys Phe
                 20                  25                  30

Leu Asn Trp Tyr Gln Gln Lys Pro Gly Lys Ala Pro Lys Leu Leu Ile
            35                  40                  45

Tyr Phe Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Thr Leu Pro Phe
                 85                  90                  95

Thr Phe Gly Gln Gly Thr Lys Val Glu Ile Lys
            100                 105
```

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Glu Phe
                 20                  25                  30

Leu Asn Trp Tyr Gln Gln Lys Pro Gly Lys Ala Pro Lys Leu Leu Ile
            35                  40                  45

Tyr Phe Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala His Ser Phe Pro Leu
                 85                  90                  95

Thr Phe Gly Gln Gly Thr Lys Val Glu Ile Lys
            100                 105
```

```
<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Asn Phe
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Asp Phe Pro Leu
                85                  90                  95

Thr Phe Gly Gln Gly Thr Lys Val Glu Ile Lys
            100                 105

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Asp Phe
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Asp Phe Pro Leu
                85                  90                  95

Thr Phe Gly Gln Gly Thr Lys Val Glu Ile Lys
            100                 105

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Glu Phe
```

```
                    20                  25                  30

Leu Asn Trp Tyr Gln Gln Lys Pro Gly Lys Ala Pro Lys Leu Leu Ile
            35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Asp Phe Pro Leu
                85                  90                  95

Thr Phe Gly Gln Gly Thr Lys Val Glu Ile Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Gly Phe
            20                  25                  30

Leu Asn Trp Tyr Gln Gln Lys Pro Gly Lys Ala Pro Lys Leu Leu Ile
            35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Leu Pro Ile
                85                  90                  95

Thr Phe Gly Gln Gly Thr Lys Val Glu Ile Lys
            100                 105

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Lys Ser
            20                  25                  30

Leu Asn Trp Tyr Gln Gln Lys Pro Gly Lys Ala Pro Lys Leu Leu Ile
            35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Phe Pro Leu
                85                  90                  95

Thr Phe Gly Gln Gly Thr Lys Val Glu Ile Lys
```

<210> SEQ ID NO 43
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asp Phe
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Thr Leu Pro Leu
                85                  90                  95

Thr Phe Gly Gln Gly Thr Lys Val Glu Ile Lys
            100                 105

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Gly Ala
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Asp Phe Pro Leu
                85                  90                  95

Thr Phe Gly Gln Gly Thr Lys Val Glu Ile Lys
            100                 105

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 45

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Asn Asn Phe
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Asn Leu Pro Ile
                85                  90                  95

Thr Phe Gly Gln Gly Thr Lys Val Glu Ile Lys
            100                 105

<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Arg Ala
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Asp Phe Pro Leu
                85                  90                  95

Thr Phe Gly Gln Gly Thr Lys Val Glu Ile Lys
            100                 105

<210> SEQ ID NO 47
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Ser Ser
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Asp Leu Pro Leu
                85                  90                  95
```

```
Thr Phe Gly Gln Gly Thr Lys Val Glu Ile Lys
            100                 105

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Glu Phe
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 49
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Phe
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Phe Pro Ile
                85                  90                  95

Thr Phe Gly Gln Gly Thr Lys Val Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Glu Tyr
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser His Ser Leu Pro Ile
                85                  90                  95

Thr Phe Gly Gln Gly Thr Lys Val Glu Ile Lys
            100                 105
```

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Gly Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser His Asp Phe Pro Leu
                85                  90                  95

Thr Phe Gly Gln Gly Thr Lys Val Glu Ile Lys
            100                 105
```

<210> SEQ ID NO 52
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Gly Val
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80
```

Glu Asp Phe Ala Thr Tyr Tyr Cys Gln Gln Ser His Asp Phe Pro Leu
                85                  90                  95

Thr Phe Gly Gln Gly Thr Lys Val Glu Ile Lys
            100                 105

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Gly Ala
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Asp Phe Pro Leu
                85                  90                  95

Thr Phe Gly Gln Gly Thr Lys Val Glu Ile Lys
            100                 105

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Asp Phe
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Phe Pro Leu
                85                  90                  95

Thr Phe Gly Gln Gly Thr Lys Val Glu Ile Lys
            100                 105

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Asn His
            20                  25                  30

Leu Asn Trp Tyr Gln Gln Lys Pro Gly Lys Ala Pro Lys Leu Leu Ile
        35                  40                  45

Tyr Phe Ala Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Asn Phe Pro Leu
                85                  90                  95

Thr Phe Gly Gln Gly Thr Lys Val Glu Ile Lys
            100                 105

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Ser
            20                  25                  30

Leu Asn Trp Tyr Gln Gln Lys Pro Gly Lys Ala Pro Lys Leu Leu Ile
        35                  40                  45

Lys Trp Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Asp Trp Pro Leu
                85                  90                  95

Thr Phe Gly Gln Gly Thr Lys Val Glu Ile Lys
            100                 105

<210> SEQ ID NO 57
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Asn Asn
            20                  25                  30

Asn Leu Asn Trp Tyr Gln Gln Lys Pro Gly Lys Ala Pro Lys Leu Leu
        35                  40                  45

Ile His Trp Ala Ser Ser Leu Gln Ser Gly Val Pro Ser Arg Phe Ser
50                  55                  60

Gly Ser Gly Ser Gly Thr Asp Phe Thr Leu Thr Ile Ser Ser Leu Gln

```
65                  70                  75                  80

Pro Glu Asp Phe Ala Thr Tyr Tyr Cys Gln Gln Gly Tyr Asp Thr Pro
                85                  90                  95

Phe Thr Phe Gly Gln Gly Thr Lys Val Glu Ile Lys
            100                 105

<210> SEQ ID NO 58
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Leu
            20                  25                  30

Asn Trp Tyr Gln Gln Lys Pro Gly Lys Ala Pro Lys Leu Leu Ile Tyr
        35                  40                  45

Trp Ala Ser Ser Leu Gln Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Gly Tyr Asp Thr Pro Phe Thr
                85                  90                  95

Phe Gly Gln Gly Thr Lys Val Glu Ile Lys
            100                 105

<210> SEQ ID NO 59
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Asn
            20                  25                  30

Asn Leu Asn Trp Tyr Gln Gln Lys Pro Gly Lys Ala Pro Lys Leu Leu
        35                  40                  45

Ile His Trp Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Tyr Asp Thr Pro
                85                  90                  95

Phe Thr Phe Gly Gln Gly Thr Lys Val Glu Ile Lys
            100                 105

<210> SEQ ID NO 60
<211> LENGTH: 108
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Asn
            20                  25                  30

Ser Leu Asn Trp Tyr Gln Gln Lys Pro Gly Lys Ala Pro Lys Leu Leu
        35                  40                  45

Ile Tyr Gly Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Asp Tyr Asn Trp Pro
                85                  90                  95

Ile Thr Phe Gly Gln Gly Thr Lys Val Glu Ile Lys
            100                 105

<210> SEQ ID NO 61
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Ser
            20                  25                  30

Tyr Leu Asn Trp Tyr Gln Gln Lys Pro Gly Lys Ala Pro Lys Leu Leu
        35                  40                  45

Ile Tyr Gly Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Trp Asp Trp Pro
                85                  90                  95

Leu Thr Phe Gly Gln Gly Thr Lys Val Glu Ile Lys
            100                 105

<210> SEQ ID NO 62
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Asn Thr
            20                  25                  30

Asn Leu Asn Trp Tyr Gln Gln Lys Pro Gly Lys Ala Pro Lys Leu Leu
        35                  40                  45

Ile His Trp Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Tyr Asp Asn Pro
                85                  90                  95

Leu Thr Phe Gly Gln Gly Thr Lys Val Glu Ile Lys
            100                 105

<210> SEQ ID NO 63
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Asn
                20                  25                  30

Asn Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Tyr Asp Trp Pro
                85                  90                  95

Leu Thr Phe Gly Gln Gly Thr Lys Val Glu Ile Lys
            100                 105

<210> SEQ ID NO 64
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Asn
                20                  25                  30

Ser Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Asp Tyr Asn Trp Pro
                85                  90                  95

Leu Thr Phe Gly Gln Gly Thr Lys Val Glu Ile Lys
            100                 105

<210> SEQ ID NO 65
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Tyr Leu
            20                  25                  30

Asn Trp Tyr Gln Gln Lys Pro Gly Lys Ala Pro Lys Leu Leu Ile Tyr
        35                  40                  45

Gly Ala Ser Ser Leu Gln Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser His Asp Trp Pro Ile Thr
                85                  90                  95

Phe Gly Gln Gly Thr Lys Val Glu Ile Lys
            100                 105

<210> SEQ ID NO 66
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Asn
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Tyr Asp Thr Pro
                85                  90                  95

Leu Thr Phe Gly Gln Gly Thr Lys Val Glu Ile Lys
            100                 105

<210> SEQ ID NO 67
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Ser
            20                  25                  30

Asn Leu Asn Trp Tyr Gln Gln Lys Pro Gly Lys Ala Pro Lys Leu Leu
        35                  40                  45

```
Ile His Trp Ala Ser Ser Leu Gln Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Trp Tyr Asp His Pro
                 85                  90                  95

Leu Thr Phe Gly Gln Gly Thr Lys Val Glu Ile Lys
            100                 105
```

<210> SEQ ID NO 68
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Arg Asn Thr
                 20                  25                  30

Asn Leu Asn Trp Tyr Gln Gln Lys Pro Gly Lys Ala Pro Lys Leu Leu
             35                  40                  45

Ile His Trp Ala Ser Ser Leu Gln Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Gly Tyr Asp Thr Pro
                 85                  90                  95

Phe Thr Phe Gly Gln Gly Thr Lys Val Glu Ile Lys
            100                 105
```

<210> SEQ ID NO 69
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ala Asn Asn
                 20                  25                  30

Asp Leu Asn Trp Tyr Gln Gln Lys Pro Gly Lys Ala Pro Lys Leu Leu
             35                  40                  45

Ile His Trp Ala Ser Ser Leu Gln Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Asp Tyr Asp Trp Pro
                 85                  90                  95

Leu Thr Phe Gly Gln Gly Thr Lys Val Glu Ile Lys
            100                 105
```

<210> SEQ ID NO 70
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Gly Phe
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Ile
                85                  90                  95

Thr Phe Gly Gln Gly Thr Lys Val Glu Ile Lys
            100                 105

<210> SEQ ID NO 71
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Gly Phe
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Leu Pro Ile
                85                  90                  95

Thr Phe Gly Gln Gly Thr Lys Val Glu Ile Lys
            100                 105

<210> SEQ ID NO 72
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
gatattcaga tgacccagag cccgagcagc ctgagcgcga gcgtgggcga tcgcgtgacc    60
attacctgcc gcgcgagcca gagcattgat gggttcctga actggtatca gcagaaaccg   120
ggcaaagcgc cgaaactgct gatttatttc gcgagcagcc tgcagagcgg cgtgccgagc   180
cgctttagcg gcagcggcag cggcaccgat tttaccctga ccattagcag cctgcagccg   240
```

```
gaagattttg cgacctatta ttgccagcag tcctacgacc tcccgattac atttggccag    300
ggcaccaaag tggaaattaa a                                              321
```

<210> SEQ ID NO 73
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Gly Ala
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Asp Phe Pro Leu
                85                  90                  95

Thr Phe Gly Gln Gly Thr Lys Val Glu Ile Lys
            100                 105
```

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Gly Tyr
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Asp Phe Pro Leu
                85                  90                  95

Thr Phe Gly Gln Gly Thr Lys Val Glu Ile Lys
            100                 105
```

<210> SEQ ID NO 75
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Ala
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Asp Phe Pro Leu
                85                  90                  95

Thr Phe Gly Gln Gly Thr Lys Val Glu Ile Lys
            100                 105

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Ser Ile Ala Asp Phe
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Ser Ile Ala Glu Phe
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Ser Ile Ala Asn Asn Asn
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Ser Ile Ala Asn Thr Asn
1               5

-continued

```
<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Ser Ile Asp Gly Ala
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Ser Ile Asp Gly Phe
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Ser Ile Asp Asn Ser Tyr
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Ser Ile Asp Arg Ala
1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Ser Ile Glu Gly Ala
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85
```

```
Gln Ser Ile Gly Asp Phe
1               5

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Ser Ile Gly Lys Ser
1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Ser Ile Gly Ser Ala
1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Ser Ile Asn Gly Val
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Ser Ile Arg Asn Thr Asn
1               5

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Ser Ile Ser Ser Ala
1               5

<210> SEQ ID NO 91
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 91

Gln Ser Ile Ser Ser Phe
1               5

<210> SEQ ID NO 92
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
gacatccaaa tgacgcagtc tccgagctct ctgagcgcat ccgtgggcga tcgcgtaact      60
atcacttgtc gcgcctccca gagcattgat aactcctatc tcaattggta tcaacaaaaa    120
ccgggtaagg caccgaaact gctgatttac ggagcgtcct ctctgcagtc cggtgtgccg    180
tcccgtttct ccggcagcgg ttctggtacc gatttcacgc tgaccatcag ctctctgcaa    240
ccggaggact ttgctacgta ctactgccaa cagggctacg atttccctct cacattcggc    300
caaggtacca aagtggaaat taaa                                           324

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Phe Ala Ser
1

<210> SEQ ID NO 94
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Ala Ser
1

<210> SEQ ID NO 95
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Ala Ser
1

<210> SEQ ID NO 96
<211> LENGTH: 9
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 96

Gln Gln Ala Leu Asp Phe Pro Leu Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Gln Ala Tyr Asp Phe Pro Leu Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Gln Gly Trp Asp Trp Pro Leu Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Gln Gly Tyr Asp Phe Pro Leu Thr
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Gln Gly Tyr Asp Thr Pro Phe Thr
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Gln Ser Phe Asp Phe Pro Leu Thr
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gln Gln Ser His Asp Phe Pro Leu Thr
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Gln Ser His Ser Phe Pro Leu Thr
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Gln Ser Ile Asp Phe Pro Leu Thr
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Gln Ser Tyr Asp Phe Pro Leu Thr
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Gln Ser Tyr Asp Leu Pro Ile Thr
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Gln Trp Tyr Asp Asn Pro Leu Thr
1               5

<210> SEQ ID NO 108
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
gatattcaga tgacccagag cccgagcagc ctgagcgcga gcgtgggcga tcgcgtgacc       60
attacctgcc gcgcgagcca gagcatcgat ggcgccctga actggtatca gcagaaaccg      120
ggcaaagcgc cgaaactgct gatttatttc gcgagcagcc tgcagagcgg cgtgccgagc      180
cgctttagcg gcagcggcag cggcaccgat tttaccctga ccattagcag cctgcagccg      240
gaagattttg cgacctatta ttgccagcag gcctacgact ttccgttgac atttggccag      300
ggcaccaaag tggaaattaa a                                                321

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Tyr Ser Phe Thr Ser Tyr Trp
1               5

<210> SEQ ID NO 110
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
gaggtgcagc tggtgcagag cggcgccgag gtgaagaagc ccggcgagag cctgaagatc       60
agctgcaagg gcagcggcta cagcttcacc agctactgga tcggctgggt gcggcagatg      120
cccggcaagg gcctggagtg gatgggcatc atcgacccca gcgacagcga cacccggtac      180
agccccagct ccagggcca ggtgaccatc agcgccgaca gagcatcag caccgcctac       240 ctgcagtgga gcagcctgaa ggccagcgac accgccatgt actactgcgc ccggcacccc      300
ggcctgaact gggccccccga cttcgactac tggggccagg gcaccctggt gaccgtgagc      360
agc                                                                    363

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ile Ala Pro Ser Asp Ser Asp Thr

```
<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ile Asp Ala Ser Asp Ser Asp Thr
1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ile Asp Pro Ser Asp Ser Asp Thr
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp or Ala
<220> FEATURE:
<221> NAME/KEY: MOD_RES
<222> LOCATION: (3)..(3)
<223> OTHER INFORMATION: Pro or Ala

<400> SEQUENCE: 114

Ile Xaa Xaa Ser Asp Ser Asp Thr
1               5

<210> SEQ ID NO 115
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Arg His Pro Gly Leu Ala Trp Ala Pro Asp Phe Asp Tyr
1               5                   10

<210> SEQ ID NO 116
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Arg His Pro Gly Leu Asn Trp Ala Pro Asp Phe Asp Tyr
1               5                   10
```

<210> SEQ ID NO 117
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
gaggtgcagc tggtgcagag cggcgccgag gtgaagaagc ccggcgagag cctgaagatc     60
agctgcaagg gcagcggcta cagcttcacc agctactgga tcggctgggt gcggcagatg    120
cccggcaagg gcctggagtg gatgggcatc atcgacgcca gcgacagcga caccggtac    180 agccccagct tccagggcca ggtgaccatc agcgccgaca gagcatcag caccgcctac    240 ctgcagtgga gcagcctgaa ggccagcgac accgccatgt actactgcgc ccggcacccc    300
ggcctgaact gggccccga cttcgactac tggggccagg gcaccctggt gaccgtgagc    360
agc                                                                  363

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Gly, Asp, Ala, Arg, Glu, Ser or Asn
<220> FEATURE:
<221> NAME/KEY: MOD_RES
<222> LOCATION: (5)..(5)
<223> OTHER INFORMATION: Asp, Gly, Asn, Ser, Arg, Glu or Lys
<220> FEATURE:
<221> NAME/KEY: MOD_RES
<222> LOCATION: (6)..(6)
<223> OTHER INFORMATION: Phe, Ala, Asn, Thr, Ser or Val
<220> FEATURE:
<221> NAME/KEY: MOD_RES
<222> LOCATION: (7)..(7)
<223> OTHER INFORMATION: Tyr, Asn or not present

<400> SEQUENCE: 118

Gln Ser Ile Xaa Xaa Xaa Xaa
1               5

<210> SEQ ID NO 119
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Trp or Gly

<400> SEQUENCE: 119

Xaa Ala Ser
1

<210> SEQ ID NO 120
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala, Gly, Ser or Trp
<220> FEATURE:
<221> NAME/KEY: MOD_RES
<222> LOCATION: (4)..(4)
<223> OTHER INFORMATION: Leu, Tyr, His, Trp, Phe or Ile
<220> FEATURE:
<221> NAME/KEY: MOD_RES
<222> LOCATION: (5)..(5)
<223> OTHER INFORMATION: Asp or Ser
<220> FEATURE:
<221> NAME/KEY: MOD_RES
<222> LOCATION: (6)..(6)
<223> OTHER INFORMATION: Phe, Thr, Leu, Asn or Trp
<220> FEATURE:
<221> NAME/KEY: MOD_RES
<222> LOCATION: (8)..(8)
<223> OTHER INFORMATION: Leu, Phe or Ile

<400> SEQUENCE: 120

Gln Gln Xaa Xaa Xaa Xaa Pro Xaa Thr
1               5

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ala or Asn

<400> SEQUENCE: 121

Ala Arg His Pro Gly Leu Xaa Trp Ala Pro Asp Phe Asp Tyr
1               5                   10

<210> SEQ ID NO 122
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
gaggtgcagc tggtgcagag cggcgccgag gtgaagaagc ccggcgagag cctgaagatc      60
agctgcaagg gcagcggcta cagcttcacc agctactgga tcggctgggt gcggcagatg     120
cccggcaagg gcctggagtg gatgggcatc atcgacccca gcgacagcga caccggtac      180 agccccagct ccagggcca ggtgaccatc agcgccgaca gagcatcag caccgcctac      240 ctgcagtgga gcagcctgaa ggccagcgac accgccatgt actactgcgc ccggcacccc     300
ggcctggcct gggcccccga cttcgactac tggggccagg gcaccctggt gaccgtgagc     360
agc                                                                  363

<210> SEQ ID NO 123
<211> LENGTH: 107
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Phe
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Leu Pro Ile
                85                  90                  95

Thr Phe Gly Gln Gly Thr Lys Val Glu Ile Lys
            100                 105

<210> SEQ ID NO 124
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Gly Phe
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Leu Pro Ile
                85                  90                  95

Thr Phe Gly Gln Gly Thr Lys Val Glu Ile Lys
            100                 105

<210> SEQ ID NO 125
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Gly Tyr
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Leu Pro Ile
                 85                  90                  95

Thr Phe Gly Gln Gly Thr Lys Val Glu Ile Lys
            100                 105
```

<210> SEQ ID NO 126
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Asp Ile Gln Met Thr Gln Ser Pro Ser Ser Leu Ser Ala Ser Val Gly
 1                5                  10                  15

Asp Arg Val Thr Ile Thr Cys Arg Ala Ser Gln Ser Ile Asp Gly Phe
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Leu Pro Ile
                 85                  90                  95

Thr Phe Gly Gln Gly Thr Lys Val Glu Ile Lys
            100                 105
```

<210> SEQ ID NO 127
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Asp Ile Gln Met Thr Gln Ser Pro Ser Ser Leu Ser Ala Ser Val Gly
 1                5                  10                  15

Asp Arg Val Thr Ile Thr Cys Arg Ala Ser Gln Ser Ile Asp Gly Phe
                 20                  25                  30

Leu Asn Trp Tyr Gln Gln Lys Pro Gly Lys Ala Pro Lys Leu Leu Ile
             35                  40                  45

Tyr Ile Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Leu Pro Ile
                 85                  90                  95

Thr Phe Gly Gln Gly Thr Lys Val Glu Ile Lys
            100                 105
```

<210> SEQ ID NO 128
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Gly Phe
            20                  25                  30

Leu Asn Trp Tyr Gln Gln Lys Pro Gly Lys Ala Pro Lys Leu Leu Ile
        35                  40                  45

Tyr Leu Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Leu Pro Ile
                85                  90                  95

Thr Phe Gly Gln Gly Thr Lys Val Glu Ile Lys
            100                 105

<210> SEQ ID NO 129
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Gly Phe
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Leu Pro Ile
                85                  90                  95

Thr Phe Gly Gln Gly Thr Lys Val Glu Ile Lys
            100                 105

<210> SEQ ID NO 130
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Gly Tyr
            20                  25                  30

Leu Asn Trp Tyr Gln Gln Lys Pro Gly Lys Ala Pro Lys Leu Leu Ile
        35                  40                  45
```

```
Tyr Phe Ala Ser Ser Leu Gln Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Leu Pro Ile
                 85                  90                  95

Thr Phe Gly Gln Gly Thr Lys Val Glu Ile Lys
                100                 105

<210> SEQ ID NO 131
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Glu Gly Phe
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Leu Pro Ile
                 85                  90                  95

Thr Phe Gly Gln Gly Thr Lys Val Glu Ile Lys
                100                 105

<210> SEQ ID NO 132
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Glu Gly Phe
                 20                  25                  30

Leu Asn Trp Tyr Gln Gln Lys Pro Gly Lys Ala Pro Lys Leu Leu Ile
             35                  40                  45

Tyr Ile Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Leu Pro Ile
                 85                  90                  95

Thr Phe Gly Gln Gly Thr Lys Val Glu Ile Lys
                100                 105

<210> SEQ ID NO 133
<211> LENGTH: 107
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Gly Phe
            20                  25                  30

Leu Asn Trp Tyr Gln Gln Lys Pro Gly Lys Ala Pro Lys Leu Leu Ile
        35                  40                  45

Tyr Leu Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Leu Pro Ile
                85                  90                  95

Thr Phe Gly Gln Gly Thr Lys Val Glu Ile Lys
            100                 105

<210> SEQ ID NO 134
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Gly Phe
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Leu Pro Ile
                85                  90                  95

Thr Phe Gly Gln Gly Thr Lys Val Glu Ile Lys
            100                 105

<210> SEQ ID NO 135
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Asn Trp Tyr Gln Gln Lys Pro Gly Lys Ala Pro Lys Leu Leu Ile

```
                35                  40                  45

Tyr Phe Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Leu Pro Ile
                 85                  90                  95

Thr Phe Gly Gln Gly Thr Lys Val Glu Ile Lys
            100                 105
```

<210> SEQ ID NO 136
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Phe Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Leu Pro Ile
                 85                  90                  95

Thr Phe Gly Gln Gly Thr Lys Val Glu Ile Lys
            100                 105
```

<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Gly Asp Phe
             20                  25                  30

Leu Asn Trp Tyr Gln Gln Lys Pro Gly Lys Ala Pro Lys Leu Leu Ile
         35                  40                  45

Tyr Tyr Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Leu Pro Ile
                 85                  90                  95

Thr Phe Gly Gln Gly Thr Lys Val Glu Ile Lys
            100                 105
```

-continued

<210> SEQ ID NO 138
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Gly Tyr
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Leu Pro Ile
                85                  90                  95

Thr Phe Gly Gln Gly Thr Lys Val Glu Ile Lys
            100                 105

<210> SEQ ID NO 139
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Gly Phe
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Leu Pro Ile
                85                  90                  95

Thr Phe Gly Gln Gly Thr Lys Val Glu Ile Lys
            100                 105

<210> SEQ ID NO 140
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Asn Trp Tyr Gln Gln Lys Pro Gly Lys Ala Pro Lys Leu Leu Ile
            35                  40                  45

Tyr Tyr Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Leu Pro Ile
                85                  90                  95

Thr Phe Gly Gln Gly Thr Lys Val Glu Ile Lys
            100                 105

<210> SEQ ID NO 141
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Ala
            20                  25                  30

Leu Asn Trp Tyr Gln Gln Lys Pro Gly Lys Ala Pro Lys Leu Leu Ile
            35                  40                  45

Tyr Phe Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Asp Phe Pro Leu
                85                  90                  95

Thr Phe Gly Gln Gly Thr Lys Val Glu Ile Lys
            100                 105

<210> SEQ ID NO 142
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Gly Tyr
            20                  25                  30

Leu Asn Trp Tyr Gln Gln Lys Pro Gly Lys Ala Pro Lys Leu Leu Ile
            35                  40                  45

Tyr Phe Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Asp Phe Pro Leu
                85                  90                  95

Thr Phe Gly Gln Gly Thr Lys Val Glu Ile Lys
            100                 105

<210> SEQ ID NO 143
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Gly Ala
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Asp Leu Pro Leu
                85                  90                  95

Thr Phe Gly Gln Gly Thr Lys Val Glu Ile Lys
            100                 105

<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Phe Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Asp Phe Pro Leu
                85                  90                  95

Thr Phe Gly Gln Gly Thr Lys Val Glu Ile Lys
            100                 105

<210> SEQ ID NO 145
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Ala
            20                  25                  30

Leu Asn Trp Tyr Gln Gln Lys Pro Gly Lys Ala Pro Lys Leu Leu Ile
         35                  40                  45

Tyr Phe Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Asp Leu Pro Leu
             85                  90                  95

Thr Phe Gly Gln Gly Thr Lys Val Glu Ile Lys
            100                 105

<210> SEQ ID NO 146
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
         35                  40                  45

Tyr Phe Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Asp Leu Pro Leu
             85                  90                  95

Thr Phe Gly Gln Gly Thr Lys Val Glu Ile Lys
            100                 105

<210> SEQ ID NO 147
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Asp Phe
            20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Asp Leu Pro Leu
             85                  90                  95

```
Thr Phe Gly Gln Gly Thr Lys Val Glu Ile Lys
            100                 105
```

<210> SEQ ID NO 148
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Ser
            20                  25                  30

Tyr Leu Asn Trp Tyr Gln Gln Lys Pro Gly Lys Ala Pro Lys Leu Leu
        35                  40                  45

Ile Tyr Gly Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Tyr Asp Trp Pro
                85                  90                  95

Leu Thr Phe Gly Gln Gly Thr Lys Val Glu Ile Lys
            100                 105
```

<210> SEQ ID NO 149
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Ser
            20                  25                  30

Tyr Leu Asn Trp Tyr Gln Gln Lys Pro Gly Lys Ala Pro Lys Leu Leu
        35                  40                  45

Ile Tyr Gly Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Trp Asp Phe Pro
                85                  90                  95

Leu Thr Phe Gly Gln Gly Thr Lys Val Glu Ile Lys
            100                 105
```

<210> SEQ ID NO 150
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Asp Ile Gln Met Thr Gln Ser Pro Ser Ser Leu Ser Ala Ser Val Gly
```

```
                1               5                   10                  15
Asp Arg Val Thr Ile Thr Cys Arg Ala Ser Gln Ser Ile Asp Asn Ser
                20                  25                  30

Tyr Leu Asn Trp Tyr Gln Gln Lys Pro Gly Lys Ala Pro Lys Leu Leu
            35                  40                  45

Ile Tyr Gly Ala Ser Ser Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Tyr Asp Phe Pro
                85                  90                  95

Leu Thr Phe Gly Gln Gly Thr Lys Val Glu Ile Lys
            100                 105

<210> SEQ ID NO 151
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Gln Ser
                20                  25                  30

Tyr Leu Asn Trp Tyr Gln Gln Lys Pro Gly Lys Ala Pro Lys Leu Leu
            35                  40                  45

Ile Tyr Gly Ala Ser Ser Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Tyr Asp Phe Pro
                85                  90                  95

Leu Thr Phe Gly Gln Gly Thr Lys Val Glu Ile Lys
            100                 105

<210> SEQ ID NO 152
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Thr Ser
                20                  25                  30

Tyr Leu Asn Trp Tyr Gln Gln Lys Pro Gly Lys Ala Pro Lys Leu Leu
            35                  40                  45

Ile Tyr Gly Ala Ser Ser Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Tyr Asp Phe Pro
```

Leu Thr Phe Gly Gln Gly Thr Lys Val Glu Ile Lys
            100                 105

<210> SEQ ID NO 153
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Thr
            20                  25                  30

Tyr Leu Asn Trp Tyr Gln Gln Lys Pro Gly Lys Ala Pro Lys Leu Leu
        35                  40                  45

Ile Tyr Gly Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Tyr Asp Phe Pro
                85                  90                  95

Leu Thr Phe Gly Gln Gly Thr Lys Val Glu Ile Lys
            100                 105

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gln Gln Ser Tyr Asp Phe Pro Leu
1               5

<210> SEQ ID NO 155
<211> LENGTH: 98
<212> TYPE: PRT
<213> ORGANISM: Homo sapiens

<400> SEQUENCE: 155

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg

<210> SEQ ID NO 156
<211> LENGTH: 107
<212> TYPE: PRT
<213> ORGANISM: Homo sapiens

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 157
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Ala Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Gly Leu Asn Trp Ala Pro Asp Phe Asp Tyr Trp Gly
            100                 105                 110

Gln Gly Thr Leu Val Thr Val Ser Ser
        115                 120

<210> SEQ ID NO 158
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr

```
                    20                  25                  30
Trp Ile Gly Trp Val Arg Gln Met Pro Gly Lys Gly Leu Glu Trp Met
            35                  40                  45

Gly Ile Ile Asp Ala Ser Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Gly Leu Asn Trp Ala Pro Asp Phe Asp Tyr Trp Gly
            100                 105                 110

Gln Gly Thr Leu Val Thr Val Ser Ser
        115                 120

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Gly, Asp, Ala, Glu, Ser or Asn
<220> FEATURE:
<221> NAME/KEY: MOD_RES
<222> LOCATION: (5)..(5)
<223> OTHER INFORMATION: Asp, Gly, Asn, Ser or Arg
<220> FEATURE:
<221> NAME/KEY: MOD_RES
<222> LOCATION: (6)..(6)
<223> OTHER INFORMATION: Phe, Ala, Asn, Ser or Val
<220> FEATURE:
<221> NAME/KEY: MOD_RES
<222> LOCATION: (7)..(7)
<223> OTHER INFORMATION: Tyr, Asn or not present

<400> SEQUENCE: 159

Gln Ser Ile Xaa Xaa Xaa Xaa
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala, Gly or Ser
<220> FEATURE:
<221> NAME/KEY: MOD_RES
<222> LOCATION: (4)..(4)
<223> OTHER INFORMATION: Tyr, His, Trp or Phe
<220> FEATURE:
<221> NAME/KEY: MOD_RES
<222> LOCATION: (5)..(5)
<223> OTHER INFORMATION: Asp or Ser
<220> FEATURE:
<221> NAME/KEY: MOD_RES
<222> LOCATION: (6)..(6)
<223> OTHER INFORMATION: Phe, Thr, Leu or Trp
<220> FEATURE:
<221> NAME/KEY: MOD_RES
<222> LOCATION: (8)..(8)
<223> OTHER INFORMATION: Leu, Phe or Ile
```

```
<400> SEQUENCE: 160

Gln Gln Xaa Xaa Xaa Xaa Pro Xaa Thr
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala or Asp
<220> FEATURE:
<221> NAME/KEY: MOD_RES
<222> LOCATION: (5)..(5)
<223> OTHER INFORMATION: Asn or Gly
<220> FEATURE:
<221> NAME/KEY: MOD_RES
<222> LOCATION: (6)..(6)
<223> OTHER INFORMATION: Phe, Asn or Ser
<220> FEATURE:
<221> NAME/KEY: MOD_RES
<222> LOCATION: (7)..(7)
<223> OTHER INFORMATION: Tyr, Asn or not present

<400> SEQUENCE: 161

Gln Ser Ile Xaa Xaa Xaa Xaa
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly or Ser
<220> FEATURE:
<221> NAME/KEY: MOD_RES
<222> LOCATION: (6)..(6)
<223> OTHER INFORMATION: Phe, Thr or Leu
<220> FEATURE:
<221> NAME/KEY: MOD_RES
<222> LOCATION: (8)..(8)
<223> OTHER INFORMATION: Leu, Phe or Ile

<400> SEQUENCE: 162

Gln Gln Xaa Tyr Asp Xaa Pro Xaa Thr
1               5
```

INTERFERON ALPHA AND OMEGA ANTIBODY ANTAGONISTS

CROSS-REFERENCE TO RELATED APPLICATION

This application is a continuation of U.S. application Ser. No. 16/222,285, filed 17 Dec. 2018, now U.S. Pat. No. 10,358,491, granted 23 Jul. 2019, which is a divisional of U.S. application Ser. No. 14/745,939, filed 22 Jun. 2015, now U.S. Pat. No. 10,208,113, issued 19 Feb. 2019, which claims the benefit of U.S. Provisional Application Ser. No. 62/015,765, filed 23 Jun. 2014. The entire contents of the aforementioned application are incorporated herein by reference in their entireties.

FIELD OF THE INVENTION

The present invention relates to antibodies that broadly neutralize interferon-α and interferon-ω, polynucleotides encoding the antibodies or fragments, and methods of making and using the foregoing.

BACKGROUND OF THE INVENTION

Type I interferons (IFNs) (IFN-I) are a family of cytokines that signal through a ubiquitously expressed heterodimeric receptor IFNAR (heterodimer of IFNAR1 and IFNAR2) resulting in antiviral, antiproliferative and immunomodulatory effects. In humans, type I IFN is composed of at least 12 IFN-α protein subtypes and 1 subtype each for IFN-β, IFN-ε, IFN-κ, and IFN-ω. IFN-I release occurs in response to both microbial and sterile ligands. Upon receptor binding, IFN-I initiates a signaling cascade through activation of JAK1 and TYK2 leading to the phosphorylation of several STAT family members including STATs 1-6. STAT1 and STAT2 activation leads to the formation of a complex with IFN-regulatory factor 9 (IRF9) and this complex, also known as the IFN-stimulated gene factor 3 (ISGF3) complex, binds to IFN-stimulated response elements (ISREs) in the nucleus resulting in the transcription of many interferon-stimulated genes (ISGs) including IRF7 and CXCL10 (IP-10) (Gonzalez-Navajas et al., *Nature reviews. Immunology* 12, 125 (February, 2012). IFN-I also modulates cellular function through other pathways including the v-crk sarcoma virus CT10 oncogene homolog (avian)-like (CRKL), mitogen-activated protein kinase (MAPK), phosphoinositide 3-kinase (PI3K), and through nuclear factor kappa-light-chain-enhancer of activated B cells (NF-κβ) (Hervas-Stubbs et al., *Clinical cancer research: an official journal of the American Association for Cancer Research* 17, 2619 (May 1, 2011)).

Several immune-mediated inflammatory diseases or autoimmune diseases, such as lupus, including Systemic Lupus Erythematosus (SLE) and cutaneous lupus erythematosus (CLE), type I diabetes, psoriasis, Sjögren's disease, systemic sclerosis, rheumatoid arthritis, immune thrombocytopenia (ITP), Aicardi-Goutieres syndrome (AGS), myositis, common variable immune deficiency (CVID) and autoimmune thyroid disease are associated at least in a sub-population of patients with overexpression of IFN-inducible gene transcripts commonly called the IFN signature present in whole blood and/or tissue, or with elevated IFN-I.

SLE is a chronic autoimmune or immune-mediated inflammatory disease in which the production of pathogenic autoantibodies and immune complexes result in tissue damage across multiple organ systems. The disease displays a broad range of symptoms with heterogeneous clinical presentation and may include systemic, cutaneous, renal, musculoskeletal, neurological and hematological manifestations. SLE varies greatly in severity and is chronic, remitting or relapsing with flares of activity cycling with periods of improvement or remission that may last weeks, months, or years. IFN-α is elevated in SLE patients and is believed to promote a loss of tolerance to self. IFN-α has been shown to contribute to sustained dendritic cell activation and thus antigen presentation, and suppression of Treg function contributing to SLE. IFN-α also induces BLyS expression, a target for the marketed SLE therapeutic BENLYSTA™. A number of polymorphisms associated with production or response to IFN-I have been identified and account for over half of confirmed polymorphisms associated with SLE (Ghodke-Puranik & Niewold, *International journal of clinical rheumatology* 8, doi:10.2217/ijr.13.58 (2013)). Antibodies neutralizing various IFN-α subtypes (pan-IFN-α antibodies) are being evaluated in clinical trials for SLE (see, for example, Int. Pat. Publ. No. WO02/066649, Int Pat. Publ. No. WO05/059106, Int. Pat. Publ. No. WO06/086586, Int. Pat. Publ. No. WO09/135861).

IFN-ω constitutes approximately 15% of the total IFN-I activity in human leukocyte IFN preparations produced after viral infection (Adolf, *Virology* 175, 410 (April, 1990). IFN-ω gene expression has been reported to be elevated in SLE patients (Han et al., *Genes and immunity* 4, 177 (April, 2003); Yao et al., *Hum Genomics Proteomics* 2009, (2009)), and the ability of IFN-ω to induce DC differentiation has been reported (Walker and Tough, *European journal of immunology* 36, 1827 (July, 2006)). The anti-IFN-α antibodies currently in clinical trials (sifalimumab (MEDI-545), rontalizumab and AGS-009) do not neutralize IFN-ω. Clinical trial data with these antibodies indicate partial reduction of the type I IFN signature in patients after treatment with anti-IFN-α antibodies (Merrill et al., Ann Rheum Dis 70:1905-1913, 2011; Yao et al., Arthritis Rheum 60:1785-1796, 2009), and Phase 2 trial data with rontalizumab (a pan-anti-IFN-α antibody) indicated improvement in signs and symptoms of SLE, flare rates, and steroid burden at week 24 in a pre-specified biomarker defined group of Interferon Signature Metric (ISM)-Low moderate to severely active lupus subjects. No efficacy was seen in patients having higher levels of IFN-inducible gene expression pre-defined as ISM-High (Kalunian et al., 2012 ACR/ARHP Annual Meeting; Abstract #2622, 2012).

In addition to anti-IFN antibodies, anti-IFNAR1 antibodies are being investigated for the treatment of lupus (Wang et al., 2013; Clinical Pharmacology & Therapeutics accepted article preview 14 Feb. 2013; doi: 10.1038/clpt.2013.35). IFNAR1 blockage is likely to abolish IFN signaling induced by all type I IFNs, including IFN-β. IFN-β may play a more critical role in antiviral defense, as specific deletion of the gene encoding IFN-β incurs substantial susceptibility to a host of viruses when compared to similarly exposed mice having functional IFN-β (Lazear et al., J Virol 85:7186-7194; Deonarain et al., J Virol 74(7): 3404-340, 2000; Deonarain et al., Circulation 110: 3540-3543, 2004; Gerlach, et al., J Virol 80: 3438-3444, 2006). Therefore, anti-IFNAR1 antibodies may increase the risk of side effects.

Current standard of care for SLE includes corticosteroids, antimalarial drugs, immunosuppressants or B cell modulators. These therapeutics may exhibit toxicity and other serious side effects, and may not be suitable for treatment of all lupus patients. Thus, there is a need for additional therapeutic treatments for lupus and other immune-mediated inflammatory or autoimmune diseases.

BRIEF DESCRIPTION OF THE DRAWINGS

FIG. 10 shows the $IC_{50}$ values for select antibodies to various Type I IFNs in an ISRE assay.

SUMMARY OF THE INVENTION

Figure 1A:
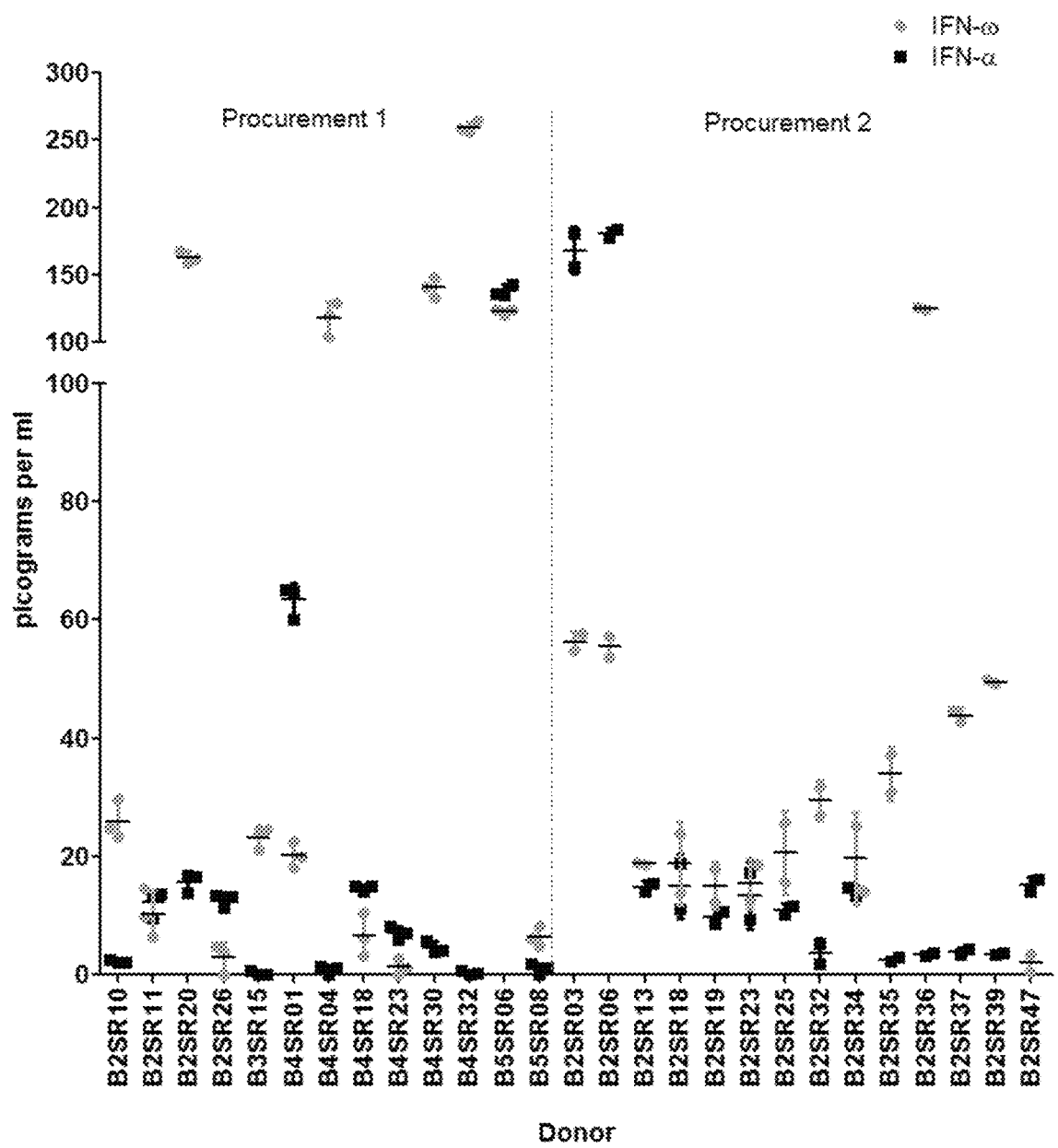
FIG. 1A shows IFN-ω and IFN-α levels (pg/ml) in plasma from Chinese SLE patients. Horizontal bars in the figure indicate mean ELISA value of replicate samples, vertical bars indicate standard deviation (SD).

One embodiment of the invention is an isolated monoclonal antibody that binds to and neutralizes a biological activity of a human interferon omega (IFN-ω) and at least three, four, five, six, seven, eight, nine, ten or eleven human interferon alpha (IFN-α) subtypes.

Another embodiment of the invention is an isolated monoclonal antibody that binds to and neutralizes a biological activity of a human interferon omega (IFN-ω) and at least three, four, five, six, seven, eight, nine, ten or eleven human interferon alpha (IFN-α) subtypes, wherein the antibody neutralizes the biological activity of the human IFN-ω with an $IC_{50}$ of at least about $1\times10^{-9}$ M or less, about $1\times10^{-10}$ M or less, about $5\times10^{-11}$ M or less, or about $1\times10^{-11}$ M or less.

In other embodiments, the antibody of the invention neutralizes the activity of at least three, four, five, six, seven, eight, nine, ten or eleven human IFN-α subtypes with an $IC_{50}$ value of at least about $2\times10^{-10}$ M or less, about $1.5\times10^{-10}$ M or less, or about $1\times10^{-10}$ M or less.

In other embodiments, the antibody comprises heavy chain complementarity determining region (HCDR) 1 (HCDR1), 2 (HCDR2) and 3 (HCDR3) amino acid sequences of SEQ ID NOs: 109, 114 and 121, respectfully, and light chain complementarity determining region (LCDR) 1 (LCDR1), 2 (LCDR2) and 3 (LCDR3) amino acid sequences of SEQ ID NOs: 118, 119 and 120.

In other embodiments, the antibody comprises the HCDR1, the HCDR2, the HCDR3, the LCDR1, the LCDR2 and the LCDR3 amino acid sequences of SEQ ID NOs: 109, 114, 121, 159, 119 and 160, respectively.

In other embodiments, the antibody neutralizes at least ten human IFN-α subtypes selected from the group consisting of IFN-αA, IFN-αB2, IFN-αC, IFN-αF, IFN-αG, IFN-αH2, IFN-αI, IFN-αJ1, IFN-αK, IFN-αWA and IFN-α4a.

In other embodiments, the antibody binds human IFN-ω of SEQ ID NO: 1 at least at amino acid residues F27, L30 and R33.

In other embodiments, the antibody comprises the HCDR1, the HCDR2, the HCDR3, the LCDR1, the LCDR2 and the LCDR3 amino acid sequences of SEQ ID NOs: 109, 114, 121, 161, 119 and 162, respectively.

In other embodiments, the antibody neutralizes at least the human IFN-α subtypes IFN-αA, IFN-αB2, IFN-αC, IFN-αF, IFN-αG, IFN-αH2, IFN-αJ1 and IFN-α4a.

In other embodiments, the antibody comprises a heavy chain variable region (VH) amino acid sequence at least 90%, 91%, 92%, 93%, 94%, 95%, 96%, 97%, 98% or 99% identical to SEQ ID NO: 28 and a light chain variable region (VL) amino acid sequences at least 90%, 91%, 92%, 93%, 94%, 95%, 96%, 97%, 98% or 99% identical to SEQ ID NO: 150.

In other embodiments, the antibody comprises certain HCDR and LCDR sequences as described herein.

In other embodiments, the antibody comprises certain VH and VL sequences as described herein.

Another embodiment of the invention is a pharmaceutical composition comprising the antibody of the invention and a pharmaceutically accepted carrier.

Another embodiment of the invention is a polynucleotide encoding the antibody VH and/or the VL of the invention.

Another embodiment of the invention is a vector comprising the polynucleotide of the invention.

Another embodiment of the invention is a host cell comprising the vector of the invention.

Another embodiment of the invention is a method of producing the antibody of the invention, comprising culturing the host cell of the invention in conditions that the antibody is expressed, and recovering the antibody produced by the host cell.

Another embodiment of the invention is a method of treating an immune-mediated inflammatory disease or an autoimmune disease, comprising administering a therapeutically effective amount of an isolated antibody of the invention to a patient in need thereof for a time sufficient to treat or prevent the disease.

In some embodiments, the immune-mediated inflammatory disease or the autoimmune disease is lupus, psoriasis, immune thrombocytopenia (ITP), Aicardi-Goutieres syndrome (AGS), systemic sclerosis, Sjögren's syndrome, myositis, common variable immune deficiency (CVID), autoimmune thyroid disease, type I diabetes, rheumatoid arthritis, transplant rejection or graft versus host disease (GVHD).

DETAILED DESCRIPTION OF THE INVENTION

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein can be used in the practice for testing of the present invention, exemplary materials and methods are described herein. In describing and claiming the present invention, the following terminology will be used.

The term "specific binding" or "specifically binds" or "binds" as used herein refers to antibody binding to an antigen or an epitope within the antigen with greater affinity than for other antigens. Typically, the antibody binds to the antigen or the epitope within the antigen with a dissociation constant ($K_D$) of $1 \times 10^{-8}$ M or less, for example $1 \times 10^{-9}$ M or less, $1 \times 10^{-10}$ M or less, $1 \times 10^{-11}$ M or less, or $1 \times 10^{-12}$ M or less, typically with a $K_D$ that is at least ten fold less than its $K_D$ for binding to a non-specific antigen (e.g., BSA, casein). The dissociation constant can be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno) or *Pan troglodytes* (chimpanzee, chimp). Antibodies that specifically bind to the antigen or the epitope within the antigen can further bind an epitope that is shared between two or more distinct antigens such as at least one interferon alpha (IFN-α) subtype and interferon omega (IFN-ω); i.e. antibodies cross-react with IFN-α subtypes and IFN-ω.

The term "neutralizing" or "neutralizes" or "neutralizing antibody" or "antibody antagonist" as used herein refers to an antibody or antibody fragment that partially or completely inhibits biological activity of recombinant human interferon omega (IFN-ω) and/or at least one recombinant human interferon alpha (IFN-α) subtype. Neutralizing antibodies may be identified using assays for IFN-α and/or IFN-ω biological activity as described herein. IFN-α and/or IFN-ω neutralizing antibody may inhibit measured IFN-α and/or IFN-ω biological activity by 20%, 30%, 40%, 50%, 60%, 70%, 75%, 80%, 85%, 90%, 95%, 96%, 97%, 98%, 99% or 100%.

The term "interferon-α" (IFN-α) as used herein refers to all native subtypes of human alpha interferons. Native IFN-α consists of at least 12 closely related protein subtypes encoded by distinct genes with a high degree of structural homology (Weissmann and Weber, Prog Nucl Acid Res Mol Biol., 33: 251, 1986; Roberts et al., J Interferon Cytokine Res. 18: 805-816, 1998). Nomenclature for human interferons is found at: hUp://www_genenames_org/genefamilies/_IFN. Table 4 shows the sequences of the IFN-α subtypes used herein, in addition to other Type I IFNs.

The term IFN-ω as used herein refers to human IFN-ω having the amino acid sequence shown in SEQ ID NO: 1 and UniProt accession number P05000. Human IFN-ω also includes the variant of SEQ ID NO: 2 having a threonine to glutamic acid substitution at position 80 (T80).

The term "type I interferon" or "IFN-I" refers to all native subtypes of human interferon-α and one subtype of interferon-β, interferon-ε, interferon-ω and interferon-κ which bind to a common interferon receptor IFNAR.

As used herein the term "IFNAR" refers to the well-known interferon receptor which is a heterodimer or IFNAR1 and IFNAR2. IFNAR1 and IFNAR2 protein sequences are shown in SEQ ID NOs: 26 and 27, respectively. IFNAR1 mature extracellular domain spans residues 28-436 of SEQ ID NO: 26 and IFNAR2 mature extracellular domain spans residues 27-243 of SEQ ID NO: 27.

The term "antibodies" as used herein is meant in a broad sense and includes immunoglobulin molecules including polyclonal antibodies, monoclonal antibodies including murine, human, humanized and chimeric monoclonal antibodies, antibody fragments, bispecific or multispecific antibodies formed from at least two intact antibodies or antibody fragments, dimeric, tetrameric or multimeric antibodies, single chain antibodies, domain antibodies and any other modified configuration of the immunoglobulin molecule that comprises an antigen recognition site of the required specificity.

Immunoglobulins can be assigned to five major classes, IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (κ) and lambda (λ), based on the amino acid sequences of their constant domains.

The term "antibody fragments" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include well known Fab, F(ab')2, Fd and Fv fragments as well as domain antibodies (dAb) consisting one VH domain. VH and VL domains can be linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO1992/01047.

An antibody variable region consists of a "framework" region interrupted by three "antigen binding sites". The antigen binding sites are defined using various terms: (i) Complementarity Determining Regions (CDRs), three in the VH(HCDR1, HCDR2, HCDR3), and three in the VL (LCDR1, LCDR2, LCDR3), are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3), refer to the regions of an antibody variable domains which are hypervariable in structure as defined by Chothia and Lesk (Chothia and Lesk, Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003.

"Monoclonal antibody" as used herein refers to a homogenous antibody population with singular molecular composition. Monoclonal antibody may be nonspecific or multispecific.

"Chothia residues" as used herein are the antibody VL and VH residues numbered according to Al-Lazikani (Al-Lazikani et al., J Mol Biol 273:927-48, 1997).

"Framework" or "framework sequences" are the remaining sequences of a variable region other than those defined to be antigen binding site. Because the antigen binding site can be defined by various terms as described above, the exact amino acid sequence of a framework depends on how the antigen-binding site was defined.

"Humanized antibodies" refers to antibodies in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human-adapted" antibodies or "human framework adapted (HFA)" antibodies refers to humanized antibodies adapted according to methods described in U.S. Pat. Publ. No. US2009/0118127. Human-adapted antibodies are humanized by selecting the acceptor human frameworks based on the maximum CDR and FR similarities, length compatibilities and sequence similarities of CDR1 and CDR2 loops and a portion of light chain CDR3 loops.

"Human antibody" refers to an antibody having heavy and light chain variable regions in which both the framework and the antigen binding site regions are derived from sequences of human origin. If the antibody contains a constant region, the constant region also is derived from sequences of human origin.

Human antibody comprises heavy or light chain variable regions that are "derived from" sequences of human origin if the variable regions of the antibody are obtained from a system that uses human germline immunoglobulin or rearranged immunoglobulin genes. Such exemplary systems are human immunoglobulin gene libraries displayed on phage, and transgenic non-human animals such as mice carrying human immunoglobulin loci as described herein. "Human antibody" may contain amino acid differences when compared to the human germline or rearranged immunoglobulin sequences due to for example naturally occurring somatic mutations or intentional introduction of substitutions. Typically, "human antibody" is at least about 80%, 81%, 82%, 83%, 84%, 85%, 86%, 87%, 88%, 89%, 90%, 91%, 92%, 93%, 94%, 95%, 96%, 97%, 98%, 99% or 100% % identical in amino acid sequence to an amino acid sequence encoded by a human germline or rearranged immunoglobulin gene. In some cases, "human antibody" may contain consensus framework sequences derived from human framework sequence analyses, for example as described in Knappik et al (2000) *J. Mol. Biol.* 296:57-86), or synthetic HCDR3 incorporated into human immunoglobulin gene libraries displayed on phage, for example as described in Shi et al (2010) *J. Mol. Biol.* 397:385-96, 2010 and Int. Pat. Publ. No. WO2009/085462.

Isolated humanized antibodies are synthetic. Human antibodies, while derived from human immunoglobulin sequences, may be generated using systems such as phage display incorporating synthetic CDRs and/or synthetic frameworks, or can be subjected to in vitro mutagenesis to improve antibody properties, resulting in antibodies that do not naturally exist within the human antibody germline repertoire in vivo.

Human antibodies may include substitutions in the framework or in the antigen binding site so that they may not be exact copies of expressed human immunoglobulin or germline gene sequences. However, antibodies in which antigen binding sites are derived from a non-human species are not included in the definition of "human antibody".

The term "recombinant" as used herein, includes antibodies and other proteins, such as various IFN-α subtypes or IFN-ω that are prepared, expressed, created or isolated by recombinant means.

The term "epitope" as used herein means a portion of an antigen to which an antibody specifically binds. Epitopes usually consist of chemically active (such as polar, nonpolar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Bispecific" as used herein refers to an antibody that binds two distinct antigens or two distinct epitopes within an antigen. The bispecific antibody may have cross-reactivity to other related antigens or can bind an epitope that is shared between two or more distinct antigens such as at least one IFN-α subtype and IFN-ω.

The term "in combination with" as used herein means that the drugs or therapeutics can be administered to an animal species such as human together in a mixture, concurrently as single agents or sequentially as single agents in any order.

The terms "IFN-α biological activity" and "IFN-ω biological activity" as used herein refer to any activity occurring as a result of IFN-α and IFN-ω, respectively, binding to its receptor IFNAR. One IFN-α and IFN-ω biological activity is the ability of IFN-α and IFN-ω to induce secreted embryonic alkaline phosphatase (SEAP) expression under the interferon inducible promoter such as ISG54 in HEK293 cells stably expressing signal transducer and activator of transcription 2 (STAT2), interferon regulatory factor 9 (IRF9) and SEAP using standard methods. Another IFN-α and IFN-ω biological activity is the induction of chemokine IP-10 (CXCL10) production from peripheral blood mononuclear cells (PBMCs) or whole blood as described herein.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "polypeptide" or "protein" means a molecule that comprises at least two amino acid residues linked by a peptide bond to form a polypeptide. Small polypeptides of less than 50 amino acids may be referred to as "peptides".

Conventional one and three-letter amino acid codes are used herein as shown in Table 1.

TABLE 1

| Amino acid | Three-letter code | One-letter code |
|---|---|---|
| Alanine | ala | A |
| Arginine | arg | R |
| Asparagine | asn | N |
| Aspartate | asp | D |
| Cysteine | cys | C |
| Glutamate | glu | E |
| Glutamine | gln | Q |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

Compositions of Matter

The present invention provides monoclonal antibodies that bind to and neutralize activity of human interferon omega (IFN-ω) and multiple human interferon alpha (IFN-α) subtypes (anti-IFN-α/ω antibodies). The invention is based on, at least part, in the appreciation of the role of INF-ω in lupus pathogenesis with similar immunomodulatory effects than those of IFN-α alone. IFN-ω was found to be present and active in serum of lupus patients, and IFN-ω was found to induce similar cytokine release and gene expression profiles, dendritic cell differentiation, and T-cell independent B cell activation when compared to IFN-α; providing the basis for the rationale for neutralizing both IFN-α and IFN-ω to maximize therapeutic effect. The invention is also based, at least in part, on the identification of a minimal neutralizing epitope shared by IFN-ω and multiple IFN-α subtypes to which the IFN-α/ω antibodies of the invention bind. The IFN-α/ω antibodies of the invention may neutralize IFN-ω and multiple IFN-α subtypes with high efficacy, and thus they may be more potent in neutralizing SLE-relevant preparations of type I IFN and IFN signatures than antibodies neutralizing multiple IFN-α subtypes but not IFN-ω. Therefore, the antibodies of the invention may be more efficacious in treating immune-mediated inflammatory diseases or autoimmune diseases including lupus. As the IFN-α/ω antibodies of the invention do not neutralize IFN-β, they may have more favorable safety and PK profiles when compared to the anti-IFNAR therapies, which are expected to block all type I IFNs.

One embodiment of the invention described herein, and in some embodiments of each and every one of the numbered embodiments listed below is an isolated monoclonal antibody that binds to and neutralizes a biological activity of a human interferon omega (IFN-ω) and at least three, four, five, six, seven, eight, nine, ten or eleven human interferon alpha (IFN-α) subtypes.

In some embodiments described herein, and in some embodiments of each and every one of the numbered embodiments listed below, the antibody of the invention neutralizes the activity of the human IFN-ω with an IC$_{50}$ of at least about $1\times10^{-9}$ M or less, about $1\times10^{-10}$ M or less, about $5\times10^{-11}$ M or less, or about $1\times10^{-11}$ M or less, when the activity of the human IFN-ω is the human IFN-ω-induced expression of secreted embryonic alkaline phosphatase (SEAP) under interferon inducible ISG54 promoter in HEK293 cells stably expressing signal transducer and activator of transcription 2 (STAT2), interferon regulatory factor 9 (IRF9) and SEAP ("ISRE assay" as described herein).

In some embodiments described herein, and in some embodiments of each and every one of the numbered embodiments listed below, the antibody of the invention neutralizes IFN-ω and at least three, four, five, six, seven, eight, nine, ten or eleven human interferon alpha (IFN-α) subtypes selected from the group consisting of IFN-αA, IFN-αB2, IFN-αC, IFN-αF, IFN-αG, IFN-αH2, IFN-αI, IFN-αJ1, IFN-αK, IFN-αWA and IFN-α4a.

In some embodiments described herein, and in some embodiments of each and every one of the numbered embodiments listed below, the antibody of the invention neutralizes IFN-ω and IFN-αA, IFN-αH2 and IFN-αK.

In some embodiments described herein, and in some embodiments of each and every one of the numbered embodiments listed below, the antibody of the invention neutralizes IFN-ω and IFN-αA, IFN-αG, IFN-αH2 and IFN-αK.

In some embodiments described herein, and in some embodiments of each and every one of the numbered embodiments listed below, the antibody of the invention neutralizes IFN-ω and IFN-αF, IFN-αG, IFN-αH2 and IFN-αK.

In some embodiments described herein, and in some embodiments of each and every one of the numbered embodiments listed below, the antibody of the invention neutralizes IFN-ω and IFN-αA, IFN-αF, IFN-αG, IFN-αH2 and IFN-αK.

In some embodiments described herein, and in some embodiments of each and every one of the numbered embodiments listed below, the antibody of the invention neutralizes IFN-ω and IFN-αA, IFN-αF, IFN-αG, IFN-αH2, IFN-αJ1 and IFN-αK.

In some embodiments described herein, and in some embodiments of each and every one of the numbered embodiments listed below, the antibody of the invention neutralizes IFN-ω and IFN-αA, IFN-αB, IFN-αG, IFN-αH2 and IFN-αK.

In some embodiments described herein, and in some embodiments of each and every one of the numbered embodiments listed below, the antibody of the invention neutralizes IFN-ω and IFN-αA, IFN-αB, IFN-αF, IFN-αG, IFN-αH2 and IFN-αK.

In some embodiments described herein, and in some embodiments of each and every one of the numbered embodiments listed below, the antibody of the invention neutralizes IFN-ω and IFN-αA, IFN-αB, IFN-αC, IFN-αG, IFN-αH2 and IFN-αK.

In some embodiments described herein, and in some embodiments of each and every one of the numbered embodiments listed below, the antibody of the invention neutralizes IFN-ω and IFN-αA, IFN-αB, IFN-αC, IFN-αF, IFN-αG and IFN-α4a.

In some embodiments described herein, and in some embodiments of each and every one of the numbered embodiments listed below, the antibody of the invention neutralizes IFN-ω and IFN-αA, IFN-αB, IFN-αF, IFN-αG, IFN-αH2, IFN-αI and IFN-αK.

In some embodiments described herein, and in some embodiments of each and every one of the numbered embodiments listed below, the antibody of the invention neutralizes IFN-ω and IFN-αA, IFN-αB, IFN-αF, IFN-αG, IFN-αH2, IFN-αJ1 and IFN-αK.

In some embodiments described herein, and in some embodiments of each and every one of the numbered embodiments listed below, the antibody of the invention neutralizes IFN-ω and IFN-αA, IFN-αB, IFN-αC, IFN-αF, IFN-αG, IFN-αH2, IFN-αJ1 and IFN-αK.

In some embodiments described herein, and in some embodiments of each and every one of the numbered embodiments listed below, the antibody of the invention neutralizes IFN-ω and IFN-αA, IFN-αB, IFN-αC, IFN-αF, IFN-αG, IFN-αH2, IFN-αI, IFN-αJ1, IFN-αK and IFN-α4a.

In some embodiments described herein, and in some embodiments of each and every one of the numbered embodiments listed below, the antibody of the invention neutralizes IFN-ω and IFN-αA, IFN-αB, IFN-αC, IFN-αF, IFN-αG, IFN-αH2, IFN-αI, IFN-αJ1, IFN-αWA and IFN-α4a.

In some embodiments described herein, and in some embodiments of each and every one of the numbered embodiments listed below, the antibody of the invention neutralizes IFN-ω and IFN-αA, IFN-αB, IFN-αC, IFN-αF, IFN-αG, IFN-αH2, IFN-αK, IFN-αWA and IFN-α4a.

In some embodiments described herein, and in some embodiments of each and every one of the numbered embodiments listed below, the antibody of the invention neutralizes IFN-ω and IFN-αA, IFN-αB, IFN-αC, IFN-αF, IFN-αG, IFN-αH2, IFN-αI, IFN-αJ1, IFN-αK, IFN-αWA and IFN-α4a.

Antibodies of the invention described herein, and in some embodiments of each and every one of the numbered embodiments listed below, may bind and neutralize at least three, four, five, six, seven, eight, nine, ten or eleven IFN-α subtypes in addition to neutralizing IFN-ω. The IFN-α subtypes and IFN-ω may be produced by recombinant expression using standard methods. Exemplary signal sequences that can be used for directing secretion are shown in SEQ ID NOs: 21-25.

The antibodies of the invention described herein, and in some embodiments of each and every one of the numbered embodiments listed below, may be tested for their ability to neutralize IFN-α and IFN-ω in a reporter gene assay using cell lines expressing reporter genes under an interferon responsive promoter, and stimulating cells with various IFN-α subtypes and/or IFN-ω. For example, HEK-Blue™ IFN-α/β cells (InvivoGen, San Diego, Calif.) engineered to express a fully active type I IFN signaling pathway (stably expressing STAT2 and IRF9) and transfected with a SEAP reporter gene under the control of the IFNα/β inducible ISG54 promoter can be used as described herein. Signal from the alkaline phosphatase may be detected an $IC_{50}$ may be calculated for the inhibition using well known methods.

In some embodiments described herein, and in some embodiments of each and every one of the numbered embodiments listed below, the antibodies of the invention neutralize the biological activity of the human IFN-ω with an $IC_{50}$ value of about $1 \times 10^{-9}$ M or less, about $1 \times 10^{-10}$ M or less, about $5 \times 10^{-11}$ M or less, or about $1 \times 10^{-11}$ M or less, when the biological activity of the human IFN-ω is inhibition of secreted embryonic alkaline phosphatase (SEAP) expression under the interferon inducible ISG54 promoter in HEK293 cells stably expressing signal transducer and activator of transcription 2 (STAT2), interferon regulatory factor 9 (IRF9) and SEAP, using the assay "ISRE reporter gene assay" as described herein in Example 1.

In some embodiments described herein, and in some embodiments of each and every one of the numbered embodiments listed below, the antibodies of the invention neutralize the biological activity of the human IFN-ω with an $IC_{50}$ value of at least about $1 \times 10^{-10}$ M or less, when the $IC_{50}$ is measured in the "ISRE reporter gene assay" described herein.

In some embodiments described herein, and in some embodiments of each and every one of the numbered embodiments listed below, the antibodies of the invention neutralize the biological activity of the human IFN-ω with an $IC_{50}$ value between about $1 \times 10^{-10}$ M to about $6 \times 10^{-12}$ M, when the $IC_{50}$ is measured in the "ISRE reporter gene assay" described herein. Skilled in the art will appreciate that the assay deviation for the ISRE reporter gene assay may typically be approximately within $pIC_{50}$ of about 0.28 (log (M)). Therefore the term "about" reflects the typical standard deviation in the assay. For example, the typical SD for an $IC_{50}$ of $1 \times 10^{-9}$ M is between about $0.53 \times 10^{-9}$ to $1.9 \times 10^{-9}$.

In some embodiments described herein, and in some embodiments of each and every one of the numbered embodiments listed below, the antibodies of the invention neutralize the biological activity at least three, four, five, six, seven, eight, nine, ten or eleven human IFN-α subtypes with an $IC_{50}$ value of at least about $2 \times 10^{-10}$ M or less, about $1.5 \times 10^{-10}$ M or less, or about $1 \times 10^{-10}$ M or less.

In some embodiments described herein, and in some embodiments of each and every one of the numbered embodiments listed below, the antibody of the invention neutralizes the activity of the human IFN-ω with an $IC_{50}$ value of at least about $1 \times 10^{-10}$ M or less, and at least 6 human IFN-α subtypes with an $IC_{50}$ value of about $2 \times 10^{-10}$ M or less, about $1.5 \times 10^{-10}$ M or less, or about $1 \times 10^{-10}$ M or less, when the $IC_{50}$ value is measured using the "ISRE reporter gene assay" described herein.

In some embodiments described herein, and in some embodiments of each and every one of the numbered embodiments listed below, the antibody of the invention neutralizes the activity of the human IFN-ω with an $IC_{50}$ value of at least about $1 \times 10^{-10}$ M or less, and at least 10 human IFN-α subtypes with an $IC_{50}$ value of about $2 \times 10^{-10}$ M or less, about $1.5 \times 10^{-10}$ M or less, or about $1 \times 10^{-10}$ M or less, when the $IC_{50}$ value is measured using the "ISRE reporter gene assay" described herein.

In some embodiments described herein, and in some embodiments of each and every one of the numbered embodiments listed below, the antibody of the invention neutralizes the activity of the human IFN-ω with an $IC_{50}$ value of at least about $1 \times 10^{-10}$ M or less, and at least 6 human IFN-α subtypes with an $IC_{50}$ value of about $1 \times 10^{-10}$ M or less, when the $IC_{50}$ value is measured using the "ISRE reporter gene assay" described herein.

In some embodiments described herein, and in some embodiments of each and every one of the numbered embodiments listed below, the antibody of the invention neutralizes the activity of the human IFN-ω with an $IC_{50}$ value of at least about $1 \times 10^{-10}$ M or less, and at least 10 human IFN-α subtypes with an $IC_{50}$ value of about $1 \times 10^{-10}$ M or less, when the $IC_{50}$ value is measured using the "ISRE reporter gene assay" described herein.

In some embodiments described herein, and in some embodiments of each and every one of the numbered embodiments listed below, the antibodies of the invention inhibit leukocyte interferon-induced IP-10 release in whole blood induced by 250 U/ml of interferon by about 50% or more in the presence of 10 μg/ml antibody than in the absence of the antibody.

In some embodiments described herein, and in some embodiments of each and every one of the numbered embodiments listed below, the antibodies of the invention inhibit systemic lupus erythematosus (SLE) immune complex-induced IP-10 release in whole blood by about 50% or more in the presence of 10 μg/ml antibody than in the absence of the antibody.

Antibodies of the invention described herein, and in some embodiments of each and every one of the numbered embodiments listed below, can be tested for their neutralizing ability by assessing their ability to inhibit IFN-induced cytokine release, such as IP-10 release from IFN-induced peripheral blood mononuclear cells (PBMCs) or whole blood. For example, PBMCs are isolated from heparinized whole blood from healthy volunteers using standard protocols, treated with a preformed complex of IFN and antibody to be tested, and IP-10 release is measured using standard methods such as Milliplex cytokine/chemokine kit (Millipore, Premixed 39 plex). Antibodies of the invention may inhibit IP-10 release by at least 30%, 40%, 50%, 60%, 70%, 75%, 80%, 85%, 90%, 95%, 96%, 97%, 98%, 99% or 100% when compared to IFN-induced IP-10 release in the absence of the antibody.

In some embodiments described herein, and in some embodiments of each and every one of the numbered embodiments listed below, the antibodies of the invention bind human IFN-ω with a dissociation constant ($K_D$) of about $1 \times 10^{-10}$ M or less, about $5 \times 10^{-11}$ M or less, about $1 \times 10^{-11}$ M or less or about $5 \times 10^{-12}$ M or less.

In some embodiments described herein, and in some embodiments of each and every one of the numbered embodiments listed below, the antibody of the invention binds IFN-ω and at least three, four, five, six, seven, eight, nine, ten or eleven human interferon alpha (IFN-α) subtypes selected from the group consisting of IFN-αA, IFN-αB2, IFN-αC, IFN-αF, IFN-αG, IFN-αH2, IFN-αI, IFN-αJ1, IFN-αK, IFN-αWA and IFN-α4a with a $K_D$ of about $5 \times 10^{-10}$ M or less, about $1 \times 10^{-10}$ M or less, about $5 \times 10^{-11}$ M or less, about $1 \times 10^{-11}$ M or less, or about $5 \times 10^{-12}$ M or less.

The affinity of an antibody to IFN-ω or to various IFN-α subtypes may be determined experimentally using any suitable method. Such methods may utilize ProteOn XPR36, Biacore 3000 or KinExA instrumentation, ELISA or competitive binding assays known to those skilled in the art. The measured affinity of a particular antibody/IFN-ω or antibody/IFN-α subtypes interaction may vary if measured under different conditions (e.g., osmolarity, pH). Thus, measurements of affinity and other binding parameters (e.g., $K_D$, $K_{on}$, $K_{off}$) are preferably made with standardized conditions and a standardized buffer, such as the buffer described herein. Skilled in the art will appreciate that the internal error for affinity measurements for example using Biacore 3000 or ProteOn (measured as standard deviation, SD) can typically be within 5-33% for measurements within the typical limits of detection. Therefore the term "about" reflects the typical standard deviation in the assay. For example, the typical SD for a $K_D$ of $1 \times 10^{-9}$ M is up to $\pm 0.33 \times 10^{-9}$ M.

The antibodies binding human IFN-ω and IFN-α subtypes with a desired affinity and neutralization profile may be selected from libraries of variants or fragments by panning with human IFN-ω and/or IFN-α subtypes and optionally by further antibody affinity maturation. In an exemplary panning campaign, phage libraries may be panned sequentially or using a mixture of chimpanzee IFN-ω and human IFN-α subtypes IFN-α2, IFN-αI, IFN-αH2, IFN-αG and IFN-αF. Alternatively, antibodies of the invention may be generated by immunizing mice with chimpanzee and cynomolgus IFN-ω, human IFN-α subtypes IFN-αD, IFN-αJ1, IFN-αC, IFN-αB2, IFN-αH2, IFN-αA, IFN-α4a, IFN-αG, IFN-αF, IFN-αWA and IFN-αI, and screening the hybriomas for binding to IFN-ω and various IFN-α subtypes, and subsequently assessing the neutralization ability of the antibodies using methods described herein.

In some embodiments described herein, and in some embodiments of each and every one of the numbered embodiments listed below, the antibody of the invention comprises heavy chain complementarity determining region (HCDR) 1 (HCDR1), 2 (HCDR2) and 3 (HCDR3) amino acid sequences of SEQ ID NOs: 109, 114 and 121, respectfully, and light chain complementarity determining region (LCDR) 1 (LCDR1), 2 (LCDR2) and 3 (LCDR3) amino acid sequences of SEQ ID NOs: 118, 119 and 120.

Exemplary such antibodies are antibodies IFWM3308, IFWM3307, IFWM3410, IFWM3322, IFWM3385, IFWM3416, IFWM3310, IFWM3400, IFWM3321, IFWM3522, IFWM3524, IFWM3320, IFWM3304, IFWM3520, IFWM3399, IFWM3314, IFWM3331, IFWM3405, IFWM3442, IFWM3525, IFWM3423, IFWM3444 and IFWM3421. These antibodies neutralize human IFN-ω and at least three IFN-α subtypes with an $IC_{50}$ value of about $1\times10^{-10}$ M or less, and comprise a consensus LCDR1 (SEQ ID NO: 118), LCDR2 (SEQ ID NO: 119), LCDR3 (SEQ ID NO: 120), HCDR2 (SEQ ID NO: 114) and HCDR3 (SEQ ID NO: 121) amino acid sequences and a constant HCDR1 (SEQ ID NO: 109) amino acid sequence. Antibodies having substitutions at least at VH residue position 103 of SEQ ID NOs: 28, 31, 157 or 158, VL residue positions 30, 31, 32, 50, 91-94 or 96 of SEQ ID NOs: 35, 39, 40, 42, 46, 52, 53, 54, 71, 73, 75 or 135, and VL residues positions 30, 31, 32, 50, 51, 92-95 or 97 of SEQ ID NOs: 57, 61, 62, 68 and 150 resulted in antibodies having improved potency when compared to the parental IFWM371 antibody.

SEQ ID NO: 118
$QSIX_1X_2X_3X_4$; wherein
$X_1$ is G, D, A, R, E, S, or N;
$X_2$ is D, G, N, S, R, E or K;
$X_3$ is F, A, N, T, S or V;
$X_4$ is Y, N or deleted.
SEQ ID NO: 119
$X_5AS$; wherein
$X_5$ is F, W or G.
SEQ ID NO: 120
$QQX_6X_7X_8X_9PX_{10}T$; wherein
$X_6$ is A, G, S or W;
$X_7$ is L, Y, H, W, F or I;
$X_8$ is D or S;
$X_9$ is F, T, L, N or W; and
$X_{10}$ is L, F or I.
SEQ ID NO: 114
$IX_{11}X_{12}SDSDT$; wherein
$X_{11}$ is D or A; and
$X_{12}$ is P or A.
SEQ ID NO: 121
$ARHPGLX_{13}WAPDFDY$; wherein
$X_{13}$ is A or N.
SEQ ID NO: 109
GYSFTSYW In some embodiments described herein, and in some embodiments of each and every one of the numbered embodiments listed below, the antibody of the invention comprises the HCDR1, the HCDR2, theHCDR3, the LCDR1, the LCDR2 and the LCDR3 amino acid sequences of SEQ ID NOs: 109, 114, 121, 159, 119 and 160, respectively.

Exemplary such antibodies are antibodies IFWM3400, IFWM3321, IFWM3522, IFWM3524, IFWM3320, IFWM3304, IFWM3520, IFWM3399, IFWM3314, IFWM3331, IFWM3405, IFWM3442, IFWM3525, IFWM3423, IFWM3444 and IFWM3421. These antibodies neutralize human IFN-ω and at least six IFN-α subtypes with an $IC_{50}$ value of about $1\times10^{-10}$ M or less, and comprise a consensus LCDR1 (SEQ ID NO: 159), LCDR2 (SEQ ID NO: 119), LCDR3 (SEQ ID NO: 160), HCDR2 (SEQ ID NO: 114) and HCDR3 (SEQ ID NO: 121) amino acid sequences and a constant HCDR1 (SEQ ID NO: 109) amino acid sequence.

SEQ ID NO: 159
$QSIX_{14}X_{15}X_{16}X_{17}$; wherein
$X_{14}$ is G, D, A, E, S, or N;
$X_{15}$ is D, G, N, S or R;
$X_{16}$ is F, A, N, S or V; and
$X_{17}$ is Y, N or deleted.
SEQ ID NO: 160
$QQX_{18}X_{19}X_{20}X_{21}PX_{22}T$; wherein
$X_{18}$ is A, G or S;
$X_{19}$ is Y, H, W or F;
$X_{20}$ is D or S;
$X_{21}$ is F, T, L or W; and
$X_{22}$ is L, F or I.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 114, 121, 161, 119 and 162, respectively.

Exemplary such antibodies are antibodies IFWM3405, IFWM3442, IFWM3525, IFWM3423, IFWM3444 and IFWM3421. These antibodies neutralize human IFN-ω and at least ten IFN-α subtypes with an $IC_{50}$ value of at least about $2\times10^{-10}$ M or less, about $1.5\times10^{-10}$ M or less, or about $1\times10^{-10}$ M or less, and comprise a consensus LCDR1 (SEQ ID NO: 161), LCDR2 (SEQ ID NO: 119), LCDR3 (SEQ ID NO: 162), HCDR2 (SEQ ID NO: 114) and HCDR3 (SEQ ID NO: 121) sequences and a constant HCDR1 (SEQ ID NO: 109) sequence.

SEQ ID NO: 161
$QSIX_{23}X_{24}X_{25}X_{26}$; wherein
$X_{23}$ is A or D;
$X_{24}$ is N or G;
$X_{25}$ is F, N or S; and
$X_{26}$ is Y, N or deleted.
SEQ ID NO: 162
$QQX_{27}X_{28}X_{29}X_{30}PX_{31}T$; wherein
$X_{27}$ is G or S;
$X_{28}$ is Y;
$X_{29}$ is D;
$X_{30}$ is F, T or L; and
$X_{31}$ is L, F or I.

In some embodiments described herein, and in some embodiments of each and every one of the numbered embodiments listed below, the antibody of the invention neutralizes human IFN-ω and at least ten human IFN-α subtypes selected from the group consisting of IFN-αA, IFN-αB2, IFN-αC, IFN-αF, IFN-αG, IFN-αH2, IFN-αI, IFN-αJ1, IFN-αK, IFN-αWA and IFN-α4a.

In some embodiments of the invention described herein, and in some embodiments of each and every one of the numbered embodiments listed below, the antibody neutralizes human IFN-ω and at least the human IFN-α subtypes IFN-αA, IFN-αB2, IFN-αC, IFN-αF, IFN-αG, IFN-αH2, IFN-αJ1 and IFN-α4a.

In some embodiments of the invention described herein, and in some embodiments of each and every one of the numbered embodiments listed below, the antibody does not bind or neutralize IFN-αD or IFN-α1.

In some embodiments of the invention described herein, and in some embodiments of each and every one of the numbered embodiments listed below, the antibody does not bind or neutralize IFN-β.

In some embodiments described herein, and in some embodiments of each and every one of the numbered embodiments listed below, the antibody of the invention comprises
  the HCDR1 amino acid sequence of SEQ ID NO: 109;
  the HCDR2 amino acid sequence of SEQ ID NOs: 111, 112 or 113;
  the HCDR3 amino acid sequence of SEQ ID NOs: 115 or 116;
  the LCDR1 amino acid sequence of SEQ ID NOs: 76, 77, 78, 79, 80, 81, 82, 83, 84, 85, 86, 87, 88, 89, 90 or 91;
  the LCDR2 amino acid sequence of SEQ ID NOs: 93, 94 or 95; and
  the LCDR3 amino acid sequence of SEQ ID NOs: 96, 97, 98, 99, 100, 101, 102, 103, 104, 105, 106 or 107.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs:
  a) 109, 113, 116, 77, 93 and 104, respectively;
  b) 109, 113, 116, 85, 93 and 96, respectively;
  c) 109, 113, 115, 79, 95 and 107, respectively;
  d) 109, 113, 116, 76, 93 and 103, respectively;
  e) 109, 113, 115, 85, 93 and 96, respectively;
  f) 109, 113, 115, 89, 95 and 100, respectively;
  g) 109, 113, 116, 86, 93 and 105, respectively;
  h) 109, 113, 115, 76, 93 and 103, respectively;
  i) 109, 113, 116, 80, 93 and 97, respectively;
  j) 109, 113, 116, 84, 93 and 97, respectively;
  k) 109, 113, 116, 90, 93 and 97, respectively;
  l) 109, 113, 116, 88, 93 and 102, respectively;
  m) 109, 113, 116, 87, 93 and 105, respectively;
  n) 109, 113, 116, 91, 93 and 106, respectively;
  o) 109, 113, 115, 80, 93 and 97, respectively;
  p) 109, 113, 116, 83, 93 and 101, respectively;
  q) 109, 113, 116, 82, 94 and 98, respectively;
  r) 109, 113, 115, 78, 95 and 100, respectively;
  s) 109, 111, 116, 81, 93 and 106, respectively;
  t) 109, 113, 116, 82, 94 and 99, respectively;
  u) 109, 113, 115, 81, 93 and 106, respectively;
  v) 109, 112, 116, 81, 93 and 106, respectively; or
  w) 109, 113, 116, 81, 93 and 106, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 77, 93 and 104, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 85, 93 and 96, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 115, 79, 95 and 107, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 76, 93 and 103, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 115, 85, 93 and 96, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 115, 89, 95 and 100, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 86, 93 and 105, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 115, 76, 93 and 103, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 80, 93 and 97, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 84, 93 and 97, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 90, 93 and 97, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 88, 93 and 102, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 87, 93 and 105, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 91, 93 and 106, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 115, 80, 93 and 97, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 83, 93 and 101, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 82, 94 and 98, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 115, 78, 95 and 100, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 111, 116, 81, 93 and 106, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 82, 94 and 99, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 115, 81, 93 and 106, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 112, 116, 81, 93 and 106, respectively.

In some embodiments described herein, and in some embodiments of each and every one of the numbered embodiments listed below, the antibody of the invention comprises the HCDR1, the HCDR2, the HCDR3, the LCDR1, the LCDR2 and the LCDR3 amino acid sequences of SEQ ID NOs: 109, 113, 116, 81, 93 and 106, respectively.

In some embodiments described herein, and in some embodiments of each and every one of the numbered embodiments listed below, the antibody comprises the VH and the VL wherein the VH comprises the amino acid sequence of SEQ ID NOs: 28, 31, 157 or 158.

In some embodiments described herein, and in some embodiments of each and every one of the numbered embodiments listed below, the antibody comprises the VH and the VL, wherein the VL comprises the amino acid sequence of SEQ ID NOs: 35, 39, 40, 42, 46, 52, 53, 54, 57, 61, 62, 68, 71, 73, 75, 135 or 150.

In some embodiments described herein, and in some embodiments of each and every one of the numbered embodiments listed below, the antibody comprises the VH of SEQ ID NOs: 28, 31, 157 or 158, and the VL of SEQ ID NOs: 35, 39, 40, 42, 46, 52, 53, 54, 57, 61, 62, 68, 71, 73, 75, 135 or 150.

In some embodiments described herein, and in some embodiments of each and every one of the numbered embodiments listed below, the antibody of the invention comprises the VH and the VL of SEQ ID NOs: 28 and 40, 28 and 39, 31 and 62, 28 and 54, 31 and 39, 31 and 68, 28 and 42, 31 and 54, 28 and 53, 28 and 73, 28 and 75, 28 and 52, 28 and 35, 28 and 135, 31 and 53, 28 and 46, 28 and 61, 31 and 57, 157 and 71, 28 and 150, 31 and 71, 158 and 71, or 28 and 71.

In some embodiments described herein, and in some embodiments of each and every one of the numbered embodiments listed below, the antibody comprises the VH and the VL, wherein the VH comprises the amino acid sequence of SEQ ID NOs: 28, 30, 31, 157 or 158.

In some embodiments described herein, and in some embodiments of each and every one of the numbered embodiments listed below, the antibody comprises the HCDR1, HCDR2 and HCDR3 amino acid sequences of the VH of SEQ ID NOs: 28, 30, 31, 157 or 158, and the LCDR1, LCDR2 and LCDR3 amino acid sequences of the VL of SEQ ID NOs: 29, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 73, 74, 75, 123, 124, 125, 126, 127, 128, 129, 130, 131, 132, 133, 134, 135, 136, 137, 138, 139, 140, 141, 142, 143, 144, 145, 146, 147, 74, 148, 149, 150, 151, 152 or 153, wherein the CDRs are defined according to Kabat, Chothia and/or IMGT.

In some embodiments described herein, and in some embodiments of each and every one of the numbered embodiments listed below, the antibody comprises the VH and the VL, wherein the VL comprises the amino acid sequence of SEQ ID NOs: 29, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 73, 74, 75, 123, 124, 125, 126, 127, 128, 129, 130, 131, 132, 133, 134, 135, 136, 137, 138, 139, 140, 141, 142, 143, 144, 145, 146, 147, 74, 148, 149, 150, 151, 152 or 153.

In some embodiments described herein, and in some embodiments of each and every one of the numbered embodiments listed below, the antibody comprises the VH and the VL, wherein the VH comprises the amino acid sequence of SEQ ID NOs: 28, 30, 31, 157 or 158, and the VL comprises the amino acid sequence of SEQ ID NOs: 29, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 73, 74, 75, 123, 124, 125, 126, 127, 128, 129, 130, 131, 132, 133, 134, 135, 136, 137, 138, 139, 140, 141, 142, 143, 144, 145, 146, 147, 74, 148, 149, 150, 151, 152 or 153.

In some embodiments described herein, and in some embodiments of each and every one of the numbered embodiments listed below, the antibody of the invention comprises the VH of SEQ ID NO: 28 and the VL of SEQ ID NO: 29.

In some embodiments described herein, and in some embodiments of each and every one of the numbered embodiments listed below, the antibody of the invention comprises the VH of SEQ ID NO: 28 and the VL of SEQ ID NO: 32.

In some embodiments described herein, and in some embodiments of each and every one of the numbered embodiments listed below, the antibody of the invention comprises the VH of SEQ ID NO: 28 and the VL of SEQ ID NO: 33.

In some embodiment described herein, and in some embodiments of each and every one of the numbered embodiments listed below s, the antibody of the invention comprises the VH of SEQ ID NO: 28 and the VL of SEQ ID NO: 34.

In some embodiments described herein, and in some embodiments of each and every one of the numbered embodiments listed below, the antibody of the invention comprises the VH of SEQ ID NO: 28 and the VL of SEQ ID NO: 35.

In some embodiments described herein, and in some embodiments of each and every one of the numbered embodiments listed below, the antibody of the invention comprises the VH of SEQ ID NO: 28 and the VL of SEQ ID NO: 36.

In some embodiments described herein, and in some embodiments of each and every one of the numbered embodiments listed below, the antibody of the invention comprises the VH of SEQ ID NO: 28 and the VL of SEQ ID NO: 37.

In some embodiments described herein, and in some embodiments of each and every one of the numbered embodiments listed below, the antibody of the invention comprises the VH of SEQ ID NO: 28 and the VL of SEQ ID NO: 38.

In some embodiments described herein, and in some embodiments of each and every one of the numbered embodiments listed below, the antibody of the invention comprises the VH of SEQ ID NO: 28 and the VL of SEQ ID NO: 39.

In some embodiments described herein, and in some embodiments of each and every one of the numbered embodiments listed below, the antibody of the invention comprises the VH of SEQ ID NO: 28 and the VL of SEQ ID NO: 40.

In some embodiments described herein, and in some embodiments of each and every one of the numbered embodiments listed below, the antibody of the invention comprises the VH of SEQ ID NO: 28 and the VL of SEQ ID NO: 41.

In some embodiments described herein, and in some embodiments of each and every one of the numbered embodiments listed below, the antibody of the invention comprises the VH of SEQ ID NO: 28 and the VL of SEQ ID NO: 42.

In some embodiments described herein, and in some embodiments of each and every one of the numbered embodiments listed below, the antibody of the invention comprises the VH of SEQ ID NO: 28 and the VL of SEQ ID NO: 43.

In some embodiments described herein, and in some embodiments of each and every one of the numbered embodiments listed below, the antibody of the invention comprises the VH of SEQ ID NO: 28 and the VL of SEQ ID NO: 44.

In some embodiments described herein, and in some embodiments of each and every one of the numbered embodiments listed below, the antibody of the invention comprises the VH of SEQ ID NO: 28 and the VL of SEQ ID NO: 45.

In some embodiments described herein, and in some embodiments of each and every one of the numbered embodiments listed below, the antibody of the invention comprises the VH of SEQ ID NO: 28 and the VL of SEQ ID NO: 46.

In some embodiments described herein, and in some embodiments of each and every one of the numbered embodiments listed below, the antibody of the invention comprises the VH of SEQ ID NO: 28 and the VL of SEQ ID NO: 47.

In some embodiments described herein, and in some embodiments of each and every one of the numbered embodiments listed below, the antibody of the invention comprises the VH of SEQ ID NO: 28 and the VL of SEQ ID NO: 48.

In some embodiments described herein, and in some embodiments of each and every one of the numbered embodiments listed below, the antibody of the invention comprises the VH of SEQ ID NO: 28 and the VL of SEQ ID NO: 49.

In some embodiments described herein, and in some embodiments of each and every one of the numbered embodiments listed below, the antibody of the invention comprises the VH of SEQ ID NO: 28 and the VL of SEQ ID NO: 50.

In some embodiments described herein, and in some embodiments of each and every one of the numbered embodiments listed below, the antibody of the invention comprises the VH of SEQ ID NO: 28 and the VL of SEQ ID NO: 51.

In some embodiments described herein, and in some embodiments of each and every one of the numbered embodiments listed below, the antibody of the invention comprises the VH of SEQ ID NO: 28 and the VL of SEQ ID NO: 52.

In some embodiments described herein, and in some embodiments of each and every one of the numbered embodiments listed below, the antibody of the invention comprises the VH of SEQ ID NO: 28 and the VL of SEQ ID NO: 53.

In some embodiments described herein, and in some embodiments of each and every one of the numbered embodiments listed below, the antibody of the invention comprises the VH of SEQ ID NO: 28 and the VL of SEQ ID NO: 54.

In some embodiments described herein, and in some embodiments of each and every one of the numbered embodiments listed below, the antibody of the invention comprises the VH of SEQ ID NO: 28 and the VL of SEQ ID NO: 55.

In some embodiments described herein, and in some embodiments of each and every one of the numbered embodiments listed below, the antibody of the invention comprises the VH of SEQ ID NO: 28 and the VL of SEQ ID NO: 56.

In some embodiments described herein, and in some embodiments of each and every one of the numbered embodiments listed below, the antibody of the invention comprises the VH of SEQ ID NO: 28 and the VL of SEQ ID NO: 57.

In some embodiments described herein, and in some embodiments of each and every one of the numbered embodiments listed below, the antibody of the invention comprises the VH of SEQ ID NO: 28 and the VL of SEQ ID NO: 58.

In some embodiments described herein, and in some embodiments of each and every one of the numbered embodiments listed below, the antibody of the invention comprises the VH of SEQ ID NO: 28 and the VL of SEQ ID NO: 59.

In some embodiments described herein, and in some embodiments of each and every one of the numbered embodiments listed below, the antibody of the invention comprises the VH of SEQ ID NO: 28 and the VL of SEQ ID NO: 60.

In some embodiments described herein, and in some embodiments of each and every one of the numbered embodiments listed below, the antibody of the invention comprises the VH of SEQ ID NO: 28 and the VL of SEQ ID NO: 61.

In some embodiments described herein, and in some embodiments of each and every one of the numbered embodiments listed below, the antibody of the invention comprises the VH of SEQ ID NO: 28 and the VL of SEQ ID NO: 62.

In some embodiments described herein, and in some embodiments of each and every one of the numbered embodiments listed below, the antibody of the invention comprises the VH of SEQ ID NO: 28 and the VL of SEQ ID NO: 63.

In some embodiments described herein, and in some embodiments of each and every one of the numbered embodiments listed below, the antibody of the invention comprises the VH of SEQ ID NO: 28 and the VL of SEQ ID NO: 64.

In some embodiments described herein, and in some embodiments of each and every one of the numbered embodiments listed below, the antibody of the invention comprises the VH of SEQ ID NO: 28 and the VL of SEQ ID NO: 65.

In some embodiments described herein, and in some embodiments of each and every one of the numbered embodiments listed below, the antibody of the invention comprises the VH of SEQ ID NO: 28 and the VL of SEQ ID NO: 66.

In some embodiments described herein, and in some embodiments of each and every one of the numbered embodiments listed below, the antibody of the invention comprises the VH of SEQ ID NO: 28 and the VL of SEQ ID NO: 67.

In some embodiments described herein, and in some embodiments of each and every one of the numbered embodiments listed below, the antibody of the invention comprises the VH of SEQ ID NO: 28 and the VL of SEQ ID NO: 68.

In some embodiments described herein, and in some embodiments of each and every one of the numbered embodiments listed below, the antibody of the invention comprises the VH of SEQ ID NO: 28 and the VL of SEQ ID NO: 69.

In some embodiments described herein, and in some embodiments of each and every one of the numbered embodiments listed below, the antibody of the invention comprises the VH of SEQ ID NO: 30 and the VL of SEQ ID NO: 32.

In some embodiments described herein, and in some embodiments of each and every one of the numbered embodiments listed below, the antibody of the invention comprises the VH of SEQ ID NO: 30 and the VL of SEQ ID NO: 33.

In some embodiments described herein, and in some embodiments of each and every one of the numbered embodiments listed below, the antibody of the invention comprises the VH of SEQ ID NO: 30 and the VL of SEQ ID NO: 34.

In some embodiments described herein, and in some embodiments of each and every one of the numbered embodiments listed below, the antibody of the invention comprises the VH of SEQ ID NO: 30 and the VL of SEQ ID NO: 35.

In some embodiments described herein, and in some embodiments of each and every one of the numbered embodiments listed below, the antibody of the invention comprises the VH of SEQ ID NO: 30 and the VL of SEQ ID NO: 36.

In some embodiments described herein, and in some embodiments of each and every one of the numbered embodiments listed below, the antibody of the invention comprises the VH of SEQ ID NO: 30 and the VL of SEQ ID NO: 37.

In some embodiments described herein, and in some embodiments of each and every one of the numbered embodiments listed below, the antibody of the invention comprises the VH of SEQ ID NO: 30 and the VL of SEQ ID NO: 38.

In some embodiments described herein, and in some embodiments of each and every one of the numbered embodiments listed below, the antibody of the invention comprises the VH of SEQ ID NO: 30 and the VL of SEQ ID NO: 39.

In some embodiments described herein, and in some embodiments of each and every one of the numbered embodiments listed below, the antibody of the invention comprises the VH of SEQ ID NO: 30 and the VL of SEQ ID NO: 40.

In some embodiments described herein, and in some embodiments of each and every one of the numbered embodiments listed below, the antibody of the invention comprises the VH of SEQ ID NO: 30 and the VL of SEQ ID NO: 41.

In some embodiments described herein, and in some embodiments of each and every one of the numbered embodiments listed below, the antibody of the invention comprises the VH of SEQ ID NO: 30 and the VL of SEQ ID NO: 42.

In some embodiments described herein, and in some embodiments of each and every one of the numbered embodiments listed below, the antibody of the invention comprises the VH of SEQ ID NO: 30 and the VL of SEQ ID NO: 43.

In some embodiments described herein, and in some embodiments of each and every one of the numbered embodiments listed below, the antibody of the invention comprises the VH of SEQ ID NO: 30 and the VL of SEQ ID NO: 44.

In some embodiments described herein, and in some embodiments of each and every one of the numbered embodiments listed below, the antibody of the invention comprises the VH of SEQ ID NO: 30 and the VL of SEQ ID NO: 45.

In some embodiments described herein, and in some embodiments of each and every one of the numbered embodiments listed below, the antibody of the invention comprises the VH of SEQ ID NO: 30 and the VL of SEQ ID NO: 46.

In some embodiments described herein, and in some embodiments of each and every one of the numbered embodiments listed below, the antibody of the invention comprises the VH of SEQ ID NO: 30 and the VL of SEQ ID NO: 47.

In some embodiments described herein, and in some embodiments of each and every one of the numbered embodiments listed below, the antibody of the invention comprises the VH of SEQ ID NO: 30 and the VL of SEQ ID NO: 48.

In some embodiments described herein, and in some embodiments of each and every one of the numbered embodiments listed below, the antibody of the invention comprises the VH of SEQ ID NO: 30 and the VL of SEQ ID NO: 49.

In some embodiments described herein, and in some embodiments of each and every one of the numbered embodiments listed below, the antibody of the invention comprises the VH of SEQ ID NO: 30 and the VL of SEQ ID NO: 50.

In some embodiments described herein, and in some embodiments of each and every one of the numbered embodiments listed below, the antibody of the invention comprises the VH of SEQ ID NO: 30 and the VL of SEQ ID NO: 51.

In some embodiments described herein, and in some embodiments of each and every one of the numbered embodiments listed below, the antibody of the invention comprises the VH of SEQ ID NO: 30 and the VL of SEQ ID NO: 52.

In some embodiments described herein, and in some embodiments of each and every one of the numbered embodiments listed below, the antibody of the invention comprises the VH of SEQ ID NO: 30 and the VL of SEQ ID NO: 53.

In some embodiments described herein, and in some embodiments of each and every one of the numbered embodiments listed below, the antibody of the invention comprises the VH of SEQ ID NO: 30 and the VL of SEQ ID NO: 54.

In some embodiments described herein, and in some embodiments of each and every one of the numbered embodiments listed below, the antibody of the invention comprises the VH of SEQ ID NO: 30 and the VL of SEQ ID NO: 56.

In some embodiments described herein, and in some embodiments of each and every one of the numbered embodiments listed below, the antibody of the invention comprises the VH of SEQ ID NO: 30 and the VL of SEQ ID NO: 57.

In some embodiments described herein, and in some embodiments of each and every one of the numbered embodiments listed below, the antibody of the invention comprises the VH of SEQ ID NO: 30 and the VL of SEQ ID NO: 58.

In some embodiments described herein, and in some embodiments of each and every one of the numbered embodiments listed below, the antibody of the invention comprises the VH of SEQ ID NO: 30 and the VL of SEQ ID NO: 59.

In some embodiments described herein, and in some embodiments of each and every one of the numbered embodiments listed below, the antibody of the invention comprises the VH of SEQ ID NO: 30 and the VL of SEQ ID NO: 60.

In some embodiments described herein, and in some embodiments of each and every one of the numbered embodiments listed below, the antibody of the invention comprises the VH of SEQ ID NO: 30 and the VL of SEQ ID NO: 61.

In some embodiments described herein, and in some embodiments of each and every one of the numbered embodiments listed below, the antibody of the invention comprises the VH of SEQ ID NO: 30 and the VL of SEQ ID NO: 62.

In some embodiments described herein, and in some embodiments of each and every one of the numbered embodiments listed below, the antibody of the invention comprises the VH of SEQ ID NO: 30 and the VL of SEQ ID NO: 63.

In some embodiments described herein, and in some embodiments of each and every one of the numbered embodiments listed below, the antibody of the invention comprises the VH of SEQ ID NO: 30 and the VL of SEQ ID NO: 64.

In some embodiments described herein, and in some embodiments of each and every one of the numbered embodiments listed below, the antibody of the invention comprises the VH of SEQ ID NO: 30 and the VL of SEQ ID NO: 65.

In some embodiments described herein, and in some embodiments of each and every one of the numbered embodiments listed below, the antibody of the invention comprises the VH of SEQ ID NO: 30 and the VL of SEQ ID NO: 66.

In some embodiments described herein, and in some embodiments of each and every one of the numbered embodiments listed below, the antibody of the invention comprises the VH of SEQ ID NO: 30 and the VL of SEQ ID NO: 67.

In some embodiments described herein, and in some embodiments of each and every one of the numbered embodiments listed below, the antibody of the invention comprises the VH of SEQ ID NO: 30 and the VL of SEQ ID NO: 68.

In some embodiments described herein, and in some embodiments of each and every one of the numbered embodiments listed below, the antibody of the invention comprises the VH of SEQ ID NO: 30 and the VL of SEQ ID NO: 69.

In some embodiments described herein, and in some embodiments of each and every one of the numbered embodiments listed below, the antibody of the invention comprises the VH of SEQ ID NO: 31 and the VL of SEQ ID NO: 32.

In some embodiments described herein, and in some embodiments of each and every one of the numbered embodiments listed below, the antibody of the invention comprises the VH of SEQ ID NO: 31 and the VL of SEQ ID NO: 33.

In some embodiments described herein, and in some embodiments of each and every one of the numbered embodiments listed below, the antibody of the invention comprises the VH of SEQ ID NO: 31 and the VL of SEQ ID NO: 34.

In some embodiments described herein, and in some embodiments of each and every one of the numbered embodiments listed below, the antibody of the invention comprises the VH of SEQ ID NO: 31 and the VL of SEQ ID NO: 35.

In some embodiments described herein, and in some embodiments of each and every one of the numbered embodiments listed below, the antibody of the invention comprises the VH of SEQ ID NO: 31 and the VL of SEQ ID NO: 36.

In some embodiments described herein, and in some embodiments of each and every one of the numbered embodiments listed below, the antibody of the invention comprises the VH of SEQ ID NO: 31 and the VL of SEQ ID NO: 37.

In some embodiments described herein, and in some embodiments of each and every one of the numbered embodiments listed below, the antibody of the invention comprises the VH of SEQ ID NO: 31 and the VL of SEQ ID NO: 38.

In some embodiments described herein, and in some embodiments of each and every one of the numbered embodiments listed below, the antibody of the invention comprises the VH of SEQ ID NO: 31 and the VL of SEQ ID NO: 39.

In some embodiments described herein, and in some embodiments of each and every one of the numbered embodiments listed below, the antibody of the invention comprises the VH of SEQ ID NO: 31 and the VL of SEQ ID NO: 40.

In some embodiments described herein, and in some embodiments of each and every one of the numbered embodiments listed below, the antibody of the invention comprises the VH of SEQ ID NO: 31 and the VL of SEQ ID NO: 41.

In some embodiments described herein, and in some embodiments of each and every one of the numbered embodiments listed below, the antibody of the invention comprises the VH of SEQ ID NO: 31 and the VL of SEQ ID NO: 42.

In some embodiments described herein, and in some embodiments of each and every one of the numbered embodiments listed below, the antibody of the invention comprises the VH of SEQ ID NO: 31 and the VL of SEQ ID NO: 43.

In some embodiments described herein, and in some embodiments of each and every one of the numbered embodiments listed below, the antibody of the invention comprises the VH of SEQ ID NO: 31 and the VL of SEQ ID NO: 44.

In some embodiments described herein, and in some embodiments of each and every one of the numbered embodiments listed below, the antibody of the invention comprises the VH of SEQ ID NO: 31 and the VL of SEQ ID NO: 45.

In some embodiments described herein, and in some embodiments of each and every one of the numbered embodiments listed below, the antibody of the invention comprises the VH of SEQ ID NO: 31 and the VL of SEQ ID NO: 46.

In some embodiments described herein, and in some embodiments of each and every one of the numbered embodiments listed below, the antibody of the invention comprises the VH of SEQ ID NO: 31 and the VL of SEQ ID NO: 47.

In some embodiments described herein, and in some embodiments of each and every one of the numbered embodiments listed below, the antibody of the invention comprises the VH of SEQ ID NO: 31 and the VL of SEQ ID NO: 48.

In some embodiments described herein, and in some embodiments of each and every one of the numbered embodiments listed below, the antibody of the invention comprises the VH of SEQ ID NO: 31 and the VL of SEQ ID NO: 49.

In some embodiments described herein, and in some embodiments of each and every one of the numbered embodiments listed below, the antibody of the invention comprises the VH of SEQ ID NO: 31 and the VL of SEQ ID NO: 50.

In some embodiments described herein, and in some embodiments of each and every one of the numbered embodiments listed below, the antibody of the invention comprises the VH of SEQ ID NO: 31 and the VL of SEQ ID NO: 51.

In some embodiments described herein, and in some embodiments of each and every one of the numbered embodiments listed below, the antibody of the invention comprises the VH of SEQ ID NO: 31 and the VL of SEQ ID NO: 52.

In some embodiments described herein, and in some embodiments of each and every one of the numbered embodiments listed below, the antibody of the invention comprises the VH of SEQ ID NO: 31 and the VL of SEQ ID NO: 53.

In some embodiments described herein, and in some embodiments of each and every one of the numbered embodiments listed below, the antibody of the invention comprises the VH of SEQ ID NO: 31 and the VL of SEQ ID NO: 54.

In some embodiments described herein, and in some embodiments of each and every one of the numbered embodiments listed below, the antibody of the invention comprises the VH of SEQ ID NO: 31 and the VL of SEQ ID NO: 56.

In some embodiments described herein, and in some embodiments of each and every one of the numbered embodiments listed below, the antibody of the invention comprises the VH of SEQ ID NO: 31 and the VL of SEQ ID NO: 57.

In some embodiments described herein, and in some embodiments of each and every one of the numbered embodiments listed below, the antibody of the invention comprises the VH of SEQ ID NO: 31 and the VL of SEQ ID NO: 58.

In some embodiments described herein, and in some embodiments of each and every one of the numbered embodiments listed below, the antibody of the invention comprises the VH of SEQ ID NO: 31 and the VL of SEQ ID NO: 59.

In some embodiments described herein, and in some embodiments of each and every one of the numbered embodiments listed below, the antibody of the invention comprises the VH of SEQ ID NO: 31 and the VL of SEQ ID NO: 60.

In some embodiments described herein, and in some embodiments of each and every one of the numbered embodiments listed below, the antibody of the invention comprises the VH of SEQ ID NO: 31 and the VL of SEQ ID NO: 61.

In some embodiments described herein, and in some embodiments of each and every one of the numbered embodiments listed below, the antibody of the invention comprises the VH of SEQ ID NO: 31 and the VL of SEQ ID NO: 62.

In some embodiments described herein, and in some embodiments of each and every one of the numbered embodiments listed below, the antibody of the invention comprises the VH of SEQ ID NO: 31 and the VL of SEQ ID NO: 63.

In some embodiments described herein, and in some embodiments of each and every one of the numbered embodiments listed below, the antibody of the invention comprises the VH of SEQ ID NO: 31 and the VL of SEQ ID NO: 65.

In some embodiments described herein, and in some embodiments of each and every one of the numbered embodiments listed below, the antibody of the invention comprises the VH of SEQ ID NO: 31 and the VL of SEQ ID NO: 66.

In some embodiments described herein, and in some embodiments of each and every one of the numbered embodiments listed below, the antibody of the invention comprises the VH of SEQ ID NO: 31 and the VL of SEQ ID NO: 67.

In some embodiments described herein, and in some embodiments of each and every one of the numbered embodiments listed below, the antibody of the invention comprises the VH of SEQ ID NO: 31 and the VL of SEQ ID NO: 68.

In some embodiments described herein, and in some embodiments of each and every one of the numbered embodiments listed below, the antibody of the invention comprises the VH of SEQ ID NO: 31 and the VL of SEQ ID NO: 69.

In some embodiments described herein, and in some embodiments of each and every one of the numbered embodiments listed below, the antibody of the invention comprises the VH of SEQ ID NO: 28 and the VL of SEQ ID NO: 70.

In some embodiments described herein, and in some embodiments of each and every one of the numbered embodiments listed below, the antibody of the invention comprises the VH of SEQ ID NO: 31 and the VL of SEQ ID NO: 70.

In some embodiments described herein, and in some embodiments of each and every one of the numbered embodiments listed below, the antibody of the invention comprises the VH of SEQ ID NO: 30 and the VL of SEQ ID NO: 70.

In some embodiments described herein, and in some embodiments of each and every one of the numbered embodiments listed below, the antibody of the invention comprises the VH of SEQ ID NO: 28 and the VL of SEQ ID NO: 71.

In some embodiments described herein, and in some embodiments of each and every one of the numbered embodiments listed below, the antibody of the invention comprises the VH of SEQ ID NO: 31 and the VL of SEQ ID NO: 71.

In some embodiments described herein, and in some embodiments of each and every one of the numbered embodiments listed below, the antibody of the invention comprises the VH of SEQ ID NO: 28 and the VL of SEQ ID NO: 123.

In some embodiments described herein, and in some embodiments of each and every one of the numbered embodiments listed below, the antibody of the invention comprises the VH of SEQ ID NO: 28 and the VL of SEQ ID NO: 124.

In some embodiments described herein, and in some embodiments of each and every one of the numbered embodiments listed below, the antibody of the invention comprises the VH of SEQ ID NO: 28 and the VL of SEQ ID NO: 125.

In some embodiments described herein, and in some embodiments of each and every one of the numbered embodiments listed below, the antibody of the invention comprises the VH of SEQ ID NO: 28 and the VL of SEQ ID NO: 126.

In some embodiments described herein, and in some embodiments of each and every one of the numbered embodiments listed below, the antibody of the invention comprises the VH of SEQ ID NO: 28 and the VL of SEQ ID NO: 127.

In some embodiments described herein, and in some embodiments of each and every one of the numbered embodiments listed below, the antibody of the invention comprises the VH of SEQ ID NO: 28 and the VL of SEQ ID NO: 128.

In some embodiments described herein, and in some embodiments of each and every one of the numbered embodiments listed below, the antibody of the invention comprises the VH of SEQ ID NO: 28 and the VL of SEQ ID NO: 129.

In some embodiments described herein, and in some embodiments of each and every one of the numbered embodiments listed below, the antibody of the invention comprises the VH of SEQ ID NO: 28 and the VL of SEQ ID NO: 130.

In some embodiments described herein, and in some embodiments of each and every one of the numbered embodiments listed below, the antibody of the invention comprises the VH of SEQ ID NO: 28 and the VL of SEQ ID NO: 131.

In some embodiments described herein, and in some embodiments of each and every one of the numbered embodiments listed below, the antibody of the invention comprises the VH of SEQ ID NO: 28 and the VL of SEQ ID NO: 132.

In some embodiments described herein, and in some embodiments of each and every one of the numbered embodiments listed below, the antibody of the invention comprises the VH of SEQ ID NO: 28 and the VL of SEQ ID NO: 133.

In some embodiments described herein, and in some embodiments of each and every one of the numbered embodiments listed below, the antibody of the invention comprises the VH of SEQ ID NO: 28 and the VL of SEQ ID NO: 134.

In some embodiments described herein, and in some embodiments of each and every one of the numbered embodiments listed below, the antibody of the invention comprises the VH of SEQ ID NO: 28 and the VL of SEQ ID NO: 135.

In some embodiments described herein, and in some embodiments of each and every one of the numbered embodiments listed below, the antibody of the invention comprises the VH of SEQ ID NO: 28 and the VL of SEQ ID NO: 136.

In some embodiments described herein, and in some embodiments of each and every one of the numbered embodiments listed below, the antibody of the invention comprises the VH of SEQ ID NO: 28 and the VL of SEQ ID NO: 137.

In some embodiments described herein, and in some embodiments of each and every one of the numbered embodiments listed below, the antibody of the invention comprises the VH of SEQ ID NO: 28 and the VL of SEQ ID NO: 138.

In some embodiments described herein, and in some embodiments of each and every one of the numbered embodiments listed below, the antibody of the invention comprises the VH of SEQ ID NO: 28 and the VL of SEQ ID NO: 139.

In some embodiments described herein, and in some embodiments of each and every one of the numbered embodiments listed below, the antibody of the invention comprises the VH of SEQ ID NO: 28 and the VL of SEQ ID NO: 140.

In some embodiments described herein, and in some embodiments of each and every one of the numbered embodiments listed below, the antibody of the invention comprises the VH of SEQ ID NO: 28 and the VL of SEQ ID NO: 141.

In some embodiments described herein, and in some embodiments of each and every one of the numbered embodiments listed below, the antibody of the invention comprises the VH of SEQ ID NO: 28 and the VL of SEQ ID NO: 73.

In some embodiments described herein, and in some embodiments of each and every one of the numbered embodiments listed below, the antibody of the invention comprises the VH of SEQ ID NO: 28 and the VL of SEQ ID NO: 142.

In some embodiments described herein, and in some embodiments of each and every one of the numbered embodiments listed below, the antibody of the invention comprises the VH of SEQ ID NO: 28 and the VL of SEQ ID NO: 143.

In some embodiments described herein, and in some embodiments of each and every one of the numbered embodiments listed below, the antibody of the invention comprises the VH of SEQ ID NO: 28 and the VL of SEQ ID NO: 74.

In some embodiments described herein, and in some embodiments of each and every one of the numbered embodiments listed below, the antibody of the invention comprises the VH of SEQ ID NO: 28 and the VL of SEQ ID NO: 75.

In some embodiments described herein, and in some embodiments of each and every one of the numbered embodiments listed below, the antibody of the invention comprises the VH of SEQ ID NO: 28 and the VL of SEQ ID NO: 144.

In some embodiments described herein, and in some embodiments of each and every one of the numbered embodiments listed below, the antibody of the invention comprises the VH of SEQ ID NO: 28 and the VL of SEQ ID NO: 145.

In some embodiments described herein, and in some embodiments of each and every one of the numbered embodiments listed below, the antibody of the invention comprises the VH of SEQ ID NO: 28 and the VL of SEQ ID NO: 146.

In some embodiments described herein, and in some embodiments of each and every one of the numbered embodiments listed below, the antibody of the invention comprises the VH of SEQ ID NO: 28 and the VL of SEQ ID NO: 147.

In some embodiments described herein, and in some embodiments of each and every one of the numbered embodiments listed below, the antibody of the invention comprises the VH of SEQ ID NO: 28 and the VL of SEQ ID NO: 148.

In some embodiments described herein, and in some embodiments of each and every one of the numbered embodiments listed below, the antibody of the invention comprises the VH of SEQ ID NO: 28 and the VL of SEQ ID NO: 149.

In some embodiments described herein, and in some embodiments of each and every one of the numbered embodiments listed below, the antibody of the invention comprises the VH of SEQ ID NO: 28 and the VL of SEQ ID NO: 150.

In some embodiments described herein, and in some embodiments of each and every one of the numbered embodiments listed below, the antibody of the invention comprises the VH of SEQ ID NO: 28 and the VL of SEQ ID NO: 151.

In some embodiments described herein, and in some embodiments of each and every one of the numbered embodiments listed below, the antibody of the invention comprises the VH of SEQ ID NO: 28 and the VL of SEQ ID NO: 152.

In some embodiments described herein, and in some embodiments of each and every one of the numbered embodiments listed below, the antibody of the invention comprises the VH of SEQ ID NO: 28 and the VL of SEQ ID NO: 153.

In some embodiments described herein, and in some embodiments of each and every one of the numbered embodiments listed below, the antibody of the invention comprises the VH of SEQ ID NO: 157 and the VL of SEQ ID NO: 71.

In some embodiments described herein, and in some embodiments of each and every one of the numbered embodiments listed below, the antibody of the invention comprises the VH of SEQ ID NO: 158 and the VL of SEQ ID NO: 71.

Variants of the anti-IFN-ω/α antibodies of the invention comprising VH or VL amino acid sequences shown in Table 9, Table 13, Table 15, Table 17, Table 19 and Table 21 are within the scope of the invention. For example, variants may comprise 1, 2, 3, 4, 5, 6, 7, 8, 9, 10, or 11 amino acid substitutions in the VH and/or VL that do not adversely affect the antibody properties. In some embodiments, the sequence identity may be about 90%, 91%, 92%, 93%, 94%, 95%, 96%, 97%, 98% or 99% to a VH or the VL amino acid sequence of the invention. Percent identity can be determined for example by pairwise alignment using the default settings of the AlignX module of Vector NTI v.9.0.0 (Invitrogen, Carslbad, Calif.). Exemplary modifications are for example conservative amino acid substitutions in the antigen-binding site or in the framework without adversely altering the properties of the antibody. Conservative substitutions may also be made to improve antibody properties, for example stability or affinity. Conservative substitutions are those that take place within a family of amino acids that are related in their side chains. Genetically encoded amino acids can be divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5)amide (asparagine, glutamine); and (6) sulfur-containing (cysteine and methionine) (Stryer (ed.), Biochemistry, 2nd ed, WH Freeman and Co., 1981). Furthermore, any native residue in the polypeptide may also be substituted with alanine, as has been previously described for alanine scanning mutagenesis (MacLennan et al (1998) *Acta Physiol. Scand. Suppl.* 643:55-67; Sasaki et al (1998) *Adv. Biophys.* 35:1-24). Desired amino acid substitutions may be determined by those skilled in the art at the time such substitutions are desired. The resulting antibody variants may be tested for their characteristics using assays described herein.

In some embodiments described herein, and in some embodiments of each and every one of the numbered embodiments listed below, the anti-IFN-α/ω antibody of the invention comprises a heavy chain variable region (VH) amino acid sequence at least 90%, 91%, 92%, 93%, 94%, 95%, 96%, 97%, 98% or 99% identical to SEQ ID NO: 28 and a light chain variable region (VL) amino acid sequences at least 90%, 91%, 92%, 93%, 94%, 95%, 96%, 97%, 98% or 99% identical to SEQ ID NO: 71.

In some embodiments described herein, and in some embodiments of each and every one of the numbered embodiments listed below, the anti-IFN-α/ω antibody of the invention comprises a heavy chain variable region (VH) amino acid sequence at least 90%, 91%, 92%, 93%, 94%, 95%, 96%, 97%, 98% or 99% identical to SEQ ID NO: 28 and a light chain variable region (VL) amino acid sequences at least 90%, 91%, 92%, 93%, 94%, 95%, 96%, 97%, 98% or 99% identical to SEQ ID NO: 150.

In some embodiments described herein, and in some embodiments of each and every one of the numbered embodiments listed below, the anti-IFN-α/ω antibody of the invention comprises a heavy chain variable region (VH) amino acid sequence at least 95% identical to SEQ ID NO: 28 and a light chain variable region (VL) amino acid sequences at least 95% identical to SEQ ID NO: 71.

In some embodiments described herein, and in some embodiments of each and every one of the numbered embodiments listed below, the anti-IFN-α/ω antibody of the invention comprises a heavy chain variable region (VH) amino acid sequence at least 95% identical to SEQ ID NO: 28 and a light chain variable region (VL) amino acid sequences at least 95% identical to SEQ ID NO: 150.

In some embodiments described herein, and in some embodiments of each and every one of the numbered embodiments listed below, the anti-IFN-α/ω antibody of the invention comprises a heavy chain variable region (VH) amino acid sequence at least 97% identical to SEQ ID NO: 28 and a light chain variable region (VL) amino acid sequences at least 97% identical to SEQ ID NO: 71.

In some embodiments described herein, and in some embodiments of each and every one of the numbered embodiments listed below, the anti-IFN-α/ω antibody of the invention comprises a heavy chain variable region (VH) amino acid sequence at least 97% identical to SEQ ID NO: 28 and a light chain variable region (VL) amino acid sequences at least 97% identical to SEQ ID NO: 150.

Amino acid substitutions may be done for example by PCR mutagenesis (U.S. Pat. No. 4,683,195). Alternatively, libraries of variants may be generated using known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties.

Although the embodiments illustrated in the Examples comprise pairs of variable regions, one from a heavy chain and one from a light chain, a skilled artisan will recognize that alternative embodiments may comprise single heavy or light chain variable regions. The single variable region can be used to screen for variable domains capable of forming a two-domain specific antigen-binding fragment capable of, for example, binding to human IFN-ω or various human IFN-α subtypes. The screening may be accomplished by phage display screening methods using for example hierarchical dual combinatorial approach disclosed in Int. Pat. Publ. No. WO92/01047. In this approach, an individual colony containing either a H or L chain clone is used to infect a complete library of clones encoding the other chain (L or H), and the resulting two-chain specific antigen-binding domain is selected in accordance with phage display techniques as described. Therefore, the individual VH and VL polypeptide chains are useful in identifying additional antibodies specifically binding to human IFN-ω or various IFN-α subtypes using the methods disclosed in Int. Pat. Publ. No. WO92/01047.

Antibodies of the invention may be made using a variety of technologies for generating antibodies. For example, the hybridoma method of Kohler and Milstein, *Nature* 256:495, 1975 may be used to generate monoclonal antibodies. In the hybridoma method, a mouse or other host animal, such as a hamster, rat or monkey, is immunized with human IFN-ω and/or various IFN-α subtypes or fragments of these proteins, followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding, cross-reactivity or lack thereof, and affinity for the antigen.

Various host animals may be used to produce the IFN-α/ω antibodies of the invention. For example, Balb/c mice may be used to generate mouse anti-human IFN-α/ω antibodies. The antibodies made in Balb/c mice and other non-human animals may be humanized using various technologies to generate more human-like sequences. Exemplary humanization techniques including selection of human acceptor frameworks are known to skilled in the art and include CDR grafting (U.S. Pat. No. 5,225,539), SDR grafting (U.S. Pat. No. 6,818,749), Resurfacing (Padlan, Mol Immunol 28:489-499, 1991), Specificity Determining Residues Resurfacing (U.S. Pat. Publ. No. 20100261620), human-adaptation (or human framework adaptation) (U.S. Pat. Publ. No. US2009/0118127), Superhumanization (U.S. Pat. No. 7,709,226) and guided selection (Osbourn et al (2005) *Methods* 36:61-68, 2005; U.S. Pat. No. 5,565,332).

Humanized antibodies may be further optimized to improve their selectivity or affinity to a desired antigen by incorporating altered framework support residues to preserve binding affinity (backmutations) by techniques such as those disclosed as described in Int. Pat. Publ. No. WO90/007861 and in Int. Pat. Publ. No. WO92/22653.

Transgenic mice carrying human immunoglobulin (Ig) loci in their genome may be used to generate human antibodies against a target protein, and are described in for example Int. Pat. Publ. No. WO90/04036, U.S. Pat. No. 6,150,584, Int. Pat. Publ. No. WO99/45962, Int. Pat. Publ. No. WO02/066630, Int. Pat. Publ. No. WO02/43478, Lonberg et al (1994) *Nature* 368:856-9; Green et al (1994)

*Nature Genet.* 7:13-21; Green & Jakobovits (1998) *Exp. Med.* 188:483-95; Lonberg and Huszar (1995) *Int. Rev. Immunol.* 13:65-93; Bruggemann et al (1991) *Eur. J. Immunol.* 21:1323-1326; Fishwild et al (1996) *Nat. Biotechnol.* 14:845-851; Mendez et al (1997) *Nat. Genet.* 15:146-156; Green (1999) *J. Immunol. Methods* 231:11-23; Yang et al (1999) *Cancer Res.* 59:1236-1243; Bruggemann and Taussig (1997) *Curr. Opin. Biotechnol.* 8:455-458; Int. Pat. Publ. No. WO02/043478). The endogenous immunoglobulin loci in such mice may be disrupted or deleted, and at least one complete or partial human immunoglobulin locus may be inserted into the mouse genome using homologous or non-homologous recombination, using transchromosomes, or using minigenes. Companies such as Regeneron (http://_www_regeneron_com), Harbour Antibodies (http://_www_harbourantibodies_com), Open Monoclonal Technology, Inc. (OMT) (http://_www_omtinc_net), KyMab (http://_www_kymab_com), Trianni (http://_www-.trianni_com) and Ablexis (http://_www_ablexis_com) can be engaged to provide human antibodies directed against a selected antigen using technology as described above.

Human antibodies may be selected from a phage display library, where the phage is engineered to express human immunoglobulins or portions thereof such as Fabs, single chain antibodies (scFv), or unpaired or paired antibody variable regions (Knappik et al (2000) *J. Mol. Biol.* 296:57-86; Krebs et al (2001) *J. Immunol. Meth.* 254:67-84; Vaughan et al (1996) *Nature Biotechnology* 14:309-314; Sheets et al (1998) *PITAS (USA)* 95:6157-6162; Hoogenboom and Winter, (1991) *J. Mol. Biol.* 227:381; Marks et al (1991) *J. Mol. Biol.* 222:581). The antibodies of the invention may be isolated for example from phage display library expressing antibody heavy and light chain variable regions as fusion proteins with bacteriophage pIX coat protein as described in Shi et al (2010) *J. Mol. Biol.* 397:385-96 and Int. Pat. Publ. No. WO09/085462). The libraries may be screened for phage binding to human IFN-ω and IFN-α and the obtained positive clones may be further characterized, the Fabs isolated from the clone lysates, and expressed as full length IgGs. Such phage display methods for isolating human antibodies are described in for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Preparation of immunogenic antigens and monoclonal antibody production may be performed using any suitable technique, such as recombinant protein production. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

In an exemplary method, phage display libraries may be panned against biotinylated human IFN-α2 or biotinylated human IFN-αG. After three rounds of panning, a polyclonal phage ELISA using human IFN-α2, IFN-αG and IFN-ω as antigens may be performed to detect the specific enrichment of individual panning experiments. The phage demonstrating enrichment for binders to IFN-α2, IFN-αG and IFN-ω may be collected and further screened in a standard ELISA assay for binding to additional IFN-α subtypes in Fab format. The identified Fab clones may be cloned to full length antibodies and characterized further for their affinity and neutralization ability of human IFN-ω and various IFN-α subtypes using ProteOn and ISRE reporter gene assay as described herein.

The antibodies of the invention may be human or humanized.

In some embodiments described herein, and in some embodiments of each and every one of the numbered embodiments listed below, the IFN-α/ω antibodies of the invention comprise a VH framework derived from human germline gene IGHV5-51 (SEQ ID NO: 155).

In some embodiments described herein, and in some embodiments of each and every one of the numbered embodiments listed below, the IFN-α/ω antibodies of the invention comprise a VL framework derived from human germline gene IGKV1D-39 (SEQ ID NO: 156).

The antibodies of the invention described herein, and in some embodiments of each and every one of the numbered embodiments listed below, may be of IgA, IgD, IgE, IgG or IgM type. The antibodies of the invention may be of IgG1, IgG2, IgG3, IgG4 type.

Immune effector properties of the antibodies of the invention may be enhanced or silenced through Fc modifications by techniques known to those skilled in the art. For example, Fc effector functions such as C1q binding, complement dependent cytotoxicity (CDC), antibody-dependent cell-mediated cytotoxicity (ADCC), phagocytosis, down regulation of cell surface receptors (e.g., B cell receptor; BCR), etc. can be provided and/or controlled by modifying residues in the Fc responsible for these activities. Pharmacokinetic properties of the antibodies of the invention may be enhanced by mutating residues in the Fc domain that extend antibody half-life (Strohl (2009) Curr Opin Biotechnol 20:685-91). Exemplary Fc modifications are IgG4 S228P/L234A/L235A, IgG2 M252Y/S254T/T256E (Dall'Acqua et al (2006) *J. Biol. Chem.* 281:23514-24; or IgG2 V234A/G237A/P238S, V234A/G237A/H268Q, H268AN309L/A330S/P331 or V234A/G237A/P238S/H268AN309L/A330S/P331S on IgG2 (Intl. Pat. Publ. No. WO11/066501), of those described in US. Pat. No. 6,737,056 (residue numbering according to the EU numbering).

Additionally, antibodies of the invention described herein, and in some embodiments of each and every one of the numbered embodiments listed below, may be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention may be conjugated to polyethylene glycol (PEGylated) to improve their pharmacokinetic profiles. Conjugation may be carried out by techniques known to those skilled in the art. Conjugation of therapeutic antibodies with PEG has been shown to enhance pharmacodynamics while not interfering with function (Knigh et al (2004) *Platelets* 15:409-18; Leong et al (2001) *Cytokine* 16:106-19; Yang et al (2003) *Protein Eng.* 16:761-70).

Antibodies or fragments thereof of the invention modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn et al (2001) *J. Mol. Biol.* 305:989-1010). Potential structure destabilizing residues may be identified based upon the crystal structure of the antibody or by molecular modeling in certain cases, and the effect of the residues on antibody stability can be tested by generating and evaluating variants harboring mutations in the identified residues. One of the ways to increase antibody stability is to raise the thermal transition midpoint ($T_m$) as measured by differential scanning calorimetry (DSC). In general, the protein $T_m$ is correlated with its stability and inversely correlated with its susceptibility to unfolding and denaturation in solution and the degradation processes that depend on the tendency of the protein to unfold (Remmele et al (2000) *Biopharm* 13:36-46,). A number of studies have found correlation between the ranking of the physical stability of formulations measured as thermal stability by DSC and physical stability measured by other methods (Gupta et al (2003) *AAPS PharmSci* 5E8; Zhang et al (2004) *J. Pharm. Sci.* 93:3076-89; Maa et al (1996) *Int. J. Pharm.* 140:155-68; Bedu-Addo et al (2004) *Pharm. Res.* 21:1353-61; Remmele et al (1997) *Pharm. Res.* 15:200-8). Formulation studies suggest that a Fab $T_m$ has implication for long-term physical stability of a corresponding mAb. Differences in amino acids in either framework or within the CDRs could have significant effects on the thermal stability of the Fab domain (Yasui et al (1994) *FEBS Lett.* 353:143-6).

In some embodiments described herein, and in some embodiments of each and every one of the numbered embodiments listed below, the antibody of the invention competes with binding to the human IFN-ω with an isolated antibody comprising the VH of SEQ ID NO: 28 and the VL of SEQ ID NO: 71.

In some embodiments described herein, and in some embodiments of each and every one of the numbered embodiments listed below, the antibody of the invention competes with binding to the human IFN-ω with an isolated antibody comprising the VH of SEQ ID NO: 28 and the VL of SEQ ID NO: 150.

Competition between specific binding to human IFN-ω with antibodies of the invention comprising certain VH and VL sequences may be assayed in vitro using well known methods. For example, binding of MSD Sulfo-Tag™ NHS-ester-labeled antibody to human to human IFN-ω in the presence of an unlabeled antibody can be assessed by ELISA, or Biacore analyses or flow cytometry may be used to demonstrate competition with the antibodies of the current invention.

In some embodiments described herein, and in some embodiments of each and every one of the numbered embodiments listed below, the antibody of the invention binds to and neutralizes a biological activity of a human interferon omega (IFN-ω) and at least three, four, five, six, seven, eight, nine, ten or eleven human interferon alpha (IFN-α) subtypes, wherein the antibody binds IFN-ω of SEQ ID NO: 1 at least at residues F27, L30 and R33 of.

The residues F27, L30 and R33 IFN-ω define a minimal epitope required for broad neutralizing activity of the IFN-α/ω antibodies of the invention. Crystal structure of several antibody/IFN-α or antibody/IFN-ω complexes revealed the three residues provide predominant contributions to antibody binding. The F27 residue is conserved in all human IFN-αs except IFN-αD (α1), to which antibodies of the invention do not bind. Both L30 and R33 are conserved in all human IFN-αs as well as in human IFN-ω. Further confirmation of the contribution of F27 to the epitope is evident from the binding studies with various cyno IFN-α subtypes: the antibodies of the invention do not bind cyno IFN-α13, which, like human IFN-αD, has a serine at position 27 (S27).

In another embodiment described herein, and in some embodiments of each and every one of the numbered embodiments listed below, the antibody of the invention binds human IFN-ω of SEQ ID NO: 1 at least at residues S25, P26, F27, L28, L30, K31, R33, R34 and D35.

In some embodiments described herein, and in some embodiments of each and every one of the numbered embodiments listed below, the antibody of the invention binds to and neutralizes a biological activity of a human interferon omega (IFN-ω) and at least three, four, five, six, seven, eight, nine, ten or eleven human interferon alpha (IFN-α) subtypes, wherein the antibody binds human IFN-ω of SEQ ID NO: 1 at one or more residues including F27.

In some embodiments described herein, and in some embodiments of each and every one of the numbered embodiments listed below, the antibody of the invention is a bispecific antibody that binds to and neutralizes a biological activity of a human interferon omega (IFN-ω) and at least three, four, five, six, seven, eight, nine, ten or eleven human interferon alpha (IFN-α) subtypes and binds BLyS, CD40L, IL-6, CD27, BDCA2, IL-12, IL-23, IFN-αD, IL-17, CD20, IL-10, CD22, IL-21, ICOS, ICOSL or IFN-γ.

Given the presence of elevated IFN-ω in SLE patients, and the demonstration that IFN-ω can induce BLyS secretion in PBMCs in vitro, combined blockade of IFN-α/ω in SLE patients may be more effective at reducing BLyS levels in comparison to anti IFN-α specific approaches. The extent of IFN-signature and IFN activity in SLE patients appears to correlate with soluble BLyS levels.

The IFN-α/ω antibodies of the invention described herein, and in some embodiments of each and every one of the numbered embodiments listed below, may be engineered into bispecific antibodies which are also encompassed within the scope of the invention. The VL and/or the VH regions of the antibodies of the invention may be engineered using published methods into single chain bispecific antibodies as structures such as TandAb® designs (Int. Pat. Publ. No. WO99/57150; U.S. Pat. Publ. No. US2011/0206672) or into bispecific scFVs as structures such as those disclosed in U.S. Pat. No. 5,869,620; Int. Pat. Publ. No. WO95/15388, Int. Pat. Publ. No. WO97/14719 or Int. Pat. Publ. No WO11/036460.

The VL and/or the VH regions of the antibodies of the invention may be engineered into bispecific full length antibodies, where each antibody arm binds a distinct antigen or epitope. Such bispecific antibodies are typically made by modulating the CH3 interactions between the two antibody heavy chains to form bispecific antibodies using technologies such as those described in U.S. Pat. No. 7,695,936; Int. Pat. Publ. No. WO04/111233; U.S. Pat. Publ. No. 2010/0015133; U.S. Pat. Publ. No. 2007/0287170; Int. Pat. Publ. No. WO2008/119353; U.S. Pat. Publ. No. 2009/0182127; U.S. Pat. Publ. No. 2010/0286374; U.S. Pat. Publ. No. 2011/0123532; Int. Pat. Publ. No. WO2011/131746; Int. Pat. Publ. No. WO2011/143545; or U.S. Pat. Publ. No. 2012/0149876.

For example, bispecific antibodies of the invention may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody (e.g., anti-IFN-α/ω antibody of the invention) and the second monospecific bivalent antibody (e.g., anti-BLyS, anti-CD40L, anti-IL-6, anti-CD27, anti-BDCA2, anti-IL-12, anti-IL-23, anti-IFN-αD, anti-IL-17, anti-CD20, anti-IL-10, anti-CD22, anti-IL-21, anti-ICOS, anti-ICOSL or anti-IFN-γ antibody.) are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl) phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Exemplary CH3 mutations that may be used in a first heavy chain and in a second heavy chain of the bispecific antibody are K409R and/or F405L. Additional bispecific structures into which the VL and/or the VH regions of the antibodies of the invention may be incorporated are for example Dual Variable Domain Immunoglobulins (DVD) (Int. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441). DVDs are full length antibodies comprising the heavy chain having a structure VH1-linker-VH2-CH and the light chain having the structure VL1-linker-VL2-CL; linker being optional.

The VH and the VL binding BLyS, CD40L, IL-6, CD27, BDCA2, IL-12, IL-23, IFN-αD, IL-17, CD20, IL-10, CD22, IL-21, ICOS, ICOSL or IFN-γ to be incorporated into bispecific anti-IFN-α/ω antibodies may be generated de novo using methods described herein, or may be engineered from existing monospecific antibodies. Exemplary anti-BLyS antibody that may be used to generate the bispecific antibodies of the invention is BENLYSTA®. Exemplary CD40L antibodies that may be used are those described in U.S. Pat. Nos. 5,474,771, 5,747,037, Int. Pat. Publ. No. WO01/68860, Int. Pat. Publ. No. WO06/033702 or Int. Pat. Publ. No. WO08/118356. Exemplary anti-IL-6 antibodies that may be used are those described in Int. Pat. Publ. No. WO06/119115, Int. Pat. Publ. No. WO10/056948, Int. Pat. Publ. No. WO10/088444 or Int. Pat. Publ. No. WO07/076927. Exemplary anti-CD27 antibodies that may be used are those described in Int. Pat. Publ. No. WO13/138586, Int. Pat. Publ. No. WO11/130434 or Int. Pat. Publ. No. WO12/004367. Exemplary IL-12 and IL-23 antibody that may be used are STELARA® Exemplary IL-23 antibodies that may be used are those described in Int. Pat. Publ. No. WO07/005955, Int. Pat. Publ. No. WO07/027714, Int. Pat. Publ. No. WO08/103432,Int. Pat. Publ. No. WO07/106769, Int. Pat. Publ. No. WO07/147019 or Int. Pat. Publ. No. WO08/134659. Exemplary IL-17 antibodies that may be used are those described in Int. Pat. Publ. No. WO06/013107, Int. Pat. Publ. No. WO06/054059 Int. Pat. Publ. No. WO07/070750, Int. Pat. Publ. No. WO08/134659, Int. Pat. Publ. No. WO07/149032, Int. Pat. Publ. No. WO08/021156, Int. Pat. Publ. No. WO08/047134, Int. Pat. Publ. No. WO09/130459, Int. Pat. Publ. No. WO10/025400, Int. Pat. Publ. No. WO11/053763 and Int. Pat. Publ. No. WO12/095662.

Another embodiment of the invention described herein, and in some embodiments of each and every one of the numbered embodiments listed below, is an antibody that binds to and neutralizes a biological activity of a human interferon omega (IFN-ω) and at least three, four, five, six, seven, eight, nine, ten or eleven human interferon alpha (IFN-α) subtypes having certain VH and VL sequences, wherein the antibody VH is encoded by a first polynucleotide and the antibody VL is encoded by a second synthetic polynucleotide. The polynucleotide may be a complementary deoxynucleic acid (cDNA), and may be codon optimized for expression in suitable host. Codon optimization is a well-known technology.

In some embodiments described herein, and in some embodiments of each and every one of the numbered embodiments listed below, the polynucleotides encoding the antibody VH or VL of the invention comprise the sequences of SEQ ID NOs: 72, 92, 108, 110, 117 or 122.

Another embodiment of the invention is an isolated polynucleotide encoding any of the antibody heavy chain variable regions and/or the antibody light chain variable regions of the invention. Certain exemplary polynucleotides are disclosed herein, however, other polynucleotides which, given the degeneracy of the genetic code or codon preferences in a given expression system, encode the antibodies of the invention are also within the scope of the invention. Exemplary polynucleotides are for example polynucleotides having the sequences shown in SEQ ID NOs: 72, 92, 108, 110, 117 or 122. The polynucleotide sequences encoding a VH or a VL or a fragment thereof of the antibody of the invention may be operably linked to one or more regulatory elements, such as a promoter or enhancer, that allow expression of the nucleotide sequence in the intended host cell. The polynucleotide may be a cDNA.

Another embodiment of the invention is a vector comprising the polynucleotide of the invention. Such vectors may be plasmid vectors, viral vectors, vectors for baculovirus expression, transposon based vectors or any other vector suitable for introduction of the synthetic polynucleotide of the invention into a given organism or genetic background by any means. For example, polynucleotides encoding light and/or heavy chain variable regions of the antibodies of the invention, optionally linked to constant regions, are inserted into expression vectors. The light and/or heavy chains may be cloned in the same or different expression vectors. The DNA segments encoding immunoglobulin chains may be operably linked to control sequences in the expression vector(s) that ensure the expression of immunoglobulin polypeptides. Such control sequences include signal sequences, promoters (e.g. naturally associated or heterologous promoters), enhancer elements, and transcription termination sequences, and are chosen to be compatible with the host cell chosen to express the antibody. Once the vector has been incorporated into the appropriate host, the host is maintained under conditions suitable for high level expression of the proteins encoded by the incorporated polynucleotides.

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed with the desired DNA sequences.

Suitable promoter and enhancer elements are known in the art. For expression in a bacterial cell, exemplary promoters include lacI, lacZ, T3, T7, gpt, lambda P and trc. For expression in a eukaryotic cell, exemplary promoters include light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. For expression in a yeast cell, an exemplary promoter is constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PH05 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Another embodiment of the invention is a host cell comprising one or more vectors of the invention. The term "host cell" refers to a cell into which a vector has been introduced. It is understood that the term host cell is intended to refer not only to the particular subject cell but to the progeny of such a cell, and also to a stable cell line generated from the particular subject cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic cells, plant cells or archeal cells.

*Escherichia coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces* (e.g., *S. cerevisiae*) and *Pichia* are examples of suitable yeast host cells Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NSO(European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

Another embodiment of the invention is a method of producing an antibody of the invention comprising culturing the host cell of the invention in conditions that the antibody is expressed, and recovering the antibody produced by the host cell. Methods of making antibodies and purifying them are well known in the art. Once synthesized (either chemically or recombinantly), the whole antibodies, their dimers, individual light and/or heavy chains, or other antibody fragments such as VH and/or VL, may be purified according to standard procedures, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody may be substantially pure, e.g., at least about 80% to 85% pure, at least about 85% to 90% pure, at least about 90% to 95% pure, or at least about 98% to 99%, or more, pure, e.g., free from contaminants such as cell debris, macromolecules, etc. other than the subject antibody.

Another embodiment of the invention is a method for producing an antibody that binds to and neutralizes a biological activity of a human interferon omega (IFN-ω) and at least three, four, five, six, seven, eight, nine, ten or eleven human interferon alpha (IFN-α) comprising:

incorporating the first polynucleotide encoding the VH of the antibody and the second polynucleotide encoding the VL of the antibody into an expression vector;

transforming a host cell with the expression vector;

culturing the host cell in culture medium under conditions wherein the VL and the VH are expressed and form the antibody; and recovering the antibody from the host cell or culture medium.

The polynucleotides encoding certain VH or VL sequences of the invention are incorporated into vectors using standard molecular biology methods. Host cell transformation, culture, antibody expression and purification are done using well known methods.

Methods of Treatment

IFN-α/ω antibodies of the invention may be utilized to treat immune-mediated inflammatory diseases or autoimmune diseases such as lupus, including systemic lupus erythematosus (SLE) or cutaneous lupus erythematosus (CLE), or other immune-mediated inflammatory diseases such as psoriasis, immune thrombocytopenia (ITP), Aicardi-Goutieres syndrome (AGS), systemic sclerosis, Sjögren's syndrome, myositis, common variable immune deficiency (CVID), autoimmune thyroid disease, type I diabetes, rheumatoid arthritis, transplant rejection or graft versus host disease (GVHD). These diseases may be associated with increased production of IFN-α and/or IFN-ω or type I IFN signature.

One embodiment of the invention is a method of treating an immune-mediated inflammatory disease or an autoimmune disease, comprising administering a therapeutically effective amount of an isolated antibody that binds to and neutralizes a biological activity of a human interferon omega (IFN-ω) and at least three, four, five, six, seven, eight, nine, ten or eleven human interferon alpha (IFN-α) subtypes to a patient in need thereof for a time sufficient to treat the immune-mediated inflammatory disease or autoimmune disease.

Another embodiment of the invention is a method of treating lupus, comprising administering a therapeutically effective amount of an isolated antibody that binds to and neutralizes a biological activity of a human interferon omega (IFN-ω) and at least three, four, five, six, seven, eight, nine, ten or eleven human interferon alpha (IFN-α) subtypes to a patient in need thereof for a time sufficient to treat lupus.

In some embodiments, lupus is systemic lupus erythematosus (SLE) or cutaneous lupus erythematosus (CLE).

In some embodiments, the patient has lupus nephritis.

In some embodiments, the immune-mediated inflammatory disease or the autoimmune disease is psoriasis, immune thrombocytopenia (ITP), Aicardi-Goutieres syndrome (AGS), systemic sclerosis, Sjögren's syndrome, myositis, common variable immune deficiency (CVID), autoimmune thyroid disease, type I diabetes, rheumatoid arthritis, transplant rejection or graft versus host disease (GVHD).

Another embodiment of the invention is a method of treating a chronic viral infection, comprising administering a therapeutically effective amount of an isolated antibody that binds to and neutralizes a biological activity of a human interferon omega (IFN-ω) and at least three, four, five, six, seven, eight, nine, ten or eleven human interferon alpha (IFN-α) subtypes to a patient in need thereof for a time sufficient to treat the chronic viral infection.

IFN-I is well known to have a protective role in acute viral infection. Recently, IFN-I has been demonstrated to have an immunosuppressive role in chronic viral infections through a mechanism at least partially mediated by IL-10 and programmed cell death 1 ligand 1 (PDL1) (Teijaro et al., Science 340, 207-211, (2013); Wilson et al., Science 340, 202-207, 2013). Combined blockade of multiple IFN-α subtypes and IFN-ω may offer beneficial effects in patients with chronic viral infections including HIV and hepatitis C by down-modulating an immunosuppressive environment conducive to viral persistence.

In some embodiments, the chronic viral infection is HIV or hepatitis C.

"Treatment" or "treat" refers to therapeutic treatment. Patients that may be treated also include those prone to or susceptible to have the disorder, of those in which the disorder is to be prevented. Individuals in need of treatment include those already with the disorder or a symptom of the disorder. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

Exemplary antibodies that may be used in the methods of the invention comprise VH, VL, HCDR and/or LCDR regions as shown in tables 9, 13, 15, 17, 19, 21, 22, 23, 24, 25, 26 or 27, and antibodies IFWM3308, IFWM3307, IFWM3410, IFWM3322, IFWM3385, IFWM3416, IFWM3310, IFWM3400, IFWM3321, IFWM3522, IFWM3524, IFWM3320, IFWM3304, IFWM3520, IFWM3399, IFWM3314, IFWM3331, IFWM3405, IFWM3442, IFWM3525, IFWM3423, IFWM3444 and IFWM3421.

Other exemplary antibodies that may be used in the methods of the invention described herein, and in some embodiments of each and every one of the numbered embodiments listed below are antibodies that bind to and neutralize a biological activity of a human interferon omega (IFN-ω) and at least three, four, five, six, seven, eight, nine, ten or eleven human interferon alpha (IFN-α) subtypes, wherein the antibody binds IFN-ω of SEQ ID NO: 1 at least at residues F27, L30 and R33.

Other exemplary antibodies that may be used in the methods of the invention described herein, and in some embodiments of each and every one of the numbered embodiments listed below, are antibodies that bind human IFN-ω of SEQ ID NO: 1 at least at residues S25, P26, F27, L28, L30, K31, R33, R34 and D35.

The methods of the invention may be used to treat an animal patient belonging to any classification. Examples of such animals include mammals such as humans, rodents, dogs, cats and farm animals.

The antibodies of the invention may be useful in the preparation of a medicament for such treatment, wherein the medicament is prepared for administration in dosages defined herein. SLE is a chronic multiorgan autoimmune disease with both genetic and environmental factor contributing to its development.

SLE is characterized by production of pathogenic autoantibodies and tissue deposition of immune complexes, resulting in tissue damage across multiple organs. Combinations of cutaneous, musculoskeletal, hematological, neurological and renal complications are seen in patients, with periods of flare-ups and remissions. Lupus nephritis is defined as a case of SLE with a diagnosis of nephritis, proteinuria, hematuria and/or renal failure. In lupus nephritis patients, renal involvement is characterized by proteinuria (>0.5 g/24 hours), and/or red blood cells or casts in urine specimens.

Not wishing to be bound by any particular theory, it is suggested that SLE triggers, such autoantibody immune complexes, invoke type I IFN responses associated with overproduction of IFN-α and IFN-ω, but not IFN-β. Therefore, IFN-α/ω antibodies of the invention may provide a more efficacious treatment of lupus and other immune-mediated inflammatory disease, broadly inhibiting IFN-ω and multiple IFN-α subtypes while sparing IFN-β function, which may play a more critical role in antiviral defense and which molecule may have no biological releavance in lupus. For example, anti-IFN-β antibodies failed to neutralize patient serum activity from both SLE and AGS patients, a disease also associated with elevated type IFN-I activity and IFN signature (Hooks et al., Arthritis and Rheumatism 25:396-400, 1982; Hua et al., Arthritis and Rheumatism 54: 1906 (June, 2006); Rice et al., Lancet Neurology doi: 10.1016/S1474-4422(13)70258-8 (2013)).

Other types of lupus in addition to SLE include cutaneous lupus erythematosus (CLE) and pediatric lupus.

Symptoms associated with lupus include joint pain and stiffness, nonerosive arthritis, muscle aches, pains, weakness, fever, malaise, ulcers on oral tissues, cutaneous manifestations (e.g., butterfly-shaped rash across the nose and cheeks; sunlight-induced dermatological flares), unusual weight loss or weight gain, anemia, low lymphocyte and/or platelet counts, neurological or neuropsychiatric manifestations (e.g., trouble thinking, memory problems, confusion, depression, headache, seizures, strokes), kidney problems (e.g., nephritis, e.g., glomerulonephritis), sun or light sensitivity, hair loss, purple or pale fingers from stress or cold, vascular lesions or other vascular manifestations, or cardiopulmonary symptoms such as pericarditis or pleuritis. Elevated levels of interleukins IL-1, IL-6, IL-10, Il-12, IL-17, IL-18, IL-5 and IL-16; TNF-α or Type I interferons, as well as overexpression of IFN inducible genes is documented in lupus patients. Patients may have elevated levels of autoantibodies against nuclear and cellular components such as double stranded DNA (dsDNA), ribonucleoprotein (RNP), SS-a/Ro, SS-b/La, phospholipids, histones or cardiolipin. Patients may have immune complex deposition in at least one tissue.

SLE may be diagnosed or classified for example using recommendations by the American College of Rheumatology (ACR), or by the Systemic Lupus International Collaborating Clinics Criteria (SLICC) for the Classification of Systemic Lupus Erythematosus. For example, the 2012 SLICC criteria require that patients demonstrate at least 4 of 11 criteria, with at least one clinical and one immunologic criterion, or lupus nephritis verified with biopsy in the presence of anti-DNA antibodies (ADA) or anti-nucleic acid antibodies (ANA). Clinical criteria are acute cutaneous lupus, chronic cutaneous lupus, oral or nasal ulcers, non-scarring alopecia, arthritis, serositis, renal symptoms, neurologic symptoms, hemolytic anemia, leukopenia or thrombocytopenia (<100,000/mm$^3$). Immunologic criteria include ANA, ADA, anti-Sm, anti-phospholipid antibodies, low complement (C3, C4 or CH50) or direct Coombs' test, which does not count in the presence of hemolytic anemia (Petre et al., Arthritis and Rheumatism August 2012). Active disease may be defined by one British Isles Lupus Activity Group's (BILAG) "A" criteria or two BILAG "B" criteria; SLE Disease Activity Index (SLEDAI); or systemic lupus erythematosus (SLE) responder index (SRI) described in Furie et al., Arthritis Rheum. 61(9): 1143-51 (2009).

SLE severity and disease activity may be defined by a BILAG score by a clinician with expertise in SLE. The BILAG 2004 index is used to determine the BILAG score (see Yee, et al. Arthritis & Rheumatism 54:3300-3305, 2006; Isenberg et al., Rheumatology 44:902-906; 2005). The BILAG 2004 index assesses 97 clinical signs, symptoms, and laboratory parameters across nine organ system domains: constitutional, mucocutaneous, neuropsychiatric, musculoskeletal, cardiorespiratory, gastrointestinal, ophthalmic, renal, and hematological. The 97 symptoms are rated with respect to severity over the previous month (4 weeks) and with respect to any change from the previous examination (new, improving, stable, worsening, absent). A single alphabetic score (A through E) for each of the nine domains is then derived from the examination results in each organ category. Table 2 shows the BILAG categories.

TABLE 2

| Category | Definition |
|---|---|
| A | Severe disease activity requiring any of the following treatment:<br>1. Systemic high dose oral glucocorticoids (equivalent to prednisolone >20 mg/day);<br>2. Intravenous pulse glucocorticoids (equivalent to pulse methylprednisolone ≥500 mg);<br>3. Systemic immunomodulators (include biologicals, immunoglobulins and plasmapheresis);<br>4. Therapeutic high dose anticoagulation in the presence of high dose steroids or immunomodulators, e.g., warfarin with target INR 3-4. |
| B | Moderate disease activity requiring any of the following treatment:<br>1. Systemic low dose oral glucocorticoids (equivalent to prednisolone ≤20 mg/day);<br>2. Intramuscular or intra-articular or soft tissue glucocorticoids injection (equivalent to methylprednisolone <500 mg). |
| C | Stable mild disease. |
| D | Inactive disease but previously affected. |
| E | System never involved. |

CLE is further classified to acute (ACLE), subacute (SCLE), chronic (CCLE) or intermittent (ICLE) CLE depending on the constellation of clinical features and duration of the cutaneous lesions, laboratory abnormalities, and skin biopsy histological changes. Classification and clinical manifestations of the various CLE forms are reviewed in Kuhn and Landmann, J Autoimmunity 48-49: 14-19, 2014.

A type I IFN gene signature has been reported to positively correlate with both clinical and serological features of lupus (Karageorgas et al., J Biomed Biotechnol 273907, 2011 Baechler et al., Proc Natl Acad Sci USA 100:2610-2615, 2003, Bennett et al., J Exp Med 197:711-723, 2003, Dall'era et al. Ann Rheum Dis 64: 1692-1697, 2005, Niewold et al. Genes Immun 8: 492-502, 2007).). A preponderance of autoantibodies in conjunction with their impaired clearance leads to a feedback cycle of IFN production where Fc receptor-dependent internalization of immune complexes into plasmacytoid dendritic cells (pDC) leads to increased amounts of IFN and thus establishment of the IFN signature. In clinical trials, anti-IFN-α antibodies in SLE patients have demonstrated partial reduction of the type I IFN signature in the majority of patients exhibiting the IFN signature and slight efficacy in exploratory analysis (Petri et al., *Arthritis and rheumatism* 65, 1011 (April, 2013); Merrill J et al., *Annals of the rheumatic diseases* 70, 314 (2011); Kennedy et al., *The 10th International Congress on SLE, Buenos Aires, Argentina* Oral Presentation 5, 022, (Apr. 20, 2013)).

The standard of care in lupus management is based on current, accepted medical practice patterns, approved guidance documents developed by rheumatology societies (e.g. American College of Rheumatology, European League Against Rheumatism) and the discretion of treating physicians. Lupus patients continue to have disease activity long after the diagnosis is made, even with proper management, often involving new organ systems or specific organ system damage. There are three patterns of disease activity in lupus: the flare (or remitting, relapsing disease activity), chronically active disease, and long quiescence. These disease patterns are characterized using systematic clinical assessments, routine laboratory tests, standardized measures of disease activity, and integration of these assessments with the patient's own perceptions of health status and quality of life. As the patient's signs and symptoms of flare persist or worsen, the physician may find that a change in medications and/or dosages is warranted. The medications used to control lupus include, but is not limited to the following: (1) NSAIDs, including over-the-counter NSAIDs, e.g., naproxen (Aleve) and ibuprofen (Advil, Motrin, others), and stronger NSAIDs available by prescription; (2) Antimalarial drugs, e.g., hydroxychloroquine (Plaquenil); (3) Corticosteroids., e.g., Prednisone and other types of corticosteroids, and (4) Immune suppressants, e.g., cyclophosphamide (Cytoxan), azathioprine (Imuran, Azasan), mycophenolate (Cellcept), leflunomide (Arava) and methotrexate (Trexall).

The antibodies of the invention may be tested for their efficacy in vitro in disease relevant cells using disease relevant IFN preparations. Such in vitro testing may be for example evaluation of inhibition of IFN production induced by SLE patient immune complexes in whole blood, or assessment of ability of the antibodies to reduce the IFN signature in whole blood as described herein. Animal models of lupus may also be used, such as NZB/NZW F1 mice that exhibit a time-dependent and female-biased disease with several features of human lupus including glomerulonephritis. However, as mice do not produce IFN-ω their utilization as a model to assess efficacy of the antibodies of the invention is more limited.

In some embodiments, the patient exhibits a Type I interferon signature. "Type I interferon signature" or "interferon signature" as used herein refers to the upregulation of a subset of genes that are induced by IFN-I. Various type I IFN signatures are known, ranging from 3-27 genes. These signatures may be utilized for example as pharmacodynamics markers to assess target engagement of Type I IFN inhibitors for treatment of SLE and for purpose of SLE patient stratification.

An exemplary Type I interferon signature is shown in Table 3, consisting of 21 upreguated genes as described in Yao et al., *Arthritis and rheumatism* 60, 1785 (June, 2009). Other exemplary type I interferon signatures are described in Tcherepanova, I., et al., *Annals of the rheumatic diseases* 71(Supp13) (2012) and Richardson, B. et al. Development of A Quantitative PCR Method to Determine Interferon Signature Metric Status in SLE Patients: Distribution and Clinical & Serological Associations in Two Lupus Clinical Trials. *ACR/ARHP* 2012 *Annual Meeting Abstract* 620 (2012).

In some methods, the anti-IFN-α/ω antibody is a bispecific antibody.

In some methods, the anti-IFN-α/ω bispecific antibody neutralizes BLyS, CD40L, IL-6, CD27, BDCA2, IL-12, IL-23, IFN-αD, IL-17 or CD20.

TABLE 3

| Number | Gene Symbol | Gene Name |
|---|---|---|
| 1 | IFI27 | interferon, alpha-inducible protein 27 |
| 2 | IFI6 | interferon, alpha-inducible protein 6 |
| 3 | RSAD2 | radical S-adenosyl methionine domain containing 2 |
| 4 | IFI44 | Interferon-induced protein 44 |
| 5 | IFI44L | IFI44L interferon-induced protein 44-like |
| 6 | USP18 | ubiquitin specific peptidase 18 |
| 7 | LY6E | lymphocyte antigen 6 complex, locus E |
| 8 | OAS1 | 2',5'-oligoadenylate synthetase 1, 40/46 kDa |
| 9 | SIGLEC1 | SIGLEC1 sialic acid binding Ig-like lectin 1 |
| 10 | ISG15 | ISG15 ubiquitin-like modifier |
| 11 | IFIT1 | interferon-induced protein with tetratricopeptide repeats |
| 12 | OAS3 | OAS3 2'-5'-oligoadenylate synthetase 3, 100 kDa |
| 13 | HERC5 | hect domain and RLD 5 |
| 14 | MX1 | myxovirus (influenza virus) resistance 1 |
| 15 | LAMP3 | lysosomal-associated membrane protein 3 |
| 16 | EPSTI1 | epithelial stromal interaction 1 (breast) |
| 17 | IFIT3 | interferon-induced protein with tetratricopeptide repeats |
| 18 | OAS2 | 2'-5'-oligoadenylate synthetase 2, 69/71 kDa |
| 19 | RTP4 | receptor (chemosensory) transporter protein 4 |
| 20 | PLSCR1 | Phospholipid scramblase 1 |
| 21 | DNAPTP6 | DNA polymerase-transactivated protein 6 |

Administration/Pharmaceutical Compositions

The invention provides for pharmaceutical compositions comprising the anti-IFN-α/ω antibody of the invention described herein, and in some embodiments of each and every one of the numbered embodiments listed below, and a pharmaceutically acceptable carrier. For therapeutic use, anti-IFN-α/ω antibody of the invention may be prepared as pharmaceutical compositions containing an effective amount of anti-IFN-α/ω antibody as an active ingredient in a pharmaceutically acceptable carrier. The term "carrier" refers to a diluent, adjuvant, excipient, or vehicle with which the active compound is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules or antibodies of the invention in such pharmaceutical formulation may vary widely, i.e., from less than about 0.5%, usually to at least about 1% to as much as 15 or 20%, 25%, 30%, 35%, 40%, 45% or 50% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, $21^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration of the anti-IFN-α/ω antibody in the methods of the invention described herein, and in some embodiments of each and every one of the numbered embodiments listed below, may be any suitable route such as parenteral administration, e.g., intradermal, intramuscular, intraperitoneal, intravenous or subcutaneous, pulmonary, transmucosal (oral, intranasal, intravaginal, rectal) or other means appreciated by the skilled artisan, as well known in the art.

The anti-IFN-α/ω antibody in the methods of the invention described herein, and in some embodiments of each and every one of the numbered embodiments listed below, may be administered to a patient by any suitable route, for example parentally by intravenous (i.v.) infusion or bolus injection, intramuscularly or subcutaneously or intraperitoneally. i.v. infusion may be given over for, example, 15, 30, 60, 90, 120, 180, or 240 minutes, or from 1, 2, 3, 4, 5, 6, 7, 8, 9, 10, 11 or 12 hours.

The dose given to a patient having an immune-mediated inflammatory disease or an autoimmune disease such as lupus is sufficient to alleviate or at least partially arrest the disease being treated ("therapeutically effective amount") and may be sometimes 0.005 mg/kg to about 100 mg/kg, e.g. about 0.05 mg/kg to about 20 mg/kg or about 0.1 mg/kg to about 20 mg/kg, or about 1 mg to about 20 mg/kg, or about 4 mg/kg, about 8 mg/kg, about 16 mg/kg or about 24 mg/kg, or, e.g., about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m². Usually between 1 and 8 doses, (e.g., 1, 2, 3, 4, 5, 6, 7 or 8) may be administered to treat the immune-mediated inflammatory disease, such as lupus, but 9, 10, 11, 12, 13, 14, 15, 16, 17, 18, 19, 20 or more doses may be given.

The administration of the anti-IFN-α/ω antibody in the methods of the invention and in some embodiments of each and every one of the numbered embodiments listed below, may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the anti-IFN-α/ω antibody in the methods of the invention may be administered at 0.1 mg/kg, at 1 mg/kg, at 5 mg/kg, at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

The anti-IFN-α/ω antibody may be administered in the methods of the invention and in some embodiments of each and every one of the numbered embodiments listed below, by maintenance therapy, such as, e.g., once a week for a period of 6 months or more.

For example, the anti-IFN-α/ω antibody in the methods of the invention and in some embodiments of each and every one of the numbered embodiments listed below, may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The anti-IFN-α/ω antibody in the methods of the invention and in some embodiments of each and every one of the numbered embodiments listed below, may also be administered prophylactically in order to reduce the risk of developing the immune-mediated inflammatory disease or an autoimmune disease such as lupus, delay the onset of the immune-mediated inflammatory disease of the autoimmune disease, and/or reduce the risk of recurrence when the immune-mediated inflammatory disease or the autoimmune disease such as lupus is in remission.

Thus, a pharmaceutical composition of the invention for intramuscular injection may be prepared to contain 1 ml sterile buffered water, and between about 1 ng to about 100 mg/kg, e.g. about 50 ng to about 30 mg/kg or more preferably, about 5 mg to about 25 mg/kg, of the anti-IFN-α/ω antibody of the invention.

For example, a pharmaceutical composition comprising the anti-IFN-α/ω antibody in the methods of the invention described herein, and in some embodiments of each and every one of the numbered embodiments listed below, for intravenous infusion may be made up to contain about 200 ml of sterile Ringer's solution, and about 8 mg to about 2400 mg, about 400 mg to about 1600 mg, or about 400 mg to about 800 mg of the anti-INF-α/ω antibody for administration to a 80 kg patient. Methods for preparing parenterally administrable compositions are well known and are described in more detail in, for example, "Remington's Pharmaceutical Science", 15th ed., Mack Publishing Company, Easton, Pa.

The "therapeutically effective amount" of the IFN-α/ω antibodies of the invention effective in the treatment of an immune-mediated inflammatory disease or an autoimmune disease may be determined by standard research techniques. For example, in vitro assays may be employed to help identify optimal dosage ranges. Optionally, the dosage of the IFN-α/ω antibodies of the invention that may be effective in the treatment of immune-mediated inflammatory diseases or autoimmune diseases such as lupus including SLE may be determined by administering the IFN-α/ω antibodies to relevant animal models well known in the art. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems. The antibodies of the invention may be tested for their efficacy and effective dosage using any of the models described herein.

The anti-IFN-α/ω antibody in the methods of the invention described herein, and in some embodiments of each and every one of the numbered embodiments listed below, may be lyophilized for storage and reconstituted in a suitable carrier prior to use. This technique has been shown to be effective with conventional protein preparations and well known lyophilization and reconstitution techniques can be employed.

The anti-IFN-α/ω antibody in the methods of the invention described herein, and in some embodiments of each and every one of the numbered embodiments listed below, may be administered in combination with a second therapeutic agent simultaneously, sequentially or separately.

The second therapeutic agent may be a corticosteroid, an antimalarial drug, an immunosuppressant, a cytotoxic drug, or a B-cell modulator.

In some embodiments, the second therapeutic agent is prednisone, prednisolone, methylprednisolone, deflazcort, hydroxychloroquine, azathioprine, methotrexate, cyclophosphamide, mycophenolate mofetil (MMF), mycophenolate sodium, cyclosporine, leflunomide, tacrolimus, Rituximab™, or Belimumab™.

Further Embodiments of the Invention

Set out below are certain further embodiments of the invention according to the disclosures elsewhere herein. Features from embodiments of the invention set out above described as relating to the invention disclosed herein also relate to each and every one of these further numbered embodiments.

1) An isolated monoclonal antibody that binds to and neutralizes a biological activity of a human interferon omega (IFN-ω) and at least three, four, five, six, seven, eight, nine, ten or eleven human interferon alpha (IFN-α) subtypes.
2) The antibody according to embodiment 1, wherein the biological activity of the human IFN-ω and the human IFN-α subtypes is the human IFN-ω or the human IFN-α subtype-induced expression of secreted embryonic alkaline phosphatase (SEAP) under interferon inducible ISG54 promoter in HEK293 cells stably expressing signal transducer and activator of transcription 2 (STAT2), interferon regulatory factor 9 (IRF9) and SEAP.
3) The antibody according to embodiment 1 or 2, wherein the antibody neutralizes the biological activity of the human IFN-ω with an $IC_{50}$ of at least about $1\times10^{-9}$M or less, about $1\times10^{-10}$ M or less, about $5\times10^{-11}$M or less, or about $1\times10^{-11}$M or less.
4) The antibody according to any one of embodiments 1-3, wherein the antibody neutralizes the biological activity of the human IFN-ω with an $IC_{50}$ value of at least about $1\times10^{-10}$ M or less.
5) The antibody according to any one of embodiments 1-4, wherein the antibody neutralizes the activity of the human IFN-ω with an $IC_{50}$ value of between about $1\times10^{-10}$M to about $6\times10^{-12}$M.
6) The antibody according to any one of embodiments 1-5, wherein the antibody neutralizes the activity of at least three, four, five, six, seven, eight, nine, ten or eleven human IFN-α subtypes with an $IC_{50}$ value of at least about $1 \times 10^{-10}$ M or less.

7) The antibody according to embodiment 6, wherein the IFN-α subtypes are selected from the group consisting of IFN-αA, IFN-αB2, IFN-αC, IFN-αF, IFN-αG, IFN-αH2, IFN-αI, IFN-αJ1, IFN-αK, IFN-αWA and IFN-α4a.

8) The antibody according to embodiment 7, wherein the antibody comprises heavy chain complementarity determining region (HCDR) 1 (HCDR1), 2 (HCDR2) and 3 (HCDR3) amino acid sequences of SEQ ID NOs: 109, 114 and 121, respectfully, and light chain complementarity determining region (LCDR) 1 (LCDR1), 2 (LCDR2) and 3 (LCDR3) amino acid sequences of SEQ ID NOs: 118, 119 and 120.

9) The antibody according to any one of embodiments 1-5, wherein the antibody neutralizes at least six human IFN-α subtypes selected from the group consisting of IFN-αA, IFN-αB2, IFN-αC, IFN-αF, IFN-αG, IFN-αH2, IFN-αI, IFN-αJ1, IFN-αK, IFN-αWA and IFN-α4a.

10) The antibody according to embodiment 9, wherein the antibody comprises the HCDR1, the HCDR2, the HCDR3, the LCDR1, the LCDR2 and the LCDR3 amino acid sequences of SEQ ID NOs: 109, 114, 121, 159, 119 and 160, respectively.

11) The antibody according to any one of embodiments 1-5, wherein the antibody neutralizes at least ten human IFN-α subtypes selected from the group consisting of IFN-αA, IFN-αB2, IFN-αC, IFN-αF, IFN-αG, IFN-αH2, IFN-αI, IFN-αJ1, IFN-αK, IFN-αWA and IFN-α4a.

12) The antibody according to embodiment 11, wherein the antibody binds human IFN-ω of SEQ ID NO: 1 at least at amino acid residues F27, L30 and R33.

13) The antibody according to any one of embodiments 1-5, wherein the antibody comprises the HCDR1, the HCDR2, the HCDR3, the LCDR1, the LCDR2 and the LCDR3 amino acid sequences of SEQ ID NOs: 109, 114, 121, 161, 119 and 162, respectively.

14) The antibody according to any one of embodiments 11-13, wherein the antibody neutralizes at least the human IFN-α subtypes IFN-αA, IFN-αB2, IFN-αC, IFN-αF, IFN-αG, IFN-αH2, IFN-αJ1 and IFN-α4a.

15) The antibody according to embodiment 14, wherein the antibody further neutralizes IFN-αI, IFN-αK or IFN-αWA.

16) The antibody according to any one of embodiments 1-15, wherein the antibody
   a) inhibits leukocyte interferon-induced IP-10 release in whole blood induced by 250 U/ml of interferon by about 50% or more in the presence of 10 μg/ml antibody; or
   b) inhibits systemic lupus erythematosus (SLE) immune complex-induced IP-10 release in whole blood by about 50% or more in the presence of 10μ/ml antibody.

17) The antibody according to any one of embodiments 1-16, wherein the antibody comprises a heavy chain variable region (VH) amino acid sequence at least 90%, 91%, 92%, 93%, 94%, 95%, 96%, 97%, 98% or 99% identical to SEQ ID NO: 28 and a light chain variable region (VL) amino acid sequences at least 90%, 91%, 92%, 93%, 94%, 95%, 96%, 97%, 98% or 99% identical to SEQ ID NO: 150.

18) The antibody according to any one of embodiments 1-17, comprising
   a) the HCDR1 amino acid sequences of SEQ ID NOs: 109;
   b) the HCDR2 amino acid sequences of SEQ ID NOs: 111, 112 or 113;
   c) the HCDR3 amino acid sequences of SEQ ID NOs: 115 or116;
   d) the LCDR1 amino acid sequences of SEQ ID NOs: 76, 77, 78, 79, 80, 81, 82, 83, 84, 85, 86, 87, 88, 89, 90 or 91;
   e) the LCDR2 amino acid sequences of SEQ ID NOs: 93, 94 or 95; and
   f) the LCDR3 amino acid sequences of SEQ ID NOs: 96, 97, 98, 99, 100, 101, 102, 103, 104, 105, 106 or 107.

19) The antibody according to embodiment 18, comprising the HCDR1, the HCDR2, the HCDR3, the LCDR1, the LCDR2 and the LCDR3 sequences of SEQ ID NOs:
   a) 109, 113, 116, 77, 93 and 104, respectively;
   b) 109, 113, 116, 85, 93 and 96, respectively;
   c) 109, 113, 115, 79, 95 and 107, respectively;
   d) 109, 113, 116, 76, 93 and 103, respectively;
   e) 109, 113, 115, 85, 93 and 96, respectively;
   f) 109, 113, 115, 89, 95 and 100, respectively;
   g) 109, 113, 116, 86, 93 and 105, respectively;
   h) 109, 113, 115, 76, 93 and 103, respectively;
   i) 109, 113, 116, 80, 93 and 97, respectively;
   j) 109, 113, 116, 84, 93 and 97, respectively;
   k) 109, 113, 116, 90, 93 and 97, respectively;
   l) 109, 113, 116, 88, 93 and 102, respectively;
   m) 109, 113, 116, 87, 93 and 105, respectively;
   n) 109, 113, 116, 91, 93 and 106, respectively;
   o) 109, 113, 115, 80, 93 and 97, respectively;
   p) 109, 113, 116, 83, 93 and 101, respectively;
   q) 109, 113, 116, 82, 94 and 98, respectively;
   r) 109, 113, 115, 78, 95 and 100, respectively;
   s) 109, 111, 116, 81, 93 and 106, respectively;
   t) 109, 113, 116, 82, 94 and 99, respectively;
   u) 109, 113, 115, 81, 93 and 106, respectively;
   v) 109, 112, 116, 81, 93 and 106, respectively; or
   w) 109, 113, 116, 81, 93 and 106, respectively.

20) The antibody according to any one of embodiments 1-19, wherein the antibody is humanized or human.

21) The antibody according to embodiment 20, wherein the human antibody heavy chain variable region framework is derived from human germline gene IGHV5-51 (SEQ ID NO: 155).

22) The antibody according to embodiment 21, wherein the human antibody light chain variable region framework is derived from human germline gene IGKV1D-39 (SEQ ID NO: 156).

23) The antibody according to any one of embodiments 1-22, wherein the antibody is of IgG1, IgG2, IgG3 or IgG4 subtype.

24) The antibody according to embodiment 23, wherein the antibody has at least one substitution in an Fc region.

25) The antibody according to embodiment 24, wherein the wherein the substitution comprises a substitution M252Y/S254T/T256E, V234A/G237A/P238S/H28AN309L/A330S/P331S or P238S/L234A/L235A, wherein residue numbering is according to the EU numbering.

26) The antibody according to any one of embodiments 1-26, comprising a heavy chain variable region (VH) and a light chain variable region (VL), wherein the
   a) VH comprises the amino acid sequence of SEQ ID NOs: 28, 31, 157 or 158.

27) The antibody according to embodiment 26, wherein the VL comprises the amino acid sequence of SEQ ID NOs: 35, 39, 40, 42, 46, 52, 53, 54, 57, 61, 62, 68, 71, 73, 75, 135 or 150.

28) The antibody according to embodiment 27 comprising the VH and the VL of SEQ ID NOs:
a) 28 and 40, respectively;
b) 28 and 39, respectively;
c) 31 and 62, respectively;
d) 28 and 54, respectively;
e) 31 and 39, respectively;
f) 31 and 68, respectively;
g) 28 and 42, respectively;
h) 31 and 54, respectively;
i) 28 and 53, respectively;
j) 28 and 73, respectively;
k) 28 and 75, respectively;
l) 28 and 52, respectively;
m) 28 and 35, respectively;
n) 28 and 135, respectively;
o) 31 and 53, respectively;
p) 28 and 46, respectively;
q) 28 and 61, respectively;
r) 31 and 57, respectively;
s) 157 and 71, respectively;
t) 28 and 150, respectively;
u) 31 and 71, respectively;
v) 158 and 71, respectively; or
w) 28 and 71, respectively.

29) The antibody according to any one of embodiments 1-28, wherein the antibody is bispecific.

30) The antibody according to embodiment 29, wherein the antibody binds BLyS, CD40L, IL-6, CD27, BDCA2, IL-12, IL-23, IFN-αD, IL-17, CD20, IL-10, CD22, IL-21, ICOS, ICOSL or IFN-γ.

31) A pharmaceutical composition comprising the antibody according to any one of embodiments 1-30 and a pharmaceutically accepted carrier.

32) A polynucleotide encoding the antibody VH or VL or the antibody VH and VL of any one of embodiments 1-28.

33) A vector comprising the polynucleotide of embodiment 32.

34) A host cell comprising the vector of embodiment 33.

35) A method of producing the antibody of embodiment 19, comprising culturing the host cell of embodiment 33 in conditions that the antibody is expressed, and recovering the antibody produced by the host cell.

36) The antibody according to any one of embodiments 1-30 for use in the treatment of an immune-mediated inflammatory disease or an autoimmune disease.

37) The antibody according to embodiment 36 for use of
a) the immune-mediated inflammatory disease or the autoimmune disease, wherein the immune-mediated inflammatory disease or the autoimmune disease is optinally lupus, psoriasis, immune thrombocytopenia (ITP), Aicardi-Goutieres syndrome (AGS), systemic sclerosis, Sjögren's syndrome, myositis, common variable immune deficiency (CVID), autoimmune thyroid disease, type I diabetes, rheumatoid arthritis, transplant rejection or graft versus host disease (GVHD);
b) chronic viral infection, wherein the chronic viral infection is optionally HIV or hepatitis C infection.

38) The antibody according to any one of embodiments 1-30 for use in the treatment of lupus.

39) The antibody according to embodiment 38 for use of lupus, wherein lupus is systemic lupus erythematosus (SLE) or cutaneous lupus erythematosus (CLE).

40) The antibody according to any one of embodiments 1-30 for use in the treatment of an immune-mediated inflammatory disease or lupus, wherein the patient to be treated has
a) lupus nephritis; or
b) exhibits a Type I interferon signature.

41) The antibody according to any one of embodiments 1-30 for use according to embodiments 37-40 in combination with a second therapeutic agent.

42) The antibody according to embodiment 41, wherein the second therapeutic agent is
a) an antibody that binds BLyS, CD40L, IL-6, CD27, BDCA2, IL-12, IL-23, IFN-αD, IL-17, CD20, IL-10, CD22, IL-21, ICOS, ICOSL or IFN-γ;
b) a corticosteroid, an antimalarial drug, an immunosuppressant, a cytotoxic drug, or a B-cell modulator; or
c) prednisone, prednisolone, methylprednisolone, deflazcort, hydroxychloroquine, azathioprine, methotrexate, cyclophosphamide, mycophenolate mofetil (MMF), mycophenolate sodium, cyclosporine, leflunomide, tacrolimus, Rituximab™ or Belimumab™.

43) The antibody according to any one of embodiments 1-30, wherein the antibody does not neutralize IFN-αD, IFN-α1 and/or IFN-β.

The present invention will now be described with reference to the following specific, non-limiting examples.

Materials and Methods

ISRE Reporter Gene Assay ("ISRE Reporter Gene Assay")

HEK-Blue™ IFN-α/β cells (InvivoGen, San Diego, Calif.) engineered to express a fully active type I IFN signaling pathway (stably expressing STAT2 and IRF9) and transfected with a SEAP reporter gene under the control of the IFN-α/β inducible ISG54 promoter was used. The cells were grown in collagen type I coated T150 flasks in Dulbecco's modified eagle media with 10% fetal bovine serum, 100 ug/ml blasticidin and 30 ug/ml zeocin at 37° C., 5% $CO_2$. Cells were harvested and plated in 384-well plates at 50 μl per well at 50,000 cells per ml. Plated cells were incubated at 37° C., 5% $CO_2$ for 24 hr. Tested interferon samples were prepared and diluted in spent HEK ISRE serum free medium, and 50 μl of IFN sample was added to each well. Plated cells were incubated at 37° C., 5% $CO_2$ for 20 hr. Alkaline phosphatase was detected from 20 μl of plated cell supernatants with 60 μl/well QUANTI-Blue™ resuspended in filtered water after incubation for 20 min at room temperature. Optical density was read on a Biotek Synergy plate reader at 650 nm.

Some ISRE reporter gene assays were done in 96-well plates as follows: HEK-Blue™ IFN-α/β cells (InvivoGen, San Diego, Calif.) were plated at 50,000 cells per well in 100 μl of selection free media (DMEM+Glutamax/10% FBS, Gibco) and allowed to incubate overnight at 37° C. The next day, type I IFN stimuli were prepared (i.e. recombinant interferon, leukocyte IFN, IC induced IFN preps, serum, etc) with or without type I IFN inhibitors in a separate 96 well U-bottom transfer plate (BD Falcon) and prewarmed at 37° C. for 10 minutes. A plate of cells was removed from incubator and media was removed and replaced with 100 μl of appropriate treatments prepared in 96 well U-bottom transfer plate. Cells were placed back at 37° C. for 24 hours. The next day, 40 μl of supernatant was transferred to a 96 well flat bottom plate (BD Falcon) containing160 μl of QUANTI-Blue™ SEAP substrate (Invivogen). Plate was allowed to develop for about 15 minutes at which time it was read using a spectrometer at an absorbancy of 650 nm.

EXAMPLE 1

Soluble IFN-ω is Present and Active in the Blood of SLE Patients

Plasma from two independent SLE cohorts from Nanjing China and serum collected from a Caucasian cohort in the USA were analyzed for soluble IFNω and IFN-α using a multiplex ELISA using a VeriPlex human interferon multiplex ELISA kit (PBL Assay Science, cat no 51500-1) according to manufacturer's instructions. The multiplex ELISA detects many, but not all of the IFN-α subtypes and may not accurately reflect quantitative differences between total IFN-α levels versus IFN-ω.

Figure 1B:
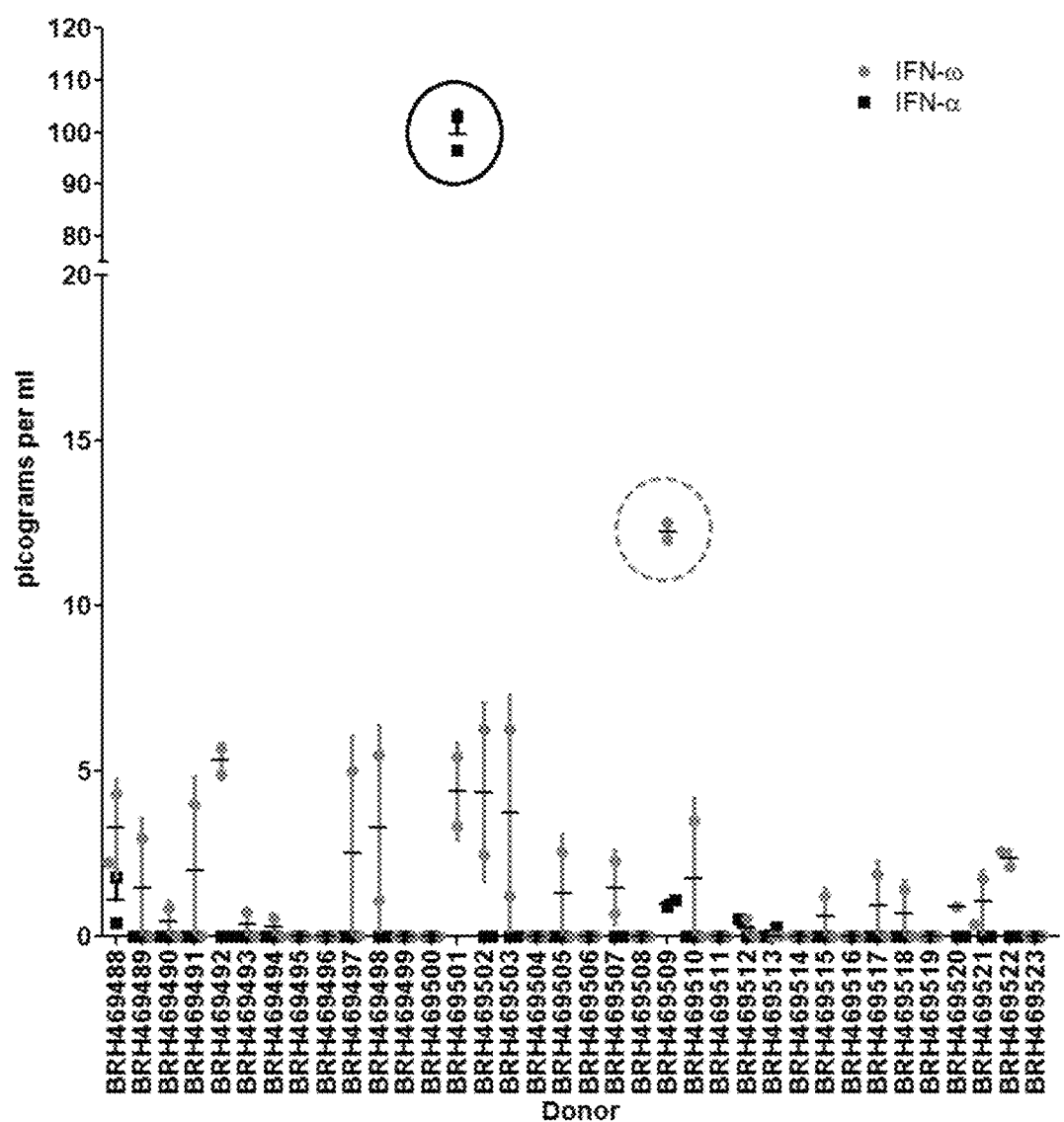
FIG. 1B shows IFN-ω and IFN-α levels (pg/ml) in serum from Caucasian SLE patients. The dark solid circle indicates the highest IFN-α levels and the dotted line circle indicate the highest IFN-ω plasma levels across the various donors. Horizontal bars in the figure indicate mean ELISA value of replicate samples, vertical bars indicate SD.
Figure 1C:
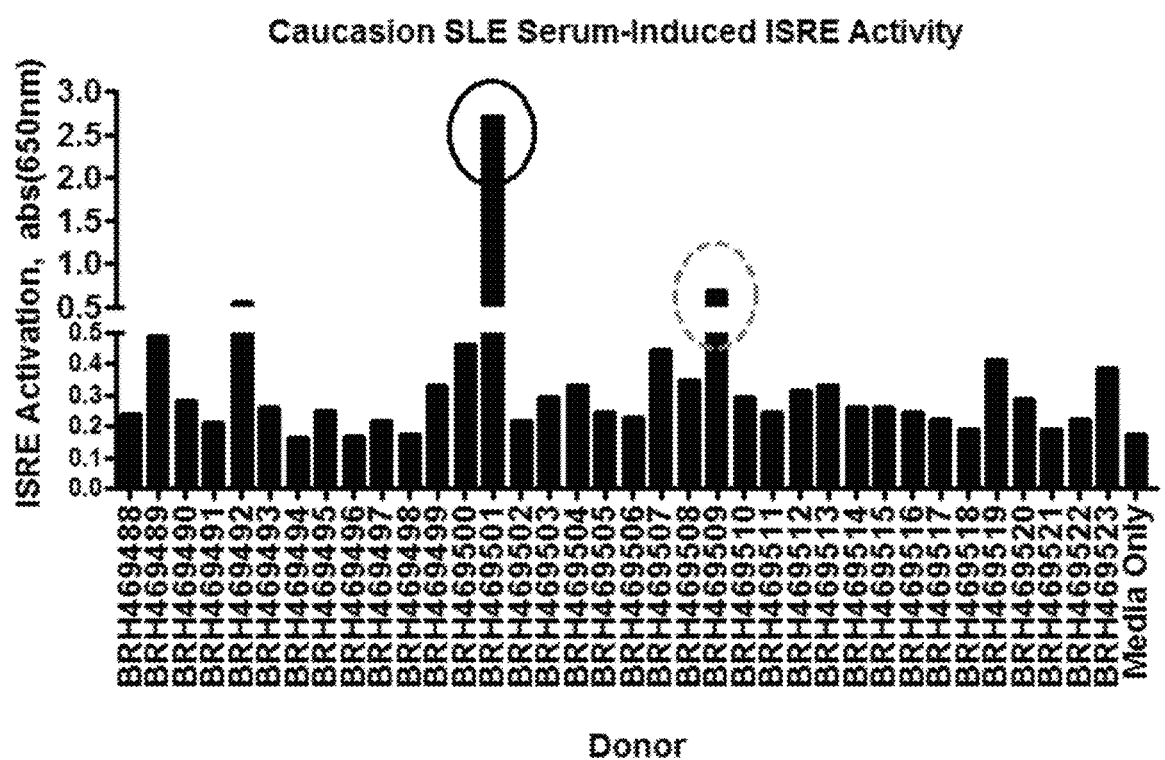
FIG. 1C shows that patient serum activates downstream interferon signaling pathways measured using ISRE reporter gene assay. The donor exhibiting the greatest amount of IFN-α protein (dark solid circle) and IFN-ω (dotted line circle) also demonstrated the greatest levels of ISRE induction in the reporter gene assay. The results are readings from a single well for each serum sample.

IFN-ω, in addition of IFN-α, was found to be elevated in certain patients from both Nanjing China cohort (FIG. 1A) and Caucasian cohort (FIG. 1B) from each cohort. FIG. 1A shows results from only those patients that were found to have elevated IFN-α or IFN-ω. Serum samples from the Caucasian group were further screened for IFN-I activity using an ISRE reporter gene assay. Donors exhibiting the greatest amount of detectable IFN protein by ELISA also demonstrated the greatest level of ISRE induction in the reporter gene assay (FIG. 1C).

EXAMPLE 2

Combined Blockade of IFN-ω and IFN-α Results in Greater Inhibition of SLE Immune Complex-Induced IFN than IFN-α Blockade Alone Effect of inhibition of IFN-α alone or both IFN-ω and IFN-α to reduce SLE immune complex-induced IFN, a stimulus better representing the type I IFN milieu present in SLE, was evaluated. SLE immune complex-induced IFN was prepared by stimulating human PBMCs with immune complexes prepared from two individual SLE donors and this conditioned media was utilized in a type I IFN-inducible reporter gene assay (ISRE reporter gene assay) in the presence of IFN inhibitors and controls.

Immune Complex Preparation

SLE donor 232 and 293 plasma (prescreened for IFN activity) and healthy control plasma (Astarte Biologics) was utilized for IgG purification using protein A/G columns (Thermo Scientific, Cat #89958) according to the manufacturer's instructions. Serum from a pooled healthy donor preparation (Life Technologies, Cat #34005100) was used for purification of healthy control IgG. To create lysates for immune complex formation, HEK293T cells (ATCC, Cat #CRL-3216) were concentrated to $5\times10^7$ cells/ml in 1× DPBS (Life Technologies, Cat #14190-250). To create lysates, freeze thawing was performed for 4 cycles of 10 minutes, freezing at −80° C. and thawing at 37° C., except for an initial freezing of 30 min. After $4^{th}$ freeze-thaw, cell debris was removed by centrifugation at 400×g for 5 minutes. Purified IgG preparations and cell lysates were then quantitated using a BCA protein assay (Pierce, Cat #23225) according to manufacturer's instructions. To create immune complexed stimulated conditioned media preparations, PBMCs from healthy donor sodium heparinized blood were isolated using Cell Preparation tubes (BD Vacutainer, Cat #362753), resuspended in RPMI 1640 (Life Technologies, Cat #11875-085)+10% FBS (Life Technologies, Cat #16140-063) media at $2\times10^6$ cells/ml and plated in 6 well plates in a volume of 2 ml/well. Purified IgG from SLE and healthy serum was premixed with cell lysates at equivalent concentrations of 500 ug/ml each and incubated at RT for 30 minutes and then added to PBMCs in a volume of 2 ml per well and incubated for 24 hours at 37° C. Plates were centrifuged at 1000 rpm for 5 minutes and PBMC immune complex-stimulated conditioned media was collected, aliquoted, and stored at −80° C. for future use.

Activity Assay

Figure 2:
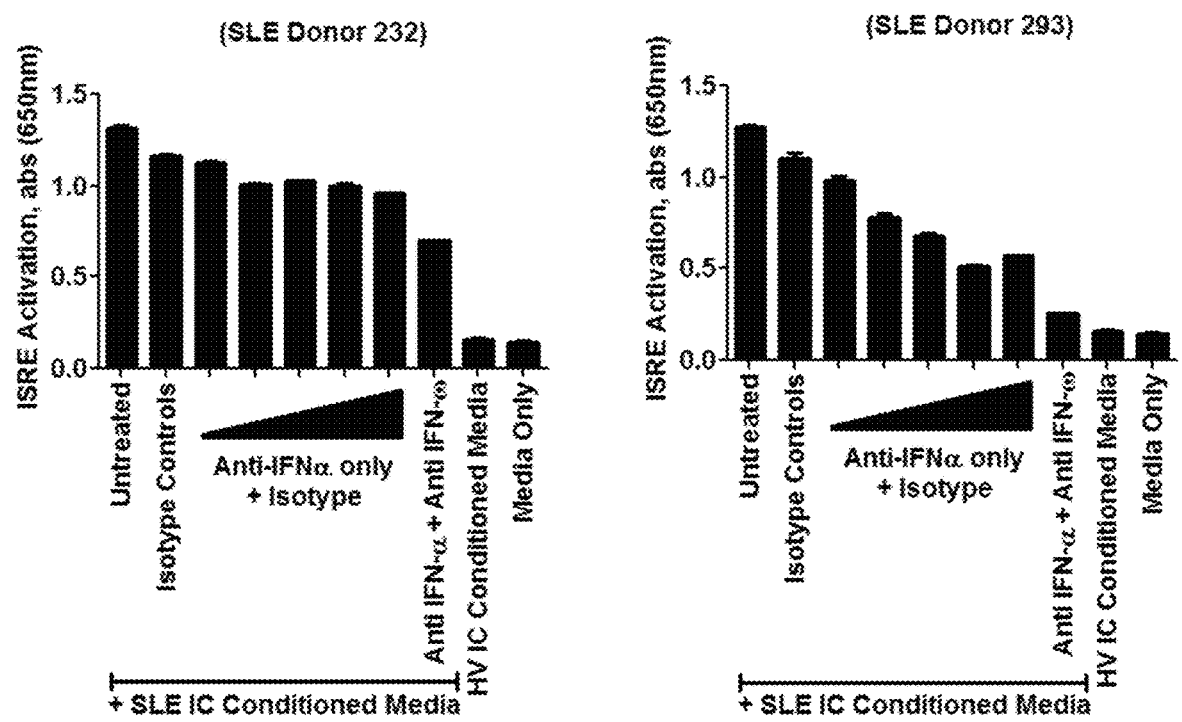
FIG. 2 shows inhibition of SLE immune complex-induced IFN with increasing concentration (0.4-100 μg/ml) of anti-IFN-α antibody alone or at 100 μg/ml in combination with anti-IFN-ω antibody (20 μg/ml). SLE immune complexes (SLE IC) were prepared from two different donors (SLE Donor 232 or 293). Combined blockage of IFN-α and IFN-ω resulted in enhanced suppression of SLE IC-induced IFN activity, as measured using the ISRE assay. HV IC conditioned media=conditioned media from PBMCs stimulated with immune complexes from healthy donors.

HEK-Blue IFNα/β cells (Invivogen) were plated in a 96 well flat bottom plate at 50,000 cells per well in 200 μl DMEM (Life Technologies)+10% fetal bovine serum (Life Technologies) and incubated for 5 hours at 37° C. to allow cells to adhere to plate. After 5 hours, Hek-Blue cells were removed from incubator and supernatants were replaced with a 1:6 dilution of donor 232 PBMC conditioned media or a 1:81 dilution of donor 293 conditioned media (using HEK-Blue cell culture media as a diluent) with or without the following treatments: broad anti-IFN-α antagonist mAb (M24, human IgG1) at 0.4, 2, 10, 50, and 100 μg/ml along with a fixed concentrations of 20 μg/ml isotype control (R&D Systems, murine IgG1), 100 μg/ml anti-IFN-α combined with 20 μg/ml anti-IFN-ω antagonist mAb (eBioscience, clone OMGS, murine IgG1), or 100 μg/ml human IgG1 isotype control (Southern Biotech) combined with 20 μg/ml murine IgG1 isotype control. Cells were incubated overnight at 37° C. The next day, 40 μl of cell supernatant from each well was removed and added to 160 μl of Quanti-Blue alkaline phosphatase substrate (Invivogen) in a separate 96 well flat bottom plate. Supernatants were allowed to react with the substrate for 10 minutes at which time the plate was read on a spectrophotometer at 650 nm wavelength. Optical densities were plotted in GraphPad Prism The additional blockade of IFN-ω in the presence of IFN-α antagonist resulted in enhanced suppression of SLE-relevant IFN-I activity than blockade of IFN-α alone (FIG. 2). As expected, conditioned media from PBMCs stimulated with immune complexes from healthy donor (HV IC Conditioned media) did not have detectable ISRE activity indicating the interferogenic potential of SLE patient immune complexes.

EXAMPLE 3

Immunomodulatory Effects of IFN-ω are Similar to Those of IFN-α

Ability of IFN-ω to induce chemokine secretion, IFN gene signature, dendritic cell maturation and activation, and B-cell maturation was evaluated in comparison to IFN-α. In these studies, IFN-αA and IFN-α2, two of the most widely used therapeutic IFN-α molecules, were primarily used as representative IFN-α subtype controls. In some assays, IFN-αB2 was used.

Induction of Chemokine Secretion and IFN Gene Signature

Figure 3:
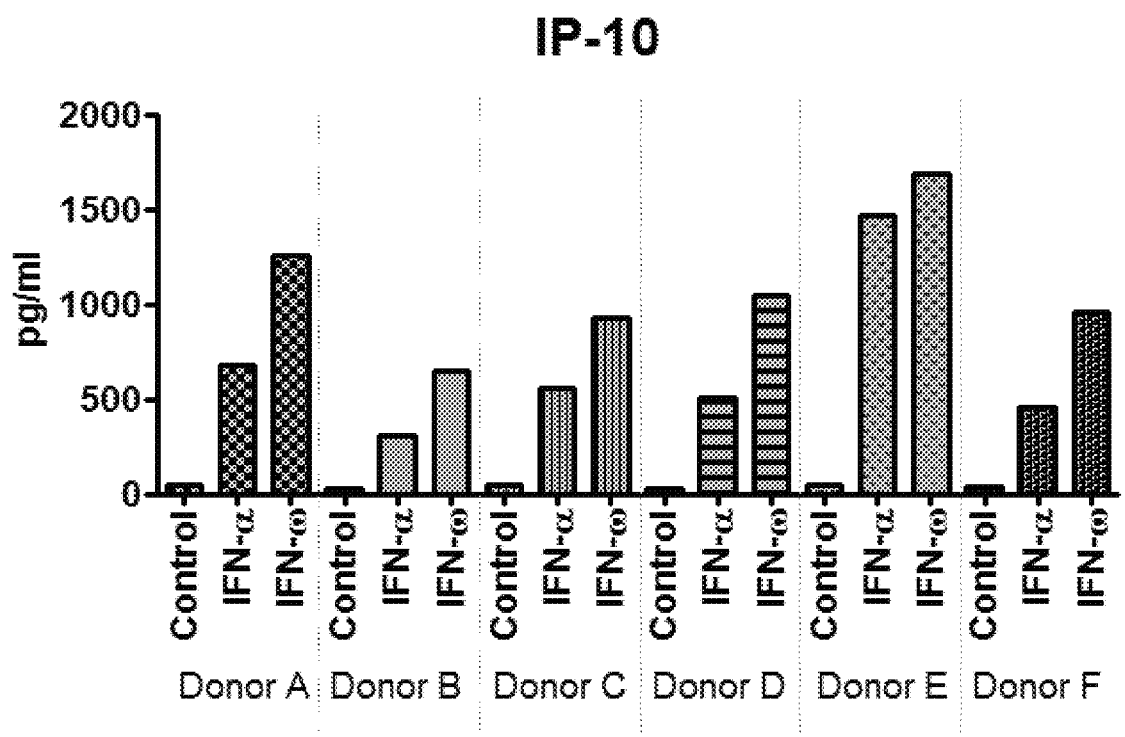
FIG. 3 shows induction of IP-10 secretion from PBMCs from 6 healthy individuals stimulated with IFN-αA or IFN-ω as indicated.

PBMCs isolated from 6 individual healthy human donors were stimulated with IFN-αA (IFN-α2) or IFN-ω, and the supernatants and pellets were collected for analyses. 3, 6 and 24 hours post-treatment. A panel of 25 cytokines were measured from the supernatants using Luminex immunoassay: IL-1β, IL-1RA, IL-2, IL-2R, IL-4, IL-5, IL-6, IL-7, IL-8, IL-10, IL-12, IL-13, IL-15, IL-17, TNFα, IFN-α, IFN-γ, GM-CSF, MIP-1α, MIP-1β, IP-10, MIG, Eotaxin, RANTES, and MCP-1. IFN-ω and IFN-α2 both enhanced the level of detectable IP-10, MCP-1, IL-1RA, IL-6, MIP-1α, and MIP-1β. FIG. 3 shows the induction of IP-10 by IFN-ω and IFN-α2. IL-8 secretion was reduced by both treatments in these experiments. IL-2R, IL-12 and RANTES levels were not altered by IFN-α or IFN-ω treatment (with the exception of one donor which had an increase in RANTES only). All other analytes in the cytokine panel did not change with respect to IFN-α or IFN-ω treatment or were below the limit of detection.

Collected pellets were processed for RNA and evaluated using a 21-gene IFN panel signature by microarray to evaluate possible similarities and/or differences in IFN-ω and IFN-α induced expression. Human PBMCs treated with IFN-ω exhibited neary indistinguishable qualitative and kinetic gene expression responses as compared to IFN-αA-treated cells. 92.5% of genes modulated by IFN-αA treatment versus untreated control were also modulated by IFN-ω treatment at 3 h. At the 6 and 24 h post-treatment time points, 97.83% and 99.25% of genes modulated by IFN-α treatment were also modulated by IFN-ω, respectively (data not shown).

In summary, IFN-α and IFN-ω induced indistinguishable qualitative cytokine release and gene expression profiles between PBMC preparations obtained from 6 individual healthy human donors suggesting that they may confer similar immunomodulatory effects.

IFN-ω Induces Differentiation of Dendritic Cells which is Inhibited by IFN-ω Blocking Antibodies Ability of IFN-ω and IFN-α to induce monocyte to DC differentiation and the functionality was evaluated.

Purified monocytes were differentiated to DC in the presence of GM-CSF alone or with IFN-α or IFN-ω in the presence or absence of 50 µg/ml anti-IFN-α or anti-IFN-ω for 3 days using standard methods. Cells were harvested and analyzed for surface marker expression by 8-color FACS. Both IFN-α and IFN-ω induced characteristic DC surface marker expression CD83, and CD80, CD86, CD40, CD11c, and reduced expression or monocyte marker CD14. Addition of either anti-IFN-α or anti-IFN-ω at concentration 50 µg/ml at the beginning of culture partially inhibited DC differentiation while the isotype antibody had no effect (data not shown).

Figure 4A:
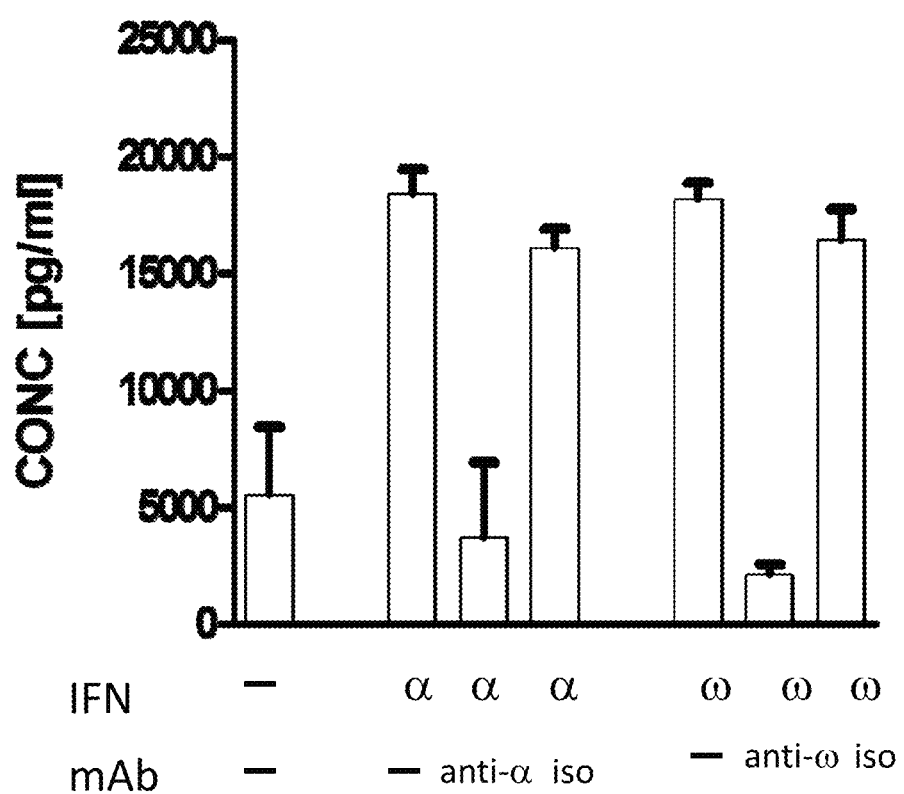
FIG. 4A shows secretion of IFN-γ by $CD4^+$ T cells in the presence of DCs differentiated in the presence of IFN-ω, IFN-α, IFN-ω and anti-IFN-ω antibody, or IFN-α and anti-IFN-α antibody, or isotype control (iso) as indicated. DCs differentiated in the presence of either IFN-ω or IFN-α induced activation of $CD4^+$ T cells to a same degree, whereas DCs differentiated in the presence of anti-IFN-ω or anti-IFN-α neutralizing antibodies did not induce $CD4^+$ T cell differentiation. The differentiated DCs were cultured with purified $CD4^+$ T cells at DC:$CD4^+$ T cells ratios of 1:20. Secreted IFN-γ was measured at day 6. Data is representative of 2 studies. Error bars indicate SD of Luminex triplicates. CONC: concentration.
Figure 4B:
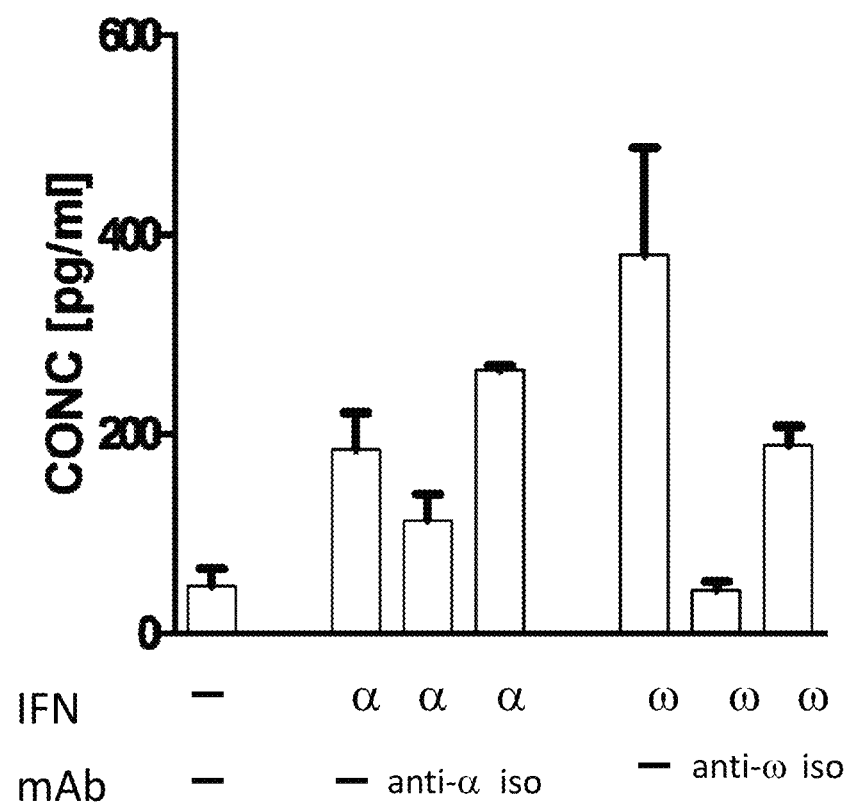
FIG. 4B shows secretion of IL-17 by $CD4^+$ T cells in the presence of DCs differentiated in the presence of IFN-ω, IFN-α, IFN-ω and anti-IFN-ω antibody, or IFN-α and anti-IFN-α antibody, or isotype control (iso) as indicated. DCs differentiated in the presence of either IFN-ω or IFN-α induced activation of $CD4^+$ T cells to a same degree, whereas DCs differentiated in the presence of anti-IFN-ω or anti-IFN-α neutralizing antibodies did not induce $CD4^+$ T cell differentiation. The differentiated DCs were cultured with purified $CD4^+$ T cells at DC:$CD4^+$ T cells ratios of 1:20. Secreted IL-17 was measured at day 6. Data is representative of 2 studies. Error bars indicate SD of Luminex triplicates. CONC: concentration.

Mixed lymphocyte reaction (MLR) was used to demonstrate the functionality of the differentiated DCs. The differentiated DCs were harvested, washed, resuspended in fresh media, and cultured with purified CD4+ T cells at DC:CD4+T cell ratios of 1:10, 1:20, and 1:100. On day 6 supernatants were collected and analyzed for secreted cytokines using a multiplex beads assay for 26 cytokines/chemokines. DCs differentiated in the presence of either IFN-α or IFN-ω activated CD4+ cells as shown by secretion of T cell specific cytokines IFN-γ and IL-17. DCs differentiated in the presence either the anti-IFN-α or the anti-IFN-ω antibody did not induce CD4+ T cell activation. FIG. 4A shows the lack of induced IFN-γ secretion from the CD4+ cells activated by DCs differentiated in the presence of anti-IFN-α or anti-IFN-ω antibodies. FIG. 4B shows the lack of induced IL-17 secretion from the CD4+ cells activated by DCs differentiated in the presence of anti-IFN-α or anti-IFN-ω antibodies. IFN-α and IFN-ω also induced secretion of IL-4, IL-5, IL-12p40 and IL-13 (data not shown). All culture conditions included GM-CSF. Data is representative of 2 studies. Error bars indicate SD of Luminex triplicates. In the experiment shown in the figure, data illustrated a DC to CD4 T cell ratio of 1:20 was used.

IFN-ω Induces T-Cell Independent B Cell Activation

B cells play a critically important role in lupus pathogenesis through the production of pathogenic autoantibodies and cytokines, and by presenting antigens to T cells. B cell activation and functional maturation can occur in a T cell-dependent (TD) or T cell-independent (TI) fashion. In TI B cell responses, B cells are released from T-dependent tolerance control as TLR ligands or dendritic cell-derived cytokines are able to substitute for T cell help. In SLE, where both TLR ligands (e.g. double-stranded DNA) and DC-derived cytokines (e.g. type I IFNs) are believed to contribute to disease pathogenesis, TI B cell activation represents a likely relevant mechanism. Besides the production of autoantibodies, autoreactive B cells are thought to play important pathogenic roles by presenting autoantigens to T cells and secreting pro-inflammatory cytokines. IFN-α has been reported to enhance the production of pro-inflammatory IL-6 by human B cells activated with antibodies against the B cell receptor (BCR) and CpG (mimicking specific antigen and TLR-signals, respectively) in the absence of T cell-derived factors. Furthermore, co-culture with plasmacytoid DCs was shown to enhance B cell activation as determined by CD86 expression levels that was dependent on soluble factors. The ability of IFN-ω to enhance CD86-expression and pro-inflammatory cytokine production by human B cells was investigated using a T cell-independent culture system Peripheral blood B cells were cultured with CpG (ODN-2006), anti-BCR, and CpG & anti-BCR, and varying concentrations of IFN-α2 (Alpha 2b) or IFN-ω as indicated (IFN concentrations in U/ml). CD86-expression (median fluorescence levels) was determined after 3 days by flow cytometry, and supernatants were analyzed by 26-plex Luminex immunoassay, including IL-6. The results were expressed as mean values of duplicate samples±SD.

Figure 5A:
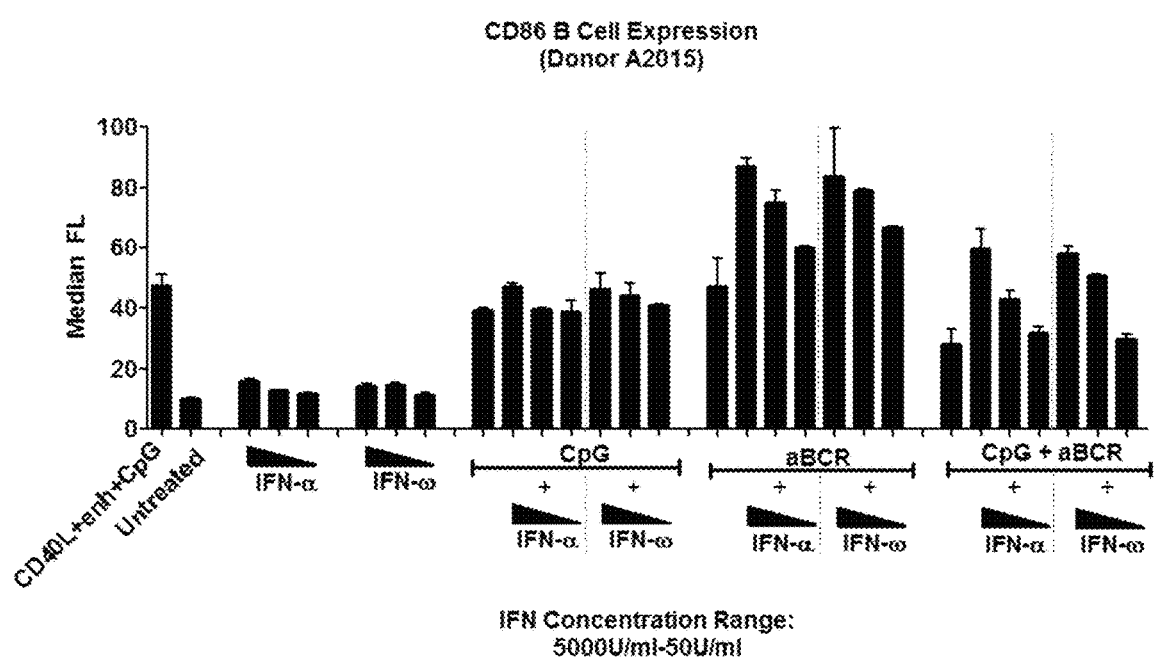
FIG. 5A shows that IFN-ω induces T-cell independent B cell activation to the same degree as IFN-α. B cell activation was assessed by CD86 surface expression using fluorescently labeled anti-CD86 antibody. T-cell independent B cell activation was induced by CpG (ODN2006) and/or anti-B cell receptor (aBCR) antibodies as indicated in the figure. IFN-ω or IFN-α (IFN-αB2) was used at indicated concentration. Median fluorescence was measured. B cells were obtained from one donor. The results were expressed as mean values of duplicate samples±SD.
Figure 5B:
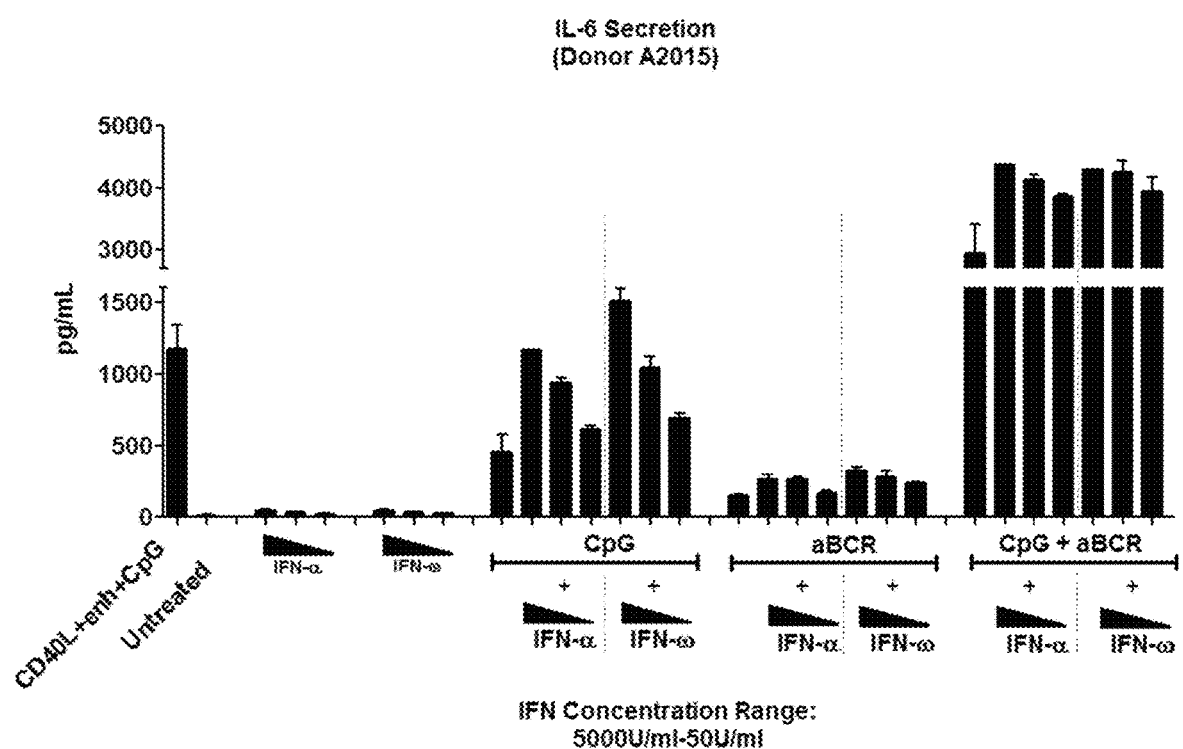
FIG. 5B shows that IFN-ω induces IL-6 secretion from B cells activated in non-T cell dependent fashion to the same degree as IFN-α. T-cell independent B cell activation was induced by CpG (ODN-2006) and/or anti-BCR antibodies (aBCR) as indicated in the figure. IFN-ω or IFN-α (IFN-α2B) was used at indicated concentration. IL-6 concentration is indicated as pg/ml. B cells were obtained from one donor. The results were expressed as mean values of duplicate samples±SD.

Dose-dependent IFN-ω-induced up-regulation of CD86 expression upon anti-BCR and anti-BCR/CpG stimulation was observed with both donor samples tested, whereas co-culture of B lymphocytes without stimulus showed only a weak effect. INF-ω induced CD86 expression to a similar extent than IFN-α2B. FIG. 5A shows the IFN-ω-induced CD86 expression from B cells from one donor. IFN-ω also dose-dependently induced IL-6-production upon CpG and anti-BCR/CpG stimulation to similar extent than IFN-α2B with both donor samples tested. FIG. 5B shows the IFN-ω-induced IL-6 secretion from B cells from one donor.

IFN-ω Induces BLyS Secretion

BLyS (BAFF) is a B cell survival factor and a clinically validated target in human SLE. IFN-α treatment has been found to induce BLyS gene expression in vivo as determined by microarray and qPCR analysis of PBMCs isolated from patients 24 h after dosing. Ability of IFN-ω to induce secretion of BLyS was therefore assessed.

PBMCs were isolated from two different normal healthy donors. Equivalent concentrations of IFN-ω and IFN-α were used to stimulate cells for 72 hours at which time supernatants were collected and analyzed by ELISA for soluble BLyS. Results were expressed as mean values of duplicate samples±SD.

Figure 6:
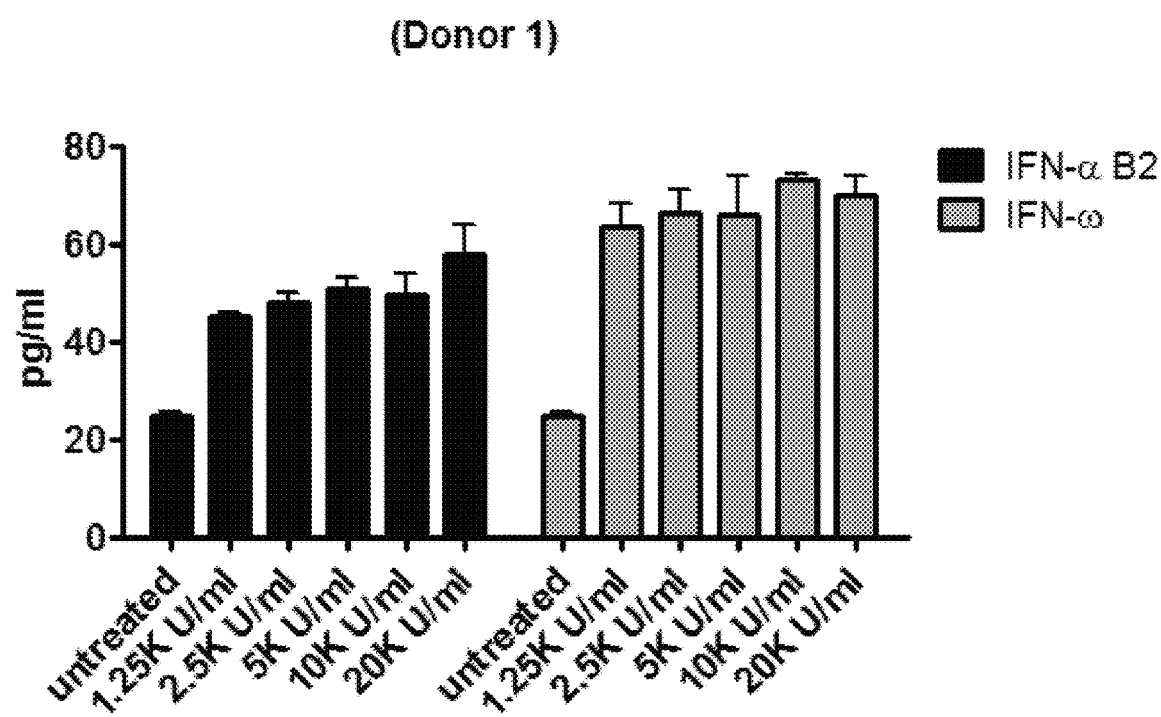
FIG. 6 shows that IFN-ω induces BLyS secretion from human PBMCs to the same degree as IFN-α (IFN-αB2). The concentration of IFN-ω or IFN-α used to stimulate PBMCs is indicated in the X-axis. BLyS concentration is shown as pg/ml. Results are expressed as mean values of duplicate samples±SD.

IFN-ω and IFN-α were similarly competent in inducing the secretion of BLyS in human PBMCs in vitro. Results from one donor are shown in FIG. 6.

EXAMPLE 4

Generation of Human Type I IFN Antigens Used for Immunization, Phage Panning, Antibody Characterization, and Crystallography Studies 20 individual recombinant human type I IFN alphas shown in Table 4 were cloned and expressed in HEK 293 cells using standard methods using signal sequences, such as SEQ ID NOs: 21-25. The proteins are human unless otherwise stated. To improve expression level and solubility, a single amino acid mutant at position 80 of human IFN-ω, IFN-ω T80E was generated and expressed in HEK 293 cells. The T80E IFN-ω variant (SEQ ID NO: 2) had comparable activity to the wild type protein. IFN-αD and IFN-α1 differ by one amino acid at position 114 (valine vs alanine). Alpha A and Alpha 2 differ by one amino acid at position 23 (lysine in Alpha A vs. arginine in Alpha 2). Alpha 4 has two forms, 4a and 4b that differ by two amino acids at position 51 (alanine in Alpha 4a and threonine in Alpha 4b) and 114 (glutamate in Alpha 4a vs valine in Alpha 4b). These variations are located outside the receptor binding region and do not affect activity. Antibodies were found to neutralize these pairs of variants (αD/α1, αA/α2 and α4a/α4b) equally well and subsequently in some experiments only one antigen of each pair was used.

TABLE 4

| IFN Protein | Alternative Name | GenBank Accession Number Adopted | SEQ ID NO: |
|---|---|---|---|
| IFN-αA | IFN-α2a | V00549 | 5 |
| IFN-αB2 | IFN-α8 | X03125 | 6 |
| IFN-αC | IFN-α10 | NM_002171.1 | 7 |
| IFN-αD | Val114 IFN-α1 | V00538 | 8 |
| IFN-αF | IFN-α21 | V00540 | 9 |
| IFN-αG | IFN-α5 | X02956 | 10 |
| IFN-αH2 | IFN-α14 | X02959 | 11 |
| IFN-αI | IFN-α17 | V00532 | 12 |
| IFN-αJ1 | IFN-α7 | X02960 | 13 |
| IFN-αK | IFN-α6 | X02958 | 14 |
| IFN-α4b | IFN-α4 | X02955 | 15 |
| IFN-αWA | IFN-α16 | X02957 | 16 |
| IFN-α2 | IFN-α2b | V00548, NM_00605.2 | 17 |
| IFN-α1 | Ala114 IFN-αD | J00210 | 18 |
| IFN-α4a | IFN-αM1 | NM_021068 | 19 |
| IFN-β | | V00534 | 20 |
| IFN-ω | | NM_002177.1 | 1 |
| IFN-ω T80E | | | 2 |
| Chimp IFN-ω | | XM_528554.1 | 3 |
| Cyno IFN-ω | | NA | 4 |

EXAMPLE 5

Generation of Antibodies Binding to IFN-α and IFN-ω

IFN-α and IFN-ω-binding Fabs were selected from de novo pIX phage display libraries as described in Shi et al., J Mol Biol 397:385-96, 2010; Int. Pat. Publ. No. WO2009/085462; U.S. Pat. Publ. No. US2010/0021477). Briefly, the libraries were generated by diversifying human scaffolds where germline VH genes IGHV1-69*01, IGHV3-23*01, and IGHV5-51*01 were recombined with the human IGHJ-4 minigene via the H3 loop, and human germline VLkappa genes O12 (IGKV1-39*01), L6 (IGKV3-11*01), A27 (IGKV3-20*01), and B3 (IGKV4-1*01) were recombined with the IGKJ-1 minigene to assemble complete VH and VL domains. The positions in the heavy and light chain variable regions around H1, H2, L1, L2 and L3 loops corresponding to positions identified to be frequently in contact with protein and peptide antigens were chosen for diversification. Sequence diversity at selected positions was limited to residues occurring at each position in the IGHV or IGLV germline gene families of the respective IGHV or IGLV genes. Diversity at the H3 loop was generated by utilizing short to mid-sized synthetic loops of lengths 7-14 amino acids. The amino acid distribution at H3 was designed to mimic the observed variation of amino acids in human antibodies. Library design is detailed in Shi et al., J Mol Biol 397:385-96, 2010. The scaffolds utilized to generate libraries were named according to their human VH and VL germline gene origin. The three heavy chain libraries were combined with the four germline light chains or germline light chain libraries to generate 12 unique VH:VL combinations for panning experiments against IFN-α and IFN-ω.

The libraries were panned against either biotinylated human IFN-α2 or biotinylated human IFN-αG. After three rounds of panning, a polyclonal phage ELISA using human IFN-α2, IFN-αG and cynomolgus IFN-ω as antigens was performed to detect the specific enrichment of individual panning experiments. The phage collected from those panning experiments which demonstrated enrichment for binders to IFN-α2, IFN-αG and IFN-ω were further screened with a monoclonal Fab ELISA in which Fab proteins expressed from individual Fab clones were used as binders. The Fab clones with binding signal to 20 nM biotinylated antigen three times higher than the negative control were selected for secondary Fab screening. Select Fabs were cloned into IgG1/κ background and characterized further using ProteOn and ISRE reporter gene assay. From these assays, mAb IFWM371 was selected for further engineering and affinity maturation.

Table 5 shows affinities ($K_D$) and $IC_{50}$ values for IFWM371 as measured using ProteOn and ISRE reporter gene assay for various Type I IFNs as well as IFN-β. Except IFN-α1 (IFN-αD), IFWM371 bound to all human IFN-alpha proteins tested ranging from 179 pM-10 nM. The antibodies did not bind IFN-α1 (IFN-αD). The antibody bound also human, chimpanzee and cynomolgus IFN-ω but did not bind IFN-β. IFWM371 demonstrated neutralizing activity to all tested IFN-α molecules except IFN-α1 (αD), which the antibody did not neutralize. IFWM371 contains the VH IFWH591 (SEQ ID NO: 28) and the VL PH9L4 (germline O12) (SEQ ID NO: 29.

TABLE 5

| | $K_D$ (pM) | $IC_{50}$ (nM) |
|---|---|---|
| IFN-αA | 813 | 8.4 |
| IFN-αB2 | 1140 | 19.3 |
| IFN-αC | 1670 | 53.9 |
| IFN-αD | NB | NN |
| IFN-αF | 5310 | 16 |
| IFN-αG | 1110 | 12.9 |
| IFN-αH2 | 179 | 9.6 |
| IFN-αJ1 | 10800 | 35.7 |
| IFN-αK | 245 | 7.3 |
| IFN-αWA | 3180 | 74.2 |
| IFN-α4a | 5390 | 32.8 |
| IFN-β | NB | NN |
| chimp IFN-ω | 1080 | |
| cyno IFN-ω | 887 | |
| human IFN-ω | ND | 43.9 |

NB: no binding
ND: not done
NN: non-neutralizing

EXAMPLE 6

Crystal Structure of IFWM371 in Complex with IFN-ω T80E

In order to reveal the epitope and paratope, the structural basis for its broad binding specificity to IFN-α subtypes and IFN-ω, and to provide support for engineering to improve affinity and specificity, the crystallography study of human IFN-ω T80E in complex with Fab of IFWM371 was performed.

His-tagged Fab IFWM371 (IgG1/kappa isotype) was cloned and expressed in HEK293 cells and purified using affinity, ion exchange and size-exclusion chromatography. The Fab was received in 20 mM Tris pH 7.4, 50 mM NaCl. Human IFN-ω T80E variant (hereafter simply IFN-ω) with a C-terminal 6x His-Tag was expressed in HEK293 cells. The protein was received in 20 mM Tris, pH 7.4, 50 mM NaCL.

The complex was prepared by mixing of IFN-ω with Fab IFWM371 in molar ratio of 1.2:1.0 (excess IFN-ω), incubated at 4° C. overnight, and purified on Superdex 200 column equilibrated with 20 mm HEPES pH 7.5, 0.25 M NaCl, then concentrated to 9.96 mg/ml using Amicon-Ultra 10 kDa cutoff. Crystals suitable for X-diffraction were obtained from 20% PEG 3K, 0.2M ammonium phosphate dibasic with MMS seeding (Obmolova, G., Malia, T. J., Teplyakov, A., Sweet, R. & Gilliland, G. L. (2010). Promoting crystallization of antibody-antigen complexes via microseed matrix screening. *Acta Crystallogr D Biol Crystallogr* 66, 927-33.).

For X-ray data collection, one crystal of IFN-ω/Fab IFWM371 complex was soaked for a few seconds in the mother liquor (20% PEG 3350, 0.2 M $(NH_4)_2HPO_4$, pH 7.9) supplemented with 20% glycerol, and flash frozen in the stream of nitrogen at 100 K. X-ray diffraction data were collected using a Rigaku MicroMax™-007HF microfocus X-ray generator equipped with an Osmic™ VariMax™ confocal optics, Saturn 944 CCD detector, and an X-stream™ 2000 cryocooling system (Rigaku, Tex.). Diffraction intensities were detected over a 205° crystal rotation in quarter-degree images. The X-ray data were processed with the program XDS. X-ray data statistics are given in Table 6.

The structure of the IFN-ω/Fab IFM371 complex was solved by molecular replacement (MR) with Phaser. The search models for MR were the crystal structure of Fab 15 (PDB ID 3NA9; Luo, J., Obmolova, G., Huang, A., Strake, B., Teplyakov, A., Malia, T., Muzammil, S., Zhao, Y., Gilliland, G. L. & Feng, Y. (2010). Coevolution of antibody stability and Vkappa CDR-L3 canonical structure. *J Mol Biol* 402, 708-19) and IFN-α4A. However, an MR solution could not be obtained for IFN-ω due to severe inter-molecular clashes. Inspection of the electron density map phased with Fab IFWM371 alone showed the electron density for over half of the IFN-ω molecule is missing. However, the remaining part of the IFN-ω molecule was readily fit in the density. The structure was then refined with PHENIX and model adjustments were carried out using COOT.

TABLE 6

| Crystal data | |
| --- | --- |
| Space group | C2 |
| Unit cell dimensions | |
| a, b, c (Å) | 153.84, 69.84, 54.69 |
| α, β, γ (°) | 90, 106.87, 90 |
| Asymmetric unit content | 1 complex |
| X-ray data | |
| Resolution (Å) | 50-1.81 (1.85-1.81)* |
| Number of measured reflections | 175,220 (1,217) |
| Number of unique reflections | 43,466 (588) |
| Completeness (%) | 85.20 (39.5) |
| $R_{merge}$ | 0.056 (0.321) |

TABLE 6-continued

| | |
| --- | --- |
| $<I/\sigma>$ | 16.1 (3.1) |
| B-factor (Wilson plot) (Å$^2$) | 20.1 |
| Refinement | |
| Resolution (Å) | 30.6-1.81 (1.84-1.81) |
| Number of refls used in refinement | 43,463 (1113) |
| Number of all atoms | 4,594 |
| Number of water molecules | 481 |
| Rcryst (%) | 18.3 (25.9) |
| Rfree (%) | 21.5 (38.1) |
| RMSD bond lengths (Å) | 0.002 |
| RMSD bond angles (°) | 0.73 |
| RMSD B-factor main-chain (Å$^2$) | 5.6 |
| Mean B-factor (Å$^2$) | 26.0 |
| Protein | 23.2 |
| Solvent | 38.0 |
| MolProbity [25] | |
| Clash score | 6.8 |
| Rotamer outliers (%) | 1.2 |
| Ramachandran favored (%) | 98.5 |
| Ramachandran outliers (%) | 0.0 |
| Cβ deviation >0.25 Å | 0 |

*Values for high-resolution shell are in parentheses

Figure 7A:
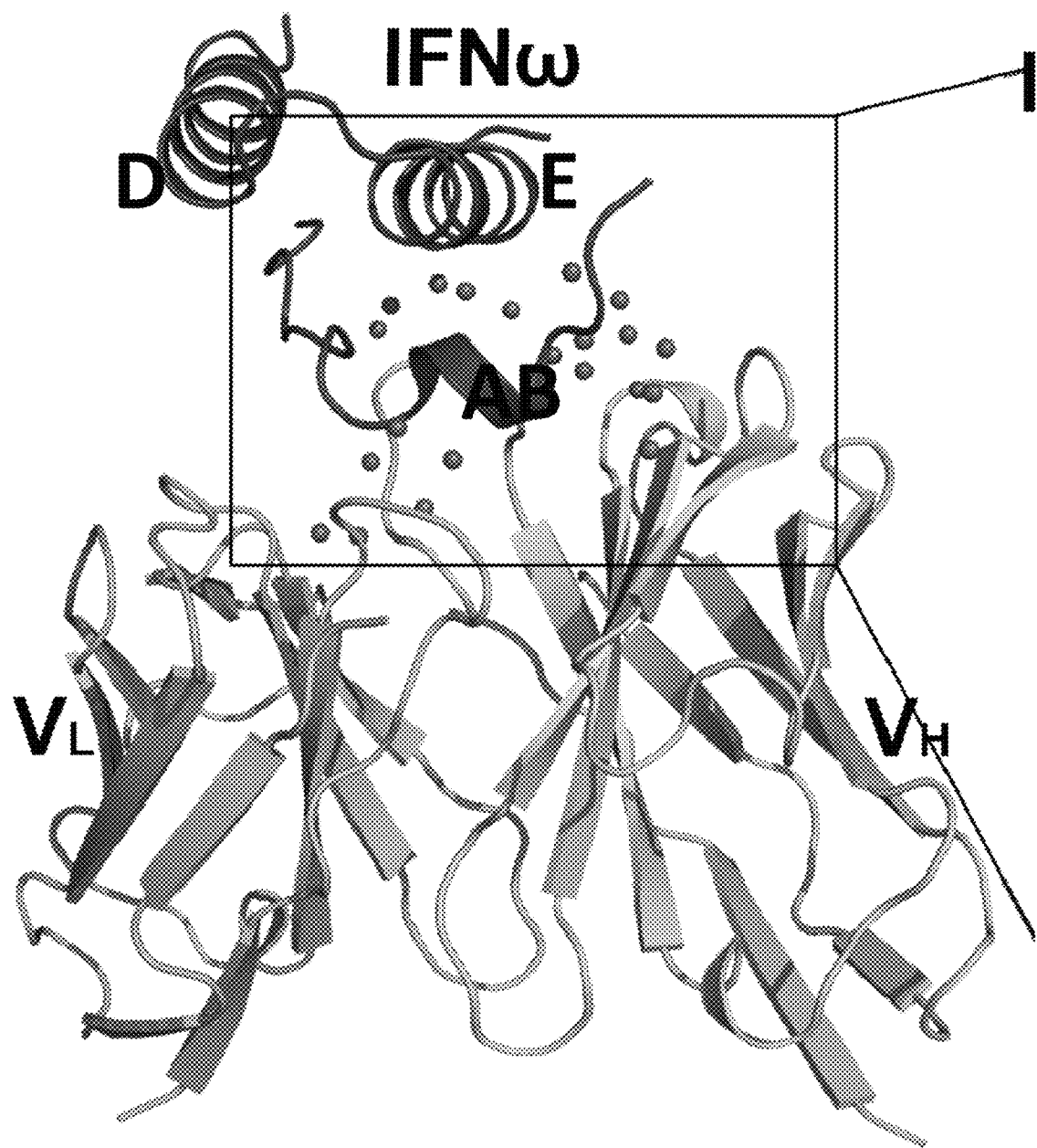
FIG. 7A shows the overall molecular structure of the IFN-ω/Fab IFWM371 complex (only the FAT for the antibody is shown). The boxed area is magnified in FIG. 7B. IFN-ω AB loop (AB), E helix (E) and D helix (D) of IFN-ω are indicated. Small circles represent water molecules. VL and VH or IFWM371 are indicated.
Figure 7B:
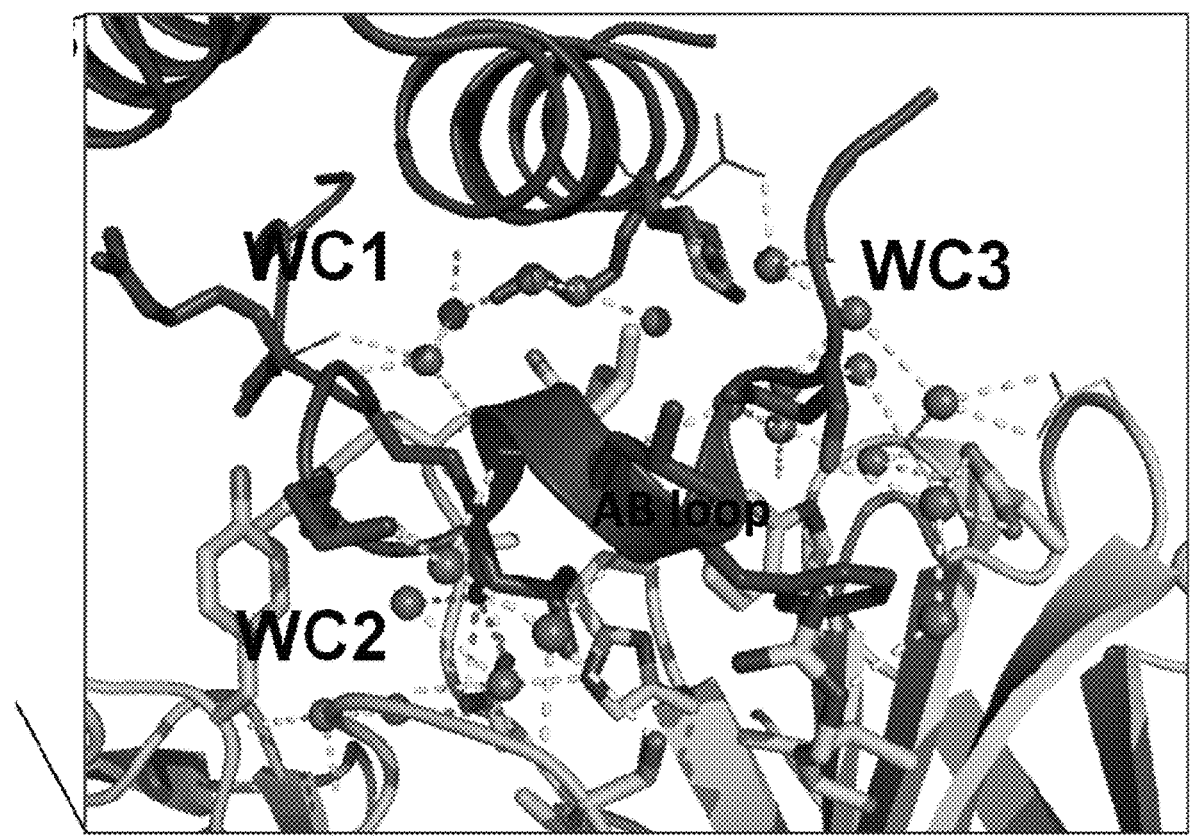
FIG. 7B shows a magnification of the boxed area of FIG. 7A, demonstrating hydrogen bonding network mediated through water molecules (water complex (WC) 1, 2, and 3) at the IFN-ω/Fab IFWM371 interface.

The overall molecular structure of the IFN-ω/Fab IFWM371 complex is shown in FIG. 7A. There was one complex in the asymmetric unit. The molecular model for the IFN-ω molecule included residues 23-39 and 119-153, corresponding to helical segment AB and helices D and E. Residue numbering is according to IFN-ω amino acid sequence shown in SEQ ID NO: 1. The helices A, B and C and the connecting loops were disordered. The Fab molecular model contained residues from 1 to 212 for the light chain (SEQ ID NO: 29) and from 1 to 222 for the heavy chain (SEQ ID NO: 28). The C-terminal 6x His tag, interchain disulfide bond and residues of 137-141 of the heavy chain were disordered. In addition, there were a number of water molecules at the antibody/antigen interface that formed an extensive H-bonding networks (FIG. 7B).

The observed parts of IFN-ω molecule were nearly identical to the corresponding parts of full-length model of a published IFN-ω (PDB id 3se4, Cα rmsd of 0.54 Å for 40 residues) and very similar to IFN-α2 with an average Cα rmsd of 0.42 Å (six IFN-α2 molecules, pdb code 1rh2) for about 40 Cα atoms. The model for IFN-ω in the IFN-ω/Fab IFWM371 contained only parts of helices C and D as well as connecting loop (loop AB). The other parts were absent in the electron density. Crystal packing analyses showed that there was not enough room for the missing helices. Careful analyses of the diffraction data indicated this was not an artifact due to abnormalities such as twinning or incorrect space group assignment. Thus, it was most likely that the IFN-ω protein had been cleaved during the crystallization process.

Figure 8A:
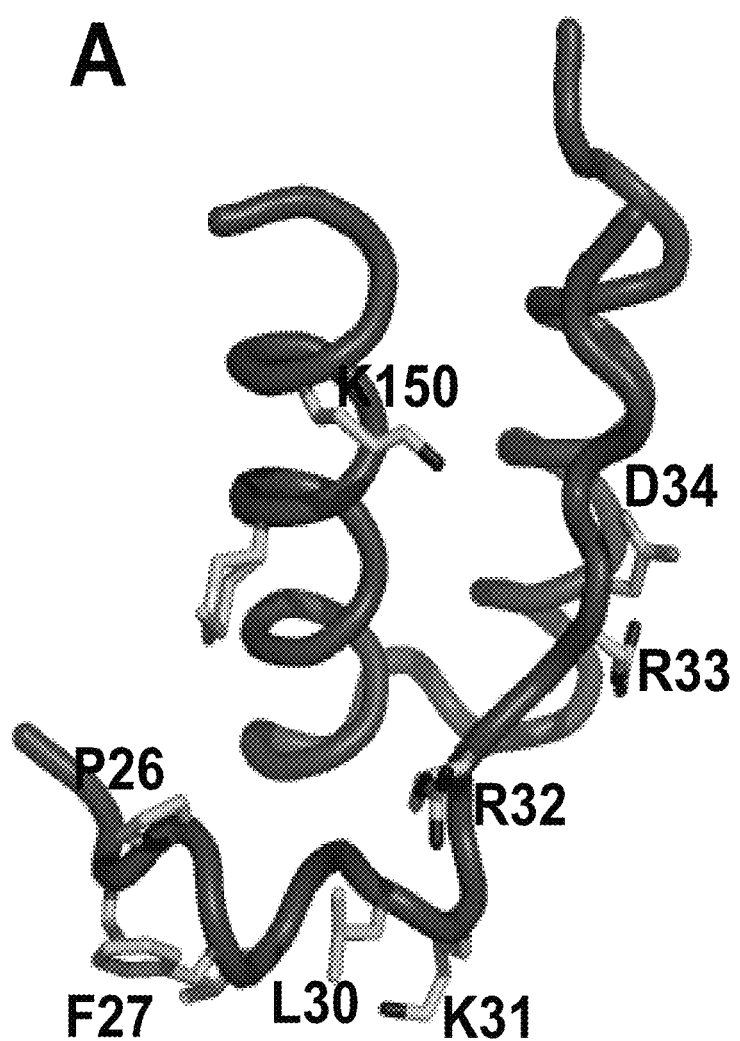
FIG. 8A shows the epitope in the IFN-ω/Fab IFWM371 complex. IFN-ω residue numbering according to SEQ ID NO: 1.
Figure 8B:
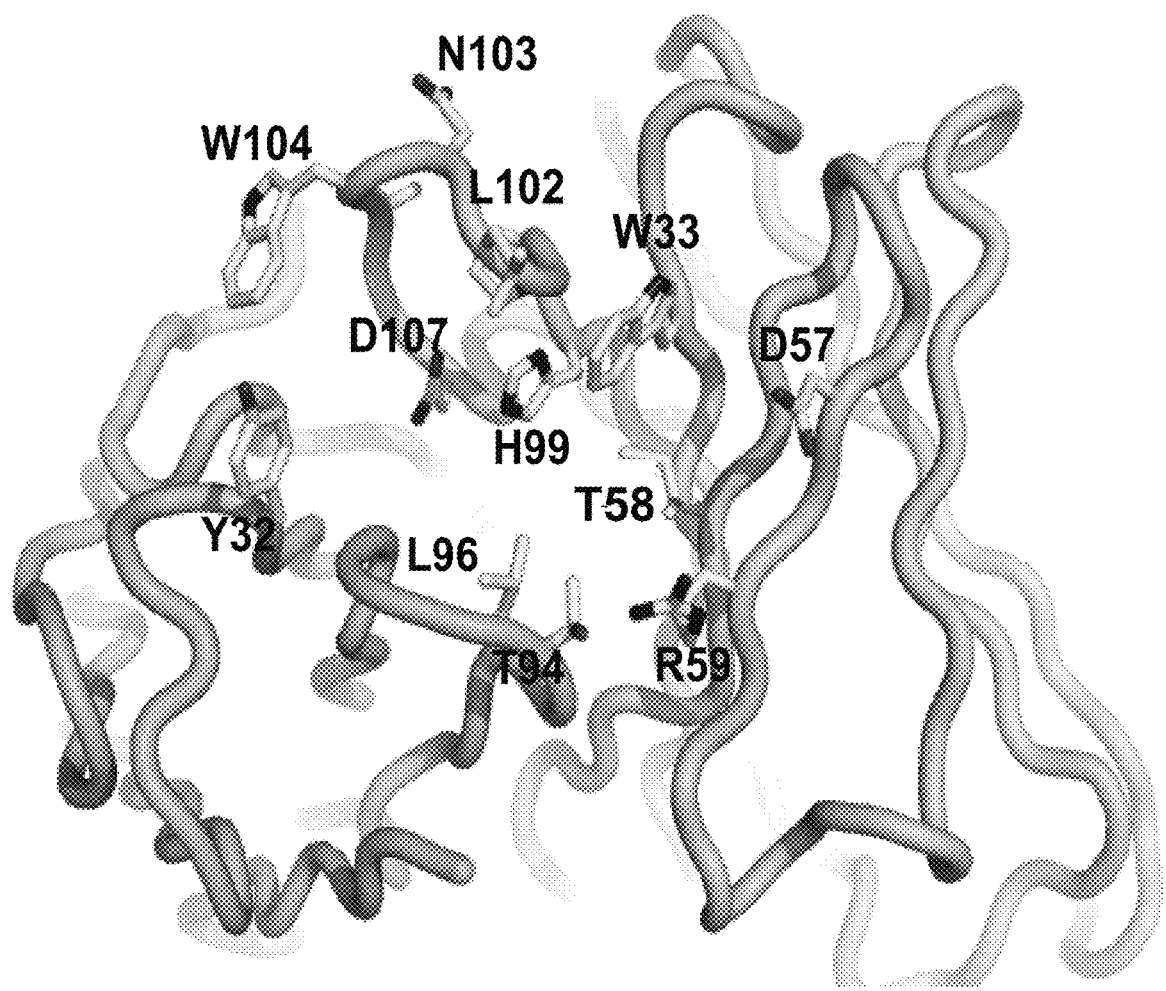
FIG. 8B shows the paratope in the IFN-ω/Fab IFWM371 complex. Residues Y32, Y92, T94 and L96 are residues in the VL, and residues W33, I50, D57, T58, R59, H99, P100, G101, L102, N103, W104, A105 and D107 are residues in the VH in contact with IFN-ω. VL: SEQ ID NO: 29; VH: SEQ ID NO: 28. T94 and A105 are not shown in the figure.
Figure 8C:
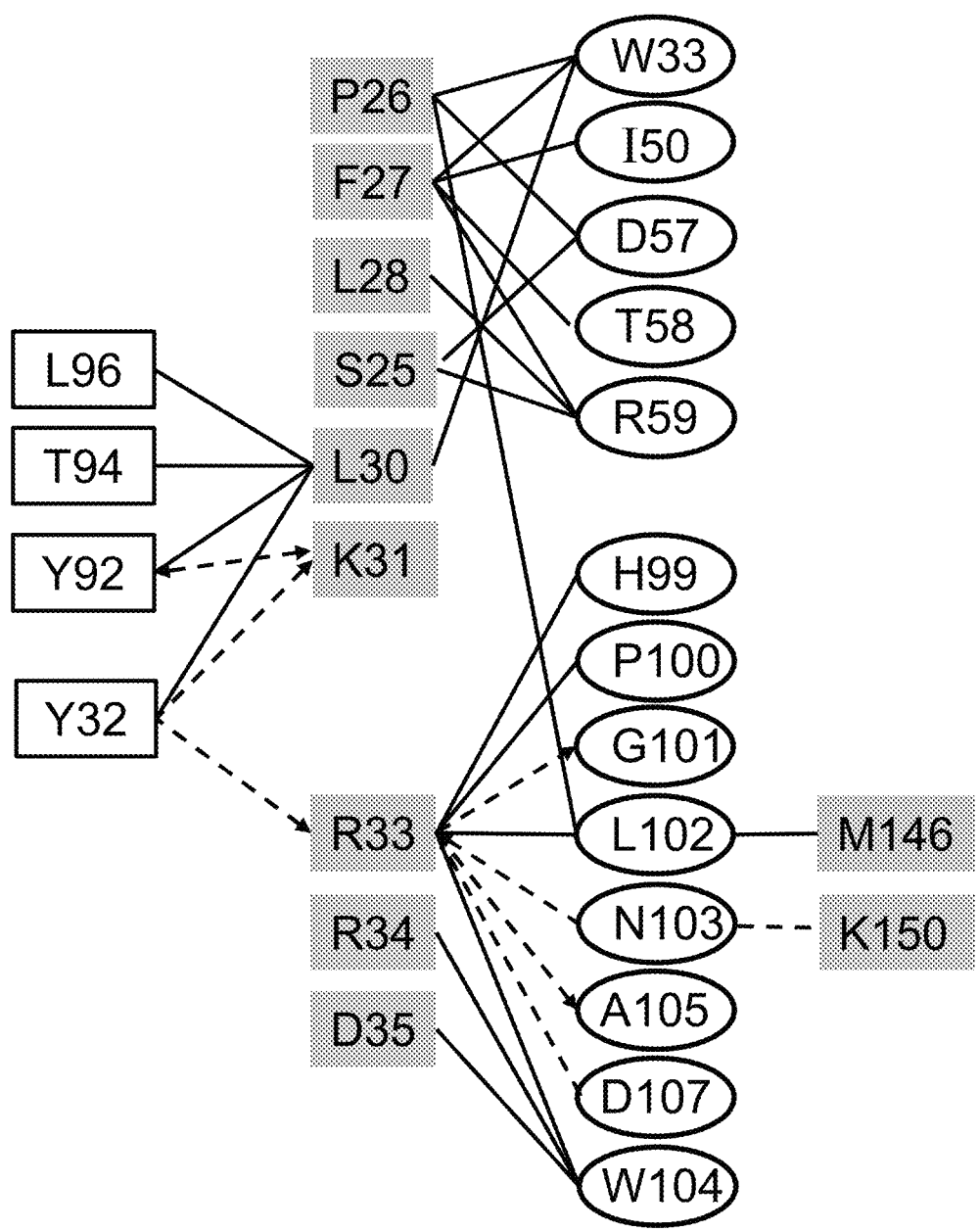
FIG. 8C shows a 2-dimensional interaction map between IFN-ω and Fab IFWM371. Boxed residues are VL paratope residues, and circled residues are VH paratope residues. Residues highlighted in gray are IFN-ω epitope residues. Numbering of VL, VH and IFN-ω residues is according to SEQ ID NOs: 29, 28 and 1, respectively. Van der Walls (VDW) and hydrophobic interactions are shown in solid lines, electrostatic and H bonds in dashed lines, arrows indicate backbone interactions with the arrows pointing to the backbone atoms. Most interactions are formed by the three IFN-ω epitope residues F27, L30 and R33.

Fab IFWM371 recognized a conformational epitope that is composed of residues of the AB loop (between S25 and D35) and residues M146, and K150 of helix E (FIG. 8A). The paratope is composed of residues from five CDRs except LCDR2. The paratope residues form a series of pockets into which dock the side chains of residues F27, L30, and R33 of the short AB helix of IFN-ω. FIG. 8B shows the paratope residues in VL and VH of IFWM371. The antibody and antigen interactions appear to be mostly van der Waals (vdw) and hydrophobic packing as well as H bonds between the antibody and antigen. FIG. 8C shows a 2D Interaction map between IFN-ω and IFWM371 interactions. In the figure, IFN-ω epitope residues are highlighted in grey, VL paratope residues are boxed, and VH paratope residues are circled. The figure demonstrates that most antigen/antibody interactions are formed by the three epitope residues F27, L30 and R33 of the IFN-ω AB helix. Thus, this region of IFN-ω constitutes the main part of the epitope. Another feature of this complex is that water molecules appeared to play a significant role mediating antigen recognition. Three water clusters (WCs) were present at the interface. WC1 contributed to H bond interactions between HCDR3 and R34, F36 and E147 of IFN-ω. WC2 mediated VH/VL pairing and H bonding between Fv and the main epitope residues L30, R33 and its neighbors. WC3 water molecules were at the periphery of the interface, probably less important for the interactions.

Figure 9:
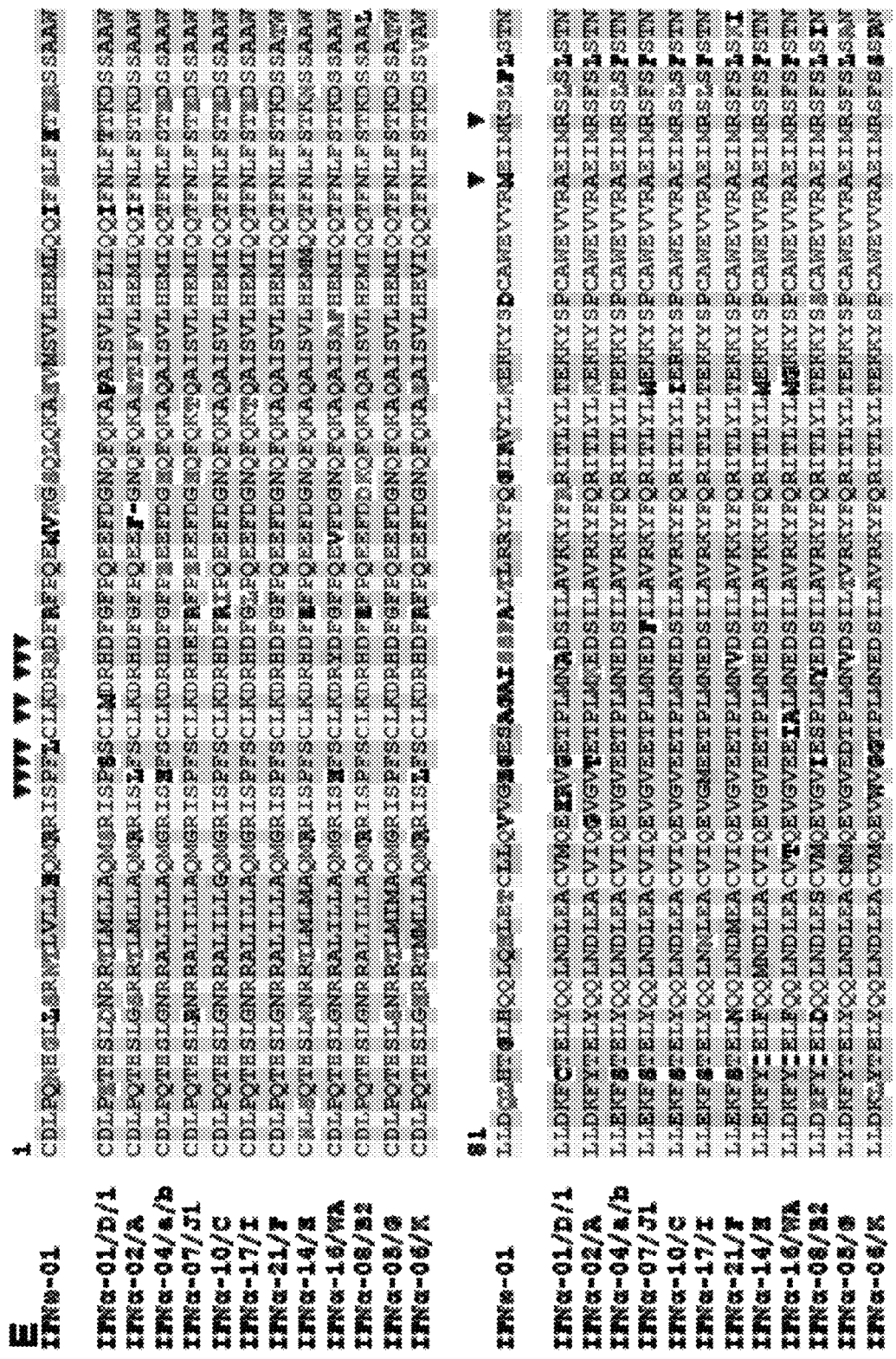
FIG. 9 shows an alignment of IFN-ω with various IFN-α subtypes. Arrows indicate epitope residues IFWM371 binds to. F27, L30 and R33 are conserved across Type I IFNs, except in IFN-αD to which IFWM371 does not bind to. Residue numbering is according to human IFN-ω SEQ ID NO: 1 (IFNω-01 in the Figure). IFNα-01/D/1: SEQ ID NO: 18; IFNα-02/A: SEQ ID NO: 5; IFNα-04/a/b: SEQ ID NO: 15; IFNα-07/J: SEQ ID NO: 13; IFNα-10/C: SEQ ID NO: 7; IFNα-17/I: SEQ ID NO: 12; IFNα-21/F: SEQ ID NO: 9; IFNα-14/H: SEQ ID NO: 11; IFNα-16/WA: SEQ ID NO: 16; IFNα-08/B2: SEQ ID NO: 6; IFNα-05/G: SEQ ID NO: 10; IFNα-06/K: SEQ ID NO: 14.

IFWM371 strongly binds a number of IFN-α subtypes and IFN-ω except IFN-αD or IFN-α1. IFWM371 does not bind IFN-β. The sequence alignment of IFNs is shown in FIG. 9. The IFWM371 epitope residues are largely conserved among the subtypes, suggesting that the broad specificity of IFNM371 is a result of epitope conservation. IFN-αD or IFN-α1, however, to which IFWM371 does not bind to, contains S27 instead of F27, leading to a loss of the majority of hydrophobic contacts of F27 side chain. Since F27 is docked in a deep pocket formed by residues of HCDR2, HCDR3 and LCDR3, loss of the side chain contacts most likely accounts for the very low or no binding by IFN-αD and IFN-α1 proteins. This also suggests that F27 is one of the binding "hot spot" residues. P26 is a residue that is less well conserved. A His or Leu residue occupies this position in several IFN-α subtypes. Because of the size and shape differences, this residue can significantly influence the local interactions between IFWM371 and IFN-α's with these mutations.

EXAMPLE 7

Alanine Scan of IFWM371

Alanine scan of IFWM371 heavy and light chain CDR residues was conducted to guide subsequent affinity-maturation efforts. All residues in the CDRs of both heavy and light chains were replaced with alanine except some low solvent exposure or non-solvent exposed residues. When native residues at CDRs were alanine, they were replaced with Tyrosine and/or Serine and/or Aspartic acid. One position with possible developability liabilities (W104 in IFWH591, SEQ ID NO 28) was replaced with Alanine, Tyrosine, Serine, and Aspartic acid. The mutated mAbs were transiently expressed in HEK 293 cells and cell supernatants were tested for binding activity to a panel of IFNs by ELISA. Two $V_H$ mutants, IFWH591 R59A (SEQ ID NO: 30) and IFWH591 N103A (SEQ ID NO: 31), had significantly improved binding compared to the parent mAb.

EXAMPLE 8

Affinity-Maturation of IFWM371

Library Design

Two distinct $V_L$ libraries (PH9L4L2 and PH9L4L3) were designed and used to affinity-mature IFWM371 light chain PH9L4 (O12) (SEQ ID NO: 29). The positions chosen for diversification of library PH9L4L2 were based on residue positions frequently found in anti-protein and anti-peptide complexes. The residues used to diversify each position were encoded within the germline gene family of IGKV genes (Shi et al (2010) J. Mol. Biol. 397:385-96). The library complexity was limited to not exceed $10^7$ library members so that the diversity could be fully assessed during affinity maturation (the actual library complexity: $3.5^7$). Table 7 shows the library design diversification scheme for LCDR1 position 30, 31 and 32, LCDR2 positions 50 and LCDR3 position 91, 92, 93, 94 and 96 of the $V_L$ PH9L4 (O12) in the library. Residue numbering is according to Kabat.

TABLE 7

| Amino acid position on O12 (SEQ ID NO: 29) | Diversified with amino acid |
|---|---|
| Ser30 | S, R, N, A, D |
| Ser31 | N, S, K, D, G |
| Tyr32 | Y, W, D, F, H, S, N, A, V |
| Ala50 | A, D, G, K, Y, F, T, N |
| Ser91 | Y, S, H, A |
| Tyr92 | Y, N, D, S, H, I, F, K, G, R, E |
| Ser93 | S, N, T, D, G, H, R |
| Thr94 | T, Y, L, V, F, S, R, G, P, I |
| Leu96 | W, Y, F, L, I, R, N |

The residue positions to be diversified in the second light chain affinity-maturation library, PH9L4L3, were chosen based on analysis of structures between antibody-protein complexes and the diversity in each position was designed based on analyzing antibody protein structures as well as the amino acid usage in germline genes for each position (G. Raghunathan et al, Antigen-binding site anatomy and somatic mutations in antibodies that recognize different types of antigens. J. Mol Recognit. 25:103-113 (2012). For LCDR3, diversity was extended beyond natural repertoire to ensure that each position has amino acids of different biochemical properties (i.e., polar/nonpolar, positively/negatively charged). Additionally, the relative frequency of each amino acid per position were varied which was made possible using the Sloning library synthesis technology. Table 8 shows the library composition of PH9L4L3. Residue numbering is according to Kabat.

TABLE 8

| Amino acid position on O12 (SEQ ID NO: 29) | Diversified with amino acid |
|---|---|
| Ser30 | S, R, N, A, D |
| Ser31 | N, S, T |
| Tyr32 | Y, N, D, S, R |
| Tyr49 | Y, K, E, H |
| Ala50 | A, Y, W, S, G, N |
| Ser91 | S, H, W, Y, E, A, G, D, N, R |
| Tyr92 | Y, S, H, W, E, A, G, D, N, R |
| Ser93 | S, H, W, Y, E, A, G, D, N, R |
| Thr94 | T, S, H, W, Y, E, A, D, N, R, G |
| Leu96 | W, Y, F, L, I |

Panning and Characterization

Affinity maturation libraries were generated by combining the light chain libraries PH9L4L2 or PH9L4L3 with the parental heavy chain IFWH591 (SEQ ID NO: 28). The libraries were then used for panning to select for high affinity antibodies. Some affinity-maturation panning experiments resulted in biased improvements in binding either only to IFN-ω or only to a few IFN-α subtypes but not both. In order to generate broadly neutralizing antibodies with improved $IC_{50}$ for most IFN-α subtypes and IFN-ω, a subset of IFN-α subtypes that were more diversified from each other (IFN-α2, IFN-α4a, IFN-αF and IFN-αG) were panned alternatively with cynomolgus monkey or human IFN-ω between each panning round. A total of three rounds of panning were carried out for each panning experiment.

Fab proteins of individual clones were expressed in TG-1 E. coli and bacterial cell lysates were used for Fab ELISAs to determine their affinities to human IFN-α4a, IFN-αF and IFN-ω compared to IFWM371. Since IFWM371 Fab bound these antigens weakly, Fab IFWF477 having higher affinity to the antigens was used as the surrogate Fab for comparison. 42 clones were identified that exhibited several folds higher binding activity than the surrogate Fab in ELISA. Some variants contained one amino acid insertion on LCDR1 which was not part of the original library design but was introduced during library synthesis. Overall, the affinity maturation of the VL resulted in a significant improvement in binding compared to the surrogate Fab. The best clones from the two libraries showed over 23-fold higher binding activity to human IFN-ω than the surrogate Fab IFWF477 respectively.

For further functional and biophysical characterization, total of 42 light chains derived from the libraries were paired with the parental heavy chain IFWH591 (SEQ ID NO: 28) as well as two $V_H$ variants with improved binding activity, IFWH624 (IFWH591 R59A, SEQ ID NO: 30) and IFWH629 (IFWH591 N103A, SEQ ID NO: 31), identified from the alanine scanning experiment described in Example 7. A total of 126 converted mAbs (42 light chains paired with three heavy chains) were then expressed and characterized further. Table 9 shows the parental and select affinity-matured antibodies and their heavy and light chain variable regions.

TABLE 9

| Antibody name | | | | | |
|---|---|---|---|---|---|
| Protein cDNA name | Protein amino acid name | VL Peptide name | VH Peptide name | VH SEQ ID NO: | VL SEQ ID NO: |
| IFWM371 | IFWB351 | PH9L4 | IFWH591 | 28 | 29 |
| IFWM3301 | IFWB3036 | IFWL983 | IFWH591 | 28 | 32 |
| IFWM3302 | IFWB3037 | IFWL991 | IFWH591 | 28 | 33 |
| IFWM3303 | IFWB3038 | IFWL992 | IFWH591 | 28 | 34 |
| IFWM3304 | IFWB3039 | IFWL997 | IFWH591 | 28 | 35 |
| IFWM3305 | IFWB3040 | IFWL998 | IFWH591 | 28 | 36 |
| IFWM3291 | IFWB3026 | IFWL999 | IFWH591 | 28 | 37 |
| IFWM3306 | IFWB3041 | IFWL1000 | IFWH591 | 28 | 38 |
| IFWM3307 | IFWB3042 | IFWL1001 | IFWH591 | 28 | 39 |
| IFWM3308 | IFWB3043 | IFWL1004 | IFWH591 | 28 | 40 |
| IFWM3309 | IFWB3044 | IFWL1006 | IFWH591 | 28 | 41 |
| IFWM3310 | IFWB3045 | IFWL1007 | IFWH591 | 28 | 42 |
| IFWM3311 | IFWB3046 | IFWL1009 | IFWH591 | 28 | 43 |
| IFWM3312 | IFWB3047 | IFWL1010 | IFWH591 | 28 | 44 |
| IFWM3313 | IFWB3048 | IFWL1013 | IFWH591 | 28 | 45 |
| IFWM3314 | IFWB3049 | IFWL1014 | IFWH591 | 28 | 46 |
| IFWM3315 | IFWB3050 | IFWL1017 | IFWH591 | 28 | 47 |
| IFWM3316 | IFWB3051 | IFWL1022 | IFWH591 | 28 | 48 |
| IFWM3317 | IFWB3052 | IFWL1026 | IFWH591 | 28 | 49 |
| IFWM3318 | IFWB3053 | IFWL1038 | IFWH591 | 28 | 50 |
| IFWM3319 | IFWB3054 | IFWL1041 | IFWH591 | 28 | 51 |
| IFWM3320 | IFWB3055 | IFWL1047 | IFWH591 | 28 | 52 |
| IFWM3321 | IFWB3056 | IFWL1048 | IFWH591 | 28 | 53 |
| IFWM3322 | IFWB3057 | IFWL1051 | IFWH591 | 28 | 54 |
| IFWM3323 | IFWB3058 | IFWL1053 | IFWH591 | 28 | 55 |
| IFWM3325 | IFWB3060 | IFWL1060 | IFWH591 | 28 | 56 |
| IFWM3327 | IFWB3062 | IFWL1063 | IFWH591 | 28 | 57 |
| IFWM3328 | IFWB3063 | IFWL1064 | IFWH591 | 28 | 58 |
| IFWM3329 | IFWB3064 | IFWL1067 | IFWH591 | 28 | 59 |
| IFWM3330 | IFWB3065 | IFWL1071 | IFWH591 | 28 | 60 |
| IFWM3331 | IFWB3066 | IFWL1073 | IFWH591 | 28 | 61 |
| IFWM3332 | IFWB3067 | IFWL1074 | IFWH591 | 28 | 62 |
| IFWM3333 | IFWB3068 | IFWL1076 | IFWH591 | 28 | 63 |
| IFWM3334 | IFWB3069 | IFWL1082 | IFWH591 | 28 | 64 |
| IFWM3335 | IFWB3070 | IFWL1084 | IFWH591 | 28 | 65 |
| IFWM3336 | IFWB3071 | IFWL1085 | IFWH591 | 28 | 66 |
| IFWM3337 | IFWB3072 | IFWL1087 | IFWH591 | 28 | 67 |
| IFWM3338 | IFWB3073 | IFWL1091 | IFWH591 | 28 | 68 |
| IFWM3339 | IFWB3074 | IFWL1093 | IFWH591 | 28 | 69 |
| IFWM3340 | IFWB3075 | IFWL983 | IFWH624 | 30 | 32 |
| IFWM3341 | IFWB3076 | IFWL991 | IFWH624 | 30 | 33 |
| IFWM3342 | IFWB3077 | IFWL992 | IFWH624 | 30 | 34 |
| IFWM3343 | IFWB3078 | IFWL997 | IFWH624 | 30 | 35 |
| IFWM3344 | IFWB3079 | IFWL998 | IFWH624 | 30 | 36 |
| IFWM3292 | IFWB3027 | IFWL999 | IFWH624 | 30 | 37 |
| IFWM3345 | IFWB3080 | IFWL1000 | IFWH624 | 30 | 38 |
| IFWM3346 | IFWB3081 | IFWL1001 | IFWH624 | 30 | 39 |
| IFWM3347 | IFWB3082 | IFWL1004 | IFWH624 | 30 | 40 |
| IFWM3348 | IFWB3083 | IFWL1006 | IFWH624 | 30 | 41 |
| IFWM3349 | IFWB3084 | IFWL1007 | IFWH624 | 30 | 42 |
| IFWM3350 | IFWB3085 | IFWL1009 | IFWH624 | 30 | 43 |
| IFWM3351 | IFWB3086 | IFWL1010 | IFWH624 | 30 | 44 |
| IFWM3352 | IFWB3087 | IFWL1013 | IFWH624 | 30 | 45 |
| IFWM3353 | IFWB3088 | IFWL1014 | IFWH624 | 30 | 46 |
| IFWM3354 | IFWB3089 | IFWL1017 | IFWH624 | 30 | 47 |
| IFWM3355 | IFWB3090 | IFWL1022 | IFWH624 | 30 | 48 |
| IFWM3356 | IFWB3091 | IFWL1026 | IFWH624 | 30 | 49 |
| IFWM3357 | IFWB3092 | IFWL1038 | IFWH624 | 30 | 50 |
| IFWM3358 | IFWB3093 | IFWL1041 | IFWH624 | 30 | 51 |
| IFWM3359 | IFWB3094 | IFWL1047 | IFWH624 | 30 | 52 |
| IFWM3360 | IFWB3095 | IFWL1048 | IFWH624 | 30 | 53 |
| IFWM3361 | IFWB3096 | IFWL1051 | IFWH624 | 30 | 54 |
| IFWM3364 | IFWB3099 | IFWL1060 | IFWH624 | 30 | 56 |
| IFWM3366 | IFWB3101 | IFWL1063 | IFWH624 | 30 | 57 |
| IFWM3367 | IFWB3102 | IFWL1064 | IFWH624 | 30 | 58 |
| IFWM3368 | IFWB3103 | IFWL1067 | IFWH624 | 30 | 59 |
| IFWM3369 | IFWB3104 | IFWL1071 | IFWH624 | 30 | 60 |
| IFWM3370 | IFWB3105 | IFWL1073 | IFWH624 | 30 | 61 |
| IFWM3371 | IFWB3106 | IFWL1074 | IFWH624 | 30 | 62 |
| IFWM3372 | IFWB3107 | IFWL1076 | IFWH624 | 30 | 63 |
| IFWM3374 | IFWB3109 | IFWL1084 | IFWH624 | 30 | 65 |
| IFWM3375 | IFWB3110 | IFWL1085 | IFWH624 | 30 | 66 |
| IFWM3376 | IFWB3111 | IFWL1087 | IFWH624 | 30 | 67 |
| IFWM3377 | IFWB3112 | IFWL1091 | IFWH624 | 30 | 68 |
| IFWM3378 | IFWB3113 | IFWL1093 | IFWH624 | 30 | 69 |
| IFWM3379 | IFWB3114 | IFWL983 | IFWH629 | 31 | 32 |
| IFWM3380 | IFWB3115 | IFWL991 | IFWH629 | 31 | 33 |
| IFWM3381 | IFWB3116 | IFWL992 | IFWH629 | 31 | 34 |
| IFWM3382 | IFWB3117 | IFWL997 | IFWH629 | 31 | 35 |
| IFWM3383 | IFWB3118 | IFWL998 | IFWH629 | 31 | 36 |
| IFWM3293 | IFWB3028 | IFWL999 | IFWH629 | 31 | 37 |
| IFWM3384 | IFWB3119 | IFWL1000 | IFWH629 | 31 | 38 |
| IFWM3385 | IFWB3120 | IFWL1001 | IFWH629 | 31 | 39 |
| IFWM3386 | IFWB3121 | IFWL1004 | IFWH629 | 31 | 40 |
| IFWM3387 | IFWB3122 | IFWL1006 | IFWH629 | 31 | 41 |
| IFWM3388 | IFWB3123 | IFWL1007 | IFWH629 | 31 | 42 |
| IFWM3389 | IFWB3124 | IFWL1009 | IFWH629 | 31 | 43 |
| IFWM3390 | IFWB3125 | IFWL1010 | IFWH629 | 31 | 44 |
| IFWM3391 | IFWB3126 | IFWL1013 | IFWH629 | 31 | 45 |
| IFWM3392 | IFWB3127 | IFWL1014 | IFWH629 | 31 | 46 |
| IFWM3393 | IFWB3128 | IFWL1017 | IFWH629 | 31 | 47 |
| IFWM3394 | IFWB3129 | IFWL1022 | IFWH629 | 31 | 48 |
| IFWM3395 | IFWB3130 | IFWL1026 | IFWH629 | 31 | 49 |
| IFWM3396 | IFWB3131 | IFWL1038 | IFWH629 | 31 | 50 |
| IFWM3397 | IFWB3132 | IFWL1041 | IFWH629 | 31 | 51 |
| IFWM3398 | IFWB3133 | IFWL1047 | IFWH629 | 31 | 52 |
| IFWM3399 | IFWB3134 | IFWL1048 | IFWH629 | 31 | 53 |
| IFWM3400 | IFWB3135 | IFWL1051 | IFWH629 | 31 | 54 |
| IFWM3401 | IFWB3136 | IFWL1053 | IFWH629 | 31 | 55 |
| IFWM3403 | IFWB3138 | IFWL1060 | IFWH629 | 31 | 56 |
| IFWM3405 | IFWB3140 | IFWL1063 | IFWH629 | 31 | 57 |
| IFWM3406 | IFWB3141 | IFWL1064 | IFWH629 | 31 | 58 |
| IFWM3407 | IFWB3142 | IFWL1067 | IFWH629 | 31 | 59 |
| IFWM3408 | IFWB3143 | IFWL1071 | IFWH629 | 31 | 60 |
| IFWM3409 | IFWB3144 | IFWL1073 | IFWH629 | 31 | 61 |
| IFWM3410 | IFWB3145 | IFWL1074 | IFWH629 | 31 | 62 |
| IFWM3411 | IFWB3146 | IFWL1076 | IFWH629 | 31 | 63 |
| IFWM3413 | IFWB3148 | IFWL1084 | IFWH629 | 31 | 65 |
| IFWM3414 | IFWB3149 | IFWL1085 | IFWH629 | 31 | 66 |
| IFWM3415 | IFWB3150 | IFWL1087 | IFWH629 | 31 | 67 |
| IFWM3416 | IFWB3151 | IFWL1091 | IFWH629 | 31 | 68 |
| IFWM3417 | IFWB3152 | IFWL1093 | IFWH629 | 31 | 69 |

TABLE 9-continued

| Protein cDNA name | Protein amino acid name | VL Peptide name | VH Peptide name | VH SEQ ID NO: | VL SEQ ID NO: |
|---|---|---|---|---|---|
| IFWM3418 | IFWB3153 | IFWL1049 | IFWH591 | 28 | 70 |
| IFWM3419 | IFWB3154 | IFWL1049 | IFWH629 | 31 | 70 |
| IFWM3420 | IFWB3155 | IFWL1049 | IFWH624 | 30 | 70 |
| IFWM3421 | IFWB3156 | IFWL984 | IFWH591 | 28 | 71 |
| IFWM3423 | IFWB3158 | IFWL984 | IFWH629 | 31 | 71 |

Affinities of the 126 generated mAbs to a panel of human IFN-ω and human IFN-α subtypes were measured by ProteOn. The mAbs were transiently transfected in triplicate along with controls in HEK 293E cells in 48-well plates and cell supernatants were used in this experiment. To increase the assay throughput, only one concentration of the individual antigen was used. Table 10 shows the $K_D$ values for the parental IFWM371 and select affinity-matured antibodies. Most of the mAbs showed significant improvement of binding affinity to all antigens tested. Some of them showed more than 100-fold improvement over the parental mAb.

TABLE 10

| Protein cDNA name | $K_D$ (pM) | | | | | | | | |
|---|---|---|---|---|---|---|---|---|---|
| | IFN-ω | IFN-αC | IFN-αF | IFN-αJ1 | IFN-α4a | IFN-αB2 | IFN-αG | IFN-αWA | IFN-α2 |
| IFWM371 | 1060 | 865 | 775 | 4230 | 4180 | 418 | 263 | 1390 | 116 |
| IFWM3301 | 18 | 24 | 29 | 74 | 146 | 39 | 29 | 79 | 42 |
| IFWM3302 | 52 | 83 | 72 | 231 | 268 | 54 | 98 | 168 | 250 |
| IFWM3303 | 13 | 79 | 134 | 157 | 299 | 32 | 82 | 168 | 63 |
| IFWM3304 | 32 | 26 | 32 | 53 | 120 | 40 | 37 | 92 | 23 |
| IFWM3305 | 31 | 114 | 113 | 154 | 223 | 17 | 127 | 201 | 245 |
| IFWM3291 | 28 | 45 | 51 | 122 | 317 | 60 | 67 | 125 | 82 |
| IFWM3306 | 20 | 27 | 25 | 86 | 147 | 30 | 29 | 70 | 38 |
| IFWM3307 | 46 | 62 | 55 | 305 | 426 | 55 | 58 | 162 | 132 |
| IFWM3308 | 38 | 52 | 53 | 203 | 246 | 49 | 45 | 99 | 109 |
| IFWM3309 | 55 | 109 | 140 | 275 | 383 | 41 | 120 | 139 | 96 |
| IFWM3310 | 65 | 57 | 40 | 101 | 177 | 63 | 54 | 91 | 384 |
| IFWM3311 | 12 | 36 | 21 | 56 | 223 | 16 | 56 | 72 | 134 |
| IFWM3312 | 13 | 22 | 20 | 68 | 144 | 22 | 13 | 38 | 35 |
| IFWM3313 | 56 | 74 | 84 | 221 | 354 | 74 | 118 | 155 | 295 |
| IFWM3314 | 20 | 26 | 21 | 39 | 92 | 16 | 28 | 42 | 57 |
| IFWM3315 | 63 | 59 | 50 | 134 | 240 | 92 | 61 | 115 | 192 |
| IFWM3316 | 42 | 42 | 33 | 70 | 168 | 57 | 87 | 73 | 123 |
| IFWM3317 | 16 | 133 | 121 | 206 | 370 | 11 | 126 | 162 | 223 |
| IFWM3318 | 18 | 30 | 34 | 119 | 252 | 48 | 40 | 91 | 64 |
| IFWM3319 | 34 | 52 | 44 | 151 | 274 | 76 | 49 | 107 | 152 |
| IFWM3320 | 21 | 20 | 13 | 61 | 89 | 26 | 33 | 41 | 24 |
| IFWM3321 | 33 | 33 | 24 | 79 | 159 | 45 | 36 | 58 | 90 |
| IFWM3322 | 40 | 42 | 33 | 127 | 272 | 56 | 58 | 86 | 37 |
| IFWM3323 | 73 | 77 | 48 | 144 | 337 | 77 | 94 | 121 | 104 |
| IFWM3325 | 11 | 22 | 32 | 92 | 111 | 6 | 33 | 91 | 55 |
| IFWM3327 | 39 | 34 | 35 | 113 | 164 | 60 | 35 | 106 | 60 |
| IFWM3328 | 108 | 99 | 91 | 360 | 410 | 132 | 72 | 207 | 482 |
| IFWM3329 | 59 | 50 | 51 | 166 | 258 | 95 | 61 | 173 | 532 |
| IFWM3330 | 45 | 112 | 366 | 631 | 375 | 58 | 82 | 175 | 38 |
| IFWM3331 | 15 | 12 | 13 | 72 | 85 | 21 | 15 | 26 | 33 |
| IFWM3332 | 34 | 31 | 54 | 135 | 139 | 55 | 50 | 76 | 68 |
| IFWM3333 | 53 | 65 | 89 | 607 | 477 | 137 | 77 | 258 | 457 |
| IFWM3334 | 345 | 620 | 5210 | 2400 | 744 | 436 | 941 | 517 | 86 |
| IFWM3335 | 42 | 49 | 61 | 245 | 336 | 111 | 77 | 137 | 151 |
| IFWM3336 | 19 | 47 | 61 | 110 | 235 | 46 | 51 | 105 | 35 |
| IFWM3337 | 20 | 17 | 16 | 71 | 91 | 22 | 34 | 37 | 43 |
| IFWM3338 | 57 | 46 | 64 | 245 | 319 | 108 | 46 | 200 | 134 |
| IFWM3339 | 49 | 59 | 65 | 161 | 235 | 94 | 79 | 141 | 115 |
| IFWM3340 | 4 | 48 | 41 | 124 | 201 | 8 | 24 | 56 | 44 |
| IFWM3341 | 8 | 104 | 88 | 275 | 445 | 7 | 63 | 134 | 151 |
| IFWM3342 | 68 | 142 | 164 | 269 | 589 | 43 | 14 | 95 | 47 |
| IFWM3343 | 20 | 65 | 63 | 157 | 237 | 60 | 60 | 83 | 106 |
| IFWM3344 | 78 | 161 | 140 | 274 | 442 | 80 | 112 | 105 | 305 |
| IFWM3292 | 18 | 123 | 98 | 295 | 613 | 21 | 49 | 72 | 254 |
| IFWM3345 | 4 | 72 | 120 | 169 | 324 | 9 | 92 | 111 | 158 |
| IFWM3346 | 52 | 105 | 117 | 505 | 480 | 44 | 86 | 170 | 183 |
| IFWM3347 | 48 | 96 | 136 | 411 | 350 | 41 | 84 | 125 | 347 |
| IFWM3348 | 50 | 83 | 64 | 164 | 89 | 58 | 20 | 49 | 42 |
| IFWM3349 | 7 | 56 | 52 | 123 | 174 | 8 | 65 | 102 | 291 |
| IFWM3350 | 20 | 57 | 54 | 55 | 161 | 33 | 98 | 66 | 366 |
| IFWM3351 | 4 | 48 | 53 | 140 | 113 | 10 | 15 | 33 | 30 |
| IFWM3352 | 60 | 121 | 152 | 287 | 267 | 48 | 90 | 87 | 193 |
| IFWM3353 | 6 | 54 | 55 | 95 | 110 | 6 | 16 | 31 | 90 |
| IFWM3354 | 17 | 43 | 32 | 98 | 123 | 23 | 43 | 52 | 360 |
| IFWM3355 | 26 | 55 | 52 | 79 | 122 | 39 | 60 | 41 | 212 |
| IFWM3356 | 274 | | | | | | | | |
| IFWM3357 | 4 | 23 | 39 | 130 | 170 | 8 | 14 | 37 | 8 |
| IFWM3358 | 18 | 54 | 47 | 223 | 319 | 62 | 48 | 123 | 103 |

TABLE 10-continued

| Protein cDNA name | K_D (pM) | | | | | | | | |
|---|---|---|---|---|---|---|---|---|---|
| | IFN-ω | IFN-αC | IFN-αF | IFN-αJ1 | IFN-α4a | IFN-αB2 | IFN-αG | IFN-αWA | IFN-α2 |
| IFWM3359 | 21 | 41 | 53 | 136 | 147 | 34 | 40 | 51 | 152 |
| IFWM3360 | 25 | 56 | 49 | 174 | 233 | 35 | 43 | 61 | 236 |
| IFWM3361 | 30 | 101 | 135 | 388 | 622 | 48 | 66 | 98 | 151 |
| IFWM3364 | 13 | 93 | 109 | 254 | 269 | 39 | 80 | 118 | 151 |
| IFWM3366 | 21 | 30 | 27 | 109 | 122 | 40 | 30 | 66 | 433 |
| IFWM3367 | 57 | 116 | 100 | 453 | 465 | 86 | 67 | 152 | 42735 |
| IFWM3368 | 28 | 62 | 59 | 181 | 203 | 62 | 48 | 103 | 47393 |
| IFWM3369 | 81 | 88 | 190 | 622 | 344 | 123 | 121 | 220 | 58 |
| IFWM3370 | 10 | 39 | 39 | 225 | 155 | 24 | 21 | 41 | 42 |
| IFWM3371 | 18 | 43 | 50 | 125 | 100 | 23 | 50 | 64 | 81 |
| IFWM3372 | 49 | 94 | 116 | 690 | 432 | 154 | 103 | 272 | 717 |
| IFWM3374 | 55 | 106 | 121 | 568 | 540 | 139 | 96 | 208 | 349 |
| IFWM3375 | 19 | 22 | 23 | 45 | 67 | 33 | 35 | 31 | 27 |
| IFWM3376 | 20 | 34 | 39 | 140 | 113 | 37 | 48 | 62 | 81 |
| IFWM3377 | 27 | 44 | 51 | 192 | 193 | 58 | 38 | 120 | 132 |
| IFWM3378 | 75 | 172 | 168 | 496 | 533 | 141 | 150 | 248 | 279 |
| IFWM3379 | 15 | 13 | 13 | 33 | 72 | 22 | 13 | 23 | 27 |
| IFWM3380 | 25 | 46 | 32 | 76 | 88 | 14 | 70 | 59 | 157 |
| IFWM3381 | 45 | 79 | 92 | 121 | 171 | 58 | 53 | 67 | 37 |
| IFWM3382 | 30 | 24 | 20 | 37 | 75 | 27 | 30 | 32 | 18 |
| IFWM3383 | 28 | 69 | 60 | 86 | 143 | 33 | 84 | 64 | 194 |
| IFWM3293 | 29 | 25 | 17 | 62 | 166 | 12 | 37 | 46 | 120 |
| IFWM3384 | 26 | 29 | 33 | 68 | 77 | 13 | 22 | 17 | 25 |
| IFWM3385 | 32 | 41 | 41 | 142 | 178 | 19 | 23 | 52 | 42 |
| IFWM3386 | 26 | 31 | 29 | 87 | 103 | 16 | 26 | 35 | 43 |
| IFWM3387 | 39 | 90 | 58 | 161 | 169 | 36 | 34 | 69 | 19 |
| IFWM3388 | 33 | 30 | 19 | 55 | 84 | 26 | 27 | 44 | 105 |
| IFWM3389 | 17 | 24 | 9 | 32 | 98 | 10 | 33 | 30 | 69 |
| IFWM3390 | 10 | 11 | 11 | 30 | 75 | 14 | 10 | 29 | 26 |
| IFWM3391 | 23 | 16 | 25 | 66 | 117 | 29 | 44 | 42 | 63 |
| IFWM3392 | 23 | 16 | 14 | 21 | 58 | 34 | 19 | 25 | 44 |
| IFWM3393 | 57 | 49 | 41 | 96 | 166 | 70 | 64 | 78 | 284 |
| IFWM3394 | 45 | 63 | 63 | 77 | 105 | 123 | 91 | 49 | 304 |
| IFWM3395 | 19 | 116 | 102 | 181 | 279 | 3 | 63 | 63 | 83 |
| IFWM3396 | 11 | 5 | 7 | 37 | 79 | 48 | 61 | 68 | 52 |
| IFWM3397 | 25 | 27 | 28 | 78 | 119 | 42 | 43 | 62 | 103 |
| IFWM3398 | 26 | 17 | 17 | 44 | 61 | 32 | 22 | 30 | 34 |
| IFWM3399 | 30 | 25 | 21 | 50 | 88 | 36 | 30 | 37 | 59 |
| IFWM3400 | 33 | 23 | 22 | 60 | 135 | 32 | 52 | 49 | 68 |
| IFWM3401 | 62 | 42 | 28 | 78 | 195 | 42 | 67 | 76 | 604 |
| IFWM3403 | 7 | 25 | 27 | 59 | 62 | 8 | 27 | 23 | 11 |
| IFWM3405 | 20 | 22 | 19 | 36 | 67 | 17 | 15 | 39 | 38 |
| IFWM3406 | 78 | 37 | 37 | 119 | 135 | 39 | 37 | 63 | 34 |
| IFWM3407 | 17 | 32 | 33 | 58 | 128 | 13 | 27 | 60 | 65 |
| IFWM3408 | 86 | 730 | 5690 | 1870 | 703 | 54 | 895 | 176 | 17 |
| IFWM3409 | 14 | 11 | 9 | 41 | 58 | 18 | 5 | 25 | 28 |
| IFWM3410 | 29 | 37 | 52 | 82 | 86 | 59 | 52 | 52 | 33 |
| IFWM3411 | 28 | 23 | 37 | 151 | 101 | 53 | 35 | 87 | 53 |
| IFWM3413 | 47 | 37 | 33 | 150 | 206 | 58 | 44 | 85 | 121 |
| IFWM3414 | 58 | 68 | 101 | 174 | 193 | 13 | 33 | 70 | 26 |
| IFWM3415 | 18 | 19 | 26 | 51 | 69 | 15 | 26 | 44 | 39 |
| IFWM3416 | 28 | 29 | 45 | 68 | 103 | 37 | 29 | 69 | 55 |
| IFWM3417 | 29 | 31 | 39 | 70 | 100 | 36 | 30 | 59 | 41 |
| IFWM3418 | 89 | 191 | 229 | 656 | 1160 | 206 | 178 | 493 | 208 |
| IFWM3419 | 86 | 126 | 158 | 399 | 582 | 90 | 81 | 193 | 87 |
| IFWM3420 | 36 | 113 | 118 | 299 | 475 | 61 | 37 | 124 | 35 |

Select antibodies from the panel of 126 were characterized in an ISRE assay for their ability to inhibit a spectrum of IFN-α subtypes and IFN-ω, and their solubility and biophysical characteristics were assessed. $IC_{50}$ values from the ISRE assay are shown in Table 11 and Table 12 for select antibodies. The $IC_{50}$ values were at double-digit pM or lower for several antibodies to 11 recombinant IFN-α subtypes and to IFN-ω. This represents more than a hundred-fold improvement over the parental mAb, IFWM371, whose $IC_{50}$ against its antigens ranging from single digit to double digit nM. As the parental antibody, the affinity-matured antibodies did not neutralize IFN-αD or IFN-β. The most potent affinity-matured antibody mAb IFWM3423 had almost a single-digit picomolar $IC_{50}$ to all interferon subtypes it bound.

TABLE 11

| mAbs | $IC_{50}$ (pM) | | | | | | |
|---|---|---|---|---|---|---|---|
| | αA | αB2 | αC | αD | αF | αG | αH2 |
| IFWM371 | 8400 | 19300 | 53900 | NN | 16000 | 12900 | 9600 |
| IFWM3304 | 29 | 39 | 117 | NN | 62 | 47 | 42 |
| IFWM3307 | 73 | 247 | 583 | NN | 170 | 95 | 88 |
| IFWM3308 | 94 | 230 | 996 | NT | 155 | 167 | 32 |
| IFWM3310 | 50 | 43 | 196 | NN | 111 | 73 | 45 |
| IFWM3314 | 29 | 33 | 157 | NN | 58 | 57 | 40 |
| IFWM3320 | 45 | 18 | 392 | NT | 54 | 82 | 23 |
| IFWM3321 | 29 | 87 | 266 | NN | 54 | 34 | 28 |
| IFWM3322 | 31 | 121 | 306 | NN | 117 | 83 | 46 |
| IFWM3328 | 216 | 520 | 1416 | NN | 631 | 486 | 440 |

TABLE 11-continued

| mAbs | αA | αB2 | αC | αD | αF | αG | αH2 |
|---|---|---|---|---|---|---|---|
| | | | IC$_{50}$ (pM) | | | | |
| IFWM3331 | 18 | 80 | 98 | NN | 48 | 27 | 33 |
| IFWM3332 | 104 | 327 | 479 | NN | 228 | 99 | 92 |
| IFWM3385 | 63 | 158 | 272 | NN | 66 | 77 | 29 |
| IFWM3399 | 43 | 62 | 189 | NN | 29 | 29 | 13 |
| IFWM3400 | 35 | 86 | 138 | NN | 43 | 35 | 15 |
| IFWM3405 | 40 | 99 | 68 | NN | 35 | 26 | 16 |
| IFWM3410 | NT | 211 | 168 | NN | 77 | 55 | 33 |
| IFWM3416 | 81 | 250 | 112 | NN | 64 | 49 | 35 |
| IFWM3421 | 13 | 16 | 20 | NN | 11 | 18 | 8 |
| IFWM3423 | 12 | 11 | 12 | NN | 8 | 9 | 4 |

NN: not neutralizing;
NT: not tested

TABLE 12

| mAbs | αI | αJ1 | αK | αWA | α4a | IFN-β | IFN-ω |
|---|---|---|---|---|---|---|---|
| | | | | IC$_{50}$ (pM) | | | |
| IFWM371 | | 35700 | 7300 | 74200 | 32800 | NN | 43900 |
| IFWM3304 | 157 | 126 | 57 | 237 | 112 | NN | 31 |
| IFWM3307 | 752 | 328 | 95 | 600 | 501 | NN | 100 |
| IFWM3308 | 478 | 363 | 59 | 894 | 295 | NN | 40 |
| IFWM3310 | 258 | 166 | 96 | 473 | 169 | NN | 81 |
| IFWM3314 | 163 | 86 | 65 | 188 | 137 | NN | 32 |
| IFWM3320 | 355 | 213 | 34 | 633 | 166 | NN | 53 |
| IFWM3321 | 301 | 114 | 46 | 267 | 295 | NN | 38 |
| IFWM3322 | 460 | 169 | 71 | 382 | 352 | NN | 59 |
| IFWM3328 | 2002 | 1657 | 321 | 3078 | 1169 | NN | 456 |
| IFWM3331 | 198 | 94 | 28 | 109 | 117 | NN | 50 |
| IFWM3332 | 893 | 487 | 76 | 947 | 519 | NN | 228 |
| IFWM3385 | 225 | 251 | 65 | 839 | 414 | NN | 68 |
| IFWM3399 | 18 | 106 | 32 | 189 | 111 | NN | 27 |
| IFWM3400 | 137 | 154 | 35 | 376 | 220 | NN | 29 |
| IFWM3405 | 72 | 26 | 22 | 216 | 86 | NN | 19 |
| IFWM3410 | 183 | 217 | 41 | 538 | 192 | NN | 89 |
| IFWM3416 | 158 | 61 | 43 | 779 | 201 | NN | 40 |
| IFWM3421 | 17 | 14 | 18 | 14 | 15 | NN | 8 |
| IFWM3423 | 4 | 6 | 9 | 10 | 8 | NN | 6 |

NN = not neutralizing

EXAMPLE 9

Engineering of Antibodies to Minimize Post-Translational Modification Risk

Based on neutralizing activity, solubility and biophysical properties, four mAbs derived from affinity maturation of IFWM371, IFWM3331 (IFWB3066), IFWM3399 (IFWB3134), IFWM3421 (IFWB3156) and IFWM3423 (IFWB3158) were analyzed further. The heavy chains of these mAbs consist of either IFWH591 (SEQ ID NO: 28) or IFWH629 (SEQ ID NO: 31) and the light chains of them consist of either IFWL984 (SEQ ID NO: 71) or IFWL1048 (SEQ ID NO: 53) or IFWL1073 (SEQ ID NO: 61).

Both VH chains contain several potential post-translational modification (PTM) motifs in their CDRs, including an acid-catalyzed hydrolysis sequence motif (D52-P53), an isomerization motif (D55-S56) on HCDR2 and potential oxidation sites on HCDR1 (W33) and CDR-H3 (W104).

The VL of IFWL984 (SEQ ID NO: 71) and IFWL1048 (SEQ ID NO: 53) contain one isomerization motif (D30-G31) on LCDR1 while the VL of IFW1073 (SEQ ID NO: 61) contains potential oxidation sites on LCDR3 (W92 and W94) and a potential deamidation site on LCDR1 (N31-S32).

To reduce PTM risks on heavy chain CDRs, D52 in HCDR2 was back-mutated to the germline residue tyrosine (D52Y). P53 was mutated to Alanine W104 in HCDR3 (VH_W104) was replaced with alanine, tyrosine, serine or aspartic acid. The mutated heavy chains were co-expressed with three different light chains and tested in the ISRE assay. From these experiments, antibodies with heavy chain IFWH615 (SEQ ID NO: 157) and IFWH617 (SEQ ID NO: 158) were characterized further.

To reduce PTM risks on VL IFWL984 (SEQ ID NO: 71) and IFWL1048 (SEQ ID NO: 53), a series of mutations to remove the potential PTM motifs were designed with the guidance of the structural information obtained from the IFWM371/IFN-ω complex structure described in Example 6. In addition, to improve the solubility of IFWM3421 (IFWB3156) and IFWM3423 (IFWB3158) having the common light chain IFWL984, a series of mutations on several hydrophobic residues in their CDRs were made to decrease the overall surface hydrophobicity of the antibody light chains. The IFWL984 variants were expressed in HEK293E cells with the parental heavy chain IFWH591 and the expressed antibody in cell supernatants were screened in the ISRE reporter gene assay for inhibition of IFN-ω and leukocyte IFN using methods described in example 11. The resulting antibodies IFWB3196 (D30E F32Y), IFWB3201 (D30S, G31S), and IFWB3202 (D30S, G31S, F32Y) retained good neutralizing activity. Table 13 shows the VL sequences of the generated antibodies having the parental IFWH591 heavy chain variable region (SEQ ID NO: 28) and a variant IFWL984 light chain. The parental IFWM3421 has the IFWH591 VH and the parental IFWM3423 has the IFWH629 VH. Table 14 shows the IC$_{50}$ values for neutralization of IFN-ω and leukocyte IFN of select generated antibodies.

TABLE 13

| Antibody DNA ID | Antibody AA ID | VL Peptide ID | VL substitution | VL SEQ ID NO: |
|---|---|---|---|---|
| IFWM3421 | IFWB3156 | IFWL984 | Parent control | 71 |
| IFWM3423 | IFWB3158 | IFWL984 | Parent control | 71 |
| IFWM3454 | IFWB3189 | IFWL1112 | IFWL984 D30S | 123 |
| IFWM3514 | IFWB3248 | IFWL1113 | IFWL984 D30E | 124 |
| IFWM3455 | IFWB3190 | IFWL1114 | IFWL984 F32Y | 125 |
| IFWM3456 | IFWB3191 | IFWL1115 | IFWL984 F50A | 126 |
| IFWM3458 | IFWB3193 | IFWL1117 | IFWL984 F50I | 127 |
| IFWM3459 | IFWB3194 | IFWL1118 | IFWL984 F50L | 128 |
| IFWM3460 | IFWB3195 | IFWL1119 | IFWL984 F50V | 129 |
| IFWM3461 | IFWB3196$^i$ | IFWL1120 | IFWL984 D30E, F32Y | 130 |
| IFWM3462 | IFWB3197 | IFWL1121 | IFWL984 D30E, F50A | 131 |
| IFWM3463 | IFWB3198 | IFWL1122 | IFWL984 D30E, F50I | 132 |

TABLE 13-continued

| Antibody DNA ID | Antibody AA ID | VL Peptide ID | VL substitution | VL SEQ ID NO: |
|---|---|---|---|---|
| IFWM3464 | IFWB3199 | IFWL1123 | IFWL984 D30E, F50L | 133 |
| IFWM3465 | IFWB3200 | IFWL1124 | IFWL984 D30E, F50V | 134 |
| IFWM3466 | IFWB3201 | IFWL1125 | IFWL984 D30S, G31S | 135 |
| IFWM3467 | IFWB3202 | IFWL1126 | IFWL984 D30S, G31S, F32Y | 136 |
| IFWM3470 | IFWB3205 | IFWL1129 | IFWL984 D30G, G31D, F50Y | 137 |
| | | IFWL1173 | IFWL984 D30E, F32Y, F50Y | 138 |
| IFWM3526 | IFWB3251 | IFWL1174 | IFWL984 D30E, F50Y | 139 |
| | | IFWL1175 | IFWL984 D30S, G31S, F50Y | 140 |

TABLE 14

| Antibody DNA ID | Antibody AA ID | IC$_{50}$ (pM) | |
|---|---|---|---|
| | | human IFN-ω | Leukocyte IFN |
| IFWM3421 | IFWB3156 | 7.4 | 0.7 |
| IFWM3423 | IFWB3158 | 10.7 | 1.1 |
| IFWM3454 | IFWB3189 | 11.2 | 1.3 |
| IFWM3514 | IFWB3248 | 10.4 | 1.4 |
| IFWM3455 | IFWB3190 | 24 | not fitted |
| IFWM3456 | IFWB3191 | 100.3 | 22.6 |

TABLE 14-continued

| Antibody DNA ID | Antibody AA ID | IC$_{50}$ (pM) | |
|---|---|---|---|
| | | human IFN-ω | Leukocyte IFN |
| IFWM3458 | IFWB3193 | 37 | 2.1 |
| IFWM3459 | IFWB3194 | 1518.9 | 4.4 |
| IFWM3460 | IFWB3195 | 43.5 | not fitted |
| IFWM3461 | IFWB3196$^i$ | 21 | 1 |
| IFWM3462 | IFWB3197 | 41.6 | 12.6 |
| IFWM3463 | IFWB3198 | 41.4 | 6.6 |
| IFWM3464 | IFWB3199 | 46.8 | 5.6 |
| IFWM3465 | IFWB3200 | 33.7 | 1.7 |
| IFWM3466 | IFWB3201 | 10.3 | 0.9 |
| IFWM3467 | IFWB3202 | 51.8 | 0.8 |
| IFWM3470 | IFWB3205 | 52.3 | 7.4 | resulting antibodies with variant IFWL1048 chains where the DG motif (D30-G31) in LCDR1 was eliminated, including IFWB3210 (D30S), IFWB3211 (D30E) and IFWB3223 (D30S, G31S), showed similar neutralization activity as the parent mAbs, IFWB3056 (VL: IFWL1048, VH: IFWH591) and IFWB3134 (VL: IFWL1048; VH: IFWH629). However, resulting antibodies with variant IFWL1048 chains with the DG motif eliminated and substitutions made to reduce hydrophobicity, including IFWB3219 (D30E, A32Y), IFWB3227 (D30S, G31S, F94L) and IFWB3230 (D30S, G31S, A32Y, F94L) demonstrated a lower activity than the parental mAbs.

TABLE 15

| Antibody DNA ID | Antibody AA ID | VL Peptide ID | Mutation | VL SEQ ID NO: |
|---|---|---|---|---|
| IFWM3321 | IFWB3056 | IFWL1048 | Parent control | 53 |
| IFWM3399 | IFWB3134 | IFWL1048 | Parent control | 53 |
| IFWM3475 | IFWB3210 | IFWL1135 | IFWL1048 D30S | 141 |
| IFWM3476 | IFWB3211 | IFWL1136 | IFWL1048 D30E | 73 |
| IFWM3477 | IFWB3212 | IFWL1137 | IFWL1048 A32Y | 142 |
| IFWM3483 | IFWB3218 | IFWL1143 | IFWL1048 F94L | 143 |
| IFWM3484 | IFWB3219 | IFWL1144 | IFWL1048 D30E, A32Y | 74 |
| IFWM3488 | IFWB3223 | IFWL1148 | IFWL1048 D30S, G31S | 75 |
| IFWM3489 | IFWB3224 | IFWL1149 | IFWL1048 D30S, G31S, A32Y | 144 |
| IFWM3492 | IFWB3227 | IFWL1152 | IFWL1048 D30S, G31S, F94L | 145 |
| IFWM3495 | IFWB3230 | IFWL1155 | IFWL1048 D30S, G31S, A32Y, F94L | 146 |
| | | IFWL1161 | IFWL1048 D30G, G31D, A32F, F50A, F94L | 147 |

TABLE 16

| Antibody DNA ID | Antibody AA ID | IC$_{50}$ (pM) | |
|---|---|---|---|
| | | human IFN-ω | Leukocyte IFN |
| IFWM3321 | IFWB3056 | 25.8 | 1.2 |
| IFWM3399 | IFWB3134 | 28.7 | 1.3 |
| IFWM3475 | IFWB3210 | 27.3 | 1.5 |
| IFWM3476 | IFWB3211 | 17.2 | 3.3 |
| IFWM3477 | IFWB3212 | 31 | 4.1 |
| IFWM3483 | IFWB3218 | 51.4 | 4.8 |
| IFWM3484 | IFWB3219 | 38.7 | 2.3 |
| IFWM3488 | IFWB3223 | 29.4 | 1 |
| IFWM3489 | IFWB3224 | 80.3 | 3.4 |
| IFWM3492 | IFWB3227 | 56.1 | 0.5 |
| IFWM3495 | IFWB3230 | 57.5 | 3.9 |

Similarly, 26 IFWL1048 variants were constructed to reduce the PTM risks. The generated light chains were co-expressed with a heavy chain IFWH591 in HEK293E cells and the supernatant containing the antibody screened with ISRE assay. Table 15 shows the VH and VL sequences of the generated antibodies, and Table 16 shows the IC$_{50}$ values of the antibodies for IFN-ω and leukocyte IFN. The Potential PTM motifs on the VL IFWL1073 of IFWB3066 included potential oxidation sites on LCDR3 (W92 and W94). The LCDR3 of IFWL1073 (QQGWDW-PLT; SEQ ID NO: 98) was replaced with a consensus LCDR3 sequence identified present in the LCDR3 of many affinity-matured antibodies (QQSYDFPLT; SEQ ID NO: 154). In addition, several mutants were designed to address a potential deamidation site (N31-S32) on LCDR1. 14 generated variants of IFWL1073 were paired with IFWH591 and expressed in 48-well HEK293E transient transfection. The cell supernatants were tested directly in ISRE assay for their neutralization activities against recombinant human IFN-ω and viral-induced leukocytes expressed IFNs. The mAbs with mutations W93Y and/or W95F showed some improvements in neutralization activity. Mutants to remove the NS motif by substitution or by shortening CDR-L1 showed reduction or loss of neutralization activity. Table 17 shows the VH and the VL sequences of the generated antibodies and Table 18 shows the $IC_{50}$ values for IFN-ω and leukocyte IFN.

TABLE 17

| Antibody DNA ID | Antibody AA ID | VL Peptide ID | VL Mutation | VL SEQ ID NO: |
|---|---|---|---|---|
| IFWM3331 | IFWB3066 | IFWL1073 | Parent control | 61 |
| IFWM3501 | IFWB3236 | IFWL1162 | IFWL1073 W93Y | 148 |
| IFWM3502 | IFWB3237 | IFWL1163 | IFWL1073 W95F | 149 |
| IFWM3503 | IFWB3238 | IFWL1164 | IFWL1073 W93Y, W95F | 150 |
| IFWM3527 | IFWB3252 | IFWL1176 | IFWL1073 N31Q, W93Y, W95F | 151 |
| IFWM3528 | IFWB3253 | IFWL1177 | IFWL1073 N31T, W93Y, W95F | 152 |
| IFWM3529 | IFWB3254 | IFWL1178 | IFWL1073 S32T, W93Y, W95F | 153 |

TABLE 18

| | | IC 50 (pM) | |
|---|---|---|---|
| Antibody DNA ID | Antibody AA ID | human IFN-ω | Leukocyte IFN |
| IFWM3331 | IFWB3066 | 40.7 | 1.5 |
| IFWM3501 | IFWB3236 | 15.1 | 2.6 |
| IFWM3502 | IFWB3237 | 28 | 2.5 |
| IFWM3503 | IFWB3238 | 12 | 2.1 |

Select VL variants derived from the engineering efforts to minimize the PTM risk were paired with either IFWH591 or IFWH629 and scaled up for expression and purification. Table 19 shows the VL/VH pairing of the antibodies. Table 20 shows the $IC_{50}$ values of the select resulting antibodies for various recombinant IFN-α subtypes and IFN-ω.

TABLE 19

| | VL | | | HC | |
|---|---|---|---|---|---|
| Antibody | Peptide ID | VL SEQ ID NO: | Description | Peptide ID | VH SEQ ID NO: |
| IFWL1073 mutants | IFWL1073 | 61 | parent | IFWH591 | 28 |
| | IFWL1164 | 150 | IFWL1073 W93Y, W95F | IFWH591 | 28 |
| | IFWL1176 | 151 | IFWL1073 N31Q, W93Y, W95F | IFWH591 | 28 |
| | IFWL1177 | 152 | IFWL1073 N31T, W93Y, W95F | IFWH591 | 28 |
| IFWL984 mutants | IFWL984 | 71 | parent | IFWH591 | 28 |
| | IFWL984 | 71 | parent | IFWH629 | 31 |
| | IFWL984 | 71 | parent | IFWH629 | 31 |
| | IFWL1125 | 135 | IFWL984 D30S, G31S | IFWH591 | 28 |
| | IFWL1126 | 136 | IFWL984 D30S, G31S, F32Y | IFWH591 | 28 |
| | IFWL1174 | 139 | IFWL984 D30E, F50Y | IFWH591 | 28 |
| | IFWL1048 | 53 | parent | IFWH591 | 28 |
| | IFWL1048 | 53 | | IFWH629 | 31 |
| | IFWL1136 | 73 | IFWL1048 D30E | IFWH591 | 28 |
| | IFWL1148 | 75 | IFWL1048 D30S, G31S | IFWH591 | 28 |

TABLE 20

| Protein DNA ID | Protein AA ID | αA | αB2 | αC | αF | αG | α4a | ω |
|---|---|---|---|---|---|---|---|---|
| IFWM3331* | IFWB3066 | 26 | 77 | 48 | 157 | 33 | | 52 |
| | | 31 | 65 | 88 | 30 | 23 | | 30 |
| IFWM3421* | IFWB3156 | 16 | 19 | 29 | 16 | 18 | 22 | 8 |
| | | 17 | 19 | 28 | 15 | 14 | 19 | 9 |
| IFWM3423* | IFWB3158 | 20 | 17 | 24 | 21 | 20 | 23 | 16 |
| | | 12 | 13 | 17 | 11 | 10 | 9 | 7 |
| IFWM3466 | IFWB3201 | 17 | 21 | 31 | 18 | 16 | 23 | 12 |
| IFWM3503 | IFWB3238 | 15 | 19 | 20 | 20 | 15 | 32 | 13 |
| IFWM3399 | IFWB3134 | 24 | 38 | 64 | 29 | 24 | 117 | 25 |
| IFWM3476 | IFWB3211 | 35 | 54 | 115 | 50 | 39 | 130 | 23 |
| IFWM3488 | IFWB3223 | 19 | 31 | 72 | 25 | 21 | 84 | 22 |

*results from two independent experiments

EXAMPLE 10

Broad Neutralizing Ability of Anti-IFN-α/ω Antibodies

Several of the generated antibodies neutralized IFN-ω and multiple IFN-α subtypes with an $IC_{50}$ of 100 pM or less, measured using the ISRE assay described above. The variable region sequences of these antibodies are shown in Table 21. Table 22 shows the LCDR1 sequences, Table 23 the LCDR2, Table 24 the LCDR3, Table 25 the HCDR1, Table 26 the HCDR2 and Table 27 the HCDR3 of the antibodies. FIG. 10 shows the IC$_{50}$ values for each Type I IFN in the ISRE assay.

TABLE 21

| mAbs cDNA | mAb protein | VH | VH SEQ ID NO: | VL | VL SEQ ID NO: |
|---|---|---|---|---|---|
| IFWM3308 | IFWB3043 | IFWH591 | 28 | IFWL1004 | 40 |
| IFWM3307 | IFWB3042 | IFWH591 | 28 | IFWL1001 | 39 |
| IFWM3410 | IFWB3145 | IFWH629 | 31 | IFWL1074 | 62 |
| IFWM3322 | IFWB3057 | IFWH591 | 28 | IFWL1051 | 54 |
| IFWM3385 | IFWB3120 | IFWH629 | 31 | IFWL1001 | 39 |
| IFWM3416 | IFWB3151 | IFWH629 | 31 | IFWL1091 | 68 |
| IFWM3310 | IFWB3045 | IFWH591 | 28 | IFWL1007 | 42 |
| IFWM3400 | IFWB3135 | IFWH629 | 31 | IFWL1051 | 54 |
| IFWM3321 | IFWB3056 | IFWH591 | 28 | IFWL1048 | 53 |
| IFWM3522 | IFWB3211 | IFWH591 | 28 | IFWL1136 | 73 |
| IFWM3524 | IFWB3223 | IFWH591 | 28 | IFWL1148 | 75 |
| IFWM3320 | IFWB3055 | IFWH591 | 28 | IFWL1047 | 52 |
| IFWM3304 | IFWB3039 | IFWH591 | 28 | IFWL997 | 35 |
| IFWM3520 | IFWB3201 | IFWH591 | 28 | IFWL1125 | 135 |
| IFWM3399 | IFWB3134 | IFWH629 | 31 | IFWL1048 | 53 |
| IFWM3314 | IFWB3049 | IFWH591 | 28 | IFWL1014 | 46 |
| IFWM3331 | IFWB3066 | IFWH591 | 28 | IFWL1073 | 61 |
| IFWM3405 | IFWB3140 | IFWH629 | 31 | IFWL1063 | 57 |
| IFWM3442 | IFWB3177 | IFWH615 | 157 | IFWL984 | 71 |
| IFWM3525 | IFWB3238 | IFWH591 | 28 | IFWL1164 | 150 |
| IFWM3423 | IFWB3158 | IFWH629 | 31 | IFWL984 | 71 |
| IFWM3444 | IFWB3179 | IFWH617 | 158 | IFWL984 | 71 |
| IFWM3421 | IFWB3156 | IFWH591 | 28 | IFWL984 | 71 |

TABLE 22

| mAbs | LCDR1 Sequence | | | | | | | SEQ ID NO: |
|---|---|---|---|---|---|---|---|---|
| IFWM3308 | Q | S | I | A | E | F | | 77 |
| IFWM3307 | Q | S | I | G | D | F | | 85 |
| IFWM3410 | Q | S | I | A | N | T | N | 79 |
| IFWM3322 | Q | S | I | A | D | F | | 76 |
| IFWM3385 | Q | S | I | G | D | F | | 85 |
| IFWM3416 | Q | S | I | R | N | T | N | 89 |
| IFWM3310 | Q | S | I | G | K | S | | 86 |
| IFWM3400 | Q | S | I | A | D | F | | 76 |
| IFWM3321 | Q | S | I | D | G | A | | 80 |
| IFWM3522 | Q | S | I | E | G | A | | 84 |
| IFWM3524 | Q | S | I | S | S | A | | 90 |
| IFWM3320 | Q | S | I | N | G | V | | 88 |
| IFWM3304 | Q | S | I | G | S | A | | 87 |
| IFWM3520 | Q | S | I | S | S | F | | 91 |
| IFWM3399 | Q | S | I | D | G | A | | 80 |
| IFWM3314 | Q | S | I | D | R | A | | 83 |
| IFWM3331 | Q | S | I | D | N | S | Y | 82 |
| IFWM3405 | Q | S | I | A | N | N | N | 78 |
| IFWM3442 | Q | S | I | D | G | F | | 81 |
| IFWM3525 | Q | S | I | D | N | S | Y | 82 |
| IFWM3423 | Q | S | I | D | G | F | | 81 |
| IFWM3444 | Q | S | I | D | G | F | | 81 |
| IFWM3421 | Q | S | I | D | G | F | | 81 |

TABLE 23

| mAbs | LCDR2 Sequence | | | SEQ ID NO: |
|---|---|---|---|---|
| IFWM3308 | F | A | S | 93 |
| IFWM3307 | F | A | S | 93 |
| IFWM3410 | W | A | S | 95 |
| IFWM3322 | F | A | S | 93 |
| IFWM3385 | F | A | S | 93 |
| IFWM3416 | W | A | S | 95 |
| IFWM3310 | F | A | S | 93 |
| IFWM3400 | F | A | S | 93 |
| IFWM3321 | F | A | S | 93 |
| IFWM3522 | F | A | S | 93 |
| IFWM3524 | F | A | S | 93 |
| IFWM3320 | F | A | S | 93 |
| IFWM3304 | F | A | S | 93 |
| IFWM3520 | F | A | S | 93 |
| IFWM3399 | F | A | S | 93 |
| IFWM3314 | F | A | S | 93 |
| IFWM3331 | G | A | S | 94 |
| IFWM3405 | W | A | S | 95 |
| IFWM3442 | F | A | S | 93 |
| IFWM3525 | G | A | S | 94 |
| IFWM3423 | F | A | S | 93 |
| IFWM3444 | F | A | S | 93 |
| IFWM3421 | F | A | S | 93 |

TABLE 24

| mAbs | LCDR3 Sequence | | | | | | | | | SEQ ID NO: |
|---|---|---|---|---|---|---|---|---|---|---|
| IFWM3308 | Q | Q | S | I | D | F | P | L | T | 104 |
| IFWM3307 | Q | Q | A | L | D | F | P | L | T | 96 |
| IFWM3410 | Q | Q | W | Y | D | N | P | L | T | 107 |
| IFWM3322 | Q | Q | S | H | S | F | P | L | T | 103 |
| IFWM3385 | Q | Q | A | L | D | F | P | L | T | 96 |
| IFWM3416 | Q | Q | G | Y | D | T | P | F | T | 100 |
| IFWM3310 | Q | Q | S | Y | D | F | P | L | T | 105 |
| IFWM3400 | Q | Q | S | H | S | F | P | L | T | 103 |
| IFWM3321 | Q | Q | A | Y | D | F | P | L | T | 97 |
| IFWM3522 | Q | Q | A | Y | D | F | P | L | T | 97 |
| IFWM3524 | Q | Q | A | Y | D | F | P | L | T | 97 |
| IFWM3320 | Q | Q | S | H | D | F | P | L | T | 102 |
| IFWM3304 | Q | Q | S | Y | D | F | P | L | T | 105 |
| IFWM3520 | Q | Q | S | Y | D | L | P | I | T | 106 |
| IFWM3399 | Q | Q | A | Y | D | F | P | L | T | 97 |

TABLE 24-continued

| | LCDR3 | | | | | | | | |
|---|---|---|---|---|---|---|---|---|---|
| mAbs | Sequence | | | | | | | | SEQ ID NO: |
| IFWM3314 | Q | Q | S | F | D | F | P | L | T | 101 |
| IFWM3331 | Q | Q | G | W | D | W | P | L | T | 98 |
| IFWM3405 | Q | Q | G | Y | D | T | P | F | T | 100 |
| IFWM3442 | Q | Q | S | Y | D | L | P | I | T | 106 |
| IFWM3525 | Q | Q | S | Y | D | F | P | L | T | 99 |
| IFWM3423 | Q | Q | S | Y | D | L | P | I | T | 106 |
| IFWM3444 | Q | Q | S | Y | D | L | P | I | T | 106 |
| IFWM3421 | Q | Q | S | Y | D | L | P | I | T | 106 |

TABLE 25

| | HCDR1 | | | | | | | |
|---|---|---|---|---|---|---|---|---|
| mAbs | Sequence | | | | | | | SEQ ID NO: |
| IFWM3308 | G | Y | S | F | T | S | Y | W | 109 |
| IFWM3307 | G | Y | S | F | T | S | Y | W | 109 |
| IFWM3410 | G | Y | S | F | T | S | Y | W | 109 |
| IFWM3322 | G | Y | S | F | T | S | Y | W | 109 |
| IFWM3385 | G | Y | S | F | T | S | Y | W | 109 |
| IFWM3416 | G | Y | S | F | T | S | Y | W | 109 |
| IFWM3310 | G | Y | S | F | T | S | Y | W | 109 |
| IFWM3400 | G | Y | S | F | T | S | Y | W | 109 |
| IFWM3321 | G | Y | S | F | T | S | Y | W | 109 |
| IFWM3522 | G | Y | S | F | T | S | Y | W | 109 |
| IFWM3524 | G | Y | S | F | T | S | Y | W | 109 |
| IFWM3320 | G | Y | S | F | T | S | Y | W | 109 |
| IFWM3304 | G | Y | S | F | T | S | Y | W | 109 |
| IFWM3520 | G | Y | S | F | T | S | Y | W | 109 |
| IFWM3399 | G | Y | S | F | T | S | Y | W | 109 |
| IFWM3314 | G | Y | S | F | T | S | Y | W | 109 |
| IFWM3331 | G | Y | S | F | T | S | Y | W | 109 |
| IFWM3405 | G | Y | S | F | T | S | Y | W | 109 |
| IFWM3442 | G | Y | S | F | T | S | Y | W | 109 |
| IFWM3525 | G | Y | S | F | T | S | Y | W | 109 |

TABLE 25-continued

| | HCDR1 | | | | | | | |
|---|---|---|---|---|---|---|---|---|
| mAbs | Sequence | | | | | | | SEQ ID NO: |
| IFWM3423 | G | Y | S | F | T | S | Y | W | 109 |
| IFWM3444 | G | Y | S | F | T | S | Y | W | 109 |
| IFWM3421 | G | Y | S | F | T | S | Y | W | 109 |

TABLE 26

| | HCDR2 | | | | | | | |
|---|---|---|---|---|---|---|---|---|
| mAbs | Sequence | | | | | | | SEQ ID NO: |
| IFWM3308 | I | D | P | S | D | S | D | T | 113 |
| IFWM3307 | I | D | P | S | D | S | D | T | 113 |
| IFWM3410 | I | D | P | S | D | S | D | T | 113 |
| IFWM3322 | I | D | P | S | D | S | D | T | 113 |
| IFWM3385 | I | D | P | S | D | S | D | T | 113 |
| IFWM3416 | I | D | P | S | D | S | D | T | 113 |
| IFWM3310 | I | D | P | S | D | S | D | T | 113 |
| IFWM3400 | I | D | P | S | D | S | D | T | 113 |
| IFWM3321 | I | D | P | S | D | S | D | T | 113 |
| IFWM3522 | I | D | P | S | D | S | D | T | 113 |
| IFWM3524 | I | D | P | S | D | S | D | T | 113 |
| IFWM3320 | I | D | P | S | D | S | D | T | 113 |
| IFWM3304 | I | D | P | S | D | S | D | T | 113 |
| IFWM3520 | I | D | P | S | D | S | D | T | 113 |
| IFWM3399 | I | D | P | S | D | S | D | T | 113 |
| IFWM3314 | I | D | P | S | D | S | D | T | 113 |
| IFWM3331 | I | D | P | S | D | S | D | T | 113 |
| IFWM3405 | I | D | P | S | D | S | D | T | 113 |
| IFWM3442 | I | A | P | S | D | S | D | T | 111 |
| IFWM3525 | I | D | P | S | D | S | D | T | 113 |
| IFWM3423 | I | D | P | S | D | S | D | T | 113 |
| IFWM3444 | I | D | A | S | D | S | D | T | 112 |
| IFWM3421 | I | D | P | S | D | S | D | T | 113 |

TABLE 27

| | HCDR3 | | | | | | | | | | | | SEQ ID NO: |
|---|---|---|---|---|---|---|---|---|---|---|---|---|---|
| mAbs | Sequence | | | | | | | | | | | | |
| IFWM3308 | A | R | H | P | G | L | N | W | A | P | D | F | D | Y | 116 |
| IFWM3307 | A | R | H | P | G | L | N | W | A | P | D | F | D | Y | 116 |
| IFWM3410 | A | R | H | P | G | L | A | W | A | P | D | F | D | Y | 115 |
| IFWM3322 | A | R | H | P | G | L | N | W | A | P | D | F | D | Y | 116 |
| IFWM3385 | A | R | H | P | G | L | A | W | A | P | D | F | D | Y | 115 |
| IFWM3416 | A | R | H | P | G | L | A | W | A | P | D | F | D | Y | 115 |
| IFWM3310 | A | R | H | P | G | L | N | W | A | P | D | F | D | Y | 116 |
| IFWM3400 | A | R | H | P | G | L | A | W | A | P | D | F | D | Y | 115 |
| IFWM3321 | A | R | H | P | G | L | N | W | A | P | D | F | D | Y | 116 |
| IFWM3522 | A | R | H | P | G | L | N | W | A | P | D | F | D | Y | 116 |
| IFWM3524 | A | R | H | P | G | L | N | W | A | P | D | F | D | Y | 116 |
| IFWM3320 | A | R | H | P | G | L | N | W | A | P | D | F | D | Y | 116 |
| IFWM3304 | A | R | H | P | G | L | N | W | A | P | D | F | D | Y | 116 |
| IFWM3520 | A | R | H | P | G | L | N | W | A | P | D | F | D | Y | 116 |
| IFWM3399 | A | R | H | P | G | L | A | W | A | P | D | F | D | Y | 115 |
| IFWM3314 | A | R | H | P | G | L | N | W | A | P | D | F | D | Y | 116 |
| IFWM3331 | A | R | H | P | G | L | N | W | A | P | D | F | D | Y | 116 |
| IFWM3405 | A | R | H | P | G | L | A | W | A | P | D | F | D | Y | 115 |
| IFWM3442 | A | R | H | P | G | L | N | W | A | P | D | F | D | Y | 116 |
| IFWM3525 | A | R | H | P | G | L | N | W | A | P | D | F | D | Y | 116 |
| IFWM3423 | A | R | H | P | G | L | A | W | A | P | D | F | D | Y | 115 |
| IFWM3444 | A | R | H | P | G | L | N | W | A | P | D | F | D | Y | 116 |
| IFWM3421 | A | R | H | P | G | L | N | W | A | P | D | F | D | Y | 116 |

EXAMPLE 11

Anti-IFN-α/ω Antibodies Neutralize Leukocyte IFN

The ability of the antibodies to neutralize leukocyte IFN was assessed by the ability of the antibodies to inhibit IFN-induced IP-10 release from whole blood.

Select antibodies from the affinity-maturation campaign or after minimizing the PTM risk were characterized further for their ability to inhibit endogenous Type I IFN. All characterized antibodies were of IgG1/κ type. Antibodies IFWM3522, IFWM3525, IFWM3399 and IFWM3423 were used in the assays.

IP-10 Release Assay:

240 μl of whole blood (Biological Specialty Corporation) was added to individual wells in 96 well U-bottom plates containing 30 μl of antibody (anti IFN-α/ω or isotype control), with or without IFN or IFN-containing conditioned media diluted in cell culture media (RPMI1640 with 10% HI FBS and 1% penn strep). For stimulation, human leukocyte IFN(Sigma-Aldrich) was utilized at 250 U/ml (final volume) and SLE immune complex-treated conditioned media at 10 μl per well. IFN and antibody mixtures were preincubated at room temperature for 20-30 min prior to adding whole blood. Plates were incubated overnight for 20-22 hours at 37° C. The following day, plates were centrifuged at 400×g for 5 minutes at room temperature and plasma removed and frozen at −20° C. Duplicate samples from each treatment were analyzed using a CXCL10/IP-10 ELISA kit from Qiagen. Upon thawing, the collected plasma was diluted 2.5 fold using sample dilution buffer and used in the assay. Manufacturer's protocol was followed with slight modification in the dilution of standards as follows. Two fold serial dilutions of the antigen standard were made starting at a concentration of 4000 pg/ml and ending at 31.25 pg/ml. Plates were read at an absorbance at 450 nm within 30 minutes of stopping the reaction. Analysis was performed using Softmax Pro.

Results

Select antibodies were characterized for their ability to neutralize endogenous IFN-I preparations in relevant cell types. IFN-I stimulation of whole blood induces IP-10 (CXCL10) release in vitro and in vivo (Arico, E. et al. Concomitant detection of IFNalpha signature and activated monocyte/dendritic cell precursors in the peripheral blood of IFNalpha-treated subjects at early times after repeated local cytokine treatments. *J Transl Med* 9, 67, doi:10.1186/1479-5876-9-67 (2011); Mohty, A. M. et al. Induction of IP-10/CXCL10 secretion as an immunomodulatory effect of low-dose adjuvant interferon-alpha during treatment of melanoma. *Immunobiology* 215, 113-123, doi:10.1016/j.imbio.2009.03.008 (2010)). IP-10 is elevated in SLE, and has been shown in several studies to correlate with disease activity and clinical manifestations of disease (Bauer, J. W. et al. Interferon-regulated chemokines as biomarkers of systemic lupus erythematosus disease activity: a validation study. *Arthritis and rheumatism* 60, 3098-3107, doi:10.1002/art.24803 (2009); Kong, K. O. et al. Enhanced expression of interferon-inducible protein-10 correlates with disease activity and clinical manifestations in systemic lupus erythematosus. *Clinical and experimental immunology* 156, 134-140, doi:10.1111/j.1365-2249.2009.03880.x (2009); Rose, T. et al. IFNalpha and its response proteins, IP-10 and SIGLEC-1, are biomarkers of disease activity in systemic lupus erythematosus. *Annals of the rheumatic diseases* 72, 1639-1645, doi:10.1136/annrheumdis-2012-201586 (2013).

Figure 11A:
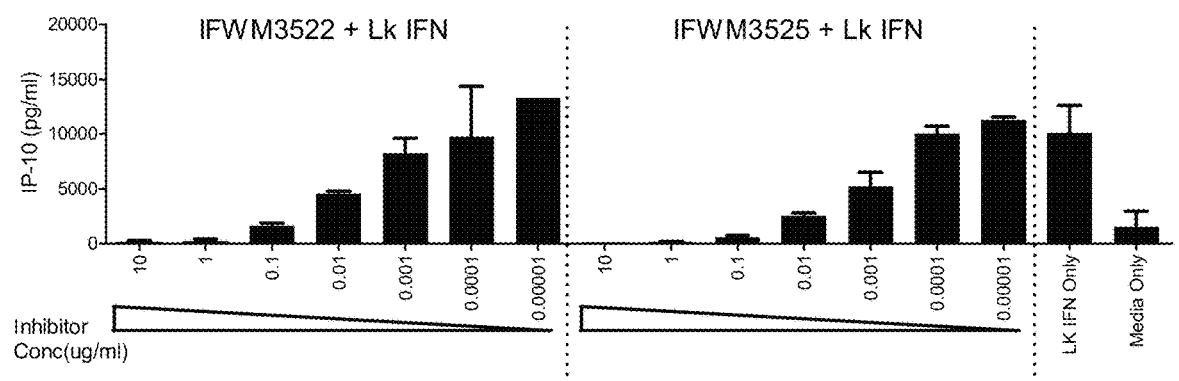
FIG. 11A shows neutralization of leukocyte IFN-induced IP10 release in human whole blood with anti-IFN-α/ω antibodies. Leukocyte IFN (Lk) was used to induce IP-10 secretion in healthy donor whole blood from 2 subjects. Whole blood was incubated with leukocyte interferon (LK) with or without anti-IFN-α/ω antibodies IFWM3522 or IFWM3525 at various concentrations (10 μg/ml-10 pg/ml) as indicated in the Figure. Bar represents mean and error bars SD from duplicate wells. Data is representative result of 2 independent experiments using whole blood from 2 different human donors.
Figure 11B:
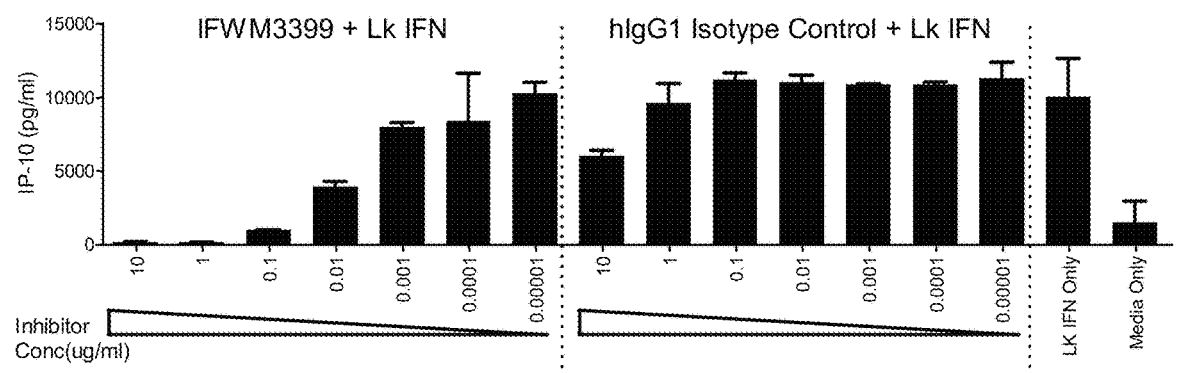
FIG. 11B shows neutralization of leukocyte IFN-induced IP-10 release in human whole blood with anti-IFN-α/ω antibodies. Leukocyte IFN (Lk) was used to induce IP-10 secretion in healthy donor whole blood from 2 subjects. Whole blood was incubated with leukocyte interferon (LK) with or without anti-IFN-α/ω antibody IFWM3399 or isotype control at various concentrations (10 μg/ml-10 pg/ml) as indicated in the Figure. Bar represents mean and error bars SD from duplicate wells. Data is representative result of 2 independent experiments using whole blood from 2 different human donors.

The ability of anti IFN-α/ω mAbs to inhibit IP-10 release in whole blood induced by leukocyte IFN was examined in vitro. IFN-I is rapidly produced in response to infectious agents, such as viruses, to help control infection. Human leukocyte IFN is a natural mixture of IFNs produced by leukocytes after viral infection and is largely composed of IFN-α subtypes and IFN-ω. IFN-ω is believed to constitute approximately 15% of the total IFN-I activity in these preparations. Importantly, infections are believed to potentially contribute to both induction and exacerbation of SLE. In this study, human leukocyte IFN was added to whole blood samples from 2 healthy human donors in the presence of inhibitors or controls and plasma was assessed for IP-10 release 24 h post IFN exposure. Anti IFN-α/ω mAbs: IFWM3522 and IFWM3525 (FIG. 11A), and IFWM3399 (FIG. 11B) all dose-dependently neutralized leukocyte IFN-induced IP-10 release in both donors tested.

EXAMPLE 12

Anti-IFN-α/ω Antibodies Neutralize SLE Immune Complexes

A hallmark of SLE is the presence of autoantibodies such as anti-double-stranded DNA (anti-dsDNA) that typically precede the development of clinically defined disease. Autoantibodies bound to nucleic acid ligands are thought to be endogenous inducers of type I IFN in SLE patients. The preponderance of autoantibodies in conjunction with impaired clearance of autoantigens leads to a feedback cycle of IFN production where Fc receptor-dependent internalization of immune complexes into plasmacytoid dendritic cells (pDC) leads to increased amounts of circulating IFN and establishment of the IFN gene signature.

We further tested the ability of the anti-IFN-α/ω antibodies to neutralize more disease relevant endogenous IFN preparations.

Figure 12A:
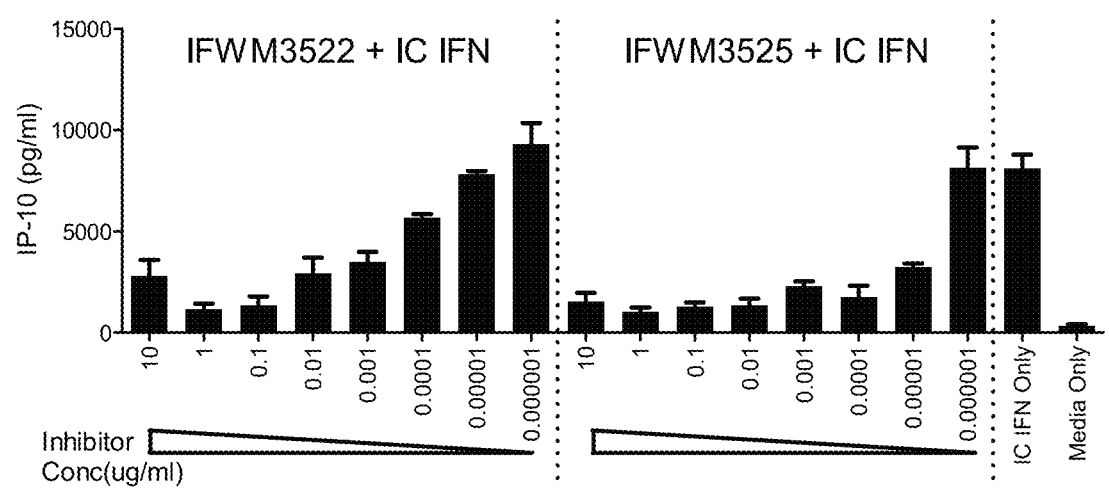
FIG. 12A shows neutralization of SLE immune complex-induced IP-10 release in human whole blood with anti-IFN-α/ω antibodies. Whole blood was incubated with SLE immune complex-induced interferon preparations with or without anti-IFN-α/ω antibodies IFWM3522 or IFWM3525 at various concentrations (10 μg/ml-10 pg/ml) as indicated in the Figure, and IP-10 was analyzed from plasma using an ELISA kit. Bar represents mean and error bars SD from duplicate wells. Data is representative result of 4 independent experiments using whole blood from 2 different human donors.
Figure 12B:
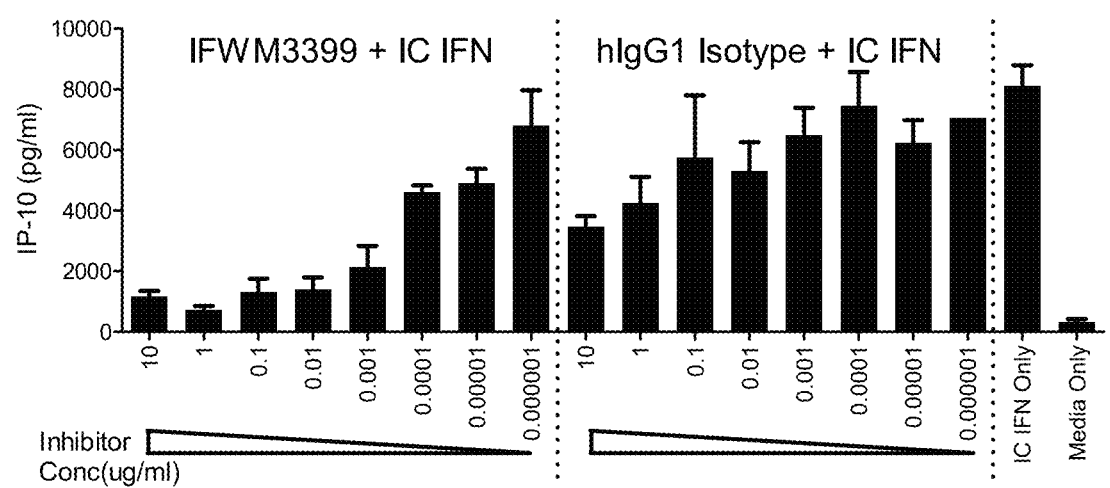
FIG. 12B shows neutralization of SLE immune complex-induced IP-10 release in human whole blood with anti-IFN-α/ω antibodies. Whole blood was incubated with SLE immune complex-induced interferon preparations with or without anti-IFN-α/ω antibody IFWM3399 or isotype control at various concentrations (10 μg/ml-10 pg/ml) as indicated in the Figure, and IP-10 was analyzed from plasma using an ELISA kit. Bar represents mean and error bars SD from duplicate wells. Data is representative result of 4 independent experiments using whole blood from 2 different human donors.

Immune complexes were prepared essentially as described in Example 1. These SLE patient-derived immune complexes were then added to healthy donor PBMCs and IFN-containing conditioned media collected from cell cultures (IC92 and IC163). Next, the conditioned media was added to healthy donor whole blood from 4 healthy donors in the presence of inhibitors or control to determine the impact of IFN-α/ω neutralization on IFN-induced IP-10 release. IFWM3522, IFWM3525, and IFWM3399 all dose-dependently neutralized IP-10 release using both SLE immune complex-induced IFN preps in all whole blood donors tested. FIG. 12A shows neutralization of SLE immune complex-induced IFN-stimulated IP-10 release in human whole blood by antibodies IFWM3522 and IFWM2525 from one donor (SLE donor 92). FIG. 12B shows the results for antibody IFWM3399 and isotype control.

EXAMPLE 13

Anti-IFN-α/ω Antibodies Neutralize SLE Plasma

Anti IFN-α/ω mAbs demonstrated potent dose-dependent neutralization of endogenous IFN-I preparations produced from human primary cells after exposure to both sterile (immune complex; Example 12) and microbial ligands (leukocyte IFN; Example 11). Potency of the IFN-α/ω mAbs to neutralize physiological Type I IFN was further assessed by the ability of the antibodies to neutralize IFN-I activity from SLE patient sera and plasma. This approach thus assesses ability of the antibodies to neutralize the actual circulating IFN-I milieu from the patient which may contain an IFN spectrum that may be difficult to recapitulate in vitro.

ISRE Assay Using SLE Serum:

HEK Blue (α/β) cells (InvivoGen) were plated at 50,000 cells per well in a total volume of 200 μl DMEM+10% FBS and incubated overnight at 37° C. The next day, pooled plasma (3 donors) or serum (13 donors) pre-selected on the basis of achieving an OD of greater than or equal to 1.0 after a 30 minute incubation in this assay was thawed and mixed at a 1:1 (v/v) ratio with DMEM+10% FBS. Supernatants were removed from the previously plated Hek Blue cells and replaced with 100 μl of the SLE plasma or serum/media mixture and allowed to incubate overnight at 37° C. The next day, 40 μl of conditioned media was removed and added to 160 μl Quanti-Blue substrate (InvivoGen) in a new plate and allowed to incubate for 30 minutes. Plates were read using a spectrophotometer at 650 nanometer wavelength and $IC_{50}$ values were calculated using GraphPad Prism.

Results

SLE serum from a Chinese cohort of patients (SLE Cohort 1) and SLE plasma from a primarily African American cohort (SLE Cohort 2) was prescreened for IFN-I activity using the ISRE assay. SLE donor serum or plasma samples having an OD of ~1.0 or greater were determined to have a sufficient window of IFN-I activity such that inhibition with antagonist antibodies could be easily measured. These donor samples were then pooled to create a serum or plasma stock to generate enough sample volume to enable repeat experiments and antibody titrations. SLE patient samples from diverse racial/ethnic cohorts were utilized to better capture the potential diversity in qualitative and quantitative IFN-I responses in SLE patients. African American and Asian donors are thought to have higher IFN-I activity than Caucasian donors. The anti-IFN-α/ω mAbs tested dose-dependently neutralized IFN-I activity in pooled SLE patient serum and plasma samples. $IC_{50}$ values from two independent experiments are shown using pooled samples from both SLE cohorts in Table 28.

TABLE 28

| | Mean $IC_{50}$ (ng/ml) +/− SD | |
|---|---|---|
| mAb | SLE Cohort 1 (serum) | SLE Cohort 2 (plasma) |
| IFWM3525 | 5.166 +/− 0.1612 | 4.255 +/− 0.8422 |
| IFWM3522 | 10.47 +/− 0.3818 | 6.059 +/− 0.3613 |
| IFWM3399 | 8.352 +/− 1.102 | 4.340 +/− 0.1223 |

EXAMPLE 14

Anti-IFN-α/ω Antibodies Neutralize IFN Gene Signature

Type I IFN induces a spectrum of genes that are also overexpressed in some SLE patients as compared to healthy controls. Plasma samples from SLE patients exhibiting this IFN gene signature are capable of inducing overexpression of a similar set of genes when added to healthy donor PBMCs or cell lines, and this activity is predominately neutralized by antibodies targeting IFN-α (Hua et al., *Arthritis and rheumatism* 54, 1906-1916, doi:10.1002/art.21890 (2006)).

An assay was developed to determine the effect of the antibodies on normalizing the IFN-I signature present in the SLE patient heparinized whole blood. IFN-I inducible gene MX1 (myxovirus resistance 1) expression was used as a marker for IFN-I activity.

Materials 2-4 h after collection of SLE or healthy blood into sodium heparin tubes, 240 μl was plated into 96 well U-bottom plates containing anti-IFN-α/ω antibodies or human IgG1 isotype control. Antibodies diluted in PBS were added at 30 μl per well to 240 μl of blood. After 24 h incubation at 37° C., 745 μl of PAXgene stabilization reagent (QIAGEN) was added to a 96 deep well plate and blood samples were transferred and mixed thoroughly by pipetting. Plates were sealed and frozen at −80° C. until further processing. After thawing, samples were transferred to 2 ml Safe-Lock tubes (Eppendorf) and spun at 5000×g for 10 minutes. Supernatants were aspirated and sample pellets resuspended in 432 μl of DNase/RNase free water by vortexing. Samples were further centrifuged at 5000×g and pellets resuspended in 350 μl BR1 buffer. 300 μl of BR2 buffer was next added followed by 40 μl of proteinase K and samples incubated at 55° C. and shaken at 800 rpm for 10 minutes. The manufacturer's protocol was followed for remainder of purification (QIAGEN, cat #762164). 120 ng of total RNA from each sample was converted to cDNA using iScript cDNA Synthesis kit (BIO-RAD) and primer/probe pairs for human MX1 and beta actin (ACTB) (cat #Hs00895608_m1 and Hs01060665_g1, respectively) were utilized for qPCR. Data was collected on a Viia7 Real Time PCR system and analyzed us GraphPad Prism representing the change in expression of MX1 relative to the ACTB (dCT).

Results

The ability of the IFN-α/ω antibodies to decrease the IFN-I signature in patient blood was assessed using MX1 gene expression as a marker for IFN-I activity.

Figure 13A:
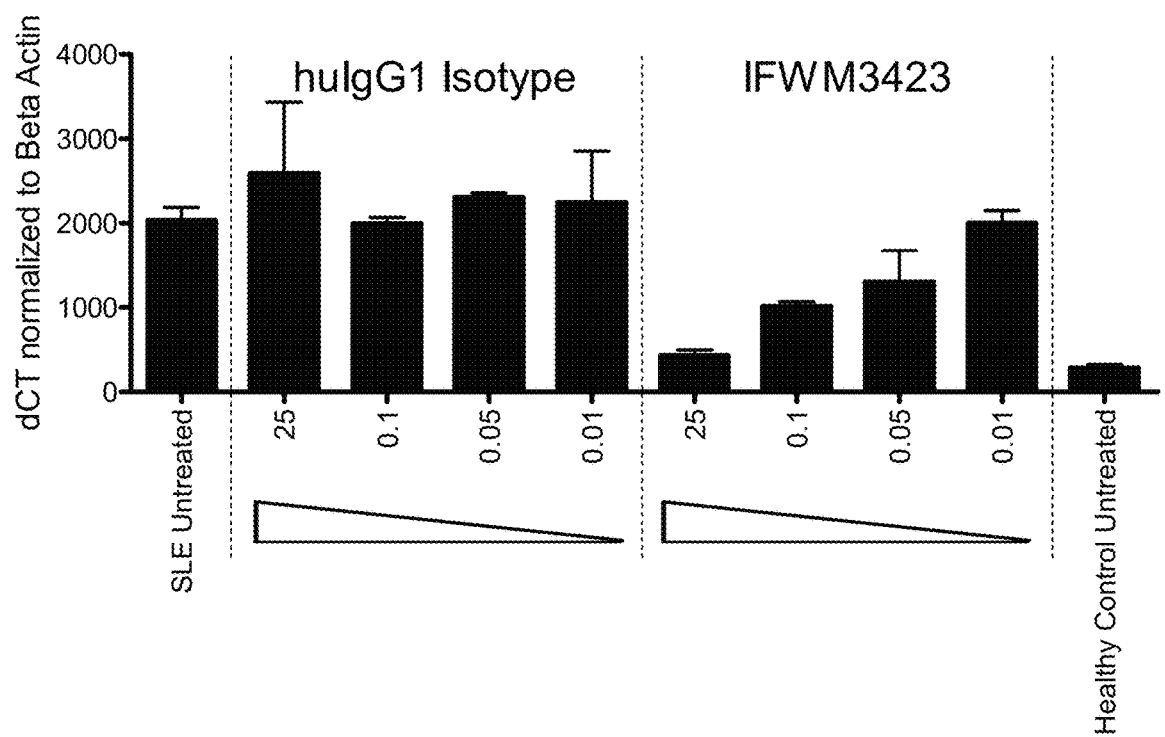
FIG. 13A shows normalization of MX1 gene expression in SLE patient blood after in vitro exposure of the blood to IFN-α/ω antibody IFWM2423 or isotype control for 24 hours at various concentrations (μg/ml) as indicated in the Figure. Bar represents mean and error bars SD from triplicate wells. MX1 gene expression was normalized to β-actin.
Figure 13B:
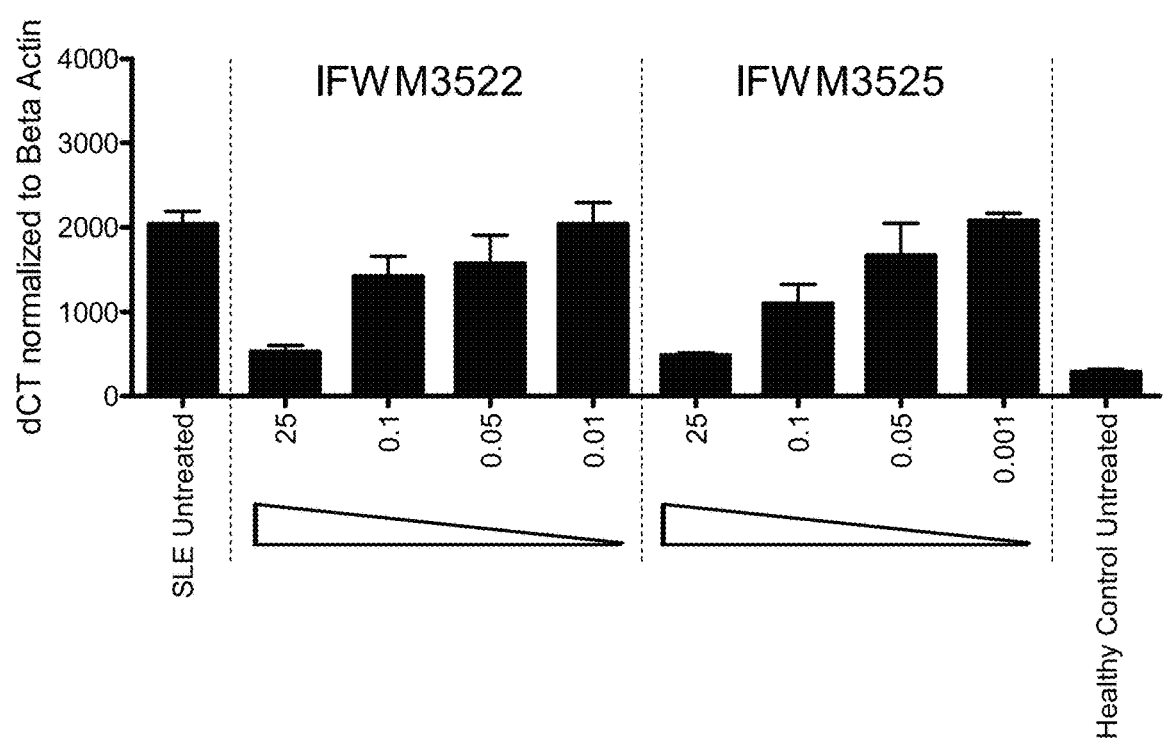
FIG. 13B shows normalization of MX1 gene expression in SLE patient blood after in vitro exposure of the blood to IFN-α/ω antibody IFWM3522 and IFWM2525 or isotype control for 24 hours at various concentrations (μg/ml) as indicated in the Figure. Bar represents mean and error bars SD from triplicate wells. MX1 gene expression was normalized to β-actin.

MX1 gene expression was increased approximately 7 fold in the blood of a SLE patient when compared to a healthy control. The tested anti-IFN-α/ω antibodies dose-dependently reduced MX1 expression in the blood of SLE patients after 24 hour incubation, and at highest antibody concentration the MX1 expression was normalized close to the levels observed in healthy control. FIG. 13 shows the effect of the antibody treatment on MX1 expression in one SLE donor normalized to beta actin expression and is representative of multiple donors having elevated baseline MX1 expression when compared to healthy controls.

EXAMPLE 15

Anti-IFN-α/ω Antibodies Neutralize Cyno Type I IFNs

The ability of the select anti-IFN-α/ω antibodies to neutralize various cyno Type I IFNs was assessed using the ISRE reporter gene assay.

Cynomolgus IFN-α2 (PBL Assay Sciences), IFN-α4 (Sino Biological), IFN-α8 (Sino Biological), and IFN-α13 (Sino Biological) were used in the assays. $IC_{50}$ values were determined using previously determined $EC_{75}$ values for each IFN. (0.078 ng/ml for IFN-α2, 2.68 ng/ml for IFN-α4, 0.66 ng/ml for IFN-α8 and 18.4 for IFN-α13). The $IC_{50}$ of select anti-IFN-α/ω mAbs is shown in Table 29). The data in table 20 is an average of two independent experiments. IFN-α/ω mAbs IFWM3525 and IFWM3522 exhibited similar cross-neutralization properties between the human and orthologous cynomolgus antigens available to test. The lack of neutralization of cynomolgus IFN-α13 was expected, as this molecule, like human IFN-αD, has a serine at position 27 (S27).

TABLE 29

| mAb | Mean IC$_{50}$ (ng/ml) +/− SD | | | | |
|---|---|---|---|---|---|
| | Cyno IFN-α13 | Cyno IFN-α4 | Cyno IFN-α2 | Cyno IFN-α8 | Cyno IFN-ω |
| IFWM3525 | 921.5 +/− 294.9 | 6.769 +/− 0.1923 | 3.346 +/− 0.1747 | 0.5668 +/− 0.07085 | 0.9568 +/− 0.1276 |
| IFWM3522 | 8063 +/− 2562 | 7.348 +/− 0.7616 | 9.887 +/− 2.918 | 0.5497 +/− 0.03734 | 2.028 +/− 0.3691 |

EXAMPLE 16

Crystal Structure of IFWM3421 in Complex with IFN-ω T80E

Crystallization, X-ray data collection and structure determination was done essentially as described in Example 6, except for following changes:

The complex was prepared by mixing IFN-ω:Fab at 1.05:1.00 ratio (excess IFN-ω), incubated at 4° C. overnight, and then concentrated without purification to 8.37 mg/mL in 20 mM Tris pH 7.4, 50 mM NaCl. Crystals for X-ray data collection were obtained from HEPES pH 7.5, 0.2 M Li2SO4, 18% PEG 3350 with MMS seeding.

For X-ray data collection for the IFNω/Fab3186 complex, a crystal was soaked in synthetic mother liquor (0.1 M HEPES, pH 7.5, 20% PEG 3350, 0.2 M LiSO4 with 20% glycerol) and flash frozen in liquid nitrogen. X-ray data were collected at APS (Argonne National Lab). ELN ATeplyak-2013-0014. The diffraction data were processed with XDS. The structure refinement statistics are given in Table 30.

TABLE 30

| | IFNω/FabM3421 |
|---|---|
| Crystal data | |
| Space group | C2 |
| Unit cell dimensions | |
| a, b, c (Å) | 77.48, 69.89, 127.38 |
| α, β, γ (°) | 90, 102.39, 90 |
| Asymmetric unit content | 1 complex |
| X-ray data | |
| Resolution (Å) | 50.00-1.90 (1.94-1.90) |
| Number of measured reflections | 160,439 (10,287) |
| Number of unique reflections | 49,423 (3,356) |
| Completeness (%) | 98.3 (91.1) |
| R$_{merge}$ | 0.095 (0.643) |
| <I/σ> | 9.8 (2.5) |
| B-factor (Wilson plot) (Å$^2$) | 26.6 |
| Refinement | |
| Resolution (Å) | 44.36-1.90 (1.94-1.90) |
| Number of refls used in refinement | 49,411 (2,292) |
| Number of all atoms | 4,249 |
| Number of water molecules | 442 |
| Rcryst (%) | 19.0 (42.1) |
| Rfree (%) | 22.8 (39.8) |
| RMSD bond lengths (Å) | 0.008 |
| RMSD bond angles (°) | 1.12 |
| RMSD B-factor main-chain (Å$^2$) | 4.9 |
| Mean B-factor (Å$^2$) | 34.1 |
| Protein | 33.6 |
| Solvent | 38.3 |

TABLE 30-continued

| | IFNω/FabM3421 |
|---|---|
| MolProbity [25] | |
| Clash score | 3.2 |
| Rotamer outliers (%) | 2.5 |
| Ramachandran favored (%) | 98.2 |
| Ramachandran outliers (%) | 0.0 |
| Cβ deviation > 0.25 Å | 0 |

*Values for high-resolution shell are in parentheses

The crystal structure of IFNω/Fab3421 was determined to 1.9 Å (Table 30). The IFN-ω model contained residues of 23-39 and 118-153. The majority of IFN-ω molecule did not have any electron density and there was no room for them in the crystal, suggesting that cleavage of IFN-ω also happened.

The overall structure of the IFN-ω/Fab3421 complex was very similar to IFNω/FabM371. The backbone structures of the individual components (VH, VL and IFNω) are all nearly identical (Cα rmsd 0.17, 0.23 and 0.36 Å, respectively).

Figure 14A:
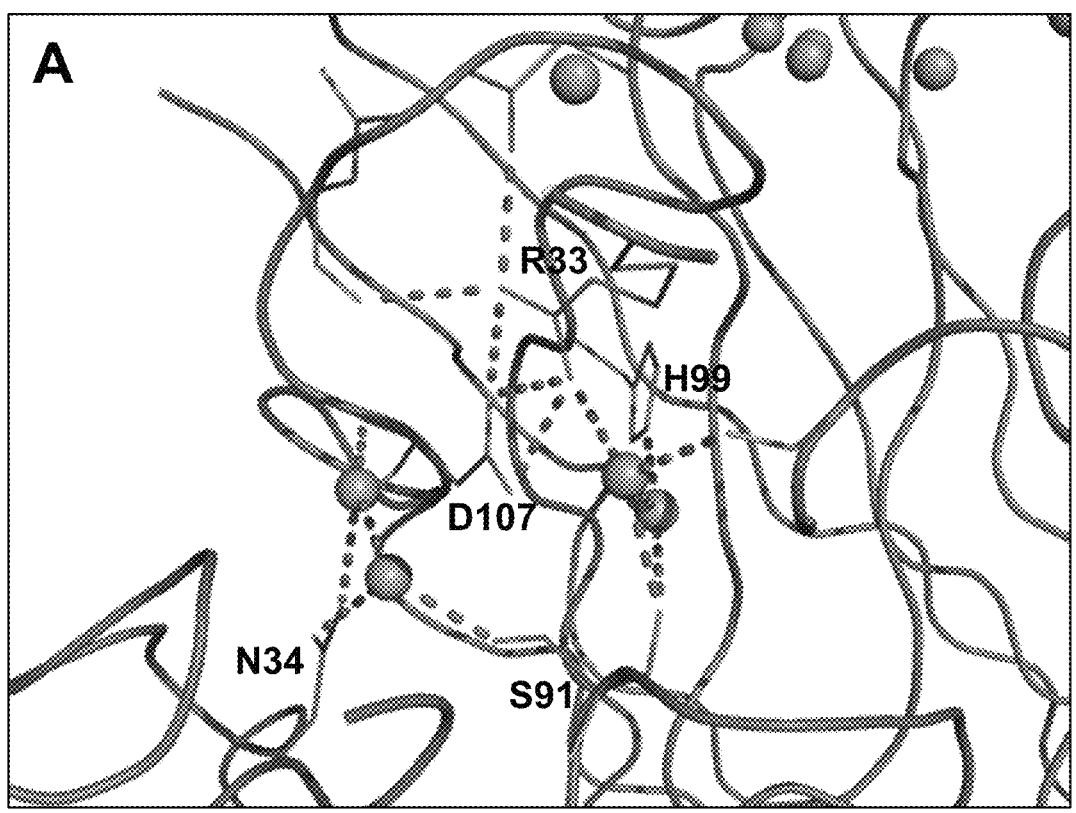
FIG. 14A shows the hydrogen (H) bond interactions between epitope residue R33 with VH of M371 as well as water molecules at the antibody/antigen interface in the IFN-ω/M341 structure.
Figure 14B:
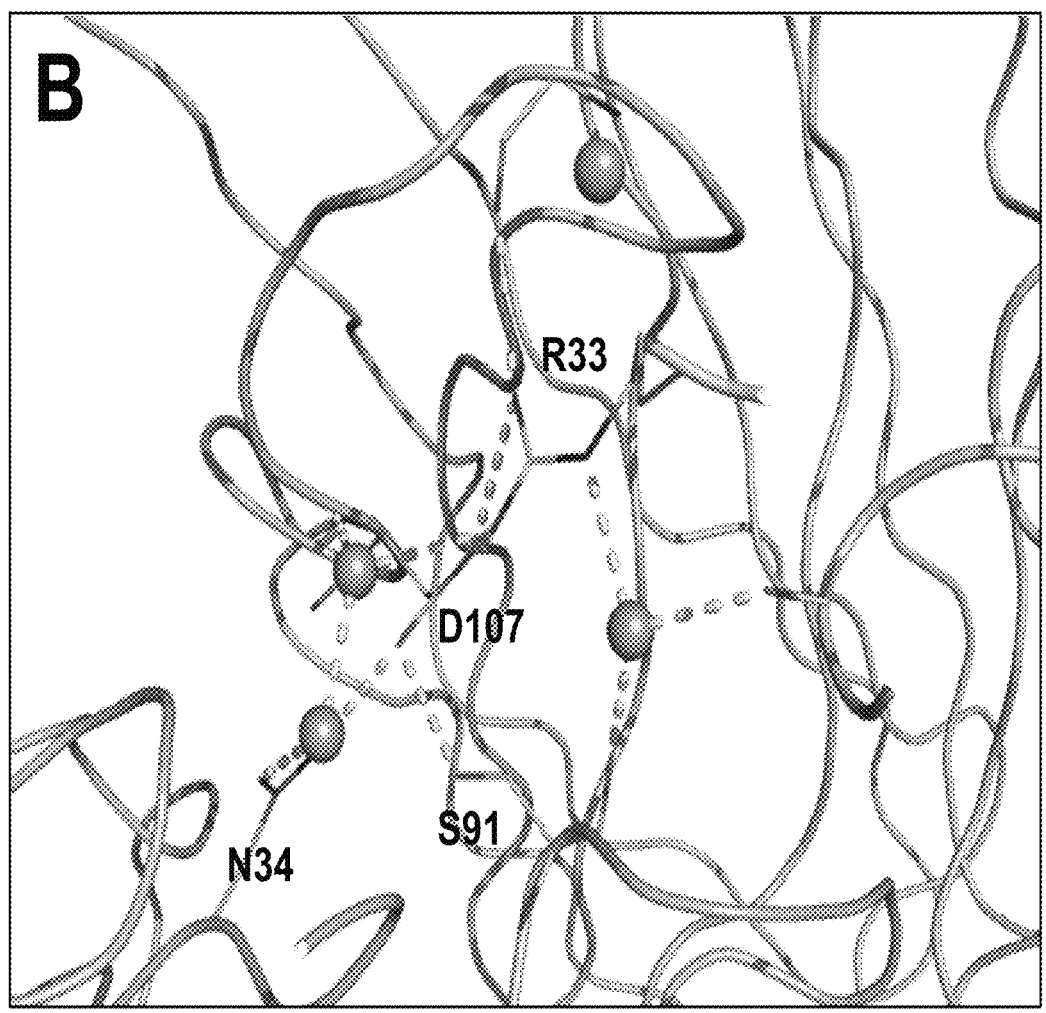
FIG. 14B shows modified H bond interactions between epitope residue R33 with VH of M3421 as well as water molecules in IFN-ω/M3421 structure.
Figure 14C:
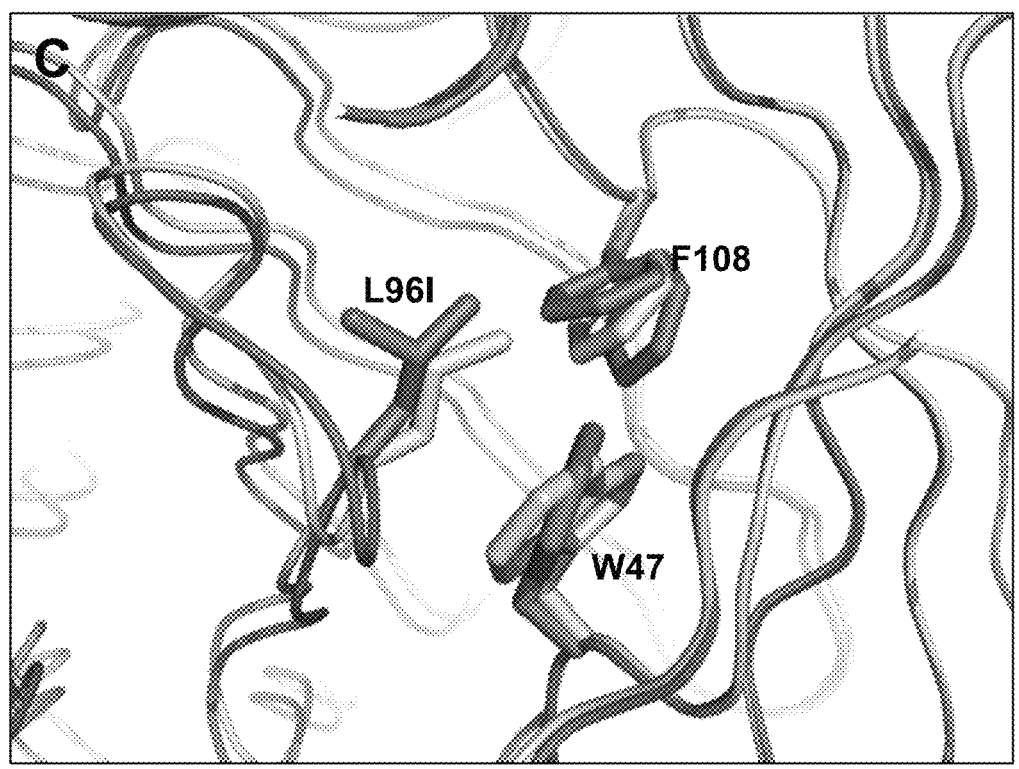
FIG. 14C shows the sequence (L961 mutation) and structural changes upon maturation of M371. In the M371 structure, F108 of VH is best described as having two alternative conformations. In the M3421 structure, they are converted into one conformation, suggesting tighter packing between VH and VL. In addition, there is a side chain rotamer flip of the W47 of VH.
Figure 14D:
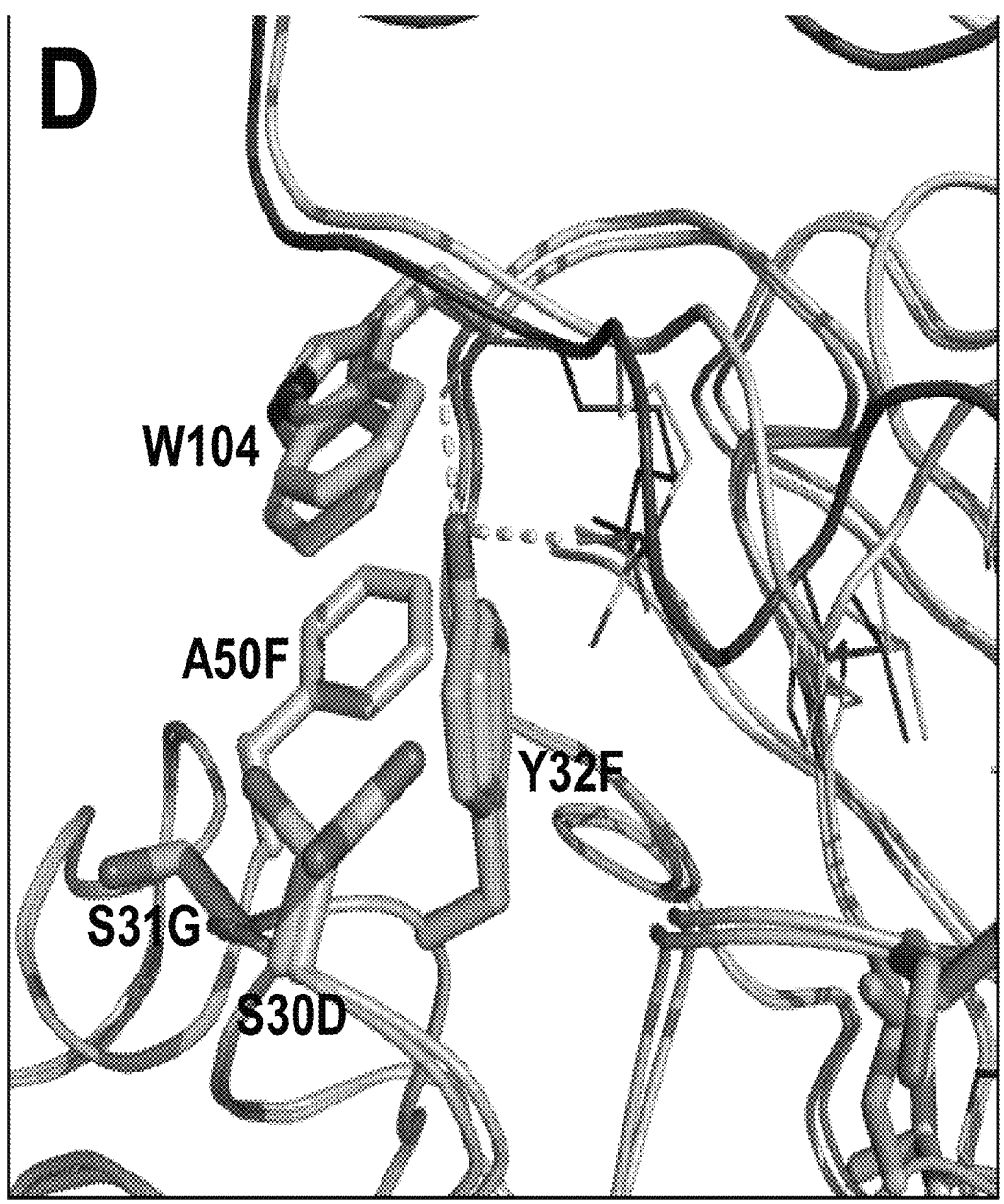
FIG. 14D shows sequence and structural changes upon M371 maturation. The VL Y32 was mutated into a more hydrophobic F(Y32F) and removing the two H bonds between Y32 in M371 and IFN-ω. VL A50 was mutated into F (A50F). This residue does not directly contact the antigen but stacks against W104 of VH that contacts the antigen. Two other changes (S31G and S30D) are not involved in antigen binding or directly impacting binding residues like A50F. These residue changes are likely to influence local hydrophobicity and optimize solvent interaction.

There were, however, a number of significant structural differences. First, when the two structures were superimposed on the VL, the VH was rotated by 4 degrees and the antigen rotated by 11 degrees, leading to a large shift of the IFN-ω molecule with respect to VL. Second, H bonding and water structures (WC2 in particular) were different between the two structures (FIGS. 14A and 14B). R33 of IFN-ω makes 6 H bonds including a salt-bridge with D107 of HCDR3 in the parent M371 complex (FIG. 14A). In the matured form, the side chain electron density for both R33 of IFN-ω and D107 of VH is less well defined (not shown) and they appear to be farther apart, thus reducing the number and strength of the charge-charge interactions (FIG. 14B). A water molecule that involves H99 of VH in M371 is now absent (FIGS. 14A, 14B). Third, F108 of HCDR3 is not involved in antigen binding, but is part of the VL/VH interface. It adopts two alternative conformations in the parent structure (FIG. 14C). The relative rotation of the VL/VH domains along with the L96I mutation in VL reduced it to a single rotamer. Thus it appears that part of the maturation mutations led to better pairing of the Fv. Fourth, two positions were mutated to F (A50F and Y32F) during maturation. Y32 forms two H bonds with the backbone of IFN-ω. But these were also lost as a result of mutation to F(FIG. 14D). The A50F mutation does not generate any new contact with the antigen. Rather its phenyl ring stacks with the VH W104, which in turn packs with the antigen (FIG. 14D). In the LCDR3, two additional hydrophobic mutations (T94L and L96I) appear to form better hydrophobic pocket for L30 and F27 of the antigen. Two additional negative charge mutations (S39D and S93D) do not form any interactions, except with solvent. Overall, affinity improvement is the result of the maturation process that reduces polar interactions but favors/strengthens hydrophobic packing with the antigen as well as better VL/VH pairing.

Figure 15:
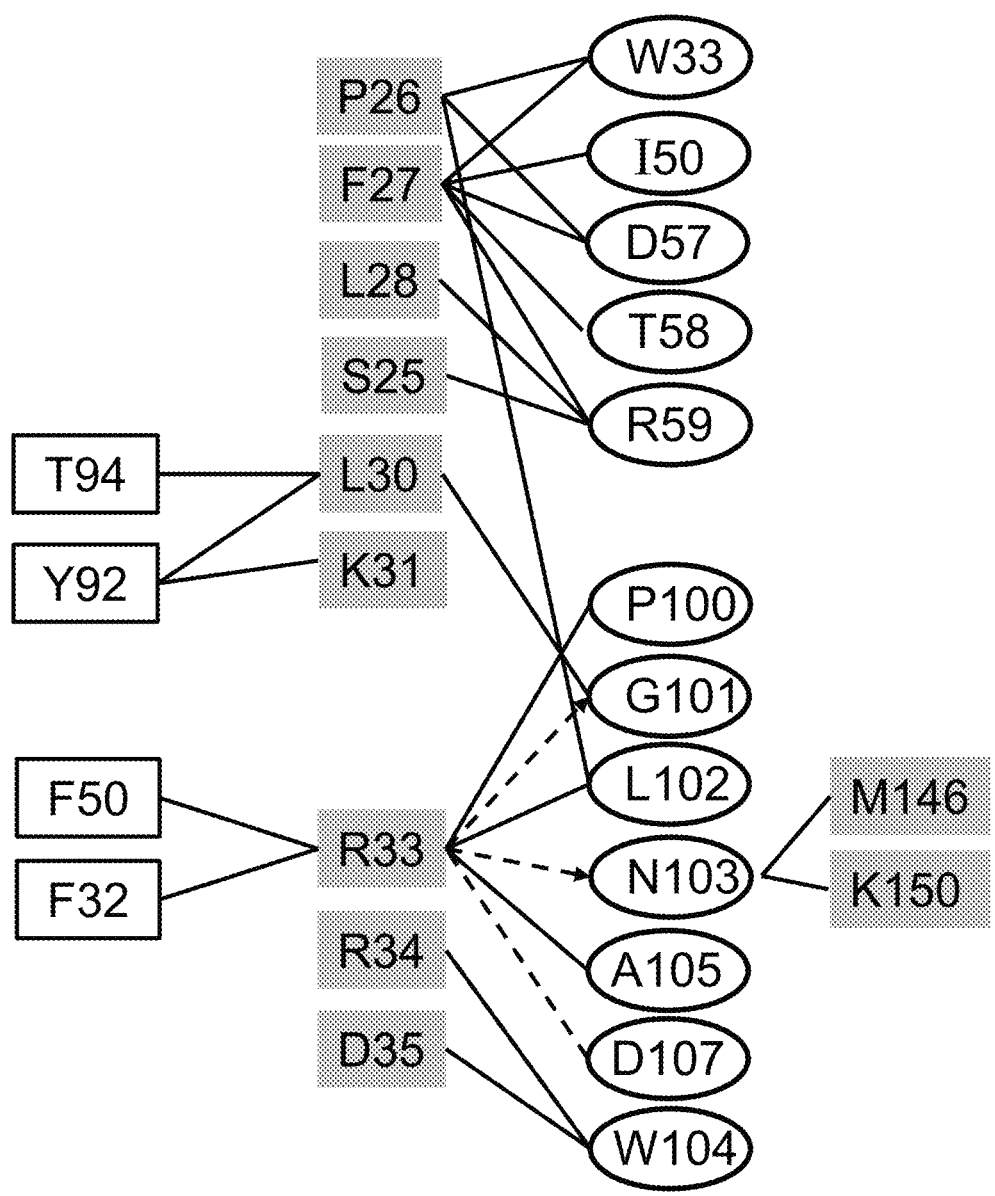
FIG. 15 shows s a 2-dimensional interaction map between IFN-ω and Fab IFWM3421. Boxed residues are VL paratope residues, and circled residues are VH paratope residues. Residues highlighted in gray are IFN-ω epitope residues. Numbering of VL, VH and IFN-ω residues is according to SEQ ID NOs: 28, 71 and 1, respectively. Van der Waals (VDW) and hydrophobic interactions are shown in solid lines, electrostatic and H bonds in dashed lines, arrows indicate backbone interactions with the arrows pointing to the backbone atoms. Most interactions are formed by the three IFN-ω epitope residues F27, L30 and R33.

The epitope and paratope residues. FIG. 15 shows the 2D interaction mAb between IFN-ω and IFWM3421. The epitope residues are identical to those in the M371 structure. The paratope residues are also almost identical (FIG. 15). However, as described above, the maturation process resulted in a number of structural and interaction differences, which likely account for the improvement in binding affinity.

EXAMPLE 17

Crystal Structure of IFWM35251 in Complex with IFN-ω T80E

Crystallization, X-ray data collection and structure determination was done essentially as described in Example 6.

The complex was prepared by mixing of IFN-ω with Fab of IFWM3525 in molar ratio of 1.05:1.0 (excess IFN-ω, 1.92:1.12 mg), incubated at 4° C. overnight, and purified on Superdex 200 column equilibrated with 20 mm HEPES pH 7.5, 0.25 M NaCl, 10% glycerol, then concentrated to 9.79 mg/ml. Crystals suitable for X-diffraction were obtained from 18% PEG 3K, 0.2 M sodium citrate by MMS seeding with seeds from IFN-ω/Fab3186 crystals.

For X-ray data collection, one crystal of IFN-ω/IFWM3525 complex was soaked for a few seconds in a synthetic mother liquor (20% PEG 3350, 0.2 M sodium citrate, 25% glycerol), and flash frozen in the liquid nitrogen. X-ray data were collected at APS (Argonne National Lab). The diffraction data were processed with XDS[10].

The structure of the IFN-ω/IFWM3525 complex was solved by molecular replacement (MR) with Phaser. The search models for MR were the crystal structure of IFN-ω/FabM371. The structure was then refined with PHENIX and model adjustments were carried out using COOT. All other crystallographic calculations were performed with the CCP4 suite of programs. All molecular graphics were generated with PyMol. The structure refinement statistics are given in Table 31.

TABLE 31

| | IFNω/Fab IFWM3525 |
|---|---|
| Crystal data | |
| Space group | C2 |
| Unit cell dimensions | |
| a, b, c (Å) | 169.53, 132.78, 144.19 |
| α, β, γ (°) | 90, 120.43, 90 |
| Asymmetric unit content | 4 complex |
| X-ray data | |
| Resolution (Å) | 50-3.14 (3.22-3.14)* |
| Number of measured reflections | 161,700 (9,097) |
| Number of unique reflections | 47,615 (3,033) |
| Completeness (%) | 98.30 (85.1) |
| $R_{merge}$ | 0.106 (0.877) |
| <I/σ> | 10.7 (1.6) |
| B-factor (Wilson plot) (Å$^2$) | 79.9 |

TABLE 31-continued

| | IFNω/Fab IFWM3525 |
|---|---|
| Refinement | |
| Resolution (Å) | 47.9-3.14 (3.20-3.14) |
| Number of refls used in refinement | 47,403 (2,685) |
| Number of all atoms | 14,880 |
| Number of solvent molecules | 0 |
| Rcryst (%) | 24.4 (37.1) |
| Rfree (%) | 28.4 (42.0) |
| RMSD bond lengths (Å) | 0.002 |
| RMSD bond angles (°) | 0.60 |
| RMSD B-factor main-chain (Å$^2$) | 5.2 |
| Mean B-factor (Å$^2$) | 88.9 |
| Protein | 88.9 |
| Solvent | N/A |
| MolProbity [25] | |
| Clash score | 3.2 |
| Rotamer outliers (%) | 0.4 |
| Ramachandran favored (%) | 96.1 |
| Ramachandran outliers (%) | 0.3 |
| Cβ deviation (>0.25 Å) | 0 |

*Values for high-resolution shell are in parentheses

The overall structure of the IFN-ω/IFWM35258 complex was very similar to IFN-ω/FabM371. The molecular models for the IFN-ω molecules includes residues 23-39 and 119-153, corresponding to helical segment AB and helices D and E. The helices A, B and C and the connecting loops are disordered. These missing parts of the IFN-ω are likely due to limited proteolysis as found for the M371 and M3421 complex structures. The Fab molecular model contains residues from 1 to 213 for the light chain and from 1 to 222 for the heavy chain. The C-terminal 6× His tag, inter-chain disulfide bond and residues of 137-141 of the heavy chain are disordered. No solvent water molecules were included due to low diffraction resolution.

Figure 16:
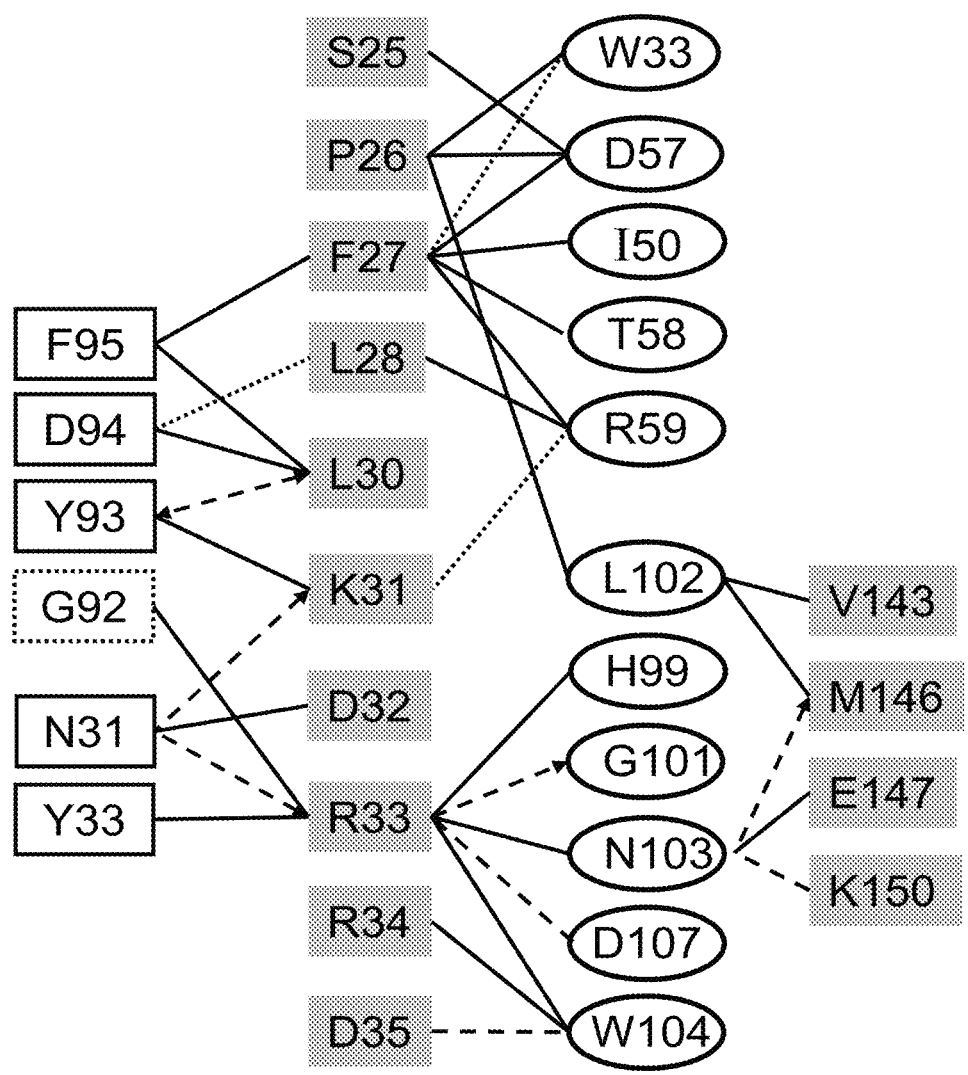
FIG. 16 shows s a 2-dimensional interaction map between IFN-ω and Fab of IFWM3525. Boxed residues are VL paratope residues, and circled residues are VH paratope residues. Residues highlighted in gray are IFN-ω epitope residues. Numbering of VL, VH and IFN-ω residues is according to SEQ ID NOs: 28, 71 and 1, respectively. Van der Waals (VDW) and hydrophobic interactions are shown in solid lines, electrostatic and H bonds in dashed lines, arrows indicate backbone interactions with the arrows pointing to the backbone atoms. Most interactions are formed by the three IFN-ω epitope residues F27, L30 and R33.

FIG. 16 shows a 2-dimensional interaction map between IFN-ω and Fab of IFWM3525. Epitope residues F27, L30, and R33 of the AB helix account for the majority of the Ab/Ag interactions. Thus, this region of IFN-ω appears to constitute the main part of the epitope. Compared with the parental M371, the epitope contains two more residues from the helix E of IFN-ω which form interactions with HCDR3 of IFWM3525.

IFWM3525 has broad binding specificity for IFNω and most of IFNα subtypes. It does not bind IFNβ and IFNα-D/1. The sequence alignment of IFNs (FIG. 9) indicates that IFWM3525 epitope residues are largely conserved among the IFN-ω and IFN-α subtypes. In addition, structural comparison of the epitope residues in IFN-α (pdb code 2RH2, which was re-built and refined using deposited data as only Cα trace was available in PDB) and IFN-ω indicate the epitope residues have very similar backbone and side chain structures. Thus, the sequence and structure conservations (or epitope conservation) likely are responsible for the broad binding of IFNα/ω by IFWM3525.

Sequence Listing

| SEQ ID NO: | Type | Species | Description | Amino acid sequence (or nucleotide sequence, as applicable) |
|---|---|---|---|---|
| 1 | PRT | Homo sapiens | human IFNw | CDLPQNHGLLSRNTLVLLHQMRRISPFLCLKDRRDFRFPQEMVKGSQLQKAHVMSVLHEMLQQIFSLFH TERSSAAWNMTLLDQLHTGLHQQLQHLETCLLQVVGEGESAGAISSPALTLRRYFQGIRVYLKEKKYSD CAWEVVRMEIMKSLFLSTNMQERLRSKDRDLGSS |

Sequence Listing

| SEQ ID NO: | Type | Species | Description | Amino acid sequence (or nucleotide sequence, as applicable) |
|---|---|---|---|---|
| 2 | PRT | *Homo sapiens* | huIFNw T80E | CDLPQNHGLLSRNTLVLLHQMRRISPFLCLKDRRDFRFPQEMVKGSQLQKAHVMSVLHEMLQQIFSLFH TERSSAAWNMELLDQLHTGLHQQLQHLETCLLQVVGEGESAGAISSPALTLRRYFQGIRVYLKEKKYSD CAWEVVRMEIMKSLFLSTNMQERLRSKDRDLGSS |
| 3 | PRT | Chimp | chimp IFNomega | CDLPQNHGLLSRNTLVLLHQMRRISPFLCLKDRRDFRFPQEMVKGSQLQKAQVMSVLHEMLQQIFSLFH TERSSAAWNMTLLDQLHTGLHQQLQHLETCLLQVMGEGESAGAISSPALTLRRYFQGIRVYLKEKKYSD CAWEVVRMEIMKSLFLSTNMQERLRSKDRDLGSSRNDSH |
| 4 | PRT | Cyno | cyno IFNomega | CDLPQNHGLLSRNTLVLLHQMRRISPFLCLKDRRDFRFPQEMVEGSQLQKAQVMSVLHEMLQQIFSLFH TEHSSAAWNTTLLDHLHTGLHRQLEHLETCLVQVMREGESAGAIRSPALTLRRYFQGIRVYLKEKKYSD CAWVVVRMEIMKSLFLSTNMQERLKSKDGDLGSS |
| 5 | PRT | *Homo sapiens* | alpha A | CDLPQTHSLGSRRTLMLLAQMRKISLFSCLKDRHDFGFPQEEFGNQFQKAETIPVLHEMIQQIFNLFST KDSSAAWDETLLDKFYTELYQQLNDLEACVIQGVGVTETPLMKEDSILAVRKYFQRITLYLKEKKYSPC AWEVVRAEIMRSFSLSTNLQESLRSKE |
| 6 | PRT | *Homo sapiens* | IFN alpha B2 | CDLPQTHSLGNRRALILLAQMRRISPFSCLKDRHDFEFPQEEFDDKQFQKAQAISVLHEMIQQTFNLFS TKDSSAALDETLLDEFYIELDQQLNDLESCVMQEVGVIESPLMYEDSILAVRKYFQRITLYLTEKKYSS CAWEVVRAEIMRSFSLSINLQKRLKSKE |
| 7 | PRT | *Homo sapiens* | alpha C | CDLPQTHSLGNRRALILLGQMGRISPFSCLKDRHDFRIPQEEFDGNQFQKAQAISVLHEMIQQTFNLFS TEDSSAAWEQSLLEKFSTELYQQLNDLEACVIQEVGVEETPLMNEDSILAVRKYFQRITLYLIERKYSP CAWEVVRAEIMRSLSFSTNLQKRLRRKD |
| 8 | PRT | *Homo sapiens* | alpha D | CDLPETHSLDNRRTLMLLAQMSRISPSSCLMDRHDFGFPQEEFDGNQFQKAPAISVLHELIQQIFNLFT TKDSSAAWDEDLLDKFCTELYQQLNDLEACVMQEERVGETPLMNVDSILAVKKYFRRITLYLTEKKYSP CAWEVVRAEIMRSLSLSTNLQERLRRKE |
| 9 | PRT | *Homo sapiens* | alpha F | CDLPQTHSLGNRRALILLAQMGRISPFSCLKDRHDFGFPQEEFDGNQFQKAQAISVLHEMIQQTFNLFS TKDSSATWEQSLLEKFSTELNQQLNDMEACVIQEVGVEETPLMNVDSILAVKKYFQRITLYLTEKKYSP CAWEVVRAEIMRSFSLSKIFQERLRRKE |
| 10 | PRT | *Homo sapiens* | alpha G | CDLPQTHSLSNRRTLMIMAQMGRISPFSCLKDRHDFGFPQEEFDGNQFQKAQAISVLHEMIQQTFNLFS TKDSSATWDETLLDKFYTELYQQLNDLEACMMQEVGVEDTPLMNVDSILTVRKYFQRITLYLTEKKYSP CAWEVVRAEIMRSFSLSANLQERLRRKE |
| 11 | PRT | *Homo sapiens* | alpha H2 | CNLSQTHSLNNRRTLMLMAQMRRISPFSCLKDRHDFEFPQEEFDGNQFQKAQAISVLHEMMQQTFNLFS TKNSSAAWDETLLEKFYIELFQQMNDLEACVIQEVGVEETPLMNEDSILAVKKYFQRITLYLMEKKYSP CAWEVVRAEIMRSLSFSTNLQKRLRRKD |
| 12 | PRT | *Homo sapiens* | IFN-aI | CDLPQTHSLGNRRALILLAQMGRISPFSCLKDRPDFGLPQEEFDGNQFQKTQAISVLHEMIQQTFNLFS TEDSSAAWEQSLLEKFSTELYQQLNNLEACVIQEVGMEETPLMNEDSILAVRKYFQRITLYLTEKKYSP CAWEVVRAEIMRSLSFSTNLQKILRRKD |
| 13 | PRT | *Homo sapiens* | alpha J1 | CDLPQTHSLRNRRALILLAQMGRISPFSCLKDRHEFRFPEEEFDGHQFQKTQAISVLHEMIQQTFNLFS TEDSSAAWEQSLLEKFSTELYQQLNDLEACVIQEVGVEETPLMNEDFILAVRKYFQRITLYLMEKKYSP CAWEVVRAEIMRSFSFSTNLKKGLRRKD |
| 14 | PRT | *Homo sapiens* | alpha K | CDLPQTHSLGHRRTMMLLAQMRRISLFSCLKDRHDERFPQEEEDGNQFQKAEAISVLHEVIQQTFNLFS TKDSSVAWDERLLDKLYTELYQQLNDLEACVMQEVWVGGTPLMNEDSILAVRKYFQRITLYLTEKKYSP CAWEVVRAEIMRSFSSSRNLQERLRRKE |
| 15 | PRT | *Homo sapiens* | alpha 4b | CDLPQTHSLGNRRALILLAQMGRISHFSCLKDRHDFGFPEEEFDGHQFQKTQAISVLHEMIQQTFNLFS TEDSSAAWEQSLLEKFSTELYQQLNDLEACVIQEVGVEETPLMNVDSILAVRKYFQRITLYLTEKKYSP CAWEVVRAEIMRSLSFSTNLQKRLRRKD |
| 16 | PRT | *Homo sapiens* | alpha WA | CDLPQTHSLGNRRALILLAQMGRISHFSCLKDRYDFGFPQEVFDGNQFQKAQAISAFHEMIQQTFNLFS TKDSSAAWDETLLDKFYIELFQQLNDLEACVTQEVGVEEIALMNEDSILAVRKYFQRITLYLMGKKYSP CAWEVVRAEIMRSFSFSTNLQKGLRRKD |
| 17 | PRT | *Homo sapiens* | IFN-a2 | CDLPQTHSLGSRRTLMLLAQMRRISLFSCLKDRHDFGFPQEEFGNQFQKAETIPVLHEMIQQIFNLFST KDSSAAWDETLLDKFYTELYQQLNDLEACVIQGVGVTETPLMKEDSILAVRKYFQRITLYLKEKKYSPC AWEVVRAEIMRSFSLSTNLQESLRSKE |
| 18 | PRT | *Homo sapiens* | IFN-a1 | CDLPETHSLDNRRTLMLLAQMSRISPSSCLMDRHDFGFPQEEFDGNQFQKAPAISVLHELIQQIFNLFT TKDSSAAWDEDLLDKFCTELYQQLNDLEACVMQEERVGETPLMNADSILAVKKYFRRITLYLTEKKYSP CAWEVVRAEIMRSLSLSTNLQERLRRKE |
| 19 | PRT | *Homo sapiens* | IFN-aa | CDLPQTHSLGNRRALILLAQMGRISHFSCLKDRHDFGFPEEEFDGHQFQKAQAISVLHEMIQQTFNLFS TEDSSAAWEQSLLEKFSTELYQQLNDLEACVIQEVGVEETPLMNEDSILAVRKYFQRITLYLTEKKYSP CAWEVVRAEIMRSLSFSTNLQKRLRRKD |

Sequence Listing

| SEQ ID NO: | Type | Species | Description | Amino acid sequence (or nucleotide sequence, as applicable) |
|---|---|---|---|---|
| 20 | PRT | Homo sapiens | IFN-b | MSYNLLGFLQRSSNFQCQKLLWQLNGRLEYCLKDRMNFDIPEEIKQLQQFQKEDAALTIYEMLQNIFAI FRQDSSSTGWNETIVENLLANVYHQINHLKTVLEEKLEKEDFTRGKLMSSLHLKRYYGRILHYLKAKEY SHCAWTIVRVEILRNFYFINRLTGYLRN |
| 21 | PRT | Artificial sequence | Signal peptide | MALTFYLLVALVVLSYKSFSSLG |
| 22 | PRT | Artificial sequence | Signal peptide | MARSFSLLMVVLVLSYKSICSLG |
| 23 | PRT | Artificial sequence | Signal peptide | MALPFALLMALVVLSCKSSCSLD |
| 24 | PRT | Artificial sequence | Signal peptide | MALSFSLLMAVLVLSYKSICSLG |
| 25 | PRT | Artificial sequence | Signal peptide | MALTFALLVALLVLSCKSSCSVG |
| 26 | PRT | Homo sapiens | IFNAR1 | 1 mmvvllgatt lvlvavapwv lsaaaggknl kspqkvevdi iddnfilrwn rsdesvgnvt<br>61 fsfdyqktgm dnwiklsgcq nitstkcnfs slklnvyeei klriraeken tsswyevdsf<br>121 tpfrkaqigp pevhleaedk aivihispgt kdsvmwaldg lsftyslviw knssgveeri<br>181 eniysrhkiy klspettycl kvkaalltsw kigvyspvhc ikttvenelp ppenievsvq<br>241 nqnyvlkwdy tyanmtfqvq wlhaflkrnp gnhlykwkqi pdcenvkttq cvfpqnvfqk<br>301 giyllrvqas dgnntsfwse eikfdteiqa fllppvfnir slsdsfhiyi gapkqsgntp<br>361 viqdypliye iifwentsna erkiiekktd vtvpnlkplt vycvkaraht mdeklnkssv<br>421 fsdavcektk pgntskiwli vgicialfal pfviyaakvf lrcinyvffp slkpssside<br>481 yfseqplknl llstseeqie kcfiienist iatveetnqt dedhkkyssq tsqdsgnysn<br>541 edesesktse elqqdfv |
| 27 | PRT | Homo sapiens | IFNAR2 | 1 mllsqnafif rslnlvlmvy islvfgisyd spdytdesct fkislrnfrs ilswelknhs<br>61 ivpthytlly timskpedlk vvkncanttr sfcdltdewr stheayvtvl egfsgnttlf<br>121 scshnfwlai dmsfeppefe ivgftnhinv mvkfpsivee elqfdlslvi eeqsegivkk<br>181 hkpeikgnms gnftyiidkl ipntnycvsv ylehsdeqav iksplkctll ppgqesesae<br>241 sakiggiitv flialvltst ivtlkwigyi clrnslpkvl rqglakgwna vaihrcshna<br>301 lqsetpelkq ssclsfpssw dykraslcps d |
| 28 | PRT | Artificial sequence | IFWH591 | EVQLVQSGAEVKKPGESLKISCKGSGYSFTSYWIGWVRQMPGKGLEWMGIIDPSDSDTRYSPSFQGQVT ISADKSISTAYLQWSSLKASDTAMYYCARHPGLNWAPDFDYWGQGTLVTVSS |
| 29 | PRT | Artificial sequence | PH9L4 | DIQMTQSPSSLSASVGDRVTITCRASQSISSYLNWYQQKPGKAPKLLIYAASSLQSGVPSRFSGSGSGT DFTLTISSLQPEDFATYYCQQSYSTPLTFGQGTKVEIK |
| 30 | PRT | Artificial sequence | IFWH624 | EVQLVQSGAEVKKPGESLKISCKGSGYSFTSYWIGWVRQMPGKGLEWMGIIDPSDSDTAYSPSFQGQVT ISADKSISTAYLQWSSLKASDTAMYYCARHPGLNWAPDFDYWGQGTLVTVSS |
| 31 | PRT | Artificial sequence | IFWH629 | EVQLVQSGAEVKKPGESLKISCKGSGYSFTSYWIGWVRQMPGKGLEWMGIIDPSDSDTRYSPSFQGQVT ISADKSISTAYLQWSSLKASDTAMYYCARHPGLAWAPDFDYWGQGTLVTVSS |
| 32 | PRT | Artificial sequence | IFWL983 | DIQMTQSPSSLSASVGDRVTITCRASQSIDGSLNWYQQKPGKAPKLLIYFASSLQSGVPSRFSGSGSGT DFTLTISSLQPEDFATYYCQQSYDFPLTFGQGTKVEIK |
| 33 | PRT | Artificial sequence | IFWL991 | DIQMTQSPSSLSASVGDRVTITCRASQSINRFLNWYQQKPGKAPKLLIYAASSLQSGVPSRFSGSGSGT DFTLTISSLQPEDFATYYCQQAIDLPFTFGQGTKVEIK |
| 34 | PRT | Artificial sequence | IFWL992 | DIQMTQSPSSLSASVGDRVTITCRASQSIGSFLNWYQQKPGKAPKLLIYFASSLQSGVPSRFSGSGSGT DFTLTISSLQPEDFATYYCQQSYSIPITFGQGTKVEIK |
| 35 | PRT | Artificial sequence | IFWL997 | DIQMTQSPSSLSASVGDRVTITCRASQSIGSALNWYQQKPGKAPKLLIYFASSLQSGVPSRFSGSGSGT DFTLTISSLQPEDFATYYCQQSYDFPLTFGQGTKVEIK |
| 36 | PRT | Artificial sequence | IFWL998 | DIQMTQSPSSLSASVGDRVTITCRASQSISKFLNWYQQKPGKAPKLLIYFASSLQSGVPSRFSGSGSGT DFTLTISSLQPEDFATYYCQQSNTLPFTFGQGTKVEIK |
| 37 | PRT | Artificial sequence | IFWL999 | DIQMTQSPSSLSASVGDRVTITCRASQSIDEFLNWYQQKPGKAPKLLIYFASSLQSGVPSRFSGSGSGT DFTLTISSLQPEDFATYYCQQAHSFPLTFGQGTKVEIK |
| 38 | PRT | Artificial sequence | IFWL1000 | DIQMTQSPSSLSASVGDRVTITCRASQSITNFLNWYQQKPGKAPKLLIYFASSLQSGVPSRFSGSGSGT DFTLTISSLQPEDFATYYCQQSLDFPLTFGQGTKVEIK |
| 39 | PRT | Artificial sequence | IFWL1001 | DIQMTQSPSSLSASVGDRVTITCRASQSIGDFLNWYQQKPGKAPKLLIYFASSLQSGVPSRFSGSGSGT DFTLTISSLQPEDFATYYCQQALDFPLTFGQGTKVEIK |

Sequence Listing

| SEQ ID NO: | Type | Species | Description | Amino acid sequence (or nucleotide sequence, as applicable) |
|---|---|---|---|---|
| 40 | PRT | Artificial sequence | IFWL1004 | DIQMTQSPSSLSASVGDRVTITCRASQSIAEFLNWYQQKPGKAPKLLIYFASSLQSGVPSRFSGSGSGT DFTLTISSLQPEDFATYYCQQSIDFPLTFGQGTKVEIK |
| 41 | PRT | Artificial sequence | IFWL1006 | DIQMTQSPSSLSASVGDRVTITCRASQSIGGFLNWYQQKPGKAPKLLIYFASSLQSGVPSRFSGSGSGT DFTLTISSLQPEDFATYYCQQSYSLPITFGQGTKVEIK |
| 42 | PRT | Artificial sequence | IFWL1007 | DIQMTQSPSSLSASVGDRVTITCRASQSIGKSLNWYQQKPGKAPKLLIYFASSLQSGVPSRFSGSGSGT DFTLTISSLQPEDFATYYCQQSYDFPLTFGQGTKVEIK |
| 43 | PRT | Artificial sequence | IFWL1009 | DIQMTQSPSSLSASVGDRVTITCRASQSIDDFLNWYQQKPGKAPKLLIYFASSLQSGVPSRFSGSGSGT DFTLTISSLQPEDFATYYCQQSHTLPLTFGQGTKVEIK |
| 44 | PRT | Artificial sequence | IFWL1010 | DIQMTQSPSSLSASVGDRVTITCRASQSIDGALNWYQQKPGKAPKLLIYFASSLQSGVPSRFSGSGSGT DFTLTISSLQPEDFATYYCQQSFDFPLTFGQGTKVEIK |
| 45 | PRT | Artificial sequence | IFWL1013 | DIQMTQSPSSLSASVGDRVTITCRASQSINNFLNWYQQKPGKAPKLLIYFASSLQSGVPSRFSGSGSGT DFTLTISSLQPEDFATYYCQQSFNLPITFGQGTKVEIK |
| 46 | PRT | Artificial sequence | IFWL1014 | DIQMTQSPSSLSASVGDRVTITCRASQSIDRALNWYQQKPGKAPKLLIYFASSLQSGVPSRFSGSGSGT DFTLTISSLQPEDFATYYCQQSFDFPLTFGQGTKVEIK |
| 47 | PRT | Artificial sequence | IFWL1017 | DIQMTQSPSSLSASVGDRVTITCRASQSITSSLNWYQQKPGKAPKLLIYFASSLQSGVPSRFSGSGSGT DFTLTISSLQPEDFATYYCQQSFDLPLTFGQGTKVEIK |
| 48 | PRT | Artificial sequence | IFWL1022 | DIQMTQSPSSLSASVGDRVTITCRASQSINEFLNWYQQKPGKAPKLLIYFASSLQSGVPSRFSGSGSGT DFTLTISSLQPEDFATYYCQQSYSTPLTFGQGTKVEIK |
| 49 | PRT | Artificial sequence | IFWL1026 | DIQMTQSPSSLSASVGDRVTITCRASQSISKFLNWYQQKPGKAPKLLIYFASSLQSGVPSRFSGSGSGT DFTLTISSLQPEDFATYYCQQSYDFPITFGQGTKVEIK |
| 50 | PRT | Artificial sequence | IFWL1038 | DIQMTQSPSSLSASVGDRVTITCRASQSISEYLNWYQQKPGKAPKLLIYFASSLQSGVPSRFSGSGSGT DFTLTISSLQPEDFATYYCQQSHSLPITFGQGTKVEIK |
| 51 | PRT | Artificial sequence | IFWL1041 | DIQMTQSPSSLSASVGDRVTITCRASQSITGFLNWYQQKPGKAPKLLIYAASSLQSGVPSRFSGSGSGT DFTLTISSLQPEDFATYYCQQSHDFPLTFGQGTKVEIK |
| 52 | PRT | Artificial sequence | IFWL1047 | DIQMTQSPSSLSASVGDRVTITCRASQSINGVLNWYQQKPGKAPKLLIYFASSLQSGVPSRFSGSGSGT DFTLTISSLQPEDFATYYCQQSHDFPLTFGQGTKVEIK |
| 53 | PRT | Artificial sequence | IFWL1048 | DIQMTQSPSSLSASVGDRVTITCRASQSIDGALNWYQQKPGKAPKLLIYFASSLQSGVPSRFSGSGSGT DFTLTISSLQPEDFATYYCQQAYDFPLTFGQGTKVEIK |
| 54 | PRT | Artificial sequence | IFWL1051 | DIQMTQSPSSLSASVGDRVTITCRASQSIADFLNWYQQKPGKAPKLLIYFASSLQSGVPSRFSGSGSGT DFTLTISSLQPEDFATYYCQQSHSFPLTFGQGTKVEIK |
| 55 | PRT | Artificial sequence | IFWL1053 | DIQMTQSPSSLSASVGDRVTITCRASQSITNHLNWYQQKPGKAPKLLIYFASSLQSGVPSRFSGSGSGT DFTLTISSLQPEDFATYYCQQAHNFPLTFGQGTKVEIK |
| 56 | PRT | Artificial sequence | IFWL1060 | DIQMTQSPSSLSASVGDRVTITCRASQSIRNSLNWYQQKPGKAPKLLIKWASSLQSGVPSRFSGSGSGT DFTLTISSLQPEDFATYYCQQLYDWPLTFGQGTKVEIK |
| 57 | PRT | Artificial sequence | IFWL1063 | DIQMTQSPSSLSASVGDRVTITCRASQSIANNLNWYQQKPGKAPKLLIHWASSLQSGVPSRFSGSGSG TDFTLTISSLQPEDFATYYCQQGYDTPFTFGQGTKVEIK |
| 58 | PRT | Artificial sequence | IFWL1064 | DIQMTQSPSSLSASVGDRVTITCRASQSINNLNWYQQKPGKAPKLLIYWASSLQSGVPSRFSGSGSGTD FTLTISSLQPEDFATYYCQQGYDTPFTFGQGTKVEIK |
| 59 | PRT | Artificial sequence | IFWL1067 | DIQMTQSPSSLSASVGDRVTITCRASQSIRNNLNWYQQKPGKAPKLLIHWASSLQSGVPSRFSGSGSG TDFTLTISSLQPEDFATYYCQQGYDTPFTFGQGTKVEIK |
| 60 | PRT | Artificial sequence | IFWL1071 | DIQMTQSPSSLSASVGDRVTITCRASQSIRNNSLNWYQQKPGKAPKLLIYGASSLQSGVPSRFSGSGSG TDFTLTISSLQPEDFATYYCQQDYNWPITFGQGTKVEIK |
| 61 | PRT | Artificial sequence | IFWL1073 | DIQMTQSPSSLSASVGDRVTITCRASQSIDNSYLNWYQQKPGKAPKLLIYGASSLQSGVPSRFSGSGSG TDFTLTISSLQPEDFATYYCQQGWDWPLTFGQGTKVEIK |
| 62 | PRT | Artificial sequence | IFWL1074 | DIQMTQSPSSLSASVGDRVTITCRASQSIANTNLNWYQQKPGKAPKLLIHWASSLQSGVPSRFSGSGSG TDFTLTISSLQPEDFATYYCQQWYDNPLTFGQGTKVEIK |
| 63 | PRT | Artificial sequence | IFWL1076 | DIQMTQSPSSLSASVGDRVTITCRASQSIDNNLNWYQQKPGKAPKLLIYAASSLQSGVPSRFSGSGSG TDFTLTISSLQPEDFATYYCQQGYDWPLTFGQGTKVEIK |

Sequence Listing

SEQ
ID                              Amino acid sequence
NO:  Type  Species    Description (or nucleotide sequence, as applicable)

64   PRT   Artificial  IFWL1082   DIQMTQSPSSLSASVGDRVTITCRASQSIRNNSLNWYQQKPGKAPKLLIYAASSLQSGVPSRFSGSGSG
           sequence               TDFTLTISSLQPEDFATYYCQQDYNWPLTFGQGTKVEIK 65   PRT   Artificial  IFWL1084   DIQMTQSPSSLSASVGDRVTITCRASQSINYLNWYQQKPGKAPKLLIYGASSLQSGVPSRFSGSGSGTD
           sequence               FTLTISSLQPEDFATYYCQQSHDWPITFGQGTKVEIK 66   PRT   Artificial  IFWL1085   DIQMTQSPSSLSASVGDRVTITCRASQSIRNNYLNWYQQKPGKAPKLLIYAASSLQSGVPSRFSGSGSG
           sequence               TDFTLTISSLQPEDFATYYCQQGYDTPLTFGQGTKVEIK 67   PRT   Artificial  IFWL1087   DIQMTQSPSSLSASVGDRVTITCRASQSISNSLNWYQQKPGKAPKLLIHWASSLQSGVPSRFSGSGSG
           sequence               TDFTLTISSLQPEDFATYYCQQWYDHPLTFGQGTKVEIK 68   PRT   Artificial  IFWL1091   DIQMTQSPSSLSASVGDRVTITCRASQSIRNTNLNWYQQKPGKAPKLLIHWASSLQSGVPSRFSGSGSG
           sequence               TDFTLTISSLQPEDFATYYCQQGYDTPFTFGQGTKVEIK 69   PRT   Artificial  IFWL1093   DIQMTQSPSSLSASVGDRVTITCRASQSIANNDLNWYQQKPGKAPKLLIHWASSLQSGVPSRFSGSGSG
           sequence               TDFTLTISSLQPEDFATYYCQQDYDWPLTFGQGTKVEIK 70   PRT   Artificial  IFWL1049   DIQMTQSPSSLSASVGDRVTITCRASQSIAGFLNWYQQKPGKAPKLLIYYASSLQSGVPSRFSGSGSGT
           sequence               DFTLTISSLQPEDFATYYCQQSYSIPITFGQGTKVEIK 71   PRT   Artificial  IFWL984    DIQMTQSPSSLSASVGDRVTITCRASQSIDGFLNWYQQKPGKAPKLLIYFASSLQSGVPSRFSGSGSGT
           sequence               DFTLTISSLQPEDFATYYCQQSYDLPITFGQGTKVEIK 72   DNA   Artificial  cDNA of    GATATTCAGATGACCCAGAGCCCGAGCAGCCTGAGCGCGAGCGTGGGCGATCGCGTGACCATTACCTGC
           sequence    IFWL984    CGCGCGAGCCAGAGCATTGATGGGTTCCTGAACTGGTATCAGCAGAAACCGGGCAAAGCGCCGAAACTG
                                  CTGATTTATTTCGCGAGCAGCCTGCAGAGCGGCGTGCCGAGCCGCTTTAGCGGCAGCGGCAGCGGCACC
                                  GATTTTACCCTGACCATTAGCAGCCTGCAGCCGGAAGATTTTGCGACCTATTATTGCCAGCAGTCCTAC
                                  GACCTCCCGATTACATTTGGCCAGGGCACCAAAGTGGAAATTAAA 73   PRT   Artificial  IFWL1136   DIQMTQSPSSLSASVGDRVTITCRASQSIEGALNWYQQKPGKAPKLLIYFASSLQSGVPSRFSGSGSGT
           sequence               DFTLTISSLQPEDFATYYCQQAYDFPLTFGQGTKVEIK 74   PRT   Artificial  IFWL1144   DIQMTQSPSSLSASVGDRVTITCRASQSIEGYLNWYQQKPGKAPKLLIYFASSLQSGVPSRFSGSGSGT
           sequence               DFTLTISSLQPEDFATYYCQQAYDFPLTFGQGTKVEIK 75   PRT   Artificial  IFWL1148   DIQMTQSPSSLSASVGDRVTITCRASQSISSALNWYQQKPGKAPKLLIYFASSLQSGVPSRFSGSGSGT
           sequence               DFTLTISSLQPEDFATYYCQQAYDFPLTFGQGTKVEIK 76   PRT   Artificial  LCDR1      QSIADF
           sequence 77   PRT   Artificial  LCDR1      QSIAEF
           sequence 78   PRT   Artificial  LCDR1      QSIANNN
           sequence 79   PRT   Artificial  LCDR1      QSIANTN
           sequence 80   PRT   Artificial  LCDR1      QSIDGA
           sequence 81   PRT   Artificial  LCDR1      QSIDGF
           sequence 82   PRT   Artificial  LCDR1      QSIDNSY
           sequence 83   PRT   Artificial  LCDR1      QSIDRA
           sequence 84   PRT   Artificial  LCDR1      QSIEGA
           sequence 85   PRT   Artificial  LCDR1      QSIGDF
           sequence 86   PRT   Artificial  LCDR1      QSIGKS
           sequence

Sequence Listing

| SEQ ID NO: | Type | Species | Description | Amino acid sequence (or nucleotide sequence, as applicable) |
|---|---|---|---|---|
| 87 | PRT | Artificial sequence | LCDR1 | QSIGSA |
| 88 | PRT | Artificial sequence | LCDR1 | QSINGV |
| 89 | PRT | Artificial sequence | LCDR1 | QSIRNTN |
| 90 | PRT | Artificial sequence | LCDR1 | QSISSA |
| 91 | PRT | Artificial sequence | LCDR1 | QSISSF |
| 92 | DNA | Artificial sequence | cDNA of IFWL1164 | GACATCCAAATGACGCAGTCTCCGAGCTCTCTGAGCGCATCCGTGGGCGATCGCGTAACTATCACTTGT CGCGCCTCCCAGAGCATTGATAACTCCTATCTCAATTGGTATCAACAAAAACCGGGTAAGGCACCGAAA CTGCTGATTTACGAGCGTCCTCTCTGCAGTCCGGTGTGCCGTCCCGTTTCTCCGGCAGCGGTTCTGGT ACCGATTTCACGCTGACCATCAGCTCTCTGCAACCGGAGGACTTTGCTACGTACTACTGCCAACAGGGC TACGATTTCCCTCTCACATTCGGCCAAGGTACCAAAGTGGAAATTAAA |
| 93 | PRT | Artificial sequence | LCDR2 | FAS |
| 94 | PRT | Artificial sequence | LCDR2 | GAS |
| 95 | PRT | Artificial sequence | LCDR2 | WAS |
| 96 | PRT | Artificial sequence | LCDR3 | QQALDFPLT |
| 97 | PRT | Artificial sequence | LCDR3 | QQAYDFPLT |
| 98 | PRT | Artificial sequence | LCDR3 | QQGWDWPLT |
| 99 | PRT | Artificial sequence | LCDR3 | QQGYDFPLT |
| 100 | PRT | Artificial sequence | LCDR3 | QQGYDTPFT |
| 101 | PRT | Artificial sequence | LCDR3 | QQSFDFPLT |
| 102 | PRT | Artificial sequence | LCDR3 | QQSHDFPLT |
| 103 | PRT | Artificial sequence | LCDR3 | QQSHSFPLT |
| 104 | PRT | Artificial sequence | LCDR3 | QQSIDFPLT |
| 105 | PRT | Artificial sequence | LCDR3 | QQSYDFPLT |
| 106 | PRT | Artificial sequence | LCDR3 | QQSYDLPIT |
| 107 | PRT | Artificial sequence | LCDR3 | QQWYDNPLT |
| 108 | DNA | Artificial sequence | cDNA of IFWL1048 | GATATTCAGATGACCCAGAGCCCGAGCAGCCTGAGCGCGAGCGTGGGCGATCGCGTGACCATTACCTGC CGCGCGAGCCAGAGCATCGATGGCGCCCTGAACTGGTATCAGCAGAAACCGGGCAAAGCGCCGAAACTG CTGATTTATTCGCGAGCAGCCTGCAGAGCGGCGTGCCGAGCCGCTTTAGCGGCAGCGGCAGCGGCACC GATTTTACCCTGACCATTAGCAGCCTGCAGCCGGAAGATTTTGCGACCTATTATTGCCAGCAGGCCTAC GACTTTCCGTTGACATTTGGCCAGGGCACCAAAGTGGAAATTAAA |

-continued

Sequence Listing

| SEQ ID NO: | Type | Species | Description | Amino acid sequence (or nucleotide sequence, as applicable) |
|---|---|---|---|---|
| 109 | PRT | Artificial sequence | HCDR1 | GYSFTSYW |
| 110 | DNA | Artificial sequence | cDNA of IFWH591 | GAGGTGCAGCTGGTGCAGAGCGGCGCCGAGGTGAAGAAGCCCGGCGAGAGCCTGAAGATCAGCTGCAAG GGCAGCGGCTACAGCTTCACCAGCTACTGGATCGGCTGGGTGCGGCAGATGCCCGGCAAGGGCCTGGAG TGGATGGGCATCATCGACCCCAGCGACAGCGACACCCGGTACAGCCCCAGCTTCCAGGGCCAGGTGACC ATCAGCGCCGACAAGAGCATCAGCACCGCCTACCTGCAGTGGAGCAGCCTGAAGGCCAGCGACACCGCC ATGTACTACTGCGCCCGGCACCCCGGCCTGAACTGGGCCCCCGACTTCGACTACTGGGGCCAGGGCACC CTGGTGACCGTGAGCAGC |
| 111 | DNA | Artificial sequence | HCDR2 | IAPSDSDT |
| 112 | DNA | Artificial sequence | HCDR2 | IDASDSDT |
| 113 | DNA | Artificial sequence | HCDR2 | IDPSDSDT |
| 114 | PRT | Artificial | HCDR2 consensus sequence mAbs neutralize at least 3 IFNalphas | I$X_{11}X_{12}$SDSDT; whrein $X_{11}$ is D or A; and $X_{12}$ is P or A. |
| 115 | PRT | Artificial | HCDR3 | ARHPGLAWAPDFDY |
| 116 | PRT | Artificial | HCDR3 | ARHPGLNWAPDFDY |
| 117 | DNA | Artificial sequence | cDNA of IFWH617 | GAGGTGCAGCTGGTGCAGAGCGGCGCCGAGGTGAAGAAGCCCGGCGAGAGCCTGAAGATCAGCTGCAAG GGCAGCGGCTACAGCTTCACCAGCTACTGGATCGGCTGGGTGCGGCAGATGCCCGGCAAGGGCCTGGAG TGGATGGGCATCATCGACGCCAGCGACAGCGACACCCGGTACAGCCCCAGCTTCCAGGGCCAGGTGACC ATCAGCGCCGACAAGAGCATCAGCACCGCCTACCTGCAGTGGAGCAGCCTGAAGGCCAGCGACACCGCC ATGTACTACTGCGCCCGGCACCCCGGCCTGAACTGGGCCCCCGACTTCGACTACTGGGGCCAGGGCACC CTGGTGACCGTGAGCAGC |
| 118 | PRT | Artificial | LCDR1 consensus sequence mAbs neutralize at least 3 IFNalphas | QSI$X_1X_2X_3X_4$; wherein $X_1$ is G, D, A, R, E, S, or N; $X_2$ is D, G, N, S, R, E or K; $X_3$ is F, A, N, T, S or V; $X_4$ is Y, N or deleted. |
| 119 | PRT | Artificial | LCDR2 consensus sequence mAbs neutralize at least 3 IFNalphas | $X_5$AS; wherein $X_5$ is F, W or G. |
| 120 | PRT | Artificial | LCDR3 consensus sequence mAbs neutralize at least 3 IFNalphas | QQ$X_6X_7X_8X_9$P$X_{10}$T; wherein $X_6$ is A, G, S or W; $X_7$ is L, Y, H, W, F or I; $X_8$ is D or S; $X_9$ is F, T, L, N or W; and $X_{10}$ is L, F or I. |
| 121 | PRT | Artificial | HCDR3 consensus sequence mAbs neutralize at least 3 IFNalphas | ARHPGL$X_{13}$WAPDFDY; wherein $X_{13}$ is A or N. |

| SEQ ID NO: | Type | Species | Description | Amino acid sequence (or nucleotide sequence, as applicable) |
|---|---|---|---|---|
| 122 | DNA | Artificial sequence | cDNA of IFWH629 | GAGGTGCAGCTGGTGCAGAGCGGCGCCGAGGTGAAGAAGCCCGGCGAGAGCCTGAAGATCAGCTGCAAG GGCAGCGGCTACAGCTTCACCAGCTACTGGATCGGCTGGGTGCGGCAGATGCCCGGCAAGGGCCTGGAG TGGATGGGCATCATCGACCCCAGCGACAGCGACACCCGGTACAGCCCCAGCTTCCAGGGCCAGGTGACC ATCAGCGCCGACAAGAGCATCAGCACCGCCTACCTGCAGTGGAGCAGCCTGAAGGCCAGCGACACCGCC ATGTACTACTGCGCCCGGCACCCCGGCCTGGCCTGGGCCCCCGACTTCGACTACTGGGGCCAGGGCACC CTGGTGACCGTGAGCAGC |
| 123 | PRT | Artificial | IFWL1112 | DIQMTQSPSSLSASVGDRVTITCRASQSISGFLNWYQQKPGKAPKLLIYFASSLQSGVPSRFSGSGSGT DFTLTISSLQPEDFATYYCQQSYDLPITFGQGTKVEIK |
| 124 | PRT | Artificial | IFWL1113 | DIQMTQSPSSLSASVGDRVTITCRASQSIEGFLNWYQQKPGKAPKLLIYFASSLQSGVPSRFSGSGSGT DFTLTISSLQPEDFATYYCQQSYDLPITFGQGTKVEIK |
| 125 | PRT | Artificial | IFWL1114 | DIQMTQSPSSLSASVGDRVTITCRASQSIDGYLNWYQQKPGKAPKLLIYFASSLQSGVPSRFSGSGSGT DFTLTISSLQPEDFATYYCQQSYDLPITFGQGTKVEIK |
| 126 | PRT | Artificial | IFWL1115 | DIQMTQSPSSLSASVGDRVTITCRASQSIDGFLNWYQQKPGKAPKLLIYAASSLQSGVPSRFSGSGSGT DFTLTISSLQPEDFATYYCQQSYDLPITFGQGTKVEIK |
| 127 | PRT | Artificial | IFWL1117 | DIQMTQSPSSLSASVGDRVTITCRASQSIDGFLNWYQQKPGKAPKLLIYIASSLQSGVPSRFSGSGSGT DFTLTISSLQPEDFATYYCQQSYDLPITFGQGTKVEIK |
| 128 | PRT | Artificial | IFWL1118 | DIQMTQSPSSLSASVGDRVTITCRASQSIDGFLNWYQQKPGKAPKLLIYLASSLQSGVPSRFSGSGSGT DFTLTISSLQPEDFATYYCQQSYDLPITFGQGTKVEIK |
| 129 | PRT | Artificial | IFWL1119 | DIQMTQSPSSLSASVGDRVTITCRASQSIDGFLNWYQQKPGKAPKLLIYVASSLQSGVPSRFSGSGSGT DFTLTISSLQPEDFATYYCQQSYDLPITFGQGTKVEIK |
| 130 | PRT | Artificial | IFWL1120 | DIQMTQSPSSLSASVGDRVTITCRASQSIEGYLNWYQQKPGKAPKLLIYFASSLQSGVPSRFSGSGSGT DFTLTISSLQPEDFATYYCQQSYDLPITFGQGTKVEIK |
| 131 | PRT | Artificial | IFWL1121 | DIQMTQSPSSLSASVGDRVTITCRASQSIEGFLNWYQQKPGKAPKLLIYAASSLQSGVPSRFSGSGSGT DFTLTISSLQPEDFATYYCQQSYDLPITFGQGTKVEIK |
| 132 | PRT | Artificial | IFWL1122 | DIQMTQSPSSLSASVGDRVTITCRASQSIEGFLNWYQQKPGKAPKLLIYIASSLQSGVPSRFSGSGSGT DFTLTISSLQPEDFATYYCQQSYDLPITFGQGTKVEIK |
| 133 | PRT | Artificial | IFWL1123 | DIQMTQSPSSLSASVGDRVTITCRASQSIEGFLNWYQQKPGKAPKLLIYLASSLQSGVPSRFSGSGSGT DFTLTISSLQPEDFATYYCQQSYDLPITFGQGTKVEIK |
| 134 | PRT | Artificial | IFWL1124 | DIQMTQSPSSLSASVGDRVTITCRASQSIEGFLNWYQQKPGKAPKLLIYVASSLQSGVPSRFSGSGSGT DFTLTISSLQPEDFATYYCQQSYDLPITFGQGTKVEIK |
| 135 | PRT | Artificial | IFWL1125 | DIQMTQSPSSLSASVGDRVTITCRASQSISSFLNWYQQKPGKAPKLLIYFASSLQSGVPSRFSGSGSGT DFTLTISSLQPEDFATYYCQQSYDLPITFGQGTKVEIK |
| 136 | PRT | Artificial | IFWL1126 | DIQMTQSPSSLSASVGDRVTITCRASQSISSYLNWYQQKPGKAPKLLIYFASSLQSGVPSRFSGSGSGT DFTLTISSLQPEDFATYYCQQSYDLPITFGQGTKVEIK |
| 137 | PRT | Artificial | IFWL1129 | DIQMTQSPSSLSASVGDRVTITCRASQSIGDFLNWYQQKPGKAPKLLIYYASSLQSGVPSRFSGSGSGT DFTLTISSLQPEDFATYYCQQSYDLPITFGQGTKVEIK |
| 138 | PRT | Artificial | IFWL1173 | DIQMTQSPSSLSASVGDRVTITCRASQSIEGYLNWYQQKPGKAPKLLIYYASSLQSGVPSRFSGSGSGT DFTLTISSLQPEDFATYYCQQSYDLPITFGQGTKVEIK |
| 139 | PRT | Artificial | IFWL1174 | DIQMTQSPSSLSASVGDRVTITCRASQSIEGFLNWYQQKPGKAPKLLIYYASSLQSGVPSRFSGSGSGT DFTLTISSLQPEDFATYYCQQSYDLPITFGQGTKVEIK |
| 140 | PRT | Artificial | IFWL1175 | DIQMTQSPSSLSASVGDRVTITCRASQSISSFLNWYQQKPGKAPKLLIYYASSLQSGVPSRFSGSGSGT DFTLTISSLQPEDFATYYCQQSYDLPITFGQGTKVEIK |
| 141 | PRT | Artificial | IFWL1135 | DIQMTQSPSSLSASVGDRVTITCRASQSISGALNWYQQKPGKAPKLLIYFASSLQSGVPSRFSGSGSGT DFTLTISSLQPEDFATYYCQQAYDFPLTFGQGTKVEIK |
| 142 | PRT | Artificial | IFWL1137 | DIQMTQSPSSLSASVGDRVTITCRASQSIDGYLNWYQQKPGKAPKLLIYFASSLQSGVPSRFSGSGSGT DFTLTISSLQPEDFATYYCQQAYDFPLTFGQGTKVEIK |
| 143 | PRT | Artificial | IFWL1143 | DIQMTQSPSSLSASVGDRVTITCRASQSIDGALNWYQQKPGKAPKLLIYFASSLQSGVPSRFSGSGSGT DFTLTISSLQPEDFATYYCQQAYDLPLTFGQGTKVEIK |
| 144 | PRT | Artificial | IFWL1149 | DIQMTQSPSSLSASVGDRVTITCRASQSISSYLNWYQQKPGKAPKLLIYFASSLQSGVPSRFSGSGSGT DFTLTISSLQPEDFATYYCQQAYDFPLTFGQGTKVEIK |

-continued

Sequence Listing

| SEQ ID NO: | Type | Species | Description | Amino acid sequence (or nucleotide sequence, as applicable) |
|---|---|---|---|---|
| 145 | PRT | Artificial | IFWL1152 | DIQMTQSPSSLSASVGDRVTITCRASQSISSALNWYQQKPGKAPKLLIYFASSLQSGVPSRFSGSGSGT DFTLTISSLQPEDFATYYCQQAYDLPLTFGQGTKVEIK |
| 146 | PRT | Artificial | IFWL1155 | DIQMTQSPSSLSASVGDRVTITCRASQSISSYLNWYQQKPGKAPKLLIYFASSLQSGVPSRFSGSGSGT DFTLTISSLQPEDFATYYCQQAYDLPLTFGQGTKVEIK |
| 147 | PRT | Artificial | IFWL1161 | DIQMTQSPSSLSASVGDRVTITCRASQSIGDFLNWYQQKPGKAPKLLIYAASSLQSGVPSRFSGSGSGT DFTLTISSLQPEDFATYYCQQAYDLPLTFGQGTKVEIK |
| 148 | PRT | Artificial | IFWL1162 | DIQMTQSPSSLSASVGDRVTITCRASQSIDNSYLNWYQQKPGKAPKLLIYGASSLQSGVPSRFSGSGSG TDFTLTISSLQPEDFATYYCQQGYDWPLTFGQGTKVEIK |
| 149 | PRT | Artificial | IFWL1163 | DIQMTQSPSSLSASVGDRVTITCRASQSIDNSYLNWYQQKPGKAPKLLIYGASSLQSGVPSRFSGSGSG TDFTLTISSLQPEDFATYYCQQGWDFPLTFGQGTKVEIK |
| 150 | PRT | Artificial | IFWL1164 | DIQMTQSPSSLSASVGDRVTITCRASQSIDNSYLNWYQQKPGKAPKLLIYGASSLQSGVPSRFSGSGSG TDFTLTISSLQPEDFATYYCQQGYDFPLTFGQGTKVEIK |
| 151 | PRT | Artificial | IFWL1176 | DIQMTQSPSSLSASVGDRVTITCRASQSIDQSYLNWYQQKPGKAPKLLIYGASSLQSGVPSRFSGSGSG TDFTLTISSLQPEDFATYYCQQGYDFPLTFGQGTKVEIK |
| 152 | PRT | Artificial | IFWL1177 | DIQMTQSPSSLSASVGDRVTITCRASQSIDTSYLNWYQQKPGKAPKLLIYGASSLQSGVPSRFSGSGSG TDFTLTISSLQPEDFATYYCQQGYDFPLTFGQGTKVEIK |
| 153 | PRT | Artificial | IFWL1178 | DIQMTQSPSSLSASVGDRVTITCRASQSIDNTYLNWYQQKPGKAPKLLIYGASSLQSGVPSRFSGSGSG TDFTLTISSLQPEDFATYYCQQGYDFPLTFGQGTKVEIK |
| 154 | PRT | Artificial | LCDR3 | QQSYDFPL |
| 155 | PRT | *Homo sapiens* | IGHV5-51 | EVQLVQSGAEVKKPGESLKISCKGSGYSFTSYWIGWVRQMPGKGLEWMGIIYPGDSDTRYSPSFQGQVT ISADKSISTAYLQWSSLKASDTAVYYCAR |
| 156 | PRT | *Homo sapiens* | IGKV1D-39 | DIQMTQSPSSLSASVGDRVTITCRASQSISSYLNWYQQKPGKAPKLLIYAASSLQSGVPSRFSGSGSGT DFTLTISSLQPEDFATYYCQQSYSTPWTFGQGTKVEIK |
| 157 | PRT | Artificial sequence | IFWH615 | EVQLVQSGAEVKKPGESLKISCKGSGYSFTSYWIGWVRQMPGKGLEWMGIIAPSDSDTRYSPSFQGQVT ISADKSISTAYLQWSSLKASDTAMYYCARHPGLNWAPDFDYWGQGTLVTVSS |
| 158 | PRT | Artificial sequence | IFWH617 | EVQLVQSGAEVKKPGESLKISCKGSGYSFTSYWIGWVRQMPGKGLEWMGIIDASDSDTRYSPSFQGQVT ISADKSISTAYLQWSSLKASDTAMYYCARHPGLNWAPDFDYWGQGTLVTVSS |
| 159 | PRT | Artificial | LCDR1 consensus sequence mAbs neutralize at least 6 IFNalphas | QSI$X_{14}X_{15}X_{16}X_{17}$; wherein $X_{14}$ is G, D, A, E, S, or N; $X_{15}$ is D, G, N, S or R; $X_{16}$ is F, A, N, S or V; and $X_{17}$ is Y, N or deleted. |
| 160 | PRT | Artificial | LCDR3 consensus sequence mAbs neutralize at least 6 IFNalphas | QQ$X_{18}X_{19}X_{20}X_{21}$P$X_{22}$T; wherein $X_{18}$ is A, G or S; $X_{19}$ is Y, H, W or F; $X_{20}$ is D or S; $X_{21}$ is F, T, L or W; and $X_{22}$ is L, F or I. |
| 161 | PRT | Artificial | LCDR1 consensus sequence mAbs neutralize at least 10 IFNalphas | QSI$X_{23}X_{24}X_{25}X_{26}$; wherein $X_{23}$ is A or D; $X_{24}$ is N or G; $X_{25}$ is F, N or S; and $X_{26}$ is Y, N or deleted. |
| 162 | PRT | Artificial | LCDR3 consensus sequence mAbs neutralize at least 10 IFNalphas | QQ$X_{27}X_{28}X_{29}X_{30}$P$X_{31}$T; wherein $X_{27}$ is G or S; $X_{28}$ is Y; $X_{29}$ is D; $X_{30}$ is F, T or L; and $X_{31}$ is L, F or I. |

We claim:

1. A method of treating lupus, comprising administering a therapeutically effective amount of an isolated antibody comprising a heavy chain variable region and a light chain variable region, the heavy chain variable region comprising heavy chain complementarity determining region (HCDR) 1 (HCDR1), 2 (HCDR2) and 3 (HCDR3) amino acid sequences of SEQ ID Nos: 109, 113 and 116, respectively, and the light chain variable region comprising light chain complementarity determining region (LCDR) 1 (LCDR1), 2 (LCDR2) and 3 (LCDR3) amino acid sequences of SEQ ID Nos: 82, 94 and 99, respectively, to a patient in need thereof for a time sufficient to treat the lupus.

2. The method of claim 1, wherein lupus is systemic lupus erythematosus (SLE) or cutaneous lupus erythematosus (CLE).

3. The method of claim 2, wherein the patient has lupus nephritis.

4. The method of claim 1, wherein the patient exhibits a Type I interferon signature.

5. The method of claim 1, wherein the antibody comprises a heavy chain variable region (VH) amino acid sequence of SEQ ID NO: 28 and a light chain variable region (VL) amino acid sequence of SEQ ID NO: 150.

6. The method of claim 5, wherein the antibody has at least one substitution in an Fc region.

7. The method of claim 6, wherein the wherein the substitution comprises a substitution M252Y/S254T/T256E, V234A/G237A/P238S/H28A/V309L/A330S/P331S or P238S/L234A/L235A, wherein residue numbering is according to the EU numbering.

8. The method of claim 1, wherein the antibody is a bispecific antibody.

9. The method of claim 8, wherein the bispecific antibody neutralizes BLyS, CD40L, IL-6, CD27, BDCA2, IL-12, IL-23, IFN-ccD, IL-17, CD20, IL-10, CD22, IL-21, ICOS, ICOSL or IFN-γ.

10. The method of claim 1, further administering a second therapeutic agent.

11. The method of claim 10, wherein the second therapeutic agent is an antibody that binds BLyS, CD40L, IL-6, CD27, BDCA2, IL-12, IL-23, IFN-ccD, IL-17, CD20, IL-10, CD22, IL-21, ICOS, ICOSL or IFN-γ.

12. The method of claim 10, wherein the second therapeutic agent is a corticosteroid, an immunosuppressant, or a B-cell modulator.

13. The method of claim 12, wherein the second therapeutic agent is prednisone, prednisolone, methylprednisolone, deflazcort, hydroxychloroquine, azathloprine, methotrexate, cyclophosphamide, mycophenolate mofetil (MMF), mycophenolate sodium, cyclosporine, taorolimus, rituximab or belirnumab.

* * * * *